US011903935B2

(12) United States Patent
Milbrandt et al.

(10) Patent No.: US 11,903,935 B2
(45) Date of Patent: Feb. 20, 2024

(54) INHIBITORS OF SARM1 NADASE ACTIVITY AND USES THEREOF

(71) Applicants: Washington University, Saint Louis, MO (US); Disarm Therapeutics, Inc., Indianapolis, IN (US)

(72) Inventors: Jeffrey Milbrandt, Saint Louis, MO (US); Kow Essuman, Saint Louis, MO (US); Yo Sasaki, Brentwood, MO (US); Aaron Diantonio, Olivette, MO (US); Xianrong Mao, Saint Louis, MO (US); Rajesh Devraj, Chesterfield, MO (US); Raul Eduardo Krauss, Chestnut Hill, MA (US); Robert Owen Hughes, Newtown, CT (US)

(73) Assignees: Washington University, Saint Louis, MO (US); Disarm Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/508,321

(22) Filed: Oct. 22, 2021

(65) Prior Publication Data
US 2022/0040164 A1 Feb. 10, 2022

Related U.S. Application Data

(63) Continuation of application No. 16/335,754, filed as application No. PCT/US2017/053098 on Sep. 22, 2017, now Pat. No. 11,253,503.

(60) Provisional application No. 62/473,916, filed on Mar. 20, 2017, provisional application No. 62/473,805, filed on Mar. 20, 2017, provisional application No. (Continued)

(51) Int. Cl.
| | |
|---|---|
| *A61K 31/4439* | (2006.01) |
| *A61K 47/55* | (2017.01) |
| *A61K 47/52* | (2017.01) |
| *A61P 25/28* | (2006.01) |
| *A61K 33/243* | (2019.01) |
| *A61K 31/047* | (2006.01) |
| *A61K 31/145* | (2006.01) |
| *A61K 31/198* | (2006.01) |
| *A61K 31/41* | (2006.01) |
| *A61K 31/437* | (2006.01) |
| *A61K 31/4375* | (2006.01) |
| *A61K 31/444* | (2006.01) |
| *A61K 31/4535* | (2006.01) |
| *A61K 31/566* | (2006.01) |
| *A61K 31/7048* | (2006.01) |
| *A61K 31/7084* | (2006.01) |
| *A61K 33/245* | (2019.01) |
| *A61K 33/28* | (2006.01) |
| *A61K 33/30* | (2006.01) |

(52) U.S. Cl.
CPC ........ *A61K 31/4439* (2013.01); *A61K 31/047* (2013.01); *A61K 31/145* (2013.01); *A61K 31/198* (2013.01); *A61K 31/41* (2013.01); *A61K 31/437* (2013.01); *A61K 31/4375* (2013.01); *A61K 31/444* (2013.01); *A61K 31/4535* (2013.01); *A61K 31/566* (2013.01); *A61K 31/7048* (2013.01); *A61K 31/7084* (2013.01); *A61K 33/243* (2019.01); *A61K 33/245* (2013.01); *A61K 33/28* (2013.01); *A61K 33/30* (2013.01); *A61K 47/52* (2017.08); *A61K 47/55* (2017.08); *A61P 25/28* (2018.01)

(58) Field of Classification Search
CPC .... A61K 31/4439; A61K 47/55; A61K 47/52; A61K 33/243; A61K 31/047; A61K 31/145; A61K 31/198; A61K 31/41; A61K 31/437; A61K 31/4375; A61K 31/444; A61K 31/4535; A61K 31/566; A61K 31/7048; A61K 31/7084; A61K 33/245; A61K 33/28; A61K 33/30; A61K 31/29; A61K 31/305; A61K 31/382; A61K 31/425; A61K 31/473; A61K 31/565; A61K 31/60; A61P 25/28; A61P 9/10; A61P 7/06; A61P 7/00; A61P 43/00; A61P 39/02; A61P 3/02; A61P 3/00; A61P 27/16; A61P 27/06; A61P 27/02; A61P 25/16; A61P 25/14; A61P 25/02; A61P 25/00; A61P 21/02; Y02A 50/30; C07K 2319/21; C07K 2319/22; C07K 2319/23; C07K 2319/70; C07K 14/705; C07K 17/70596; C12Q 1/34; C12N 9/2497

See application file for complete search history.

(56) References Cited

U.S. PATENT DOCUMENTS

| | | | |
|---|---|---|---|
| 5,045,552 A | 9/1991 | Souda et al. | |
| 2012/0328629 A1 | 12/2012 | Freeman et al. | |

FOREIGN PATENT DOCUMENTS

| | | |
|---|---|---|
| EP | 268956 A2 | 6/1988 |
| WO | 2006/084854 A2 | 8/2006 |
| WO | 2018/057989 A1 | 3/2018 |

OTHER PUBLICATIONS

Araki, T. et al., Increased nuclear NAD biosynthesis and SIRT1 activation prevent axonal degeneration, Science, 305(5686):1010-3 (2004).

(Continued)

*Primary Examiner* — Robert A Wax
*Assistant Examiner* — Quanglong N Truong
(74) *Attorney, Agent, or Firm* — Robert D. Shereda

(57) ABSTRACT

The present disclosure provides compounds useful as inhibitors of SARM1 NADase activity, compositions thereof, and methods of using the same. The present disclosure provides compounds useful for treating a neurodegenerative or neu- (Continued)

rological disease or disorder, compositions thereof, and methods of using the same.

3 Claims, 34 Drawing Sheets

Specification includes a Sequence Listing.

Related U.S. Application Data

62/473,921, filed on Mar. 20, 2017, provisional application No. 62/399,339, filed on Sep. 24, 2016.

(56) References Cited

OTHER PUBLICATIONS

Arbanas, Caroline, Major pathway identified in nerve cell death offers hope for therapies, The Source Washington University in St. Louis, Retrieved from the Internet: https://source.wustle.edu/2015/04/major-pathway-identified-in-nerve-cell-death-offers-hope-for-therapies [retrieved on Dec. 6, 2017], pp. 3-4 (Apr. 23, 2015).
Berge, S. et al., Pharmaceutical salts, J Pharm Sci, 66(1):1-19 (1977).
Breen, L. et al., beta-NAD is a novel nucleotide released on stimulation of nerve terminals in human urinary bladder detrusor muscle, Am J Physiol Renal Physiol., 290(2):F486-95 (2006).
Canto, C. et al., NAD(+) Metabolism and the Control of Energy Homeostasis: A Balancing Act between Mitochondria and the Nucleus, Cell Metab., 22(1):31-53 (2015).
De Deyn, P. et al., Aripiprazole in the treatment of Alzheimer's disease, Expert Opin Pharmacother, 14(4):459-74 (2013).
Fischer, L. et al., Axonal degeneration in motor neuron disease, Neurodegener Dis., 4(6):431-42 (2007).
Geisler, S. et al., Prevention of vincristine-induced peripheral neuropathy by genetic deletion of SARM1 in mice, Brain, 139(Pt 12):3092-3108 (2016).
Gerdts, J. et al., Axon Self-Destruction: New Links among SARM1, MAPKs, and NAD+ Metabolism, Neuron, 89(3):449-60 (2016).
Gerdts, J. et al., SARM1 activation triggers axon degeneration locally via NAD+ destruction, Science, 348(6233):453-7 (2015).
Gerdts, J. et al., Sarm1-mediated axon degeneration requires both SAM and TIR interactions, J Neurosci., 33(33):13569-80 (2013).
Hasan, M. et al., Scant Extracellular NAD Cleaving Activity of Human Neutrophils is Down-Regulated by fMLP via FPRL 1, Korean J Physiol Pharmacol., 18(6):497-502 (2014).
Henninger, N. et al., Attenuated traumatic axonal injury and improved functional outcome after traumatic brain injury in mice lackina Sarm1, Brain, 139(Pt 4):1094-105 (2016).
International Search Report for PCT/US2017/053098 (Inhibitors of SARM1 Nadase Activity and Uses Thereof, filed Sep. 22, 2017), issued by ISA/EPO, 9 pages (dated Mar. 12, 2018).
Kurowska, Z. et al., Is Axonal Degeneration a Key Early Event in Parkinson's Disease?, Journal of Parkinson's Disease, 6:703-707 (2016).
Li, P. et al., Role of ADP-ribose in 11, 12-EET-induced activation of K(Ca) channels in coronary arterial smooth muscle cells, Am J Physiol Heart Circ Physiol., 282(4):H1229-36 (2002).
O'neill, L. et al., The family of five: TIR-domain-containing adaptors in Toll-like receptor signalling, Nat Rev Immunol., 7(5):353-64 (2007).
O'neill, L. et al., The history of Toll-like receptors—redefining innate immunity, Nat Rev Immunol., 13(6):453-60 (2013).
Oliver et al., Imino-1,2,4-dithiazoles. I. Alkvlation, J. Ora. Chem, 39(15):2225-2228 (1974).
Osterloh, J. et al., dSarm/Sarm1 is required for activation of an injury-induced axon death pathwav, Science, 337(6093):481-4 (2012).
Pandeya, S. et al., Synthesis and biological activity of isodithiobiurets, dithiobiurets, and dithiazoles, Pharm Res., 4(4):321-6 (1987).
Qiao, F. et al., The many faces of SAM, Sci STKE., 2005(286):re7 (2005).
Rojo, L. et al., Selective interaction of lansoprazole and astemizole with tau polymers: potential new clinical use in diagnosis of Alzheimer's disease, J Alzheimers Dis, 19(2):573-89 (2010).
Sasaki, Y. et al., Nicotinamide mononucleotide adenylyl transferase-mediated axonal protection requires enzymatic activity but not increased levels of neuronal nicotinamide adenine dinucleotide, J Neurosci., 29(17):5525-35 (2009).
Sasaki, Y. et al., NMNAT1 inhibits axon degeneration via blockade of SARM1-mediated NAD(+) depletion, Elife, 5:e19749 (2016).
Sodhi, R. and Singh, N., Defensive effect of lansoprazole in dementia of AD type in mice exposed to streptozotocin and cholesterol enriched diet, PLOS One, 8(7):e70487 (2013).
Tewari, R. et al., Armadillo-repeat protein functions: questions for little creatures, Trends Cell Biol., 20(8):4 70-8 (2010).
Verdin, E., NAD+ in aging, metabolism, and neurodegeneration, Science, 350(6265):1208-13 (2015).
Wang, J. et al., A local mechanism mediates NAO-dependent protection of axon degeneration, J Cell Biol, 170(3):349-55 (2005).
Whitmore, A. et al., The proapoptotic proteins Bax and Bak are not involved in Wallerian degeneration, Cell Death Differ . . . 10(2):260-1 (2003).
Written Opinion for PCT/US2017/053098 (Inhibitors of SARM1 Nadase Activity and Uses Thereof, filed Sep. 22, 2017), issued by ISA/EPO, 13 pages (dated Mar. 12, 2018).

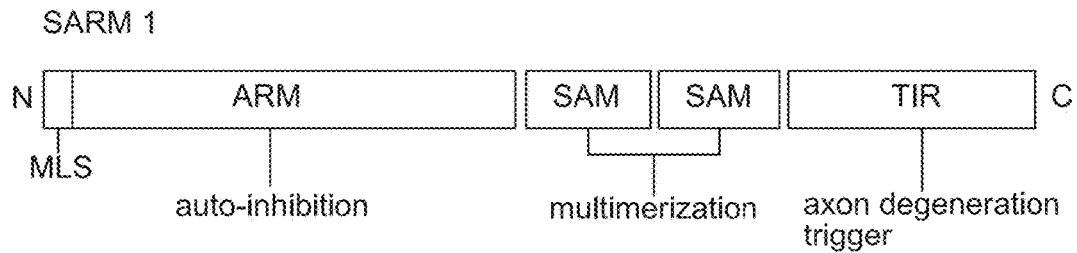
FIG. 1
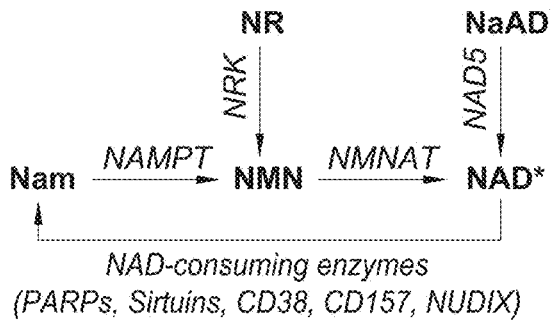
FIG. 2A
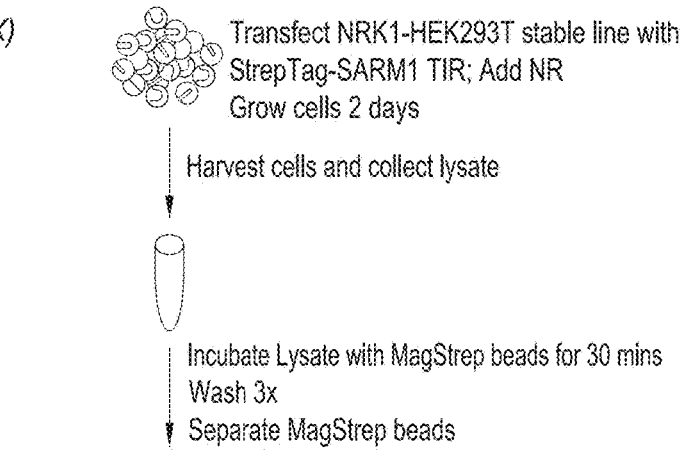
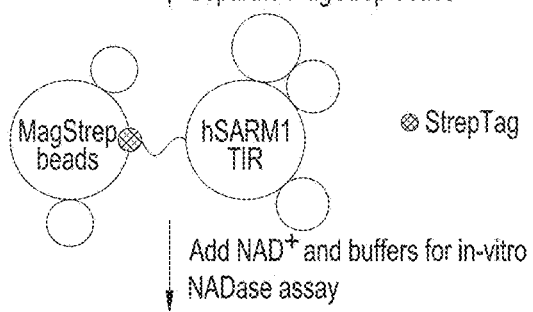
FIG. 2B

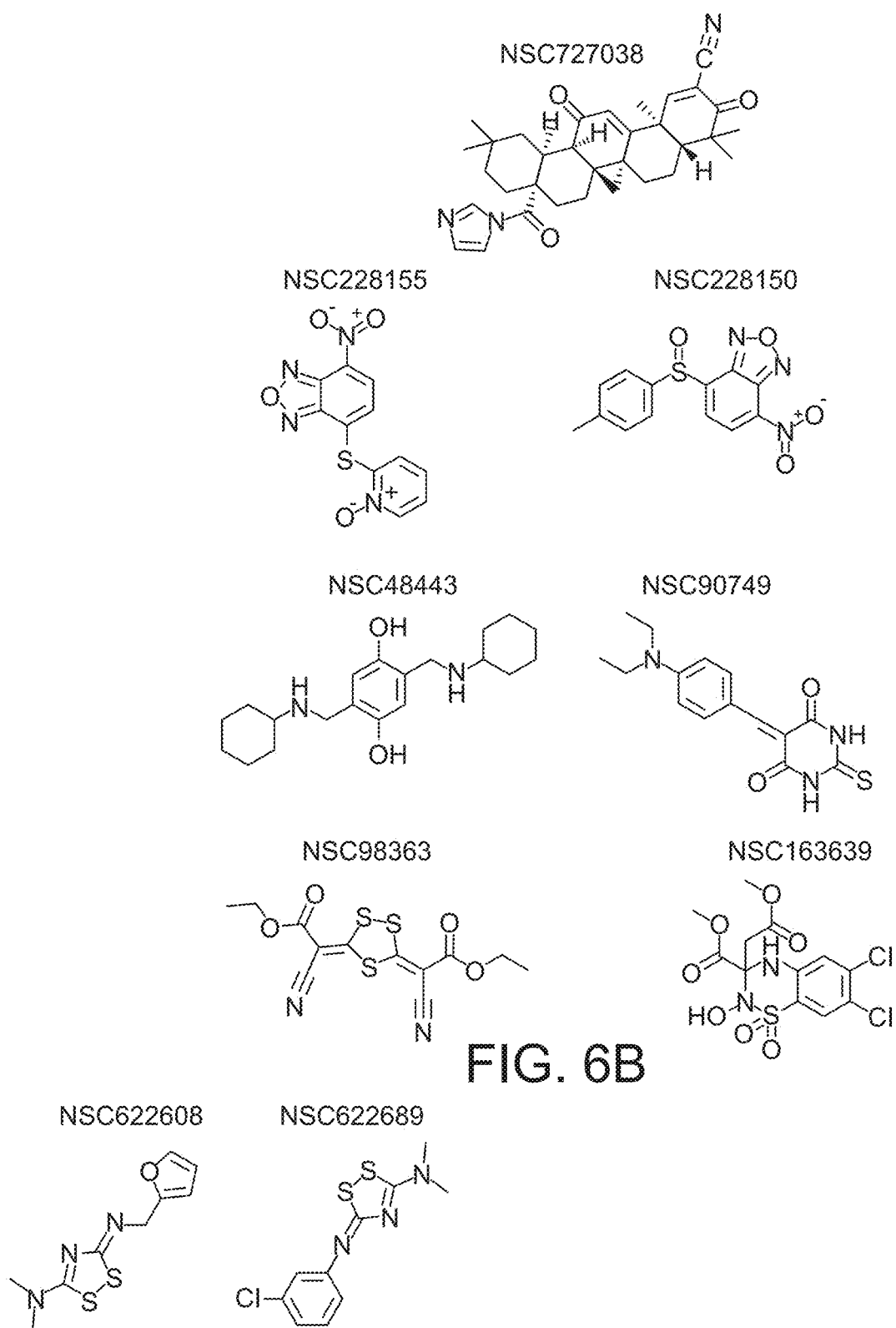

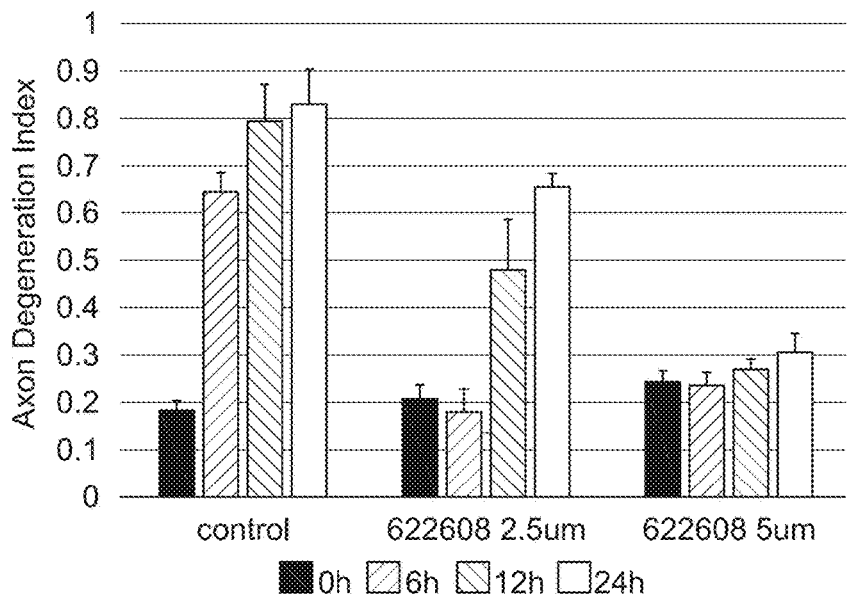
FIG. 10C
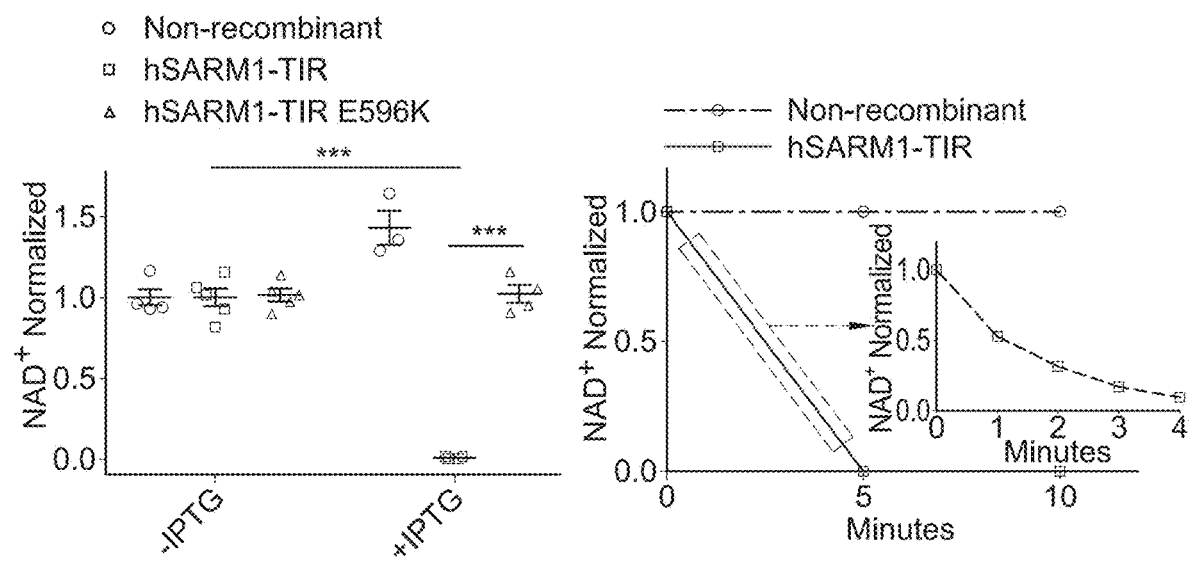
FIG. 11A
FIG. 11B

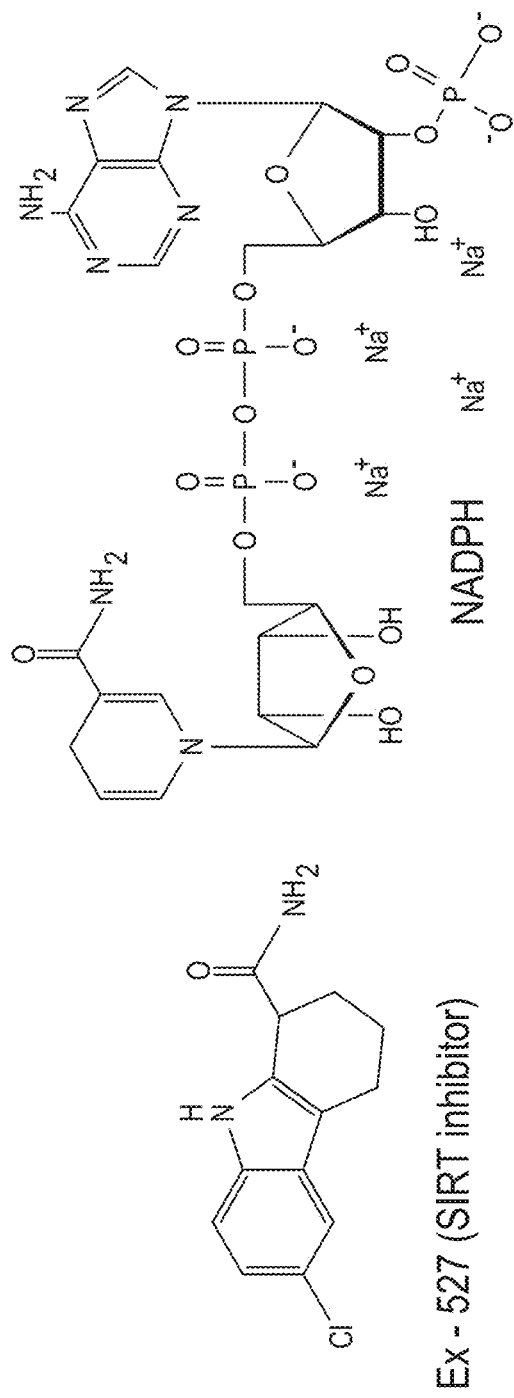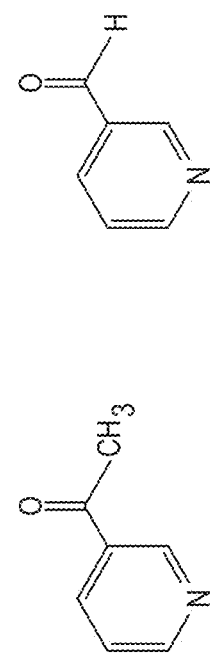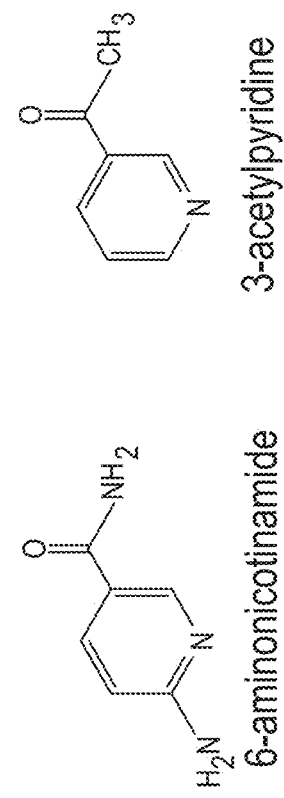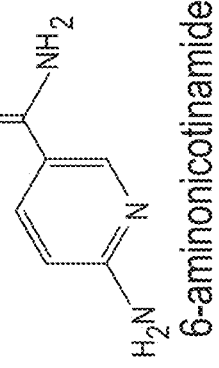
FIG. 15 (Cont.)

```
SARM1 TIR  559 GDTPDWFISY.....RNSGSQLASLKVILQLHGFSWFIDVEKLEAGK.....FEDKLIQSVMGA 614
      MiiB   13 ..VGSWRLGGPFRQLVDPRTGVMSSGDQNVFSRLIENFESRGTTWYNAHRREAWGAEFLSPAEATRLDHDEIKA  85

SARM1 TIR  615 RNKVLVLSPGALDKCMQDHDCKDWVHKEIVTALSCWNINPIIDGFRWPEPQVLPEDMQAVLTFNGIKW.SHEYQ 688
      MiiB   86 DVEAFPG..VPASP......GTHMEIGWASGMQKPMVLLERDE.....DYAFLVTGLESQANVEILRFSGT 145

SARM1 TIR  689 EATIEKIIRFLQGRSSRDSSAGSDTSLEGAAPMGPT 724
      MiiB  146 EIVMRLDGAVARVLGRAGEP 166
```

FIG. 16

TIR E642A

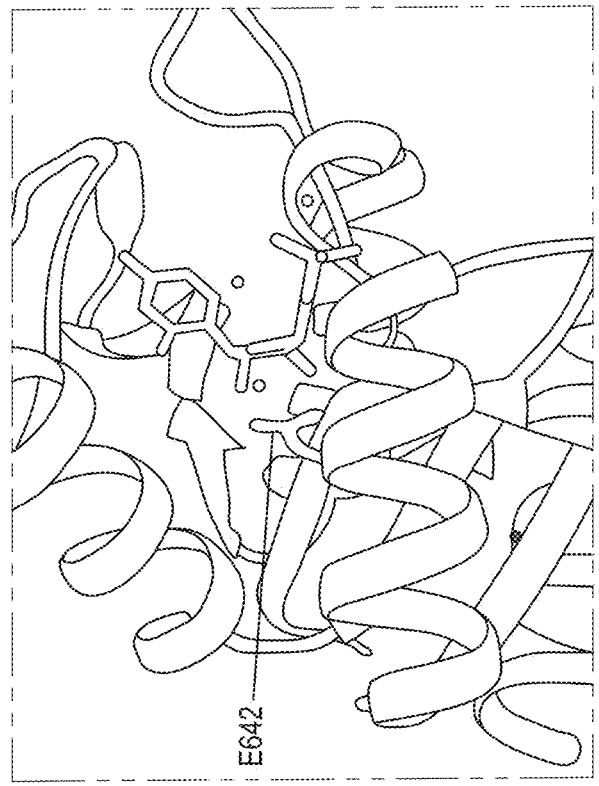

FIG. 17

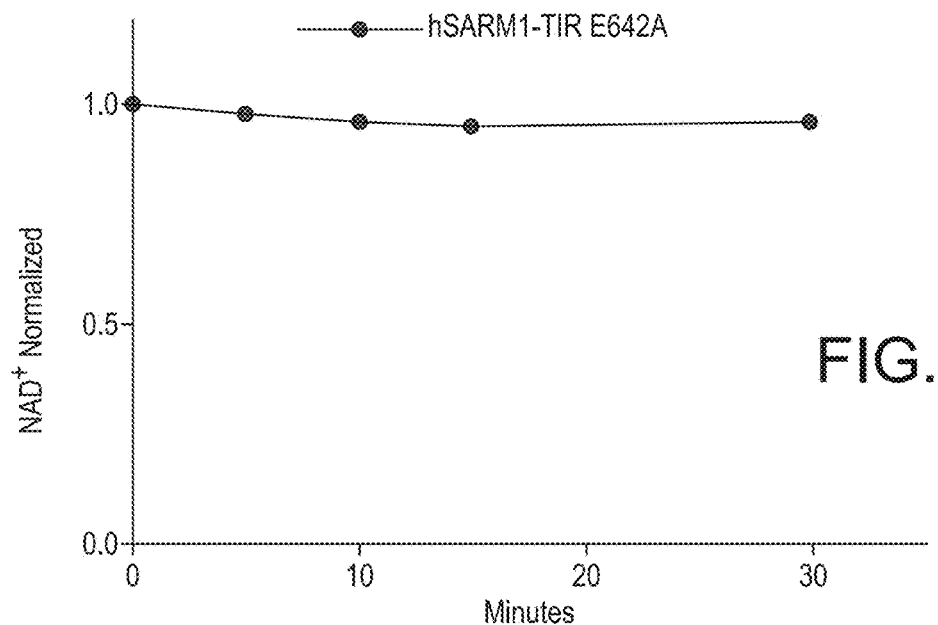
FIG. 18
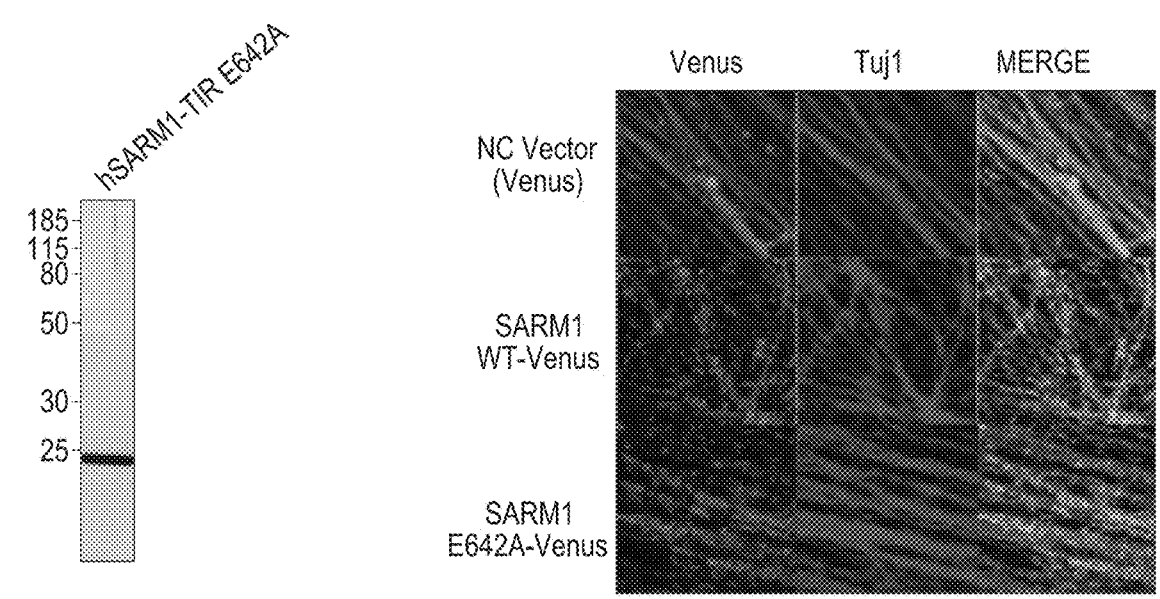
FIG. 19
FIG. 20

INHIBITORS OF SARM1 NADASE ACTIVITY AND USES THEREOF

CROSS REFERENCE TO RELATED APPLICATIONS

This application is a Continuation Patent Application of U.S. application Ser. No. 16/335,754, filed on Mar. 22, 2019, which is a U.S. National Entry claiming priority to International Application PCT/US2017/053098 filed on Sep. 22, 2017, which claims the benefit of U.S. Provisional Application 62/399,339, filed Sep. 24, 2016, U.S. Provisional Application No. 62/473,805, filed Mar. 20, 2017, U.S. Provisional Application No. 62/473,916, filed Mar. 20, 2017 and U.S. Provisional Application No. 62/473,921, filed Mar. 20, 2017, each of which is hereby incorporated by reference in its entirety.

GOVERNMENT SUPPORT

This invention was made with government support under AG013730, NS065053 and NS087632 awarded by the National Institutes of Health. The government has certain rights in the invention.

FIELD

This application relates to various compounds and compositions, and methods, useful for inhibition of SARM1 NADase activity and/or treating a neurodegenerative or neurological disease or disorder.

BACKGROUND

Axonal degeneration is a hallmark of several neurological disorders including peripheral neuropathy, traumatic brain injury, and neurodegenerative diseases (Gerdts et al., SARM1 activation triggers axon degeneration locally via NAD(+) destruction. *Science* 348 2016, pp. 453-457, hereby incorporated by reference in its entirety). In Parkinson's disease and Amyotrophic Lateral Sclerosis, for example, axonal degeneration is an early event, preceding symptom onset and widespread neuronal loss (Kurowska et al., 2017; Fischer et al., Axonal degeneration in motor neuron disease *Neurodegener. Dis.* 4 2007 pp. 431-442; both of which are hereby incorporated by reference in their entireties).

SUMMARY

In some embodiments, the present disclosure provides enzyme(s) as therapeutic target(s) for many neurological disorders that involve axon degeneration or axonopathy.

In certain embodiments, the present disclosure provides assays for identifying and/or characterizing SARM1 inhibitor. In some embodiments, the present disclosure provides certain vector constructs and polypeptides for use in these assays, including SAM-TIR in which the SARM1 N-terminal auto-inhibitory domain is deleted, as well as tagged versions of the TIR domain. In some embodiments, the present disclosure provides compositions comprising a polypeptide and a solid support which is used for screening SARM1 NADase inhibitors.

In some embodiments, the present disclosure provides methods of using SARM1 NADase inhibitors to treat, prevent or ameliorate axonal degeneration, axonopathies and neurological diseases and disorders that involve axonal degeneration. In some embodiments, the present disclosure provides inhibitors of SARM1 NADase. In some such embodiments, such compounds inhibit axonal degeneration, including axonal degeneration that results from reduction or depletion of NAD. In some embodiments, the present disclosure encompasses the recognition that Nicotinamide Hypoxanthine Dinucleotide (NHD) is useful as an inhibitor of SARM1 NADase activity.

In some embodiments, the present disclosure provides methods of treating a neuropathy or axonopathy associated with axonal degeneration. In some such embodiments, a neuropathy or axonopathy associated with axonal degeneration is selected from hereditary or congenital neuropathies or axonopathies. In some embodiments, a neuropathy or axonopathy associated with axonal degeneration is selected from or associated with Parkinson's disease, Alzheimer's disease, Herpes infection, diabetes, amyotrophic lateral sclerosis, a demyelinating disease, ischemia or stroke, chemical injury, thermal injury, and AIDS. In some embodiments, a neuropathy or axonopathy associated with axonal degeneration is selected from Parkinson's disease or non-Parkinson's diseases, and Alzheimer's disease.

It has now been found that compounds of this disclosure, and pharmaceutically acceptable compositions thereof, are effective as inhibitors of SARM1 NADase activity. In some embodiments, inhibitors of SARM1 NADase activity have the general formula $I^A$ or formula $I^B$:

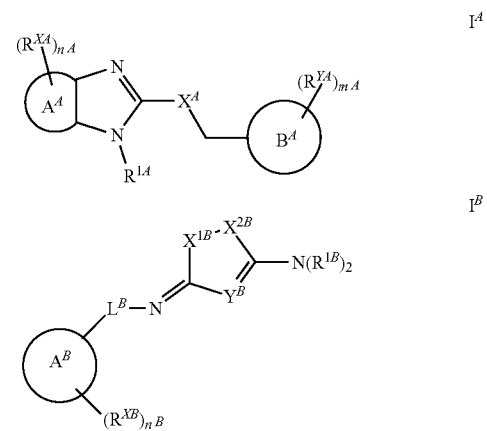

or a pharmaceutically acceptable salt thereof, wherein each variable is as defined and described herein.

In some embodiments, inhibitors of SARM1 NADase activity have the general formula $I^C$ or formula $I^D$:

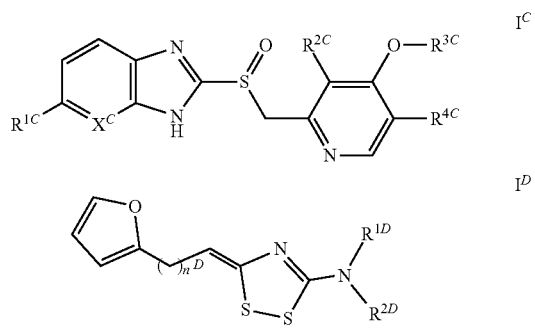

or a pharmaceutically acceptable salt thereof, wherein each variable is as defined and described herein.

In some embodiments, inhibitors of SARM1 NADase activity are selected from

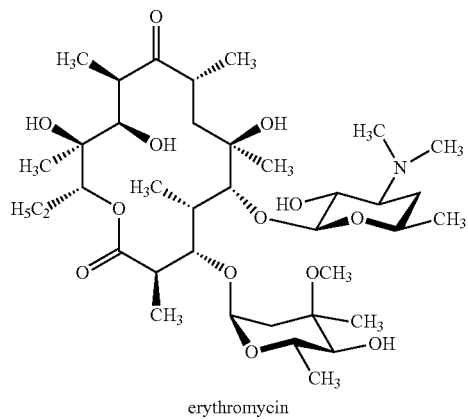
erythromycin

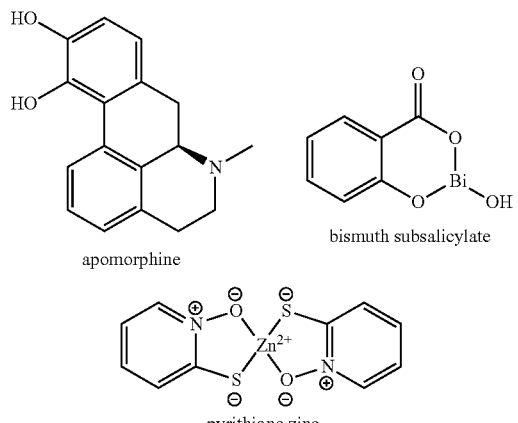
apomorphine bismuth subsalicylate

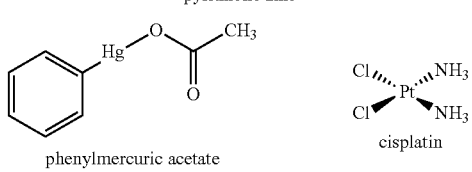
pyrithione zinc

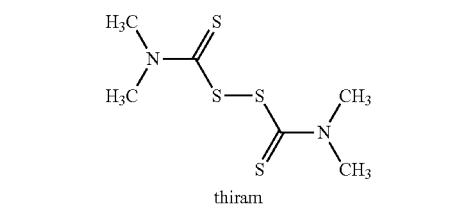
phenylmercuric acetate cisplatin

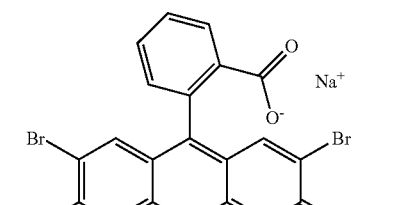
thiram

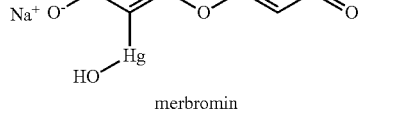
merbromin

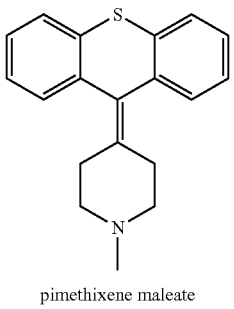
pimethixene maleate

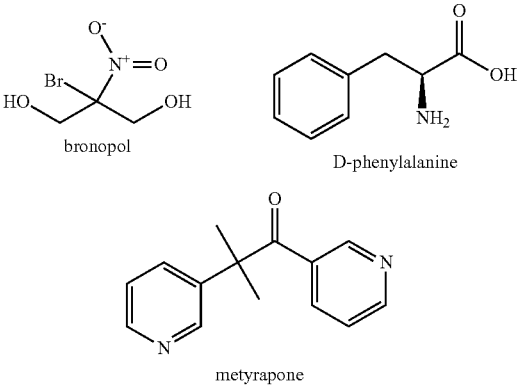
epiestriol

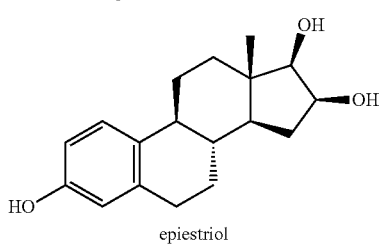
bronopol

D-phenylalanine

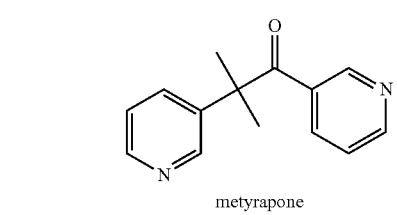
metyrapone

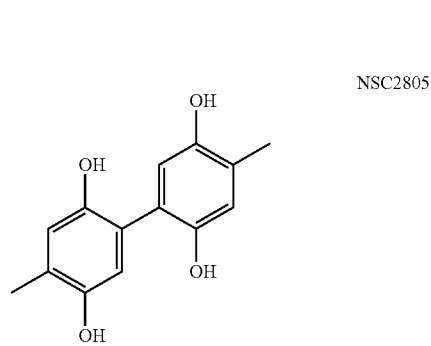
NSC2805

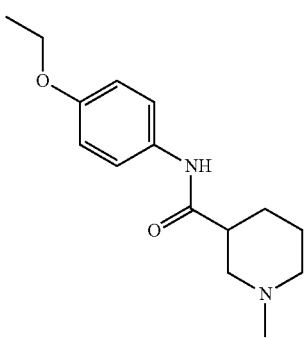
NSC1152

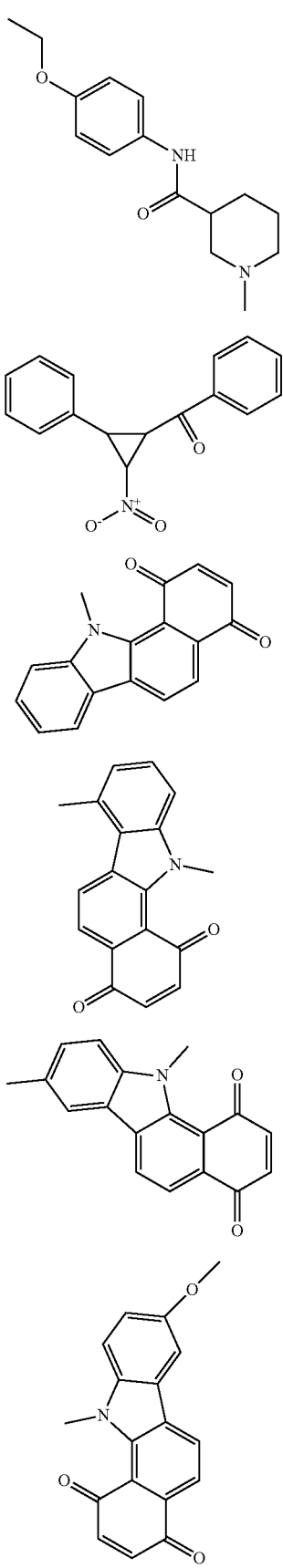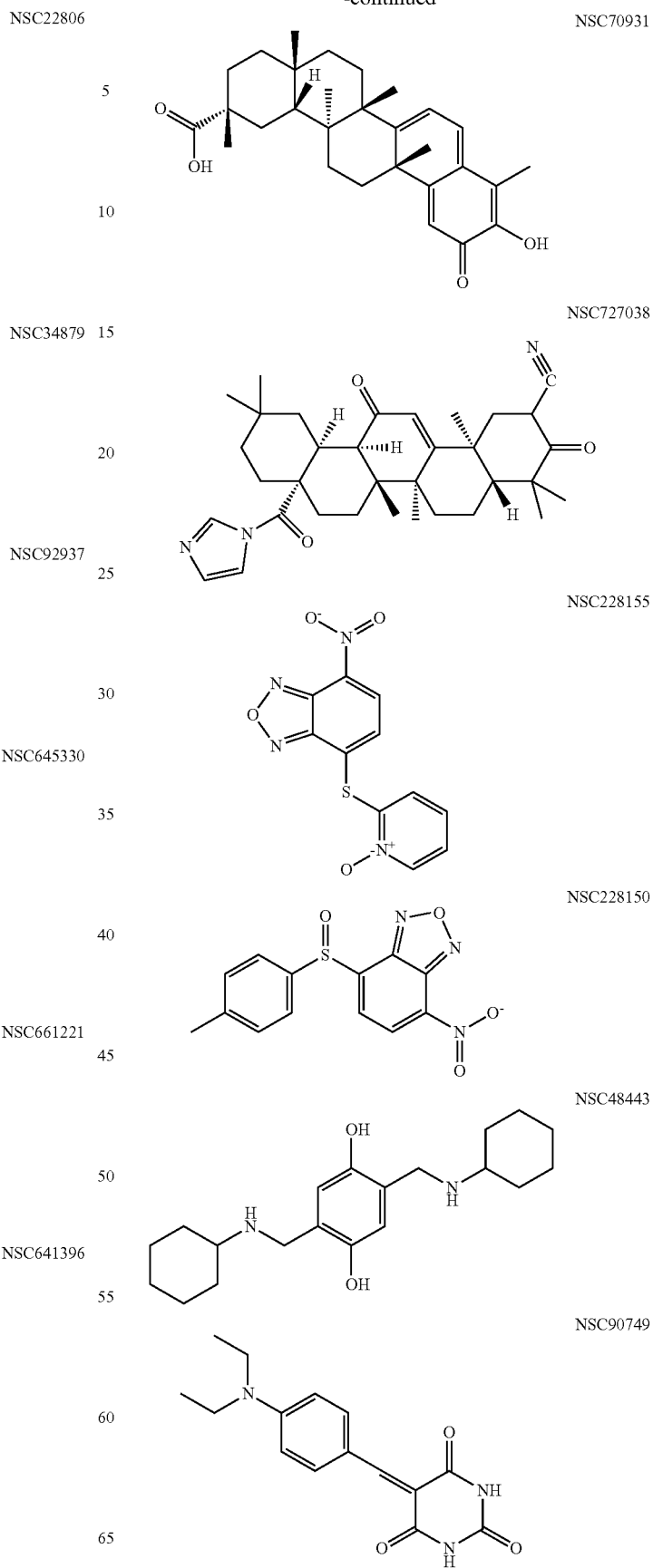

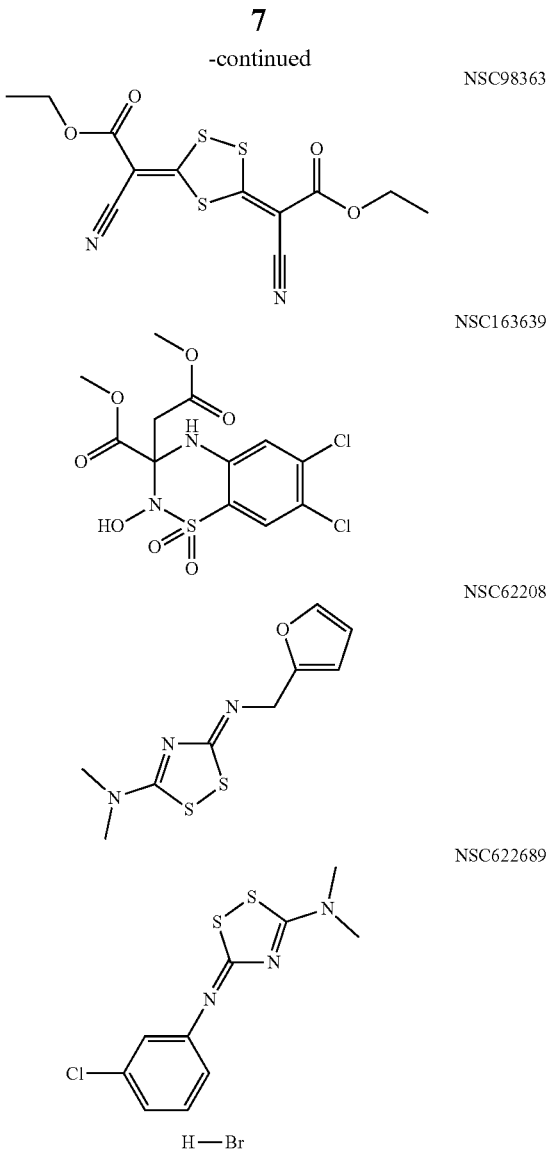

or a pharmaceutically acceptable salt thereof.

Compounds of the present disclosure, and pharmaceutically acceptable compositions thereof, are useful for treating a variety of diseases, disorders or conditions. Such diseases, disorders, or conditions include those described herein.

Compounds provided by this disclosure are also useful for the study of SARM1 NADase activity in biological and pathological phenomena; the study of intracellular signal transduction pathways occurring in lipogenic tissues; and the comparative evaluation of new SARM1 NADase activity inhibitors in vitro or in vivo.

BRIEF DESCRIPTION OF THE FIGURES

FIG. 1 illustrates the structure of the SARM1 protein.

FIG. 2A-F illustrate that native SARM1-TIR protein complex cleaves NAD+ in an in vitro assay. FIG. 2A illustrates selected pathways of NAD+ synthesis and degradation. FIG. 2B illustrates a procedure for detecting NADase activity and its inhibition. FIG. 2C illustrates NADase activity of StrepTag-hSARM1-TIR. FIG. 2D illustrates that wild type SARM1-TIR complexes do not degrade NaAD. FIG. 2E illustrates an NAD+ reaction time course of human SARM1-TIR G601P, TLR4-TIR, and MyD88-TIR laden beads in in-vitro NADase assay (normalized to control at 0 min). FIG. 2F illustrates representative SYPRO Ruby gel of SARM1-TIR G601P, TLR4-TIR, and MyD88-TIR laden beads used in assay.

FIG. 4A illustrates HPLC traces showing changes over time in levels of ADPR, NAM+ and NAD+. FIG. 4B illustrates HPLC traces showing that NADase activity is not exhibited in control lysates. FIG. 4C illustrates quantitative values of NAD+ and ADPR of HPLC traces of FIG. 4A. FIG. 4D illustrates dose-dependent cleavage of NAD+ by SARM1 SAM-TIR lysate. FIG. 4E illustrates quantitation of NAD+/ADPR ratio by SAM-TIR lysate and control.

FIG. 5A illustrates a primary screen of all 1600 compounds from the NCI diversity IV compound library. FIG. 5B illustrates re-testing of 20 positive "hits" from the primary screen.

FIG. 6A-C illustrates structures of 18 compounds that suppress SAM TIR NADase activity. NSC numbers are shown.

FIG. 7A illustrates that SAM-TIR lysate (STL) but not control (con) lysate decreases NAD+, as determined by a NAD+ Glo assay. FIG. 7B illustrates robustness of the assay. FIG. 7C illustrates that most hits identified in the initial HPLC assay (14/18) showed significant inhibition of SAM-TIR NADase activity in a NAD+-Glo assay.

FIG. 7D illustrates NADase inhibitory activity of two compounds.

FIG. 10A-C illustrates the effect of candidate inhibitors on axon degeneration. FIG. 10A illustrates testing of effects of compounds on axon degeneration index. FIG. 10B illustrates preventative effects of compound NSC622608 on axonal degeneration. FIG. 10C illustrates dose dependent inhibition of axon degeneration by compound NSC622608.

FIG. 11A-G illustrates that NAD+ cleavage enzymatic activity is intrinsic to SARM1-TIR. FIG. 11A illustrates endogenous NAD+ levels in bacteria after IPTG induction of human SARM1-TIR. FIG. 11B illustrates in vitro NAD+ cleavage reaction by human SARM1-TIR protein expressed and purified from bacteria. FIG. 11C illustrates that bacterially expressed mouse and zebrafish SARM1-TIR proteins cleave NAD+ in the in vitro assay. FIG. 11D illustrates a SYPRO Ruby gel of SARM1-TIR laden beads purified from bacteria used in NADase assay. FIG. 11E illustrates a time course of NAD+ cleavage reaction using bacterially synthesized human SARM1-TIR, purified by TAP, and subjected to 1M and 2M NaCl washes during purification (normalized to control at 0 min). FIG. 11F illustrates a time course of NAD+ cleavage reaction using bacterially synthesized human SARM1-TIR, purified by TAP, and subjected to either 0.5% Triton X-100 or 0.5% Tween-20 washes during purification (normalized to control at 0 min). FIG. 11G illustrates a reaction time course of purified components of the cell-free protein transcription/translation system incubated with NAD+ and non-recombinant plasmid.

FIGS. 12A-12E depict HPLC chromatograms showing NAD+ cleavage products of human and *Drosophila* SARM1-TIR. Retention time: Nam t~2.40 min; cADPR at t~0.85 min; ADPR at t~1.10 min. FIGS. 12F-12G illustrate quantification of metabolites generated by human FIG. 12F and drosophila FIG. 12G SARM1-TIR as displayed in FIG. 12A-E (normalized to 0 min NAD+). FIG. 12H illustrates HPLC chromatograms showing that mouse and zebrafish SARM1-TIR NAD+ cleavage reaction generate Nam and ADPR as major products, and cADPR as a minor product. FIG. 12I illustrates that kinetic assays of the SARM1-TIR enzyme revealed saturation kinetics. FIG. 12J illustrates that ADPR does not inhibit SARM1-TIR NADase activity. FIG. 12K illustrates that Nam inhibits SARM1-TIR enzymatic activity. FIG. 12L illustrates Nam dose response inhibition of SARM1-TIR enzymatic activity. FIG. 12M illustrates SARM1 is the axonal NADase.

FIG. 16 illustrates Amino acid sequence alignment of SARM1-TIR with MilB Cytidine 5' Monophosphate (CMP) Hydrolase. CMP catalytic glutamic acid is highlighted in red box and aligns to glutamic acid 642 in the SARM1-TIR domain.

FIG. 17 illustrates modeling of the SARM1-TIR domain on the crystal structure of CMP Hydrolase bound to CMP. E642 aligns with a catalytic residue of CMP Hydrolase.

FIG. 18 illustrates NAD+ reaction timecourse of human SARM1-TIR E642A purified from cell-free protein translation system (normalized to control at 0 min).

FIG. 19 illustrates a SYPRO Ruby gel of SARM1-TIR E642A purified from a cell-free protein translation system.

FIG. 20 illustrates Venus expression of indicated constructs in DRG axons, co-stained for Tuj1 to assess total axon area for each field.

P<0.01, *P<0.001 one-way ANOVA.

Figure 25:
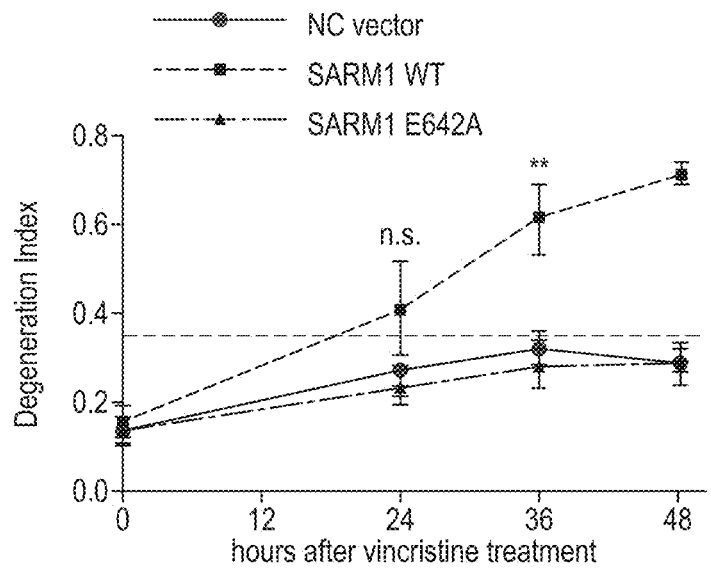
FIG. 25 illustrates axonal degeneration time course after vincristine treatment, quantified as DI. Quantification data were generated from at least three independent biological experiments. Data are presented as mean±SEM; Error bars: SEM.*P<0.05.
Figure 26:
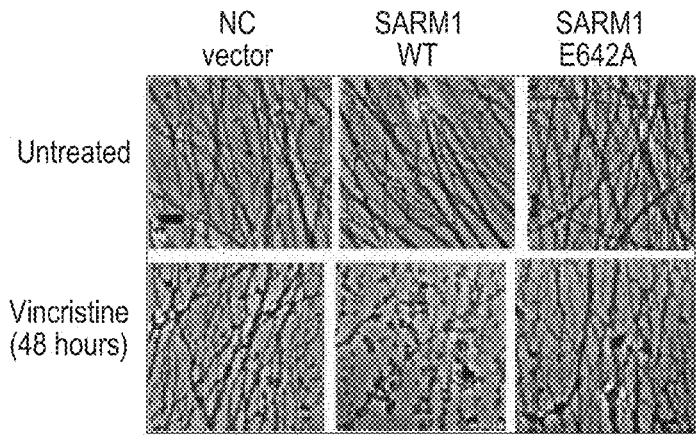

FIG. 26 illustrates bright-field micrographs of axons after vincristine treatment corresponding to selected groups in FIG. 25. Scale bar, 5 μm.

Figure 27:
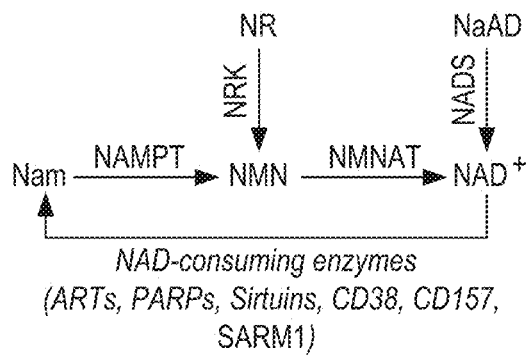

FIG. 27 illustrates selected pathways of NAD+ synthesis and degradation including SARM1 as a NAD+-consuming enzyme.

Figure 28:
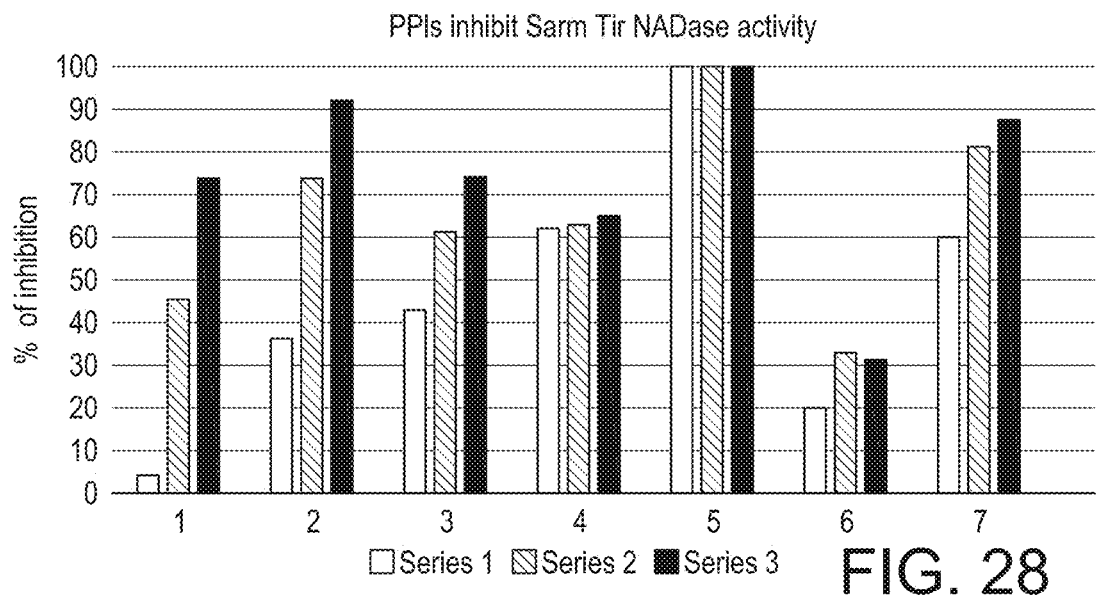

FIG. 28 illustrates SARM1-TIR NADase inhibition by members of the proton pump inhibitor family.

Figure 29:
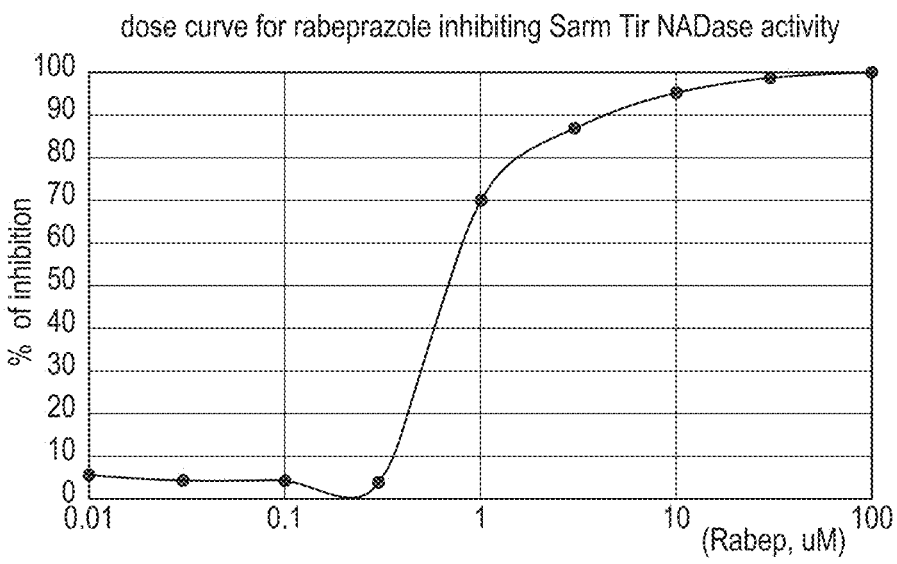

FIG. 29 shows a dose response curve for rabeprazole inhibition of SARM1-TIR NADase activity.

Figure 30:
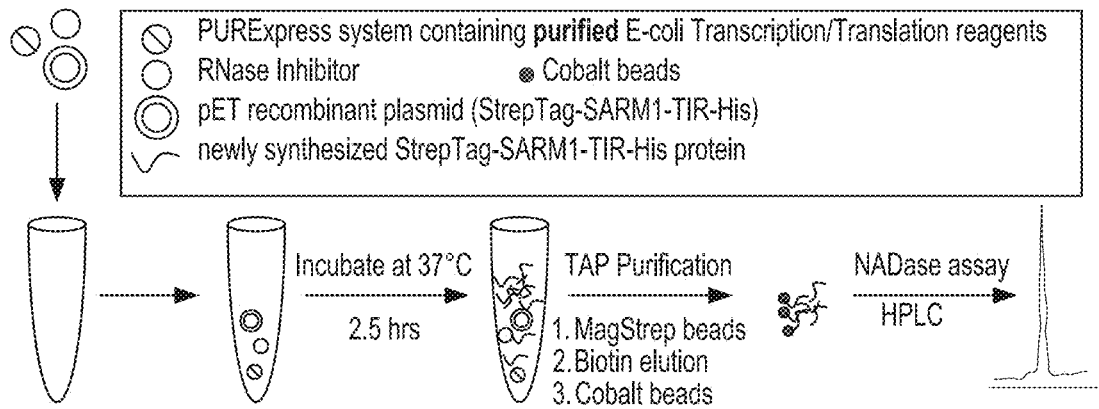

FIG. 30 shows a schematic of cell-free protein expression system.

Figure 31:
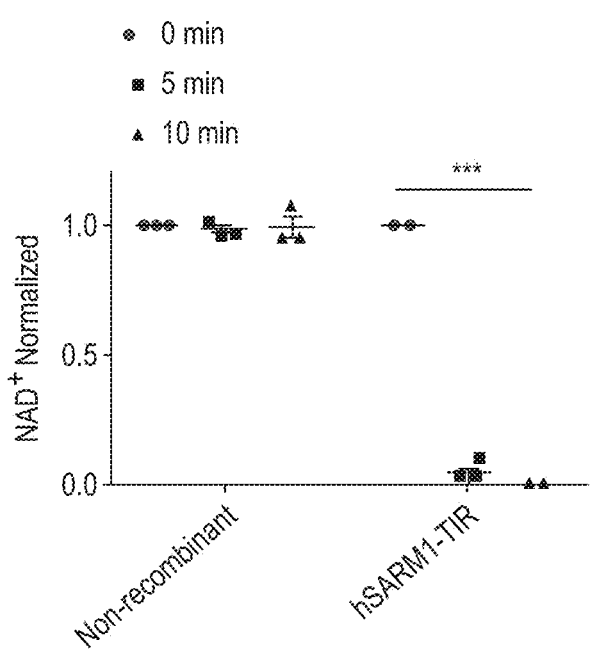

FIG. 31 illustrates that human SARM1-TIR purified from a cell-free protein expression system cleaves NAD+ in NADase assay.

Figure 32:
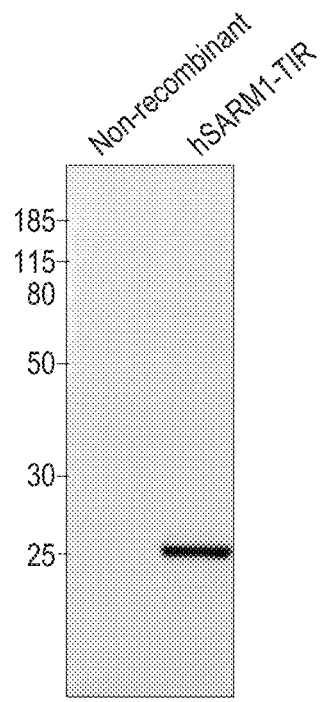

FIG. 32 illustrates a SYPRO Ruby gel of SARM1-TIR laden beads purified from a cell-free transcription/translation system.

Figure 33A:
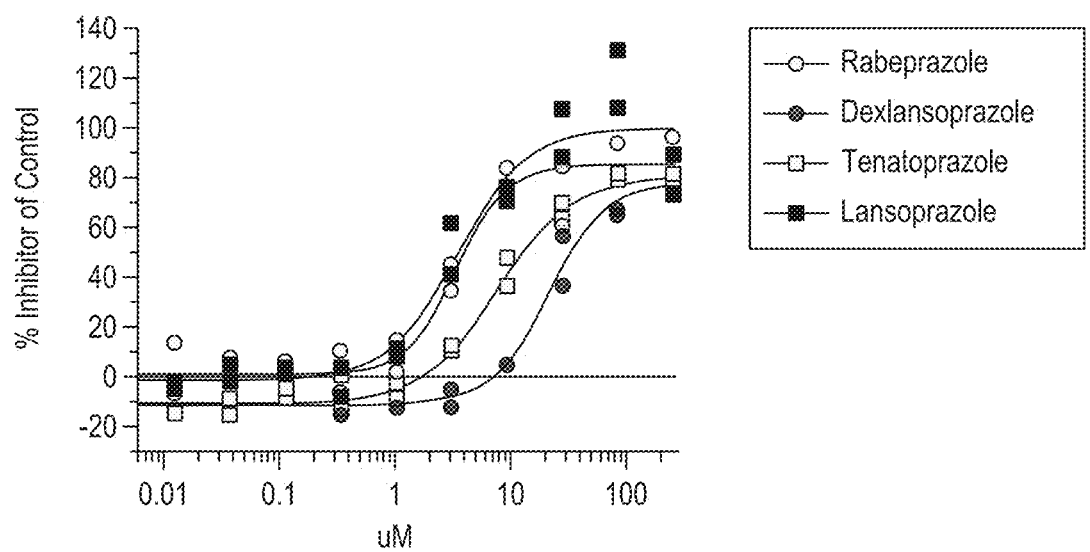
Figure 33B:
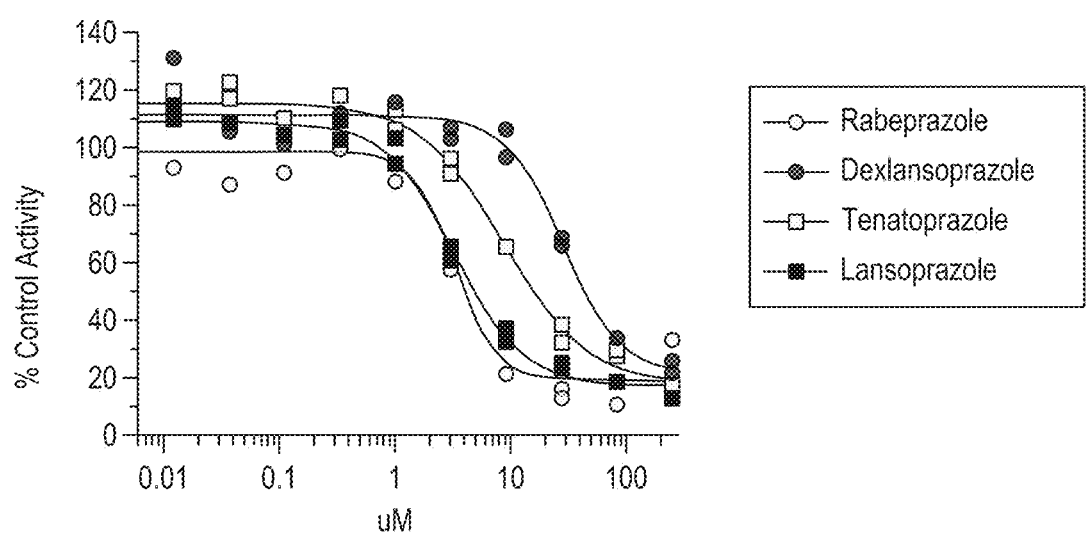

FIGS. 33A and 33B depict the dose curves of SARM1 NADase activity inhibition by compounds $I^A$-2, $I^A$-3, $I^A$-6 and $I^A$-8, whereby FIG. 33A shows % control of NAD consumption and FIG. 33B shows % control of ADPR production.

Figure 34:
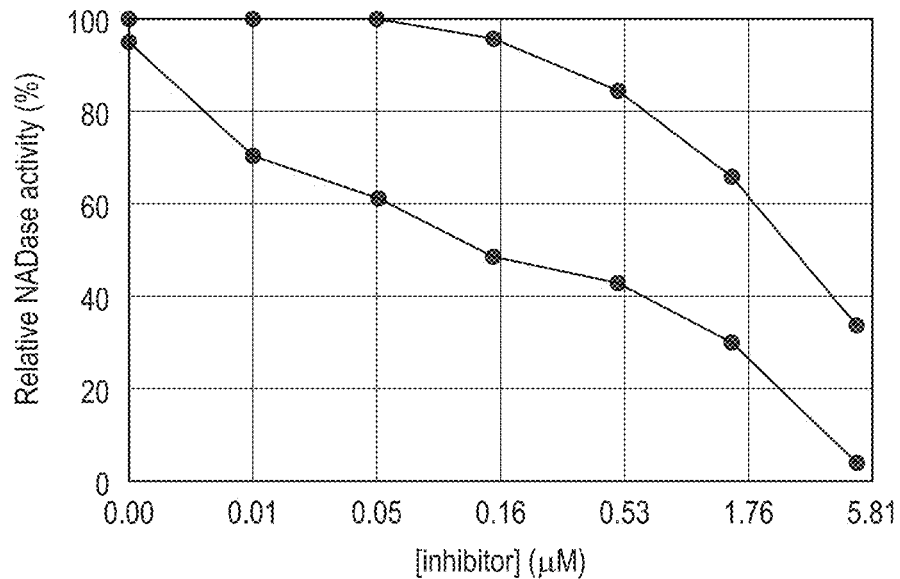

FIG. 34 depicts dose curves of SARM1 NADase activity inhibition by compounds $I^B$-1 and $I^B$-2.

Figure 35:
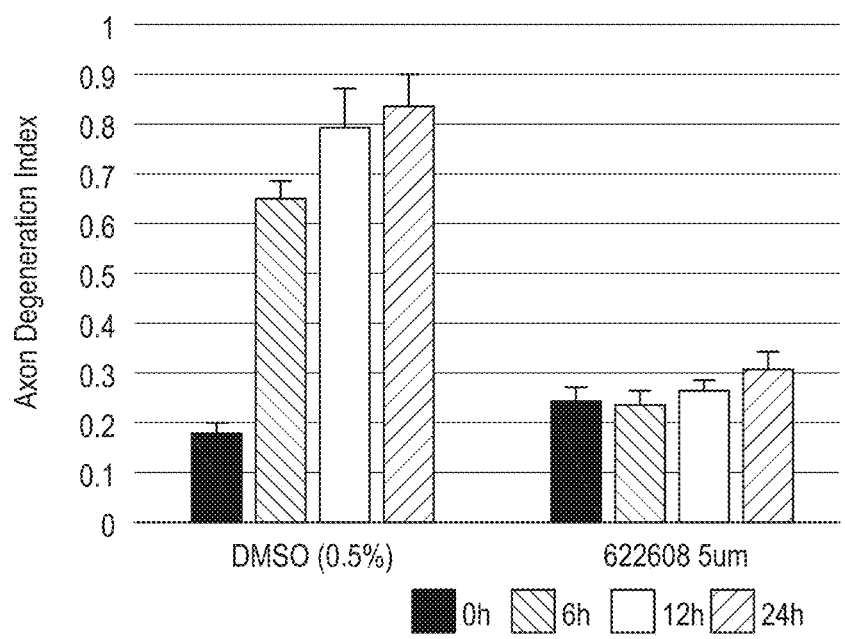

FIG. 35 depicts prevention of axonal degeneration by compound $I^B$-2 at intervals of 0 hours, 6 hours, 12 hours and 24 hours.

Figures 36A, 36B:
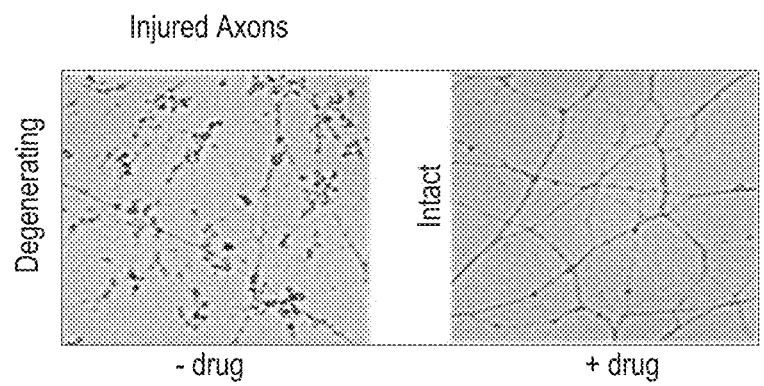

FIGS. 36A and 36B depict SEM micrographs of injured axons under degenerating conditions with (FIG. 36A) and without (FIG. 36B) exposure to compound $I^B$-2.

Figure 37A:
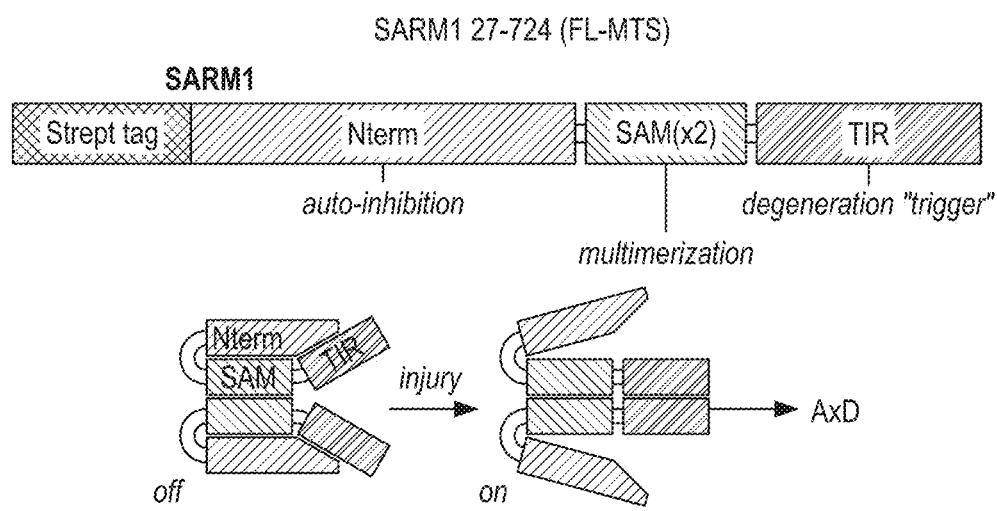
Figure 37B:
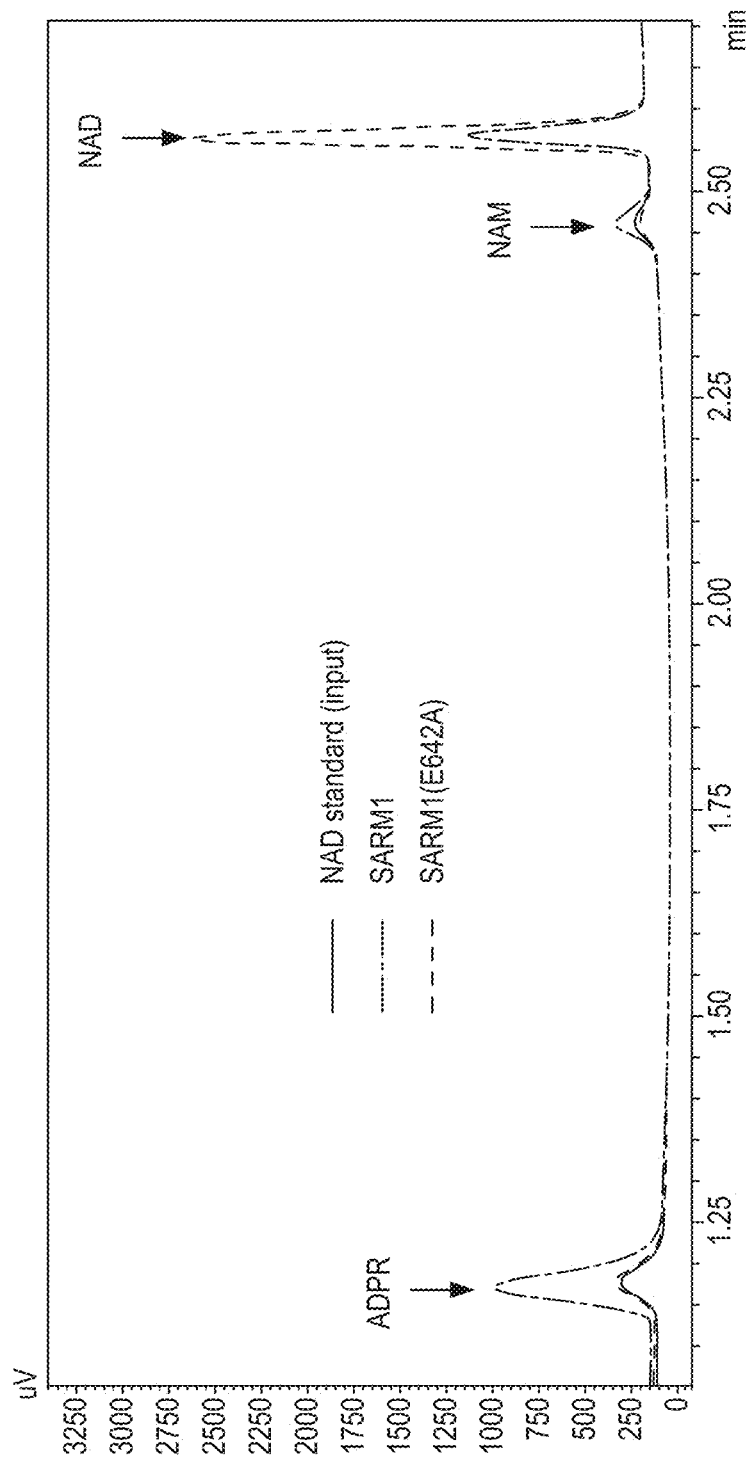
Figure 37C:
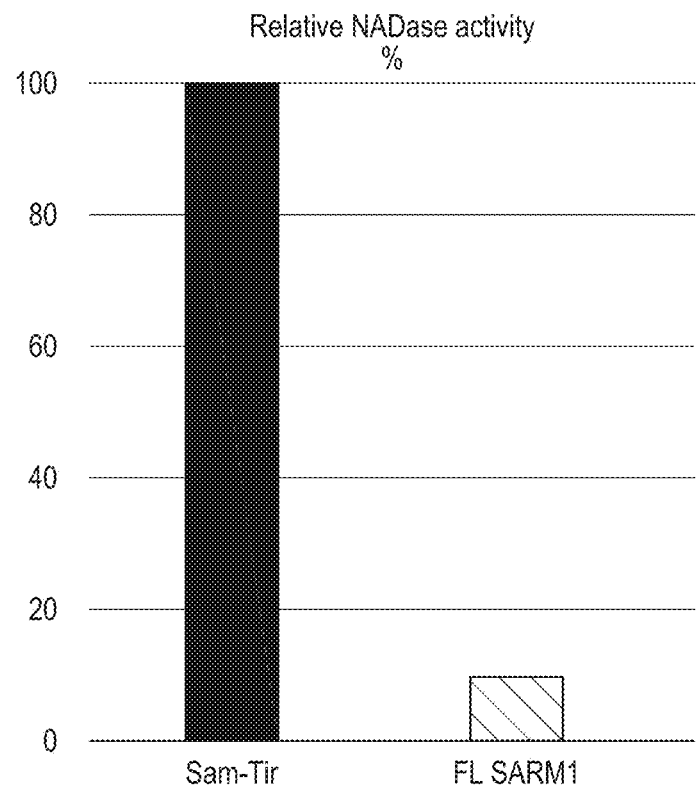
Figure 37D:
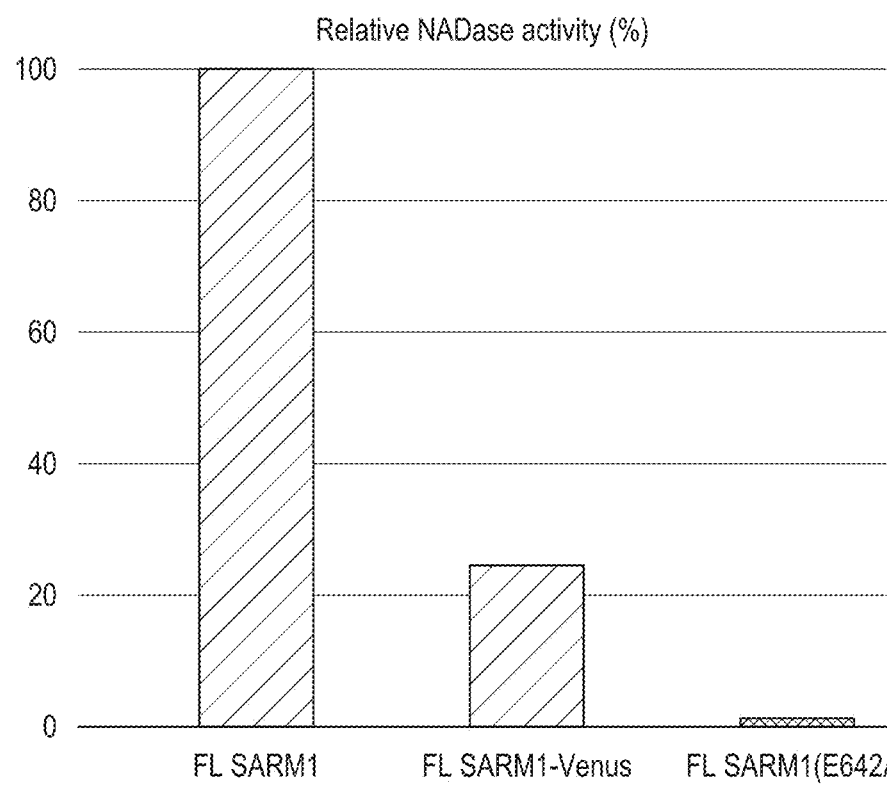

FIGS. 37A-37D depict results from an in vitro assay of full-length SARM1. FIG. 37A is a schematic showing SARM1 domains and changes including dimerization of the TIR1 domain after injury. A×D=axonal degeneration. FIG. 37B illustrates HPLC traces showing levels of ADPR, NAM and NAD. FIG. 37C shows relative NADase activity of full-length SARM1 vs that of an active SARM1 mutant (SAM-TIR). FIG. 37D shows relative NADase activity of full-length SARM1 versus that of catalytically inactive mutant (FL-MTS SARM1 (E642A)).

DETAILED DESCRIPTION OF CERTAIN EMBODIMENTS

The Toll/Interleukin-1 receptor (TIR) domain is an evolutionarily conserved protein domain present in Toll-like receptors (TLR), and their cytosolic adaptor proteins, where as a scaffolding domain, it promotes innate immune signaling to protect hosts against invading pathogens (O'Neill, L. A., et al., *Nat. Rev. Immunol.*, 2013, 13, 453-460). Sterile Alpha and TIR motif-containing 1 (SARM1) belongs to the family of cytosolic adaptor proteins, but is unique among its members because it is the most evolutionary ancient adaptor, paradoxically inhibits TLR signaling, and was recently identified as the central executioner of an injury-induced axon death pathway (O'Neill, L. A. & Bowie, A. G., *Nat. Rev. Immunol.*, 2007, 7, 353-364; Osterloh, J. M., et al., *Science*, 2012, 337, 481-484; Gerdts, J., et al., *J. Neurosci.* 33, 2013, 13569-13580). Activation of SARM1 by axonal injury or by enforced dimerization of the SARM1-TIR domain promotes the rapid and catastrophic depletion of Nicotinamide Adenine Dinucleotide (NAD+), which is followed soon after by axonal demise (Gerdts, J., et al., *Science*, 2015, 348, 453-457). Previous attempts to identify the NAD+ depleting enzyme(s) underlying this process were unsuccessful (Gerdts, J., et al., *Science*, 2015, 348, 453-457). Moreover, neither SARM1 nor TIR domains from other proteins have known enzymatic activity.

Damaged or unhealthy axons are eliminated via an intrinsic self-destruction program that is distinct from traditional cellular death pathways like apoptosis (Gerdts, J., et al., *Neuron*, 2016, 89, 449-460; Whitmore, A. V. et al., *Cell Death Differ.*, 2003, 10, 260-261). Axon degeneration is a major component of several neurological diseases, such as but not limited to Alzheimer's disease, Parkinson's disease, ALS, Multiple sclerosis, diabetic peripheral neuropathy, chemotherapy-induced peripheral neuropathy, inherited neuropathy, traumatic brain injury, and glaucoma. Among pro-degenerative genes, SARM1 is the central executioner of the degenerative program. Loss of SARM1 blocks axon degeneration for weeks after injury (Osterloh, J. M., et al., *Science*, 2012, 337, 481-484; Gerdts, J., et al. *J. Neurosci.*, 2013, 33, 13569-13580) and also improves functional outcomes in mice after traumatic brain injury (Henninger, N. et al., *Brain* 139, 2016, 1094-1105). SARM1 is also required for axon degeneration in chemotherapy-induced peripheral neuropathy; loss of SARM1 blocks the development of chemotherapy-induced peripheral neuropathy, both halting axon degeneration and the development of heightened pain sensitivity after treatment with the chemotherapeutic vincristine (Geisler et al, *Brain*, 2016, 139, 3092-3108). Activation of SARM1 on the other hand, is sufficient to induce axon degeneration in the absence of injury (Gerdts, J., et al., *Science*, 2015, 348, 453-457). SARM1 also is required for axon degeneration in chemotherapy-induced peripheral neuropathy.

The activation of SARM1 leads to the catastrophic depletion of NAD+ (Gerdts, J., et al., Science, 2015, 348, 453-457), thus highlighting the central role of NAD+ homeostasis in axonal integrity as first implied by studies with NMNAT1.

Despite these advances, the enzyme(s) underlying NAD+ breakdown in damaged axons remains unknown.

SARM1 contains multiple conserved motifs including SAM domains, ARM/HEAT motifs and a TIR domain (FIG. 1) that mediate oligomerization and protein-protein interactions (O'Neill, L. A. & Bowie, A. G., *Nat. Rev. Immunol.*, 2007, 7, 353-364; Tewari, R., et al., *Trends Cell Biol.*, 2010, 20, 470-481; Qiao, F. & Bowie, J. U., *Sci. STKE* 2005, re7, 2005). Dimerization of SARM1-TIR domains is sufficient to induce axonal degeneration and to rapidly trigger the degradation of NAD+, demonstrating that the NADase activity is either associated with or induced by dimerized SARM1-TIR domains. TIR domains are common in signaling proteins functioning in innate immunity pathways where they serve as scaffolds for protein complexes (O'Neill, L. A. & Bowie, A. G., *Nat. Rev. Immunol.*, 2007, 7, 353-364).

Several groups have previously measured NAD+ and metabolites such as ADP ribose (ADPR) (for example, Hasan, M. A. et al., *Korean J. Physiol. Pharmacol.*, 2014 18, 497-502; Breen, L. T., et al., Am. J. Physiol. Renal. Physiol., 2006, 290, F486-F495; and Li, P. L., et al., *Am. J. Physiol. Heart Circ. Physiol.*, 2002, 282, H1229-H12236). However none of these groups have specifically done so in conjunction with SARM1 activity. In some embodiments, an ADPR as mentioned herein is a cADPR, e.g., a cyclic ADPR.

Loss of SARM1 blocks axonal degeneration for weeks after injury (Gerdts et al., Sarm1-mediated axon degeneration requires both SAM and TIR interactions *J. Neurosci.* 33 2013 pp. 13569-13580; Osterloh et al., 2012 both of which are hereby incorporated by reference in their entireties) and improves functional outcomes in mice after both traumatic brain injury (Henninger et al., 2016) and vincristine-induced peripheral neuropathy (Geisler et al., 2016). Axonal injury induces NAD+ loss (Wang et al., 2005), and SARM1 is required for this injury-induced NAD+ depletion both in vitro and in vivo (Gerdts et al., SARM1 activation triggers axon degeneration locally via NAD(+) destruction *Science* 348 2015 pp. 453-457; Sasaki et al., 2016; both of which are hereby incorporated by reference in their entireties). Moreover, activation of SARM1 signaling, via enforced dimerization of its TIR domain, is sufficient to induce axonal degeneration in the absence of injury due to a catastrophic depletion of axonal NAD+ (Gerdts et al., SARM1 activation triggers axon degeneration locally via NAD(+) destruction *Science* 348 2015 pp. 453-457).

NAD+ is a dinucleotide that is essential for many redox reactions, but it is also consumed by a variety of enzymes (e.g., PARPs, CD38, Sirtuins) where the resulting metabolites influence signaling pathways via their effects on calcium mobilization or protein parylation (Cantó et al., 2015; Verdin, 2015). The identity of the NADase enzyme(s) responding to SARM1 activation and mediating NAD+ loss in injured axons has been unknown, although PARP1 and CD38 were previously eliminated as candidates (Gerdts et al., 2015; Sasaki et al., 2009). Furthermore, SARM1 is not known to have enzymatic activity, nor have TIR domains from any protein ever been associated with enzymatic activity. TIR domains are rather known for their scaffolding properties in Toll-like Receptor signaling, where they activate downstream enzymes to regulate pro-inflammatory and defense genes (O'Neill et al., 2013).

It has now been found, surprisingly, that the TIR domain of SARM1 acts as an enzyme to cleave NAD+, and that SARM1 enzymatic activity promotes axonal NAD+ depletion and axon degeneration after both traumatic and vincristine induced axonal injuries. The findings presented herein identify SARM1 enzymatic activity as novel therapeutic targets against diseases characterized by axonal degeneration including peripheral neuropathy, traumatic brain injury, and neurodegenerative diseases. More broadly, the findings presented herein show that TIR domains can possess intrinsic enzymatic activity.

1. General Description of Compounds of the Present Disclosure

In certain embodiments, the present disclosure provides a compound of formula $I^A$:

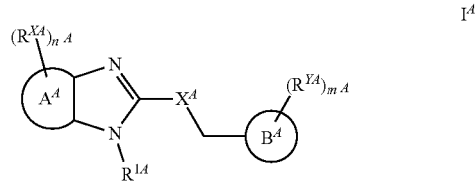

or a pharmaceutically acceptable salt thereof, wherein:
$X^A$ is —S—, —SO— or —SO$_2$—;
$R^{1A}$ is hydrogen, $C_{1-4}$ aliphatic, alkali metal, alkaline earth metal, ammonium or $N^+(C_{1-4}alkyl)_4$;
Ring $A^A$ is selected from a benzo fused ring and a 5-6 membered heteroaromatic fused ring having 1-3 heteroatoms independently selected from nitrogen, oxygen, and sulfur;
Ring $B^A$ is selected from phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^{XA}$ and $R^{YA}$ are independently hydrogen, $C_{1-4}$ aliphatic optionally substituted with 1-4 halogen, —$OR^A$, —$SR^A$, —$N(R^A)_2$, —$N(R^A)C(O)R^A$, —$C(O)N(R^A)_2$, —$N(R^A)C(O)N(R^A)_2$, —$N(R^A)C(O)OR^A$, —$OC(O)N(R^A)_2$, —$N(R^A)S(O)_2R^A$, —$S(O)_2N(R^A)_2$, —$C(O)R^A$, —$C(O)OR^A$, —$OC(O)R^A$, —$S(O)R^A$, —$S(O)_2R^A$, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^A$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$m^A$ and $n^A$ are independently 0, 1, 2, or 3.

In certain embodiments, the present disclosure provides a compound of formula $I^B$:

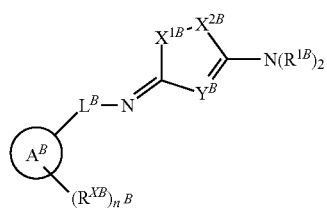

$I^B$ or a pharmaceutically acceptable salt thereof, wherein:
$X^{1B}$ and $X^{2B}$ are independently —O—, —S—, or —$NR^B$—, provided that one of $X^{1B}$ and $X^{2B}$ is —O— or —S— and both of $X^{1B}$ and $X^{2B}$ are not —O—;
$Y^B$ is —N— or —CH—;
each $R^{1B}$ is independently hydrogen or optionally substituted $C_{1-4}$ aliphatic;
Ring $A^B$ is selected from phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^{XB}$ is independently hydrogen, halogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^B$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$L^B$ is a covalent bond, a $C_{1-6}$ membered straight or branched bivalent hydrocarbon chain, cyclopropylenyl, cyclobutylenyl, or oxetanylenyl; and
$n^B$ is 0, 1, 2, 3 or 4.

2. Compounds and Definitions

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkyl" refers to a straight-chain (i.e., unbranched) or branched, substituted or unsubstituted hydrocarbon chain that is completely saturated, or a monocyclic hydrocarbon or bicyclic hydrocarbon that is completely saturated (also referred to herein as "cycloalkyl") and which has a single point of attachment to the rest of the molecule. Unless otherwise specified, alkyl groups contain 1-6 carbon atoms. In some embodiments, alkyl groups contain 1-5 carbon atoms. In other embodiments, alkyl groups contain 1-4 carbon atoms. In still other embodiments, alkyl groups contain 1-3 carbon atoms, and in yet other embodiments, alkyl groups contain 1-2 carbon atoms. In some embodiments, "cycloalkyl" refers to a monocyclic $C_3$-$C_6$ hydrocarbon that is completely saturated and has a single point of attachment to the rest of the molecule.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In some embodiments, the term "aryl" refers to a monocyclic or bicyclic ring system having a total of five to ten ring members, wherein at least one ring in the system is aromatic and wherein each ring in the system contains three to seven ring members. In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms selected from nitrogen, oxygen and sulfur. For instance, heteroaryl may refer to a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical,"

are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "measurably inhibit" refers to a measurable change in SARM1 NADase activity between a sample comprising a provided compound or composition, and SARM1 NADase and an equivalent sample comprising SARM1 NADase in the absence of a provided composition or composition. In some embodiments, a compound or composition "measurably inhibits" SARM1 NADase activity by at least 2-fold, 3-fold, 4-fold, or greater as compared to the control. In some embodiments, a compound or composition "measurably inhibits" SARM1 NADase activity by at least 10%, 20%, 25%, 50%, 75% or more as compared to control.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)$_{0-2}$OR●, —(CH$_2$)$_{0-2}$CH(OR●)$_2$, —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR●; wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺(C₁₋₄alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds of the present disclosure are within the scope of the present disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a ¹³C- or ¹⁴C-enriched carbon are within the scope of this disclosure. Such compounds are useful, for example, as analytical tools, as probes in biological assays, or as therapeutic agents in accordance with the present disclosure.

As used herein, the term "full-length," when used to refer to SARM1, refers to a SARM1 polypeptide that comprises at least: (i) the N-terminal autoinhibitory domain or a functional fragment thereof, (ii) one or more SAM domains or a functional fragment thereof, and (iii) a TIR domain or a functional fragment thereof, of a human SARM1 polypeptide having constitutive NADase activity. In some embodiments, a full-length SARM1 lacks a mitochondrial targeting sequence. In some embodiments, provided are SARM1 polypeptides comprising at least a functional fragment of a SARM1 N-terminal auto-inhibitory domain, at least a functional fragment of one or more SAM domains, and at least a functional fragment of a SARM1 TIR domain, wherein the SARM1 polypeptide lacks a mitochondrial targeting sequence.

3. Description of Exemplary Embodiments

In certain embodiments, the present disclosure provides a compound of formula I$^A$:

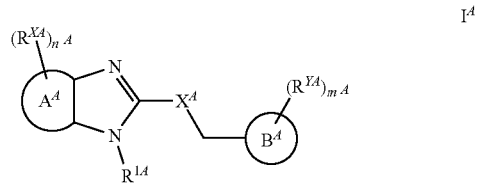

or a pharmaceutically acceptable salt thereof. In some embodiments, a compound of formula I$^A$ is an inhibitor of SARM1 NADase activity. It will be appreciated that certain compounds of formula I$^A$ are proton pump inhibitors.

As defined generally above, X$^A$ is —S—, —SO— or —SO₂—. In some embodiments, X$^A$ is —S—. In some embodiments, X$^A$ is —SO—. In some embodiments, X$^A$ is —SO₂—.

As defined generally above, R$^{1A}$ is hydrogen, C₁₋₄ aliphatic, alkali metal, alkaline earth metal, ammonium or N⁺(C₁₋₄alkyl)₄. It will be appreciated that when R$^{1A}$ is hydrogen or C₁₋₄ aliphatic, R$^{1A}$ is covalently bonded to the nitrogen atom in formula I$^A$. It will further be appreciated that when R$^{1A}$ is an alkali metal, alkaline earth metal, ammonium (i.e., NH₄⁺) or N⁺(C₁₋₄alkyl)₄, R$^{1A}$ is ionically associated with the nitrogen atom in formula I$^A$. In some embodiments, R$^{1A}$ is hydrogen or C₁₋₄ aliphatic. In some embodiments, R$^{1A}$ is selected from an alkali metal, alkaline earth metal, ammonium (i.e., NH₄⁺) or N⁺ (C₁₋₄alkyl)₄. In some embodiments, R$^{1A}$ is hydrogen. In some embodiments, R$^{1A}$ is C₁₋₄ aliphatic. In some embodiments, R$^{1A}$ is an alkali metal. In some such embodiments, R$^{1A}$ is sodium (Na⁺). In some embodiments, R$^{1A}$ is an alkaline earth metal. In some embodiments, R$^{1A}$ is ammonium. In some embodiments, R$^{1A}$ is N⁺(C₁₋₄alkyl)₄.

As defined generally above, the Ring $A^A$ group of formula $I^A$ is a benzo fused ring or a 5-6 membered heteroaromatic fused ring having 1-3 heteroatoms independently selected from nitrogen, oxygen, and sulfur. In some embodiments, Ring $A^A$ is a benzo fused ring. In some embodiments, Ring $A^A$ is a 5-6 membered heteroaromatic fused ring having 1-3 heteroatoms independently selected from nitrogen, oxygen and sulfur. In some embodiments, Ring $A^A$ is a 6 membered heteroaromatic fused ring having 1-2 nitrogens. In some embodiments, Ring $A^A$ is a pyrido fused ring, a pyrimidino fused ring, pyridazino or pyrazino fused ring. In some embodiments, Ring $A^A$ is a triazino fused ring. In some embodiments, Ring $A^A$ is a 5 membered heteroaromatic fused ring containing 1-2 heteroatoms independently selected from oxygen, nitrogen and sulfur. In some embodiments, Ring $A^A$ is a pyrrolo fused ring, a thiopheno fused ring, a furano fused ring, a thiazolofused ring, an isothiazolo fused ring, an imidazolo fused ring, a pyrazolo fused ring, an oxazolo fused ring, or an isoxazolo fused ring.

As defined generally above, the Ring $B^A$ group of formula $I^A$ is selected from phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, Ring $B^A$ is aryl. In some embodiments, Ring $B^A$ is phenyl, biphenyl, napthyl or anthracyl. In some embodiments, Ring $B^A$ is indanyl, phthalimidyl, naphthimidyl, phenanthridinyl, or tetrahydronaphthyl. In some embodiments, Ring $B^A$ is heteroaryl. In some embodiments, Ring $B^A$ is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl or pteridinyl.

As defined generally above, $R^{XA}$ and $R^{YA}$ are independently hydrogen, $C_{1-4}$ aliphatic optionally substituted with 1-4 halogen, $-OR^A$, $-SR^A$, $-N(R^A)_2$, $-N(R^A)C(O)R^A$, $-C(O)N(R^A)_2$, $-N(R^A)C(O)N(R^A)_2$, $-N(R^A)C(O)OR^A$, $-OC(O)N(R^A)_2$, $-N(R^A)S(O)_2R^A$, $-S(O)_2N(R^A)_2$, $-C(O)R^A$, $-C(O)OR^A$, $-OC(O)R^A$, $-S(O)R^A$, $-S(O)_2R^A$, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, $R^{XA}$ and $R^{YA}$ are the same. In some embodiments, $R^{XA}$ and $R^{YA}$ are both hydrogen. In some embodiments, $R^{XA}$ and $R^{YA}$ are both $C_{1-4}$ aliphatic optionally substituted with 1-4 halogen. In some embodiments, $R^{XA}$ and $R^{YA}$ are both $-OR^A$. In some embodiments, $R^{XA}$ and $R^{YA}$ are both aryl. In some embodiments, $R^{XA}$ and $R^{YA}$ are both heteroaryl.

In some embodiments, $R^{XA}$ and $R^{YA}$ are different. In some embodiments, $R^{XA}$ is hydrogen and $R^{YA}$ is $C_{1-4}$ aliphatic optionally substituted with 1-4 halogen and/or $-OR^A$. In some embodiments, $R^{XA}$ is $-OR^A$ and $R^{YA}$ is $C_{1-4}$ aliphatic optionally substituted with 1-4 halogen. In some embodiments, $R^{XA}$ is aryl and $R^{YA}$ is $-OR^A$ and/or $C_{1-4}$ aliphatic optionally substituted with 1-4 halogen. In some embodiments, $R^{XA}$ is heteroaryl and $R^{YA}$ is $-OR^A$ and/or $C_{1-4}$ aliphatic optionally substituted with 1-4 halogen.

As defined generally above, $m^A$ and $n^A$ are independently 0, 1, 2, or 3. In some embodiments, $m^A$ and $n^A$ are the same. In some embodiments, $m^A$ and $n^A$ are both zero. In some embodiments, $m^A$ and $n^A$ are both one. In some embodiments, $m^A$ and $n^A$ are both two. In some embodiments, $m^A$ and $n^A$ are both three.

In some embodiments, $m^A$ and $n^A$ are different. In some embodiments, $m^A$ is zero and $n^A$ is one, two or three. In some embodiments, $m^A$ is one and $n^A$ is zero, two or three. In some embodiments, $m^A$ is two and $n^A$ is zero, one or three. In some embodiments, $m^A$ is three and $n^A$ is zero, one or two. In some embodiments, $m^A$ is one, two or three and $n^A$ is zero. In some embodiments, $m^A$ is zero, two or three and $n^A$ is one. In some embodiments, $m^A$ is zero, one or three and $n^A$ is two. In some embodiments, $m^A$ is zero, one or two and $n^A$ is three. In some embodiments, $m^A$ is one and $n^A$ is two or three.

In some embodiments, $n^A$ is one and $R^{XA}$ is $-OCH_3$. In some embodiments, $n^A$ is one and $R^{XA}$ is $-OCHF_2$. In some embodiments, $n^A$ is one and $R^{XA}$ is a 5-membered heteroaryl ring. In some such embodiments, $n^A$ is one and $R^{XA}$ is pyrrolyl. In some embodiments, $n^A$ is one and $R^{XA}$ is $-OR^A$. In some such embodiments, $R^A$ is optionally substituted $C_{1-6}$ aliphatic. In some embodiments, $n^A$ is one and $R^{XA}$ is $-OR^A$, wherein $R^A$ is $C_{1-6}$ aliphatic substituted with phenyl.

In some embodiments, $m^A$ is two and each $R^{YA}$ is independently selected from $-OR^A$ and $C_{1-4}$ aliphatic optionally substituted with 1-4 halogen. In such embodiments, one $R^{YA}$ is $-CH_3$ and the other $R^{YA}$ is $-OCH_3$. In some embodiments, one $R^{YA}$ is $-CH_3$ and the other $R^{YA}$ is $-OCH_2CF_3$. In some embodiments, $m^A$ is two and each $R^{YA}$ is $-OCH_3$. In some embodiments, $m^A$ is two and each $R^{YA}$ is selected from $-OR^A$ and $C_{1-4}$ aliphatic optionally substituted with 1-4 halogen, wherein $R^A$ is $C_{1-6}$ aliphatic substituted with $-(CH_2)_{0-4}OR°$. In some such embodiments, one $R^{YA}$ is $-CH_3$ and the other $R^{YA}$ is $-OCH_2CH_2CH_2OCH_3$.

In some embodiments, $m^A$ is three and each $R^{YA}$ is independently selected from $-OR^A$ and $C_{1-4}$ aliphatic optionally substituted with 1-4 halogen. In some embodiments, one $R^{YA}$ is $-OCH_3$ and two $R^{YA}$ are $-CH_3$. In some embodiments, one $R^{YA}$ is $-OCH_2CF_3$ and two $R^{YA}$ are $-CH_3$.

In some embodiments, Ring $A^A$ is selected from the Ring $A^A$ groups in the compounds depicted in Table $1^A$, below. In some embodiments, Ring $B^A$ is selected from the Ring $B^A$ groups in the compounds depicted in Table $1^A$, below. In some embodiments, $R^{XA}$ is selected from the $R^{XA}$ groups in the compounds depicted in Table $1^A$, below. In some embodiments, $R^{YA}$ is selected from the $R^{YA}$ groups in the compounds depicted in Table $1^A$, below. In some embodiments, $X^A$ is selected from the $X^A$ groups in the compounds depicted in Table $1^A$, below. In some embodiments, the compounds of formula $I^A$ are selected from those depicted in Table $1^A$, below. In some embodiments, the compounds of formula $I^A$ are selected from the compounds in Table $1^A$:

TABLE $1^A$ $I^A$-1

TABLE 1^A-continued

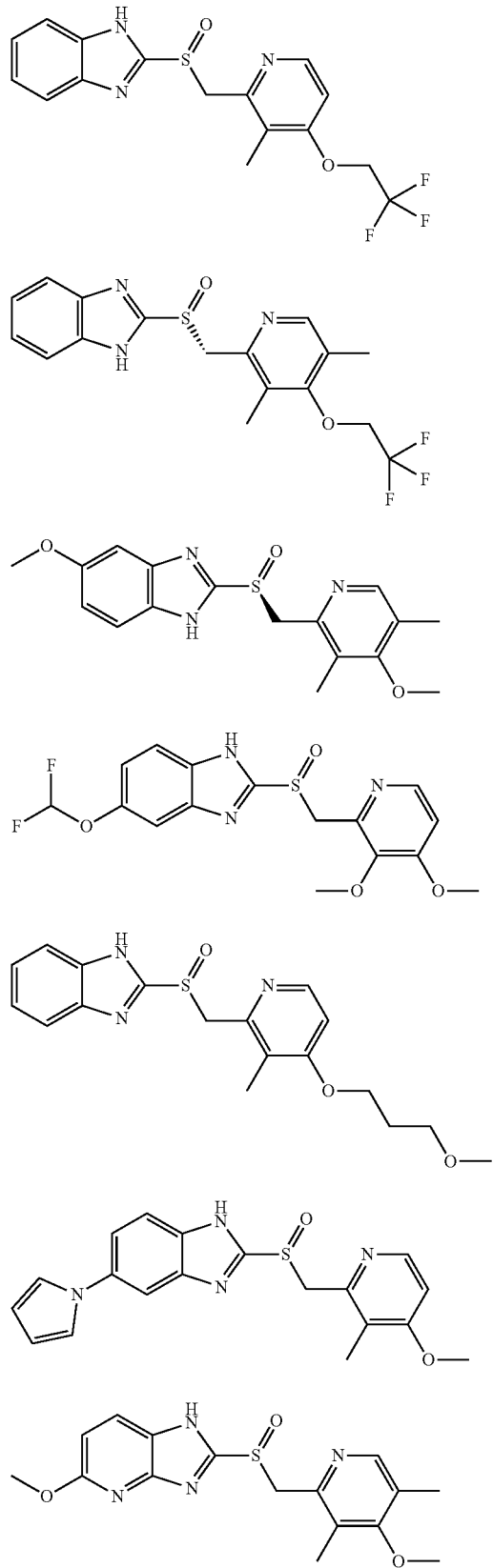

TABLE 1^A-continued

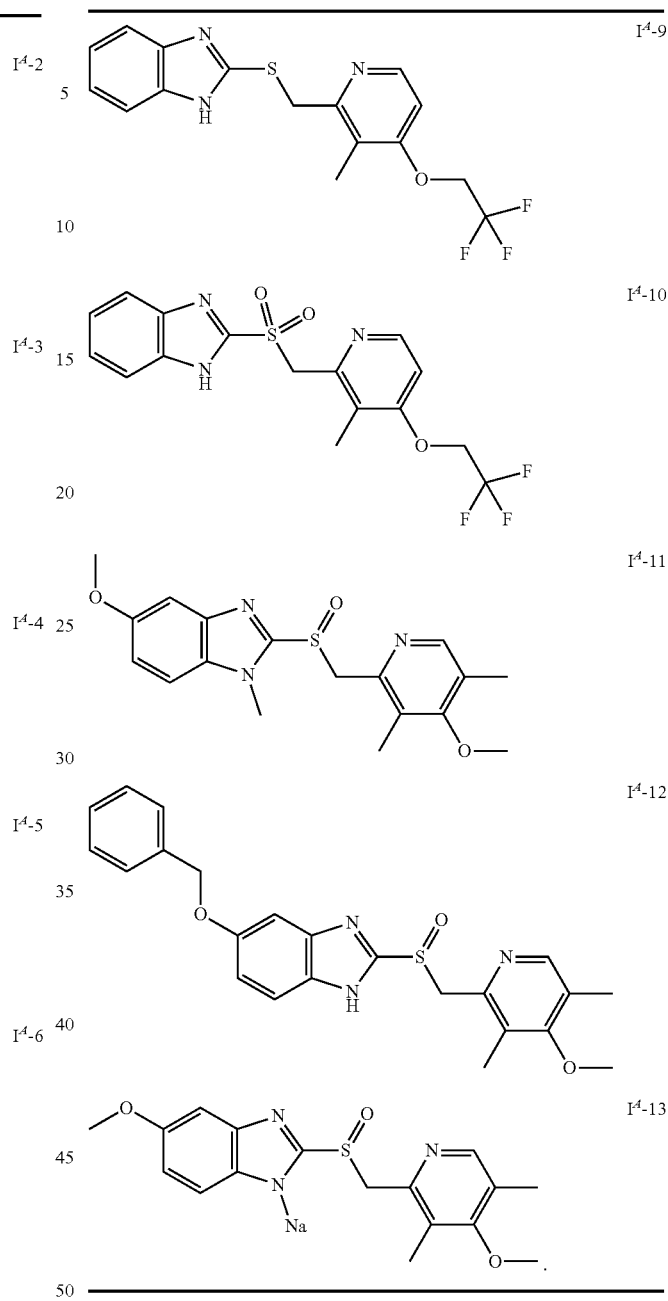

In some embodiments, $X^A$ is —SO—. In some embodiments, $n^A$ is 0 or 1 and $m^A$ is 2 or 3. In some embodiments, $R^{1A}$ is hydrogen, $C_{1-4}$ aliphatic or an alkali metal. In some embodiments, $R^{1A}$ is hydrogen, methyl or sodium. In some embodiments, $R^{YA}$ is hydrogen, $C_{1-4}$ aliphatic optionally substituted with 1-4 halogen or —$OR^A$; and $R^A$ is optionally substituted $C_{1-6}$ aliphatic. In some embodiments, $R^{YA}$ is hydrogen, —$CH_3$, —$OCH_3$, —$OCH_2CF_3$ or —$O(CH_2)_3OCH_3$. In some embodiments, $R^{XA}$ is hydrogen, —$OR^A$, or heteroaryl; and $R^A$ is optionally substituted $C_{1-6}$ aliphatic or benzyl. In some embodiments, $R^{XA}$ is hydrogen, —$OCH_3$, —$OCHCF_2$, pyrrolyl or —$OCH_2$-phenyl.

In some embodiments, Ring $A^A$ is an arylo fused ring and Ring $B^A$ is a heteroaryl ring. In some embodiments, Ring $A^A$ is a benzo fused ring and Ring $B^A$ is a pyridyl ring. In some embodiments, Ring $A^A$ is a heteroaromatic fused ring and Ring $B^A$ is a heteroaryl ring.

In some embodiments, Ring $A^A$ is selected from the group consisting of a pyrido fused ring, a pyrimidino fused ring, a pyridazino fused ring, pyrazino fused ring, a triazino fused ring, a pyrrolo fused ring, a thiopheno fused ring, a furano fused ring, a thiazolofused ring, an isothiazolo fused ring, an imidazolo fused ring, a pyrazolo fused ring, an oxazolo fused ring and an isoxazolo fused ring.

In some embodiments, Ring $B^A$ is selected from the group consisting of phenyl, biphenyl, napthyl, anthracyl, indanyl, phthalimidyl, naphthimidyl, phenanthridinyl, tetrahydronaphthyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl and pteridinyl.

In certain embodiments, the present disclosure provides a compound of formula $I^B$:

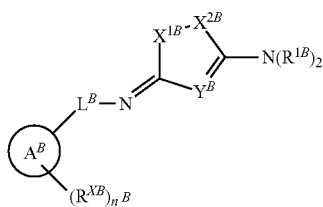

$I^B$ or a pharmaceutically acceptable salt thereof.

As defined generally above, $X^{1B}$ and $X^{2B}$ are independently —O—, —S—, or —NR$^B$—, provided that one of $X^{1B}$ and $X^{2B}$ is —O— or —S— and both of $X^{1B}$ and $X^{2B}$ are not —O—. In some embodiments, $X^{1B}$ and $X^{2B}$ are the same. In some embodiments, $X^{1B}$ and $X^{2B}$ are different. In some embodiments, $X^{1B}$ and $X^{2B}$ are —S—. In some embodiments, $X^{1B}$ is —S— and $X^{2B}$ is —O—. In some embodiments, $X^{1B}$ is —O— and $X^{2B}$ is —S—. In some embodiments, $X^{1B}$ and $X^{2B}$ are selected from the $X^{1B}$ and $X^{2B}$ groups in the compounds depicted in Table $1^B$, below.

As defined generally above, $Y^B$ is —N— or —CH—. In some embodiments, $Y^B$ is —N—. In some embodiments, $Y^B$ is —CH—. In some embodiments, $Y^B$ is selected from the $Y^B$ groups in the compounds depicted in Table $1^B$, below.

As defined generally above, $R^{1B}$ is hydrogen or optionally substituted $C_{1-4}$ aliphatic. In some embodiments, each $R^{1B}$ is the same. In some embodiments, each $R^{1B}$ is different. In some embodiments, each $R^{1B}$ is hydrogen. In some embodiments, each $R^{1B}$ is optionally substituted $C_{1-4}$ aliphatic. In some embodiments, one $R^{1B}$ is hydrogen and the other is optionally substituted $C_{1-4}$ aliphatic. In some embodiments, $R^{1B}$ is selected from the $R^{1B}$ groups in the compounds depicted in Table $1^B$, below.

As defined generally above, Ring $A^B$ is phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, Ring $A^B$ is aryl. In some embodiments, Ring $A^B$ is phenyl, biphenyl, napthyl or anthracyl. In some embodiments, Ring $A^B$ is indanyl, phthalimidyl, naphthimidyl, phenanthridinyl, or tetrahydronaphthyl. In some embodiments, Ring $A^B$ is heteroaryl. In some embodiments, Ring $A^B$ is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl or pteridinyl. In some embodiments, Ring $A^B$ is selected from the Ring $A^B$ groups in the compounds depicted in Table $1^B$, below.

As defined generally above, each $R^{XB}$ is independently hydrogen, halogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, each $R^{XB}$ is the same. In some embodiments, each $R^{XB}$ is different. In some embodiments, $R^{XB}$ is hydrogen. In some embodiments, $R^{XB}$ is halogen. In some embodiments, $R^{XB}$ is optionally substituted $C_{1-4}$ aliphatic. In some embodiments, $R^{XB}$ is aryl. In some embodiments, $R^{XB}$ is phenyl, biphenyl, napthyl or anthracyl. In some embodiments, $R^{XB}$ is indanyl, phthalimidyl, naphthimidyl, phenanthridinyl, or tetrahydronaphthyl. In some embodiments, $R^{XB}$ is heteroaryl. In some embodiments, $R^{XB}$ is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl or pteridinyl. In some embodiments, $R^{XB}$ is selected from the $R^{XB}$ groups in the compounds depicted in Table $1^B$, below.

As defined generally above, $L^B$ is a covalent bond, a $C_{1-6}$ membered straight or branched bivalent hydrocarbon chain, cyclopropylenyl, cyclobutylenyl, or oxetanylenyl. In some embodiments, $L^B$ is a covalent bond. In some embodiments, $L^B$ is a $C_{1-6}$ membered straight or branched bivalent hydrocarbon chain. In some embodiments, $L^B$ is cyclopropylenyl. In some embodiments, $L^B$ is cyclobutylenyl. In some embodiments, $L^B$ is oxetanylenyl. In some embodiments, $L^B$ is —C(CH$_3$)$_2$—. In some embodiments, $L^B$ is —CH$_2$—. In some embodiments, $L^B$ is —CH(CH$_3$)—. In some embodiments, $L^B$ is —CH(CH$_3$)— with (S) configuration at the chiral center. In some embodiments, $L^B$ is —CH(CH$_3$)— with an (R) configuration at the chiral center. In some embodiments, $L^B$ is selected from the $L^B$ groups in the compounds depicted in Table $1^B$, below.

As defined generally above, $n^B$ is 0-4. In some embodiments, $n^B$ is 0. In some embodiments, $n^B$ is 1. In some embodiments, $n^B$ is 2. In some embodiments, $n^B$ is 3. In some embodiments, $n^B$ is 4.

In some embodiments, the compounds of formula $I^B$ are selected from the compounds in Table $1^B$:

Table $1^B$.

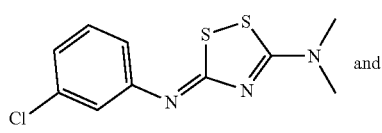

$I^B$-1 and

-continued

I$^B$-2

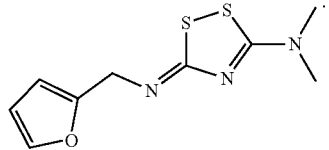

In some embodiments, $X^{1B}$ and $X^{2B}$ are —S— and $Y^B$ is —N—. In some embodiments, $R^{1B}$ is hydrogen or optionally substituted $C_{1-4}$ aliphatic. In some embodiments, $R^{1B}$ is hydrogen or methyl. In some embodiments, $L^B$ is a covalent bond or a $C_{1-6}$ membered straight or branched bivalent hydrocarbon chain. In some embodiments, $L^B$ is a covalent bond or a methylene group. In some embodiments, $R^{XB}$ is hydrogen, halogen or optionally substituted $C_{1-4}$ aliphatic. In some embodiments, $R^{XB}$ is hydrogen or —Cl.

In some embodiments, Ring $A^B$ is aryl or heteroaryl. In some embodiments, Ring $A^B$ is selected from the group consisting of phenyl, biphenyl, napthyl and anthracyl. In some embodiments, Ring $A^B$ is selected from the group consisting of indanyl, phthalimidyl, naphthimidyl, phenanthridinyl, tetrahydronaphthyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl and pteridinyl.

In some embodiments, the present disclosure provides a compound of formula $I^C$:

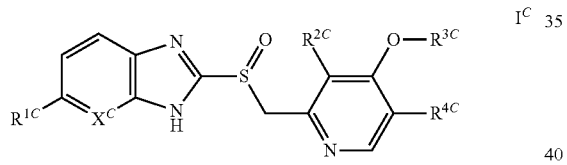

or a pharmaceutically acceptable salt thereof, wherein:
$X^C$ is N or C;
$R^{1C}$ is H, $C_1$-$C_5$ alkyl, $C_1$-$C_5$ alkoxy, or $C_1$-$C_5$ haloalkoxy;
$R^{2C}$ is $C_1$-$C_5$ alkyl or $C_1$-$C_5$ alkoxy;
$R^{3C}$ is $C_1$-$C_{10}$ alkyl, $C_1$-$C_{10}$ haloalkyl or an ether; and
$R^{4C}$ is H, $C_1$-$C_5$ alkyl or $C_1$-$C_5$ alkoxy.

In some embodiments, $X^C$ is N. In some embodiments, $X^C$ is C.

In some embodiments, $R^{1C}$ is H. In some embodiments, $R^{1C}$ is $C_1$-$C_5$ alkyl, $C_1$-$C_5$ alkoxy, or $C_1$-$C_5$ haloalkoxy.

In some embodiments, $R^{1C}$ is $C_1$-$C_5$ alkyl. In some such embodiments, $R^{1C}$ is methyl, ethyl, n-propyl or isopropyl.

In some embodiments, $R^{1C}$ is $C_1$-$C_5$ alkoxy. In some such embodiments, $R^{1C}$ is —OCH$_3$, —OCH$_2$CH$_3$, —OCH$_2$CH$_2$CH$_3$, or —OCH(CH$_3$)$_2$.

In some embodiments, $R^{1C}$ is $C_1$-$C_5$ haloalkoxy. In some embodiments, $R^{1C}$ is $C_1$-$C_5$ fluoroalkoxy. In some such embodiments, $R^{1C}$ is fluoromethoxy, difluoromethoxy, trifluoromethoxy, fluoroethoxy, difluoroethoxy, or trifluoromethoxy. In some embodiments, $R^{1C}$ is —OCH$_2$F, —OCHF$_2$, —OCF$_3$, —OCH$_2$CH$_2$F, —OCH$_2$CHF$_2$, or —OCH$_2$CF$_3$.

In some embodiments, $R^{2C}$ is $C_1$-$C_5$ alkyl. In some such embodiments, $R^{2C}$ is methyl, ethyl, n-propyl or isopropyl.

In some embodiments, $R^{2C}$ is $C_1$-$C_5$ alkoxy. In some such embodiments, $R^{2C}$ is —OCH$_3$, —OCH$_2$CH$_3$, —OCH$_2$CH$_2$CH$_3$, or —OCH(CH$_3$)$_2$.

In some embodiments, $R^{3C}$ is $C_1$-$C_{10}$ alkyl. In some such embodiments, $R^{3C}$ is methyl, ethyl, n-propyl or isopropyl.

In some embodiments, $R^{3C}$ is $C_1$-$C_{10}$ haloalkyl. In some embodiments, $R^{3C}$ is fluoroalkyl. In some such embodiments, $R^{3C}$ is fluoromethyl, difluoromethyl, trifluoromethyl, fluoroethyl, difluoroethyl, or trifluoroethyl. In some embodiments, $R^{3C}$ is —CH$_2$F, —CHF$_2$, —CF$_3$, —CH$_2$CH$_2$F, —CH$_2$CHF$_2$, or —CH$_2$CF$_3$.

In some embodiments, $R^{3C}$ is an ether. In some such embodiments, $R^{3C}$ is methoxypropyl (i.e., —CH$_2$CH$_2$CH$_2$OCH$_3$).

In some embodiments, $R^{4C}$ is H. In some embodiments, $R^{4C}$ is $C_1$-$C_5$ alkyl. In some such embodiments, $R^{4C}$ is methyl, ethyl, n-propyl or isopropyl.

In some embodiments, $R^{4C}$ is $C_1$-$C_5$ alkoxy. In some such embodiments, $R^{4C}$ is —OCH$_3$, —OCH$_2$CH$_3$, —OCH$_2$CH$_2$CH$_3$, or —OCH(CH$_3$)$_2$.

In some embodiments, the compounds of formula $I^C$ are selected from the compounds in Table $1^C$:

TABLE $1^C$

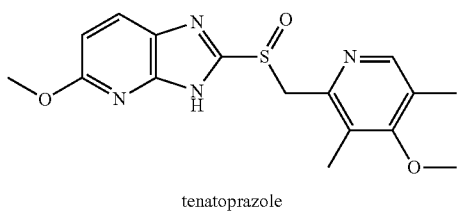

tenatoprazole

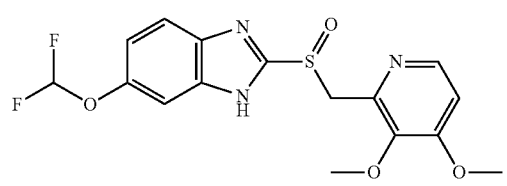

pantoprazole

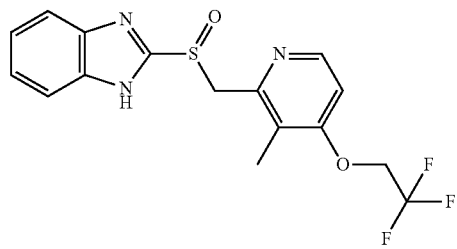

dexlansoprazole

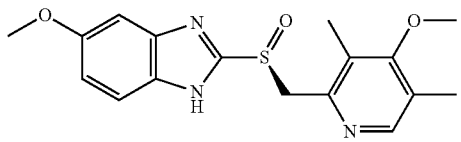

esomeprazole

TABLE 1C-continued

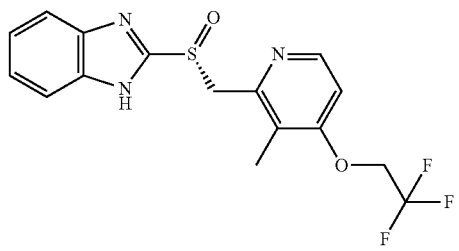

lansoprazole

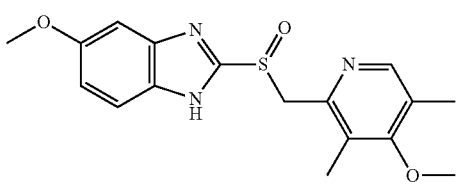

omeprazole

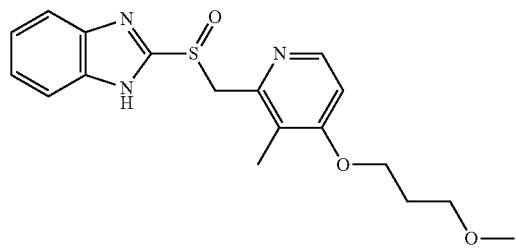

rabeprazole

In some embodiments, pantoprazole is in the form of a sodium salt:

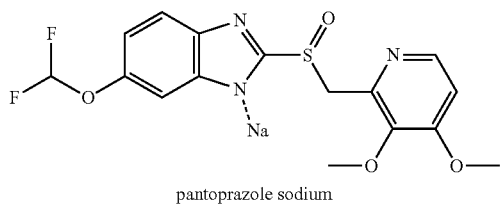

pantoprazole sodium

In some embodiments, rabeprazole is in the form of a sodium salt:

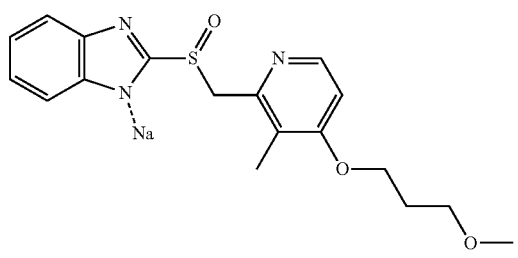

rabeprazole sodium

In some embodiments, esomeprazole is in the form of a magnesium hydrate:

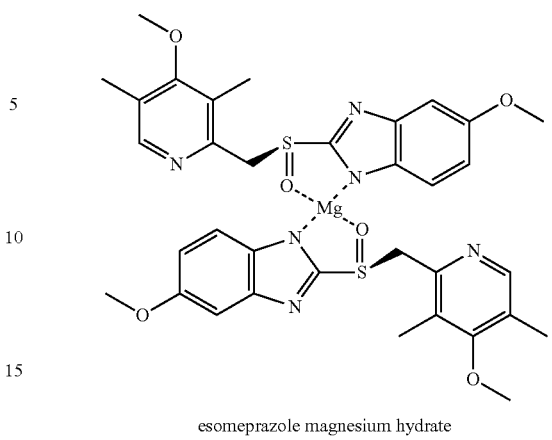

esomeprazole magnesium hydrate

In some embodiments, the present disclosure provides a compound of formula $I^D$:

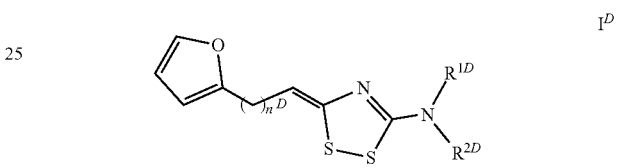

$I^D$ or a pharmaceutically acceptable salt thereof,
wherein:
$R^{1D}$ and $R^{2D}$ are each independently selected from H, $C_1$-$C_5$ alkyl, $C_1$-$C_5$ alkoxy, $C_1$-$C_5$ haloalkyl, or $C_1$-$C_5$ haloalkoxy; and
$n^D$ is an integer from 1 to 5.

In some embodiments, $R^{1D}$ and $R^{2D}$ are the same. In some embodiments, each of $R^{1D}$ and $R^{2D}$ is hydrogen.

In some embodiments, $R^{1D}$ and $R^{2D}$ are different. In some embodiments, $R^{1D}$ is hydrogen and $R^{2D}$ is $C_1$-$C_5$ alkyl.

In some embodiments, $R^{1D}$ is selected from methyl, ethyl, n-propyl or isopropyl. In some embodiments, $R^{1D}$ is selected from —OCH$_3$, —OCH$_2$CH$_3$, —OCH$_2$CH$_2$CH$_3$, or —OCH(CH$_3$)$_2$. In some embodiments, $R^{1D}$ is selected from fluoromethyl, difluoromethyl, trifluoromethyl, fluoroethyl, difluoroethyl, or trifluoroethyl. In some such embodiments, $R^{1D}$ is selected from —CH$_2$F, —CHF$_2$, —CF$_3$, —CH$_2$CH$_2$F, —CH$_2$CHF$_2$ or —CH$_2$CF$_3$. In some embodiments, $R^{1D}$ is selected from fluoromethoxy, difluoromethoxy, trifluoromethoxy, fluoroethoxy, difluoroethoxy, or trifluoroethoxy. In some such embodiments, $R^{1D}$ is selected from —OCH$_2$F, —OCHF$_2$, —OCF$_3$, —OCH$_2$CH$_2$F, —OCH$_2$CHF$_2$, or —OCH$_2$CF$_3$.

In some embodiments, $R^{2D}$ is selected from methyl, ethyl, n-propyl or isopropyl. In some embodiments, $R^{2D}$ is selected from —OCH$_3$, —OCH$_2$CH$_3$, —OCH$_2$CH$_2$CH$_3$, or —OCH(CH$_3$)$_2$. In some embodiments, $R^{2D}$ is selected from fluoromethyl, difluoromethyl, trifluoromethyl, fluoroethyl, difluoroethyl, or trifluoroethyl. In some such embodiments, $R^{2D}$ is selected from —CH$_2$F, —CHF$_2$, —CF$_3$, —CH$_2$CH$_2$F, —CH$_2$CHF$_2$ or —CH$_2$CF$_3$. In some embodiments, $R^{2D}$ is selected from fluoromethoxy, difluoromethoxy, trifluoromethoxy, fluoroethoxy, difluoroethoxy, or trifluoroethoxy. In some such embodiments, $R^{2D}$ is selected from —OCH$_2$F, —OCHF$_2$, —OCF$_3$, —OCH$_2$CH$_2$F, —OCH$_2$CHF$_2$, or —OCH$_2$CF$_3$.

In some embodiments, $n^D$ is 1-2. In some embodiments, $n^D$ is 1. In some embodiments, $n^D$ is 2. In some embodiments, $n^D$ is 3. In some embodiments, $n^D$ is 4. In some embodiments, $n^D$ is 5.

In some embodiments, a SARM1 NADase inhibitor is selected from the compounds in Table 2:

TABLE 2

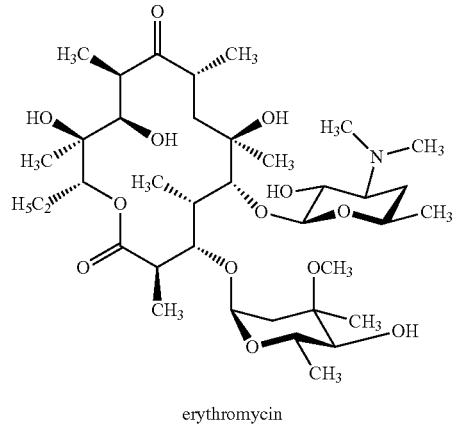

erythromycin

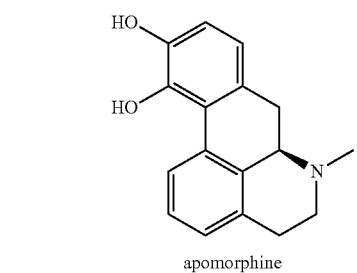 [SMILES: CN1CCc2cccc3c2[C@H]1Cc1ccc(O)c(O)c1-3]

apomorphine

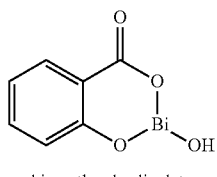

bismuth subsalicylate

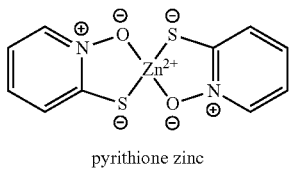

pyrithione zinc

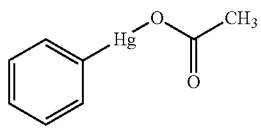

phenylmercuric acetate

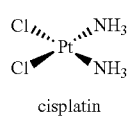

cisplatin

TABLE 2-continued

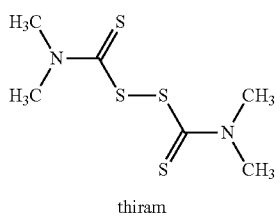

thiram

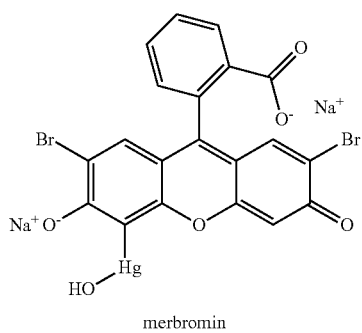

merbromin

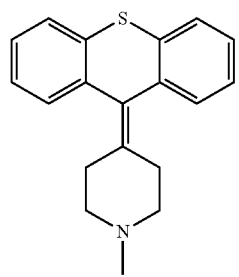

pimethixene maleate

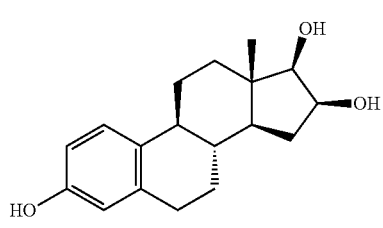

epiestriol

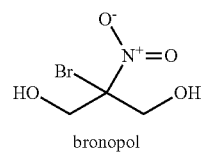

bronopol

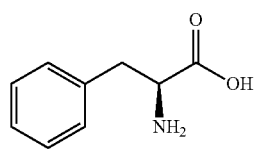

D-phenylalanine

TABLE 2-continued
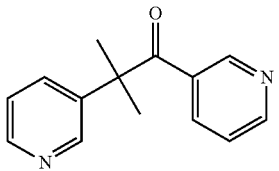
metyrapone
In some embodiments, a SARM1 NADase inhibitor is selected from the group of compounds in Table 3:
TABLE 3
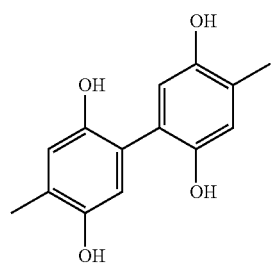
NSC2805
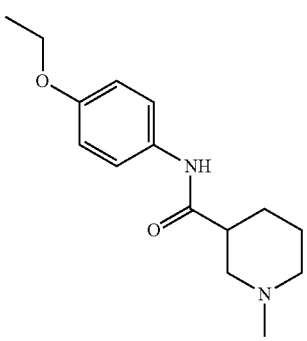
NSC1152
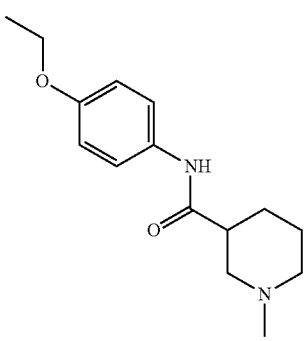
NSC22806
TABLE 3-continued
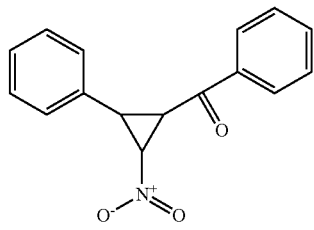
NSC34879
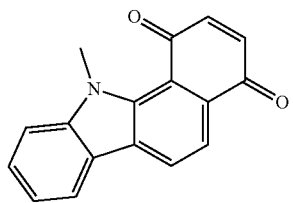
NSC92937
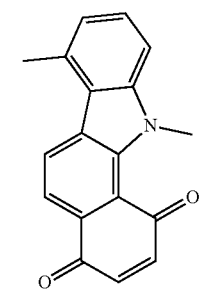
NSC645330
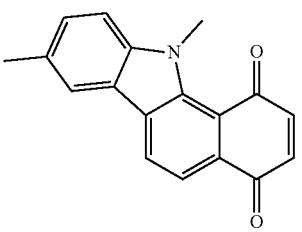
NSC661221
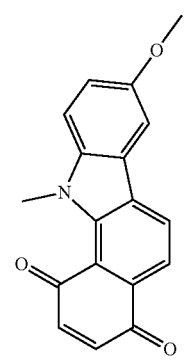
NSC641396

TABLE 3-continued

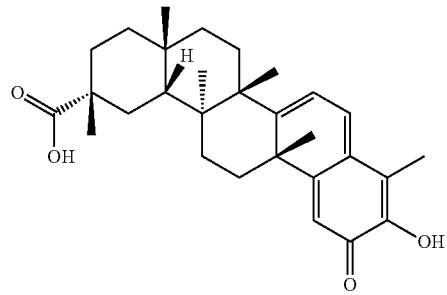

NSC70931

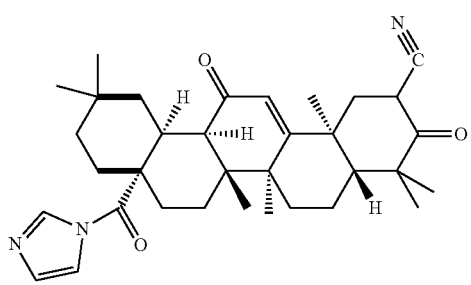

NSC727038

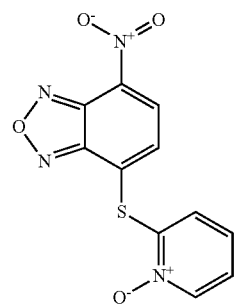

NSC228155

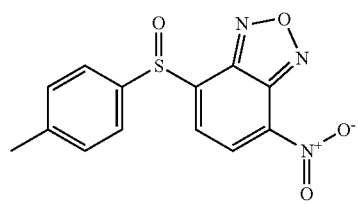

NSC228150

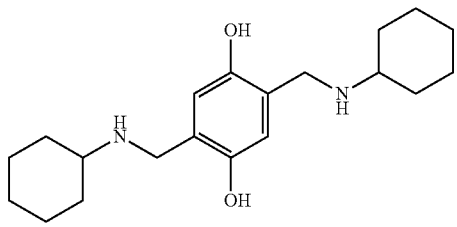

NSC48443

TABLE 3-continued

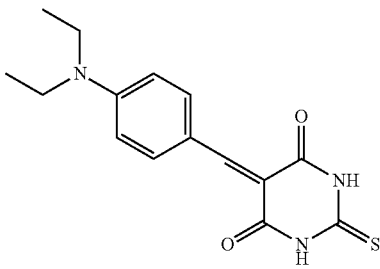

NSC90749

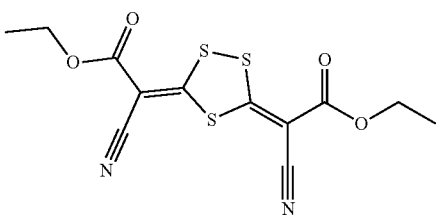

NSC98363

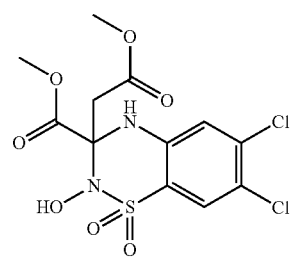

NSC163639

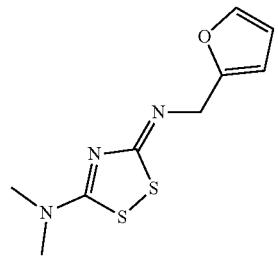

NSC62208

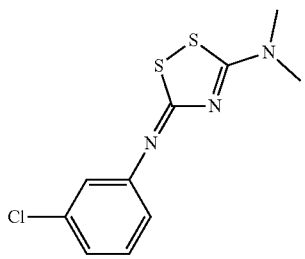

NSC622689

In some embodiments, the compounds of any of Formula $I^A$, Formula $I^B$, Formula $I^C$ and Formula $I^D$ are administered as part of a pharmaceutically acceptable composition. In some embodiments, the compounds of any of Formula $I^A$, Formula $I^B$, Formula $I^C$ and Formula $I^D$ are administered orally. In some embodiments, the compounds of any of Formula $I^A$, Formula $I^B$, Formula $I^C$ and Formula $I^D$ are administered in a range of 0.01-100 mg/kg body weight of the patient.

In some embodiments, the neurodegenerative or neurological disease or disorder is associated with axonal degeneration, axonal damage, axonopathy, a demyelinating disease, a central pontine myelinolysis, a nerve injury disease or disorder, a metabolic disease, a mitochondrial disease, metabolic axonal degeneration, axonal damage resulting from a leukoencephalopathy or a leukodystrophy. In some embodiments, the neurodegenerative or neurological disease or disorder is selected from the group consisting of spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin $B_{12}$ deficiency, isolated vitamin E deficiency syndrome, Bassen-Kornzweig syndrome, Glaucoma, Leber's hereditary optic atrophy (neuropathy), Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west nile virus encephalopathy, La Crosse virus encephalitis, Bunyavirus encephalitis, pediatric viral encephalitis, essential tremor, Charcot-Marie-Tooth disease, motorneuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss, congenital hearing loss, Lewy Body Dementia, frontotemporal dementia, amyloidosis, diabetic neuropathy, HIV neuropathy, enteric neuropathies and axonopathies, Guillain-Barre syndrome, and severe acute motor axonal neuropathy (AMAN).

In certain embodiments, the present disclosure provides any compound selected from those depicted in Table $1^A$, above, or a pharmaceutically acceptable salt thereof, for the inhibition of SARM1 NADase activity. The compounds shown in Table $1^A$ are known proton pump inhibitors, such as: omeprazole (compound $I^A$-1); lansoprazole (compound $I^A$-2); dexlansoprazole (compound $I^A$-3); esomeprazole (compound $I^A$-4); pantoprazole (compound $I^A$-5); rabeprazole (compound $I^A$-6); ilaprazole (compound $I^A$-7); tenatoprazole (compound $I^A$-8); lansoprazole sulfide (compound $I^A$-9); lansoprazole sulfone (compound $I^A$-10); N-methyl omeprazole (compound $I^A$-11); 5-benzyloxy omeprazole (compound $I^A$-12) and sodium esomeprazole (compound $I^A$-13).

In certain embodiments, the present disclosure provides any compound selected from those depicted in Table $1^B$, above, or a pharmaceutically acceptable salt thereof, for the inhibition of SARM1 NADase activity.

In certain embodiments, the present disclosure provides any compound selected from those depicted in Table $1^C$, above, or a pharmaceutically acceptable salt thereof, for the inhibition of SARM1 NADase activity.

In certain embodiments, the present disclosure provides any compound selected from those depicted in Table 2, above, or a pharmaceutically acceptable salt thereof, for the inhibition of SARM1 NADase activity.

In certain embodiments, the present disclosure provides any compound selected from those depicted in Table 3, above, or a pharmaceutically acceptable salt thereof, for the inhibition of SARM1 NADase activity.

In certain embodiments, the present disclosure provides a pharmaceutical composition comprising a compound selected from any of Tables $1^A$, $1^B$, $1^C$, 2, or 3, or a pharmaceutically acceptable salt thereof, and a pharmaceutically acceptable carrier.

4. General Methods for Providing the Present Compounds

It will be appreciated that certain compounds of formula $I^A$ are proton pump inhibitors and are commercially available from various sources.

The compounds of this disclosure and described by formula $I^A$ herein may also be synthesized according to known procedures. For instance, U.S. Pat. No. 5,045,552, filed Dec. 28, 1989 and issued on Sep. 3, 1991 ("the '552 patent," the entirety of which is hereby incorporated herein by reference), describes compounds of formula $I^A$ and their synthesis. EP 268956, filed Nov. 13, 1987 and published Jun. 1, 1988 ("EP '256," the entirety of which is hereby incorporated herein by reference), also describes compounds of formula $I^A$ and their synthesis.

General Preparation of the Compounds of Formula $I^A$:

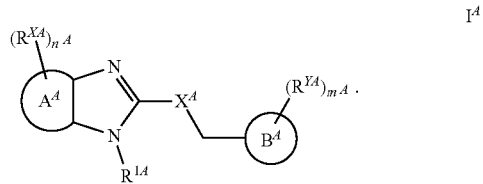

The compounds of formula $I^A$ may be prepared according to the steps and intermediates (e.g., Scheme $1^A$) described below and in the '552 patent and EP '256. In certain embodiments, compounds of the present disclosure of formula $I^A$ are generally prepared according to Scheme $1^A$ set forth below:

Scheme $1^A$

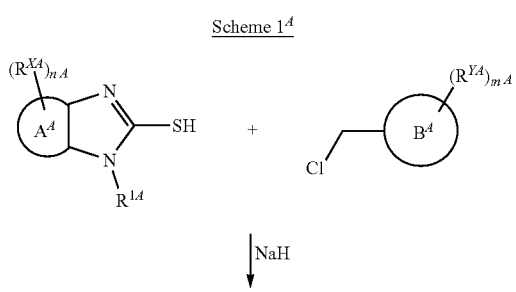

-continued

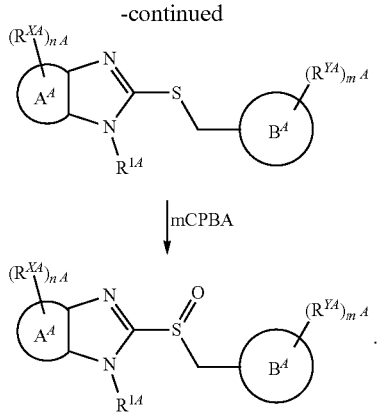

↓ mCPBA

-continued

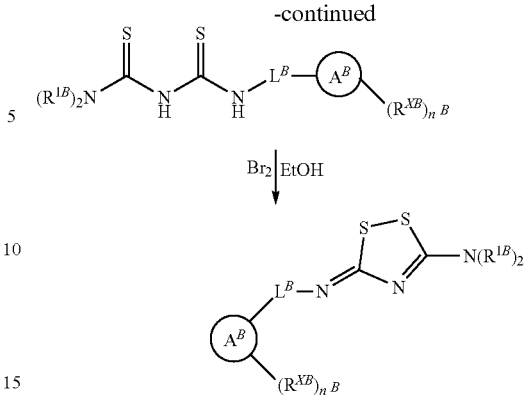

↓ Br₂ | EtOH

The compounds described by formula $I^B$ herein may be prepared or isolated in general by synthetic and/or semi-synthetic methods known to those skilled in the art for analogous compounds and by methods described in detail in the Examples, herein. For instance, the compounds described by formula $I^B$ herein may be synthesized according to WO 2006/084854, filed Feb. 8, 2006 and published on Aug. 17, 2006 ("WO '854," the entirety of which is hereby incorporated herein by reference), describes compounds of formula $I^B$ and their synthesis. Also describing synthesis of the compounds of formula $I^B$ are Oliver et al., J. Org. Chem., vol. 39, No. 15, 1974, pp. 2225-2228 and Pandeya et al., Pharmaceutical Research, vol. 4, No. 4, 1987, pp. 321-326 (the entireties of both which are hereby incorporated herein by reference).

General Preparation of the Compounds of Formula $I^B$:

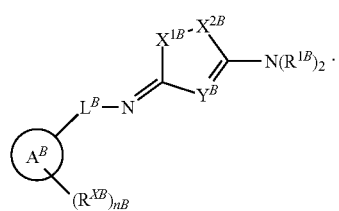

The compounds of formula $I^B$ may be prepared according to the steps and intermediates (e.g., Scheme $1^B$) described below and in WO '854. In certain embodiments, compounds of the present disclosure of formula $I^B$ are generally prepared according to Scheme $1^B$ set forth below:

Scheme $1^B$

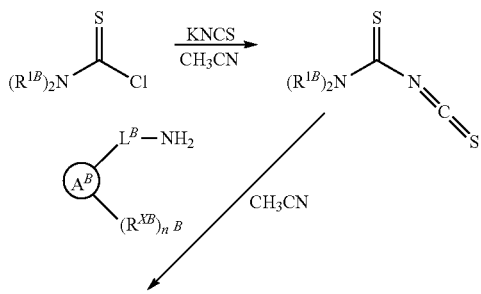

5. Uses, Formulation and Administration and Pharmaceutically Acceptable Compositions According to another embodiment, the present disclosure provides a composition comprising a compound of formula $I^A$, formula $I^B$, formula $I^C$, or formula $I^D$, or any compound selected from Tables $I^A$, $I^B$, $I^C$, 2 and 3, or a pharmaceutically acceptable salt, ester, or salt of ester thereof, and a pharmaceutically acceptable carrier, adjuvant, or vehicle. In some embodiments, the amount of compound in compositions of this disclosure is such that is effective to measurably inhibit SARM1 NADase activity and/or treat a neurodegenerative or neurological disease or disorder, in a biological sample or in a patient. In some embodiments, compositions provided herein contain and/or deliver an amount of a compound of formula $I^A$, formula $I^B$, formula $I^C$, or formula $I^D$, or any compound selected from Tables $I^A$, $I^B$, $I^C$, 2 and 3 that is effective to measurably inhibit SARM1 NADase activity in a biological sample. In some embodiments, compositions provided herein contain and/or deliver an amount of a compound of formula $I^A$, formula $I^B$, formula $I^C$, or formula $I^D$, or any compound selected from Tables $I^A$, $I^B$, $I^C$, 2 and 3 that is effective to measurably inhibit SARM1 NADase activity and/or treat a neurodegenerative or neurological disease or disorder in a patient when administered to the patient in an appropriate dosing regimen. In certain embodiments, a composition of this disclosure is formulated for administration to a patient in need of such composition. In some embodiments, a composition of this disclosure is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this disclosure that, upon administration to a recipient, is capable of providing, either directly or indirectly, a compound of this disclosure or an inhibitorily active metabolite or residue thereof.

As used herein, the term "inhibitorily active metabolite or residue thereof" means that a metabolite or residue thereof is also an inhibitor of SARM1 NADase activity.

In some embodiments, compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. In some embodiments, sterile injectable forms of the compositions of this disclosure may be aqueous or oleaginous suspension. These suspensions may be formulated according to techniques known in the art using suitable dispersing or wetting agents and suspending agents. In some embodiments, the sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some embodiments, pharmaceutically acceptable compositions of this disclosure may be orally administered in any orally acceptable dosage form including, but not limited to, capsules, tablets, aqueous suspensions or solutions. In some embodiments, in the case of tablets for oral use, carriers commonly used include lactose and corn starch. In some embodiments, lubricating agents, such as magnesium stearate, are also typically added. In some embodiments, for oral administration in a capsule form, useful diluents include lactose and dried cornstarch. In some embodiments, when aqueous suspensions are required for oral use, the active ingredient is combined with emulsifying and suspending agents. In some embodiments, certain sweetening, flavoring or coloring agents may also be added.

In some embodiments, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. In some embodiments, such materials include cocoa butter, beeswax and polyethylene glycols.

In some embodiments, pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

In some embodiments, topical application for the lower intestinal tract can be effected in a rectal suppository formulation (see above) or in a suitable enema formulation. In some embodiments, topically-transdermal patches may also be used.

For topical applications, provided pharmaceutically acceptable compositions may be formulated in a suitable ointment containing the active component suspended or dissolved in one or more carriers. In some embodiments, carriers for topical administration of compounds of this disclosure include, but are not limited to, mineral oil, liquid petrolatum, white petrolatum, propylene glycol, polyoxyethylene, polyoxypropylene compound, emulsifying wax and water. In some embodiments, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

In some embodiments, pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

In some embodiments, the amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, the amount of a compound of the present disclosure in the composition will also depend upon the particular compound in the composition.

In some embodiments, the present disclosure provides methods of identifying a SARM1 NADase inhibitor. Such methods comprise: a) providing a mixture comprising i) a mutant or fragment of SARM1, ii) NAD+, and iii) a candidate inhibitor, wherein the mutant or fragment has constitutive NADase activity; b) incubating the mixture; and c) quantifying NAD+, ADPR (and/or cADPR), nicotinamide or any combination thereof in the mixture after the incubating. In some embodiments, provided methods can further comprise d) determining the molar ratio of NAD+/ADPR (and/or NAD+/cADPR); and e) identifying a candidate inhibitor compound as an NADase inhibitor if the molar ratio of NAD+/ADPR (and/or NAD+/ADPR) is greater than that of a control mixture that does not contain the candidate inhibitor. In some embodiments, one or more of NAD+, ADPR (and/or cADPR), nicotinamide or any combination thereof is quantified by any available analytical method, such as, for example, performing an HPLC analysis, a chemiluminescence assay, a mass spectroscopy analysis, a liquid chromatography-mass spectroscopy analysis, or a combination thereof. In some embodiments, the mixture comprises a cell lysate comprising a mutant or fragment of SARM1. In some embodiments, the cell lysate is a lysate of NRK1-HEK293T cells comprising, consisting of, or consisting essentially of a mutant or fragment of SARM1 that has NADase activity. In some embodiments, the mixture can comprise a purified SAM-TIR polypeptide. In some embodiments, the NRK1-HEK293T cells is treated with nicotinamide riboside (NR), which can be useful for maintaining high NAD+ levels and increasing cell viability in the presence of constitutively active SARM1 molecules. In some embodiments, an inhibitor is identified as an NADase inhibitor if the molar ratio of NAD+ to ADPR (or cADPR) is greater than 4:1. In some embodiments, the candidate inhibitor compound is identified as an NADase inhibitor if the molar ratio of NAD+ to ADPR (or cADPR) is greater than 1:1, 2:1, 3:1, 4:1, 5:1, 6:1, 7:1, 8:1, 9:1 or 10:1.

In some embodiments, the mutant or fragment of SARM1 is a SAM-TIR fragment having constitutive NADase activity.

Fragments of SARM1 having constitutive NADase activity include, for example and without limitation, a SARM1 deleted for the autoinhibitory domain; at least one point mutation of SARM1 that renders the autoinhibitory domain inactive; a fragment of SARM1 consisting of the TIR domain; or a fragment of SARM1 consisting of the SAM and TIR domains. A polypeptide of the present teachings can further include one or more additional amino acid sequences that can act as tags, such as a His tag, a streptavidin tag, or a combination thereof. A polypeptide can include a tag at the amino terminal end, at the carboxy terminal end, or a combination thereof.

In some embodiments, SAM-TIR domains can include human SAM-TIR:

(SEQ ID NO: 1)
VPSWKEAEVQTWLQQIGFSKYCESFREQQVDGDLL

LRLTEEELQTDLGMKSGITRKRFFRELTELKTFAN

-continued
YSTCDRSNLADWLGSLDPRFRQYTYGLVSCGLDRS

LLHRVSEQQLLEDCGIHLGVHRARILTAAREMLHS

PLPCTGGKPSGDTPDVFISYRRNSGSQLASLLKVH

LQLHGFSVFIDVEKLEAGKFEDKLIQSVMGARNFV

LVLSPGALDKCMQDHDCKDWVHKEIVTALSCGKNI

VPIIDGFEWPEPQVLPEDMQAVLTFNGIKWSHEYQ

EATIEKIIRFLQGRSSRDSSAGSDTSLEGAAPMGP

T.

The present teachings also provide for the use of isolated TIR domain constructs.

These include constructs including the Human SARM1-TIR domain:

(SEQ ID NO: 2)
TPDVFISYRRNSGSQLASLLKVHLQLHGFSVFIDV

EKLEAGKFEDKLIQSVMGARNFVLVLSPGALDKCM

QDHDCKDWVHKEIVTALSCGKNIVPIIDGFEWPEP

QVLPEDMQAVLTFNGIKWSHEYQEATIEKIIRFLQ

GRSSRDSSAGSDTSLEGAAPMGPT;

Mouse SARM1-TIR:

(SEQ ID NO: 3)
TPDVFISYRRNSGSQLASLLKVHLQLHGFSVFIDV

EKLEAGKFEDKLIQSVIAARNFVLVLSAGALDKCM

QDHDCKDWVHKEIVTALSCGKNIVPIIDGFEWPEP

QALPEDMQAVLTFNGIKWSHEYQEATIEKIIRFLQ

GRPSQDSSAGSDTSLEGATPMGLP and Zebrafish SARM1-TIR:

(SEQ ID NO: 4)
PDVFISYRRTTGSQLASLLKVHLQLRGFSVFIDVE

KLEAGRFEEKLITSVQRARNFILVLSANALDKCMG

DVAMKDWVHKEIVTALNGKKNIVPVTDNFVWPDPT

SLPEDMSTILKFNGIKWSHEYQEATIEKILRFLEG

CPSQEKPDGAKTDKKEPQKK.

A skilled artisan will be able to identify mutations or fragments which lack NADase activity.

In some embodiments, an active mutant or fragment of a SARM1 protein is hSARM1-TIR (561-724), mSARM1-TIR (561-724), zfSARM1-TIR (554-713), MyD88-TIR (148-296), or TLR4-TIR (670-839).

In some embodiments, an active mutant or fragment of a SARM1 protein is hSARM1-TIR (561-724), mSARM1-TIR (561-724), zfSARM1-TIR (554-713), MyD88-TIR (148-296), or TLR4-TIR (670-839).

For ease in purification, a SARM1-TIR domain can be engineered with various protein tags. These tags include, such as and without limitation, FLAG, His, Strep-tag, and VENUS tag.

As used herein, a streptavidin tag is a protein domain that has affinity for a bioengineered streptavidin protein. It can have a sequence, such as but without limitation, of Trp-Ser-His-Pro-Gln-Phe-Glu-Lys (SEQ ID NO: 5). Expression vectors and resins are sold under the trade names such as Strep-Tag® and Strep-Tactin® (IBA, Gottingen, Germany).

As used herein, NRK1-HEK293T cells refer to an HEK293 cell line that expresses a Nicotinamide Riboside Kinase 1 (NRK1). NRK1 has sequence MKRFVI-GIGGVTNGGKTTLAKSLQKHLPNCSVISQDDFFKPE-SEIDIDENGFLQYDVL EALNMEKMMSAVSCWMEN-PGSSAGPAALESAQGVPILIIEGFLLFNYKPLDTIWNRS YFLTVPYEECKRRRSTRVYEPPDPPGYFDGHVWPM-YLKHRQEMSSITWDIVYLDGT RSEEDLF-SQVYEDVKQELEKQNGL (SEQ ID NO: 6). These cells can be stably transformed or transfected with NRK1 or transiently transformed or transfected with NRK1. In some configurations, NRK1 can be transformed or transfected from an expression vector such as but without limitation an FCIV expression vector (Araki, T., et al., Science 305:1010-1013, 2004). In some configurations, NRK1-HEK293T cells can comprise a polyclonal cell line that has been stably transfected with an FCIV expression vector that expresses human Nicotinamide Riboside Kinase 1 (NRK1).

In some embodiments, the mixture can comprise a purified SAM-TIR polypeptide. In some embodiments, the mutant or fragment of SARM1 can consist of or consist essentially of human SARM1 residues 410 to 721 (SEQ ID NO:8). In some embodiments, the mutant or fragment of SARM1 can consist of or consist essentially of human SARM1 residues 560-724. In some embodiments, the mutant or fragment of SARM1 can consist of or consist essentially of human SARM1 residues 560-723. In some embodiments, the mutant or fragment of SARM1 can consist of or consist essentially of human SARM1 residues 560-722. In some embodiments, the mutant or fragment of SARM1 can consist of or consist essentially of human SARM1 residues 560-721. In some embodiments, the mutant or fragment of SARM1 can consist of or consist essentially of a mutant or fragment of SARM1 from any species which has a polypeptide homologous to human SARM1, such as, for example and without limitation, a murine SARM1 polypeptide fragment homologous to human residues 410 to 721. In some embodiments, the SARM1 mutant or SARM1 fragment is a human SARM1 mutant or fragment, a mouse SARM1 mutant or fragment, a zebrafish SARM1 mutant or fragment, a chimpanzee SARM1 mutant or fragment, a Rhesus monkey SARM1 mutant or fragment, a canine SARM1 mutant or fragment, a rat SARM1 mutant or fragment, a chicken SARM1 mutant or fragment, Drosophila SARM1 mutant or fragment, a mosquito SARM1 mutant or fragment, a C. elegans SARM1 mutant or fragment, or a frog SARM1 mutant or fragment. In some embodiments, the mutant or fragment of SARM1 is a SARM1 polypeptide deleted for an N-terminal autoinhibitory domain. In some embodiments, a SARM1 polypeptide having constitutive NADase activity is from about 150 to about 300 amino acid residues in length. In some embodiments, a SARM1 polypeptide having constitutive NADase activity is from about 160 to about 310 amino acid residues in length. In some embodiments, a SARM1 polypeptide having constitutive NADase activity is from about 160 to about 320 amino acid residues in length.

In some embodiments, a SARM1 polypeptide having constitutive NADase activity has a sequence that has at least 70% sequence identity with a human SARM1 polypeptide having constitutive NADase activity. In some embodiments, a SARM1 polypeptide having constitutive NADase activity has a sequence that has at least 80% sequence identity with a human SARM1 polypeptide having constitutive NADase activity. In some embodiments, a SARM1 polypeptide having constitutive NADase activity has a sequence that has at least 90% sequence identity with a human SARM1 polypeptide having constitutive NADase activity. In some embodiments, a SARM1 polypeptide having constitutive NADase activity has a sequence that has at least 95% sequence identity with a human SARM1 polypeptide having constitutive NADase activity. In some embodiments, a SARM1 polypeptide having constitutive NADase activity and at least 70% sequence identity with a human SARM1 polypeptide having constitutive NADase activity, has conservative amino acid substitutions, insertions, deletions, or a combination thereof. In some embodiments, a SARM1 polypeptide having constitutive NADase activity and at least 80% sequence identity with a human SARM1 polypeptide having constitutive NADase activity, has conservative amino acid substitutions, insertions, deletions, or a combination thereof. In some embodiments, a SARM1 polypeptide having constitutive NADase activity and at least 90% sequence identity with a human SARM1 polypeptide having constitutive NADase activity, has conservative amino acid substitutions, insertions, deletions, or a combination thereof. In some embodiments, a SARM1 polypeptide having constitutive NADase activity and at least 95% sequence identity with a human SARM1 polypeptide having constitutive NADase activity, has conservative amino acid substitutions, insertions, deletions, or a combination thereof. In some embodiments, a SARM1 polypeptide having constitutive NADase activity and a sequence that has at least 70%, at least 80%, at least 90% or at least 95% sequence identity with a human SARM1 polypeptide having constitutive NADase activity, has an artificial sequence, or has a sequence identical to a homologous or orthologous sequence from SARM1 of a non-human species.

In some embodiments, a SARM1 polypeptide having constitutive NADase activity is a full-length SARM1 polypeptide.

In some embodiments, the present teachings include a host cell, e.g., a bacterium such as an E. coli that harbors a nucleic acid that encodes a mutant or fragment of SARM1 of eukaryotic origin has constitutive NADase activity. In some embodiments, the present teachings include a bacterium such as an E. coli that harbors a mutant SARM1 polypeptide of eukaryotic origin that has constitutive NADase activity.

In some embodiments, a method of identifying a SARM1 NADase inhibitor comprises: a) providing a mixture comprising i) a mutant or fragment of SARM1, ii) NAD+ and iii) a candidate inhibitor, wherein the mutant or fragment has constitutive NADase activity; b) incubating the mixture; c) quantifying NAD+ in the mixture after the incubating; and d) identifying the candidate inhibitor compound as an NADase inhibitor if the amount of NAD+ is greater than that of a control mixture that does not contain the candidate inhibitor.

In some embodiments, provided are methods of identifying a SARM1 NADase inhibitor, comprising: a) providing a mixture comprising i) a full-length SARM1, ii) NAD+ and iii) a candidate inhibitor, wherein the full-length SARM1 has constitutive NADase activity; b) incubating the mixture; c) quantifying NAD+ and ADPR (or cADPR) in the mixture after the incubating; d) determining the molar ratio of NAD+: ADPR (or cADPR); and e) identifying the candidate inhibitor compound as an NADase inhibitor if the molar ratio is greater than that of a control mixture that does not contain the candidate inhibitor.

In some embodiments, provided are methods of identifying a SARM1 NADase inhibitor, comprising: a) providing a mixture comprising a solid support to which is bound i) a full-length SARM1 and at least one tag, ii) NAD+, and iii) a candidate inhibitor; b) incubating the mixture; c) quantifying the NAD+ after the incubating; and d) identifying the candidate inhibitor compound as an NADase inhibitor if the concentration of NAD+ is greater than that of a control.

In some embodiments, provided are methods of identifying a SARM1 NADase inhibitor, comprising: a) providing a mixture comprising i) a full-length SARM1, ii) NAD+ and iii) a candidate inhibitor, wherein the full-length SARM1 has constitutive NADase activity; b) incubating the mixture; c) quantifying NAD+ in the mixture after the incubating; and d) identifying the candidate inhibitor compound as an NADase inhibitor if the amount of NAD+ is greater than that of a control mixture that does not contain the candidate inhibitor.

In some embodiments, provided are methods of identifying a SARM1 NADase inhibitor, comprising: a) providing a mixture comprising i) a full-length SARM1 that has constitutive NADase activity, ii) NAD+ and iii) a candidate inhibitor, wherein the full-length SARM1 has constitutive NADase activity; b) incubating the mixture; c) quantifying NAD+ and at least one NADase cleavage product in the mixture after the incubating; and d) identifying the candidate inhibitor compound as an NADase inhibitor if the molar ratio of NAD+ to the at least one NADase cleavage product is greater than that of a control mixture that does not contain the candidate inhibitor.

In some embodiments, the quantifying NAD+ in the mixture comprises, consists of, or consists essentially of performing a chemiluminescence assay. In some embodiments, the quantifying NAD+ in the mixture comprises, consists of, or consists essentially of performing an HPLC analysis. In some embodiments, the mixture can comprise a purified SAM-TIR fragment. In some embodiments, the mixture comprises a cell lysate comprising the mutant or fragment of SARM1. In some embodiments, the cell lysate is a lysate of NRK1-HEK293T cells comprising the mutant or fragment of SARM1. In some embodiments, the NRK1-HEK293T cells comprising the mutant or fragment of SARM1 is treated with NR. In some embodiments, the mutant or fragment of SARM1 is a SAM-TIR fragment. In some embodiments, the mutant or fragment of SARM1 comprises, consists of, or consists essentially of, human SARM1 residues 410 to 721 (SEQ ID NO:8). In some embodiments, the mutant or fragment of SARM1 comprises, consists of, or consists essentially of murine SARM1 residues homologous to those of human SARM1. In some embodiments, the mutant or fragment of SARM1 is a SARM1 polypeptide deleted for an N-terminal auto-inhibitory domain.

In some embodiments, a polypeptide comprises, consists of, or consists essentially of a) a mutant or fragment of SARM1, wherein the mutant or fragment has constitutive NADase activity; and b) at least one tag. In some embodiments, the at least one tag is selected from the group consisting of a streptavidin tag, a His tag, and a combination thereof. In some embodiments, the mutant or fragment of SARM1 is a SAM-TIR fragment. In some embodiments, a mutant or fragment comprises, consists of, or consists essentially of a SAM-TIR fragment, a His tag, and a streptavidin tag. In some embodiments, the streptavidin tag is a tandem streptavidin tag. In some embodiments, a polypeptide comprises, consists of, or consists essentially of an amino terminal tandem streptavidin, a SAM-TIR fragment, and a C-terminal His tag. In some embodiments, the mutant or fragment of SARM1 is a SARM1 polypeptide deleted for an N-terminal auto-inhibitory domain. In some embodiments, the mutant or fragment of SARM1 comprises, consists of, or consists essentially of human SARM1 residues 410 to 721 (SEQ ID NO:8). In some embodiments, the mutant or fragment of SARM1 comprises, consists of, or consists essentially of murine SARM1 residues which are homologous to those of human SARM1 residues 410 to 721 (SEQ ID NO:8). In some embodiments, the mutant or fragment of SARM1 comprises, consists of, or consists essentially of human SARM1 residues 410 to 721 In some embodiments, the polypeptide is immobilized on a solid support. In some embodiments, the solid support is a bead. In some embodiments, vectors include a plasmid or virus comprising a sequence encoding a polypeptide described herein.

In some embodiments, the present disclosure provides methods of identifying a SARM1 NADase inhibitor, which comprises: a) providing a mixture comprising NAD+ and a bead to which is bound a polypeptide consisting of a mutant or fragment of SARM1 having constitutive NADase activity; b) adding a candidate inhibitor to the mixture; c) incubating the mixture; d) quantifying the NAD+ in the mixture; and e) identifying the candidate inhibitor compound as a SARM1 inhibitor if the concentration of NAD+ is greater than that of a control. In some embodiments, provided methods include stopping NADase activity (if any) in the mixture after the incubating. In some embodiments, the polypeptide further includes at least one tag, such as an N-terminal tag. In some embodiments, the N-terminal tag is a streptavidin tag. In some embodiments, the N-terminal tag is a tandem streptavidin tag. In some embodiments, the at least one tag is a C-terminal tag. In some embodiments, the C-terminal tag is a polyhistidine tag. In some embodiments, the bead is a histidine tag purification bead. In some embodiments, the at least one tag is at least two tags. In some embodiments, the at least two tags is an N-terminal tag and a C-terminal tag. In some embodiments, the N-terminal tag is a tandem streptavidin tag and the C-terminal tag is a polyhistidine tag. In some embodiments, the quantifying NAD+ comprises performing an HPLC-based analysis. In some embodiments, the quantifying NAD+ and ADPR (or cADPR) comprises performing an LC/MS-based analysis. In some embodiments, a candidate inhibitor compound is identified as a SARM1 inhibitor if the molar ratio of NAD to ADPR (or cADPR) is greater than 4:1. In some embodiments, a candidate inhibitor compound is identified as a SARM1 inhibitor if the molar ratio of NAD to ADPR (or cADPR) is greater than 1:1, 2:1, 3:1, 4:1, 5:1, 6:1, 7:1, 8:1, 9:1, or 10:1.

In some embodiments, the present disclosure provides a SARM1 polypeptide mutant or fragment. In some embodiments, a SARM1 polypeptide mutant or fragment may be bound to a solid support such as a bead. In some embodiments, the SARM1 polypeptide mutant or fragment bound to a solid support comprises, consists of, or consists essentially of SAM-TIR, a TIR domain, or a SARM1 polypeptide deleted for an autoinhibitory domain. In some embodiments, the SARM1 polypeptide mutant or fragment is selected from the group consisting of a human SARM1 polypeptide mutant or fragment, a mouse SARM1 polypeptide mutant or fragment, and a zebrafish SARM1 polypeptide mutant or fragment. In some embodiments, the SARM1 polypeptide mutant or fragment further comprises, consists of, or consists essentially of a tag. In some embodiments, a SARM1 polypeptide mutant or fragment having NADase activity comprises, consists of, or consists essentially of a SARM1 mutant or fragment bound to a solid support via a protein tag.

In some embodiments, a method of identifying a SARM1 NADase inhibitor comprises: a) providing a mixture comprising at least one cultured neuron comprising an axon; b) adding a candidate SARM1 NADase inhibitor to the mixture; c) adding a labeled NAM to the mixture and transecting the axon; d) incubating the mixture; and e) quantifying the amount of labeled and unlabeled NAD+ in the mixture. In some embodiments, provided methods can further comprise 0 calculating the net rate of NAD+ consumption, for example by calculating the % decrease of unlabeled over total NAD+ (e.g., light NAD over total (light plus heavy) NAD+) over time. In some embodiments, the calculation is expressed, for example, as %/hr. In some embodiments, an inhibitor of SARM1 is identified when there is a decrease in the post-injury NAD+ consumption rate compared to that of a control mixture that does not contain the candidate inhibitor. In some embodiments, the labeled NAM is deuterium labeled ("heavy") NAM. In some embodiments, the labeled NAM is $d_4$-NAM. In some embodiments, the quantifying of labeled and unlabeled NAD+ is performed using analytical methods such as LC-MS/MS. In some embodiments, the at least one cultured neuron is at least one dorsal root ganglion cultured neuron.

In some embodiments, a method of identifying an inhibitor of axonal degeneration comprises, consists of, or consists essentially of: a) providing a mixture comprising at least one cultured neuron comprising an axon; b) adding a candidate inhibitor to the mixture; c) disrupting the neuron; d) calculating the degeneration index using at least one microscope image (Sasaki, Y. et al, *Journal of Neuroscience* 2009 29(17): 5525-5535); and f) identifying an inhibitor of axon degeneration when there is a significant decrease in the degeneration index compared to a control with no inhibitor. In some embodiments, disrupting the neuron comprises transecting the axon. In some embodiments, disrupting the neuron comprises adding vincristine to the mixture.

In some embodiments, the present disclosure also provides an NRK1-HEK293 cell line comprising HEK293T cells transformed with a Nicotinamide Riboside Kinase 1 (NRK1). In some embodiments, the NRK1-HEK293 cells transformed or transfected with a DNA sequence encoding Nicotinamide Riboside Kinase 1 (NRK1). In some embodiments, the DNA encoding NRK1 can be genomic or cDNA. In some embodiments, an NRK1-HEK293 cell is stably or transiently transformed or transfected with DNA encoding NRK1 from a source exogenous to the host cell. In some embodiments, an NRK1-HEK293 cell is stably or transiently transformed or transfected with DNA encoding NRK1 such that the cell expresses NRK1 at an elevated level compared to control cells. In some embodiments, the DNA encoding NRK1 is under the control of one or more exogenous regulatory sequences such as a promoter, an enhancer or a combination thereof. In some embodiments, a combination of a DNA sequence encoding NRK1 and regulatory sequences is a non-naturally occurring combination. In some embodiments, DNA encoding NRK1, either genomic or cDNA, comprises an expression vector such as an FCIV expression vector. In some embodiments, DNA encoding NRK1 originates from genomic DNA or cDNA, and can be from a vertebrate or invertebrate species such as but not limited to human, mouse, zebrafish or a *Drosophila*. In some configurations, the NRK1 DNA is a human NRK1 DNA.

Pharmaceutical Uses

In some embodiments, the present disclosure provides inhibitors of SARM1 NADase activity for treatment of neurodegenerative or neurological diseases or disorders that involve axon degeneration or axonopathy. The present disclosure also provides methods of using inhibitors of SARM1 NADase activity to treat, prevent or ameliorate axonal degeneration, axonopathies and neurodegenerative or neurological diseases or disorders that involve axonal degeneration.

In some embodiments, the present disclosure provides methods of treating neurodegenerative or neurological diseases or disorders related to axonal degeneration, axonal damage, axonopathies, demyelinating diseases, central pontine myelinolysis, nerve injury diseases or disorders, metabolic diseases, mitochondrial diseases, metabolic axonal degeneration, axonal damage resulting from a leukoencephalopathy or a leukodystrophy.

Such neurodegenerative or neurological diseases or disorders may include spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin $B_{12}$ deficiency, isolated vitamin E deficiency syndrome, Bassen-Kornzweig syndrome, Glaucoma, Leber's hereditary optic atrophy, Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west nile virus encephalopathy, La Crosse virus encephalitis, Bunyavirus encephalitis, pediatric viral encephalitis, essential tremor, Charcot-Marie-Tooth disease, motorneuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss, congenital hearing loss.

In some embodiments, a neuropathy or axonopathy associated with axonal degeneration can be any of a number of neuropathies or axonopathys such as, for example, those that are hereditary or congenital or associated with Parkinson's disease, Alzheimer's disease, Herpes infection, diabetes, amyotrophic lateral sclerosis, a demyelinating disease, ischemia or stroke, chemical injury, thermal injury, and AIDS. In addition, neurodegenerative diseases not mentioned above as well as a subset of the above mentioned diseases can also be treated with the methods of the present disclosure. Such subsets of diseases can include Parkinson's disease or non-Parkinson's diseases, or Alzheimer's disease.

Neuropathies and axonopathies can include any disease or condition involving neurons and/or supporting cells, such as for example, glia, muscle cells or fibroblasts, and, in particular, those diseases or conditions involving axonal damage. Axonal damage can be caused by traumatic injury or by non-mechanical injury due to diseases, conditions, or exposure to toxic molecules or drugs. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

Peripheral neuropathies can involve damage to the peripheral nerves, and can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa. Peripheral nerve degeneration can also result from traumatic (mechanical) damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, taxol, cisplatinin, a proteasome inhibitor, or a vinca alkaloid such as vincristine. Typical symptoms of such peripheral neuropathies include weakness, numbness, paresthesia (abnormal sensations such as burning, tickling, pricking or tingling) and pain in the arms, hands, legs and/or feet. The neuropathy can also be associated with mitochondrial dysfunction. Such neuropathies can exhibit decreased energy levels, i.e., decreased levels of NAD and ATP.

A peripheral neuropathy can also be a metabolic and endocrine neuropathy which includes a wide spectrum of peripheral nerve disorders associated with systemic diseases of metabolic origin. These diseases include, for example, diabetes mellitus, hypoglycemia, uremia, hypothyroidism, hepatic failure, polycythemia, amyloidosis, acromegaly, porphyria, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

Neuropathies can also include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins $B_{12}$ or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

Neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The exact amount required will vary from subject to subject, depending on the species, age, and general condition of the subject, the severity of the infection, the particular agent, its mode of administration, and the like. A provided compound or composition of the present disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

A pharmaceutically acceptable composition of this disclosure can be administered to humans and other animals orally, rectally, intravenously, parenterally, intracisternally, intravaginally, intraperitoneally, topically (as by powders, ointments, or drops), bucally, as an oral or nasal spray, or the like, depending on the severity of the infection being treated. In certain embodiments, a provided compound of the present disclosure may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

A provided compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body.

Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the present disclosure relates to a method of inhibiting SARM1 NADase activity in a biological sample comprising the step of contacting said biological sample with a provided compound, or a composition comprising said compound.

In certain embodiments, the present disclosure relates to a method of treating axonal degeneration in a biological sample comprising the step of contacting said biological sample with a provided compound, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present disclosure relates to a method of inhibiting SARM1 NADase activity in a patient comprising the step of administering to said patient a provided compound, or a composition comprising said compound.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this disclosure. For example, a provided compound may be administered with another therapeutic agent simultaneously or sequentially in separate unit dosage forms or together in a single unit dosage form. Accordingly, the present disclosure provides a single unit dosage form comprising a provided compound, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this disclosure should be formulated so that a dosage of between 0.01-100 mg/kg body weight/day of a provided compound can be administered.

In those compositions which comprise an additional therapeutic agent, that additional therapeutic agent and a provided compound may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in a composition comprising a provided compound will be no more than the amount that would normally be administered in a composition comprising that therapeutic agent as the only active agent. Preferably the amount of additional therapeutic agent in a provided composition will range from about 50% to 100% of the amount normally present in a composition comprising that agent as the only therapeutically active agent.

EXEMPLIFICATION

The present teachings including descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Materials and Methods for Examples 1-10

NRK1-HEK293T Cell Lines.

Figure 3:
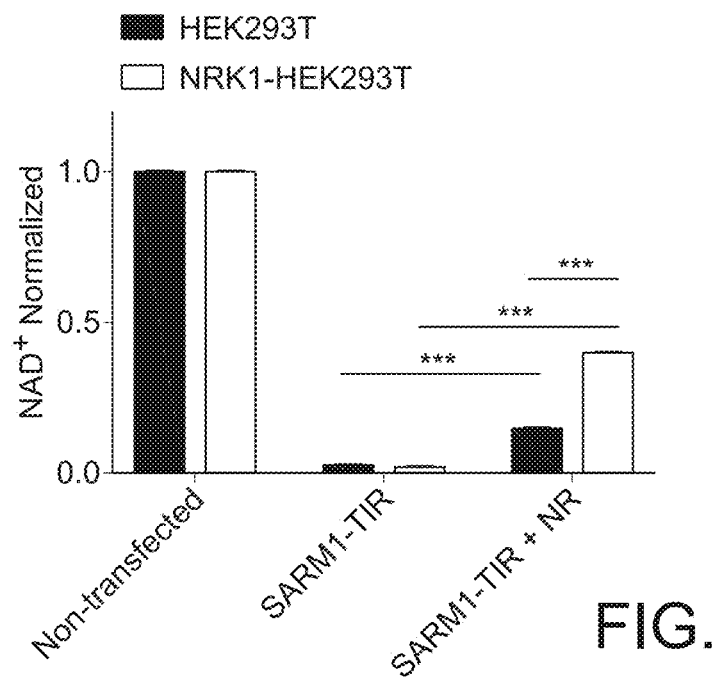
FIG. 3 illustrates that a NRK1-HEK293T stable line with NR supplementation maintains higher NAD+ levels upon SARM1-TIR expression.

A clonal HEK293T cell line (NRK1-HEK293T) that expresses Nicotinamide Riboside Kinase 1 (NRK1) was developed so that supplementation with NR during protein expression would significantly augment cellular NAD+ levels and maintain cell viability adequate for protein purification (FIG. 3). FIG. 3 illustrates that a NRK1-HEK293T stable line with NR supplementation maintains higher NAD+ levels upon SARM1-TIR expression. Data was generated from three independent NAD+ measurements from three independent transfection experiments, and normalized to data from a non-transfected experiment run concurrently. Data are presented as mean±SEM; Error bars: SEM; *** $P<0.001$ two tailed student's t-test.

Methods.

Some methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, NJ, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Reagents.

MagStrep (Strep-Tactin) type 3 XT beads (IBA-Lifesciences, 2-4090-002). Dynabeads HisTag Isolation and Pulldown (ThermoFisher, 10103D). Biotin (Sigma, B4501). β-Nicotinamide Adenine Dinucleotide (Sigma), Nicotinic Acid Adenine Dinucleotide (Sigma), SYPRO Ruby Protein Gel stain (ThermoFisher, S12000), X-tremeGENE 9 DNA transfection reagent (Roche), Shuffle T7 Express Competent *E. coli* (New England BioLabs)

Cell Culture.

HEK293T and NRK1-HEK293T cells were maintained in 10% FBS in DMEM, supplemented with penicillin/streptomycin and glutamine, and passaged by suspending in 0.05% trypsin. Cell lines were continuously monitored for contamination. A batch of HEK293T was tested for *Mycoplasma* contamination. HEK293T was obtained from ATCC. NRK1-HEK293T is a cell line developed that stably expresses Nicotinamide Riboside Kinase 1 (NRK1) so that supplementation with Nicotinamide Riboside (NR), an NAD+ biosynthetic precursor, during protein expression would significantly augment cellular NAD+ levels and maintain cell viability adequate for protein purification.

Recombinant DNA.

Mammalian Expression constructs were cloned into FCIV lentiviral vector: StrepTag-hSARM1-TIR-Venus, StrepTag-hSARM1-TIR(E596K)-Venus, StrepTag-GST-MyD88-TIR, StrepTag-GST-TLR4-TIR, StrepTag-hSARM1-TIR-Venus-HisTag, StrepTag-hSARM1-TIR(E596K)-Venus-HisTag.

Bacterial expression constructs were cloned into pET30a+: StrepTag-hSARM1-TIR-HisTag, StrepTag-mSARM1-TIR-HisTag, StrepTag-zfSARM1TIR-HisTag.

TIR Domain Residues:

hSARM1-TIR (561-724), mSARM1-TIR (561-724), zfSARM1-TIR (554-713), MyD88-TIR (148-296), TLR4-TIR (670-839).

Mouse Embryonic Dorsal Root Ganglion (DRG) Neuronal Culture.

DRG neurons were isolated from SARM1−/− E13.5 mouse embryos as previously described (Gerdts et al., 2015, Science 348, 453-457) and seeded on plates pre-coated with poly-D-Lysine (Sigma-Aldrich) and laminin (Life Technologies). DRG neurons were maintained in neurobasal medium supplemented with L-glutamine, 2% B27 (Gibco), 50 ng/mL nerve growth factor (Envigo Bioproducts), and 1 µM 5-fluoro-2'deoxyuridine plus 104 uridine (Sigma-Aldrich). On DIV 1, neurons were transduced with lentiviral particles generated from HEK293T cells as previously described (Sasaki et al., 2009, J. Neurosci., 29, 5525-5535) expressing Venus alone or the indicated SARM1 construct fused to Venus at the C-terminus. Axons from SARM1−/− DRGs expressing the indicated construct were severed with a razor blade or treated with 40 nM vincristine on DIV 7. SARM1−/− mice (C57/BL6) were housed (12 hr dark/light cycle and less than 5 mice per cage) and used under the direction of institutional animal study guidelines at Washington University in St. Louis.

Protein Expression and Purification from NRK1-HEK293T Stable Line.

Approximately 10 million cells were plated and transfected the next day with 15 µg of StrepTag SARM1-TIR construct DNA using X-tremeGENE™ 9 reagent (Sigma-Aldrich, St. Louis MO). Nicotinamide Riboside (NR) was added at a final concentration of 1 mM to improve cell viability. After 2 days the cells were harvested and lysed by sonication in binding buffer (50 mM Sodium Phosphate buffer pH 8, 300 mM Sodium Chloride, 0.01% Tween-20, protease inhibitor tablets). For single step affinity purification, the whole cell lysates were incubated with 20 µL MagStrep (Strep-Tactin) type 3 XT beads suspension (IBA Lifesciences) for 30 min. The beads were then washed three times with binding buffer and resuspended in 100 µL of binding buffer for enzymatic assays and other downstream applications.

Tandem Affinity Purification (TAP) from NRK1-HEK293T Stable Line.

Dual tagged (Strep-tag and His tag SARM1-TIR) proteins were first purified by Strep Tag affinity methods as described above. For tandem affinity purification, the proteins were then eluted from MagStrep type 3 XT beads with 22.5 mM biotin for 25 min. Supernatant containing the eluted protein was separated from MagStrep beads, and then incubated with 10 µL Co2+ Dynabead suspension for 30 min to bind SARM1-TIR proteins via the His tag. The beads were then washed at least two times with binding buffer and resuspended in 100 µL of binding buffer for downstream applications.

Bacterial Protein Expression and Tandem Affinity Purification (TAP).

The appropriate dual tag (StrepTag and HisTag) SARM1-TIR was cloned into a pET30a+ plasmid. These constructs as well as non-recombinant pET30a+ were transformed into Shuffle T7 Express Competent *E. coli* (New England Bio-Labs). Single colonies were grown overnight and the next day, cultures were diluted in LB media, grown at 30° C. until they reached A600=0.4-0.8, when IPTG (0.5 mM final concentration) was added. The bacteria were grown for an additional 4 h, pelleted by centrifugation, washed with PBS and stored at −80° C. For protein purification, the frozen bacterial pellet was thawed on ice, resuspended in binding buffer (without protease inhibitors) and incubated with 100 µg/mL lysozyme for 15 min on ice.

Protease inhibitor cocktail was then added and the cells were lysed by sonication. Tandem affinity purification was carried out as described above.

Preparation of Peptides for LC-MS.

Purified TAP complexes were eluted by boiling the cobalt magnetic beads for 15 min in Tris-HCl buffer (pH 7.6, 100 mM) (40 µL) containing 4% SDS and dithiothreitol (100 mM). The beads were spun at 16,000×g for 5 min and the eluted proteins were mixed with 300 µL of Tris-HCl buffer (pH 8.5, 100 mM) containing 8M urea. The SDS was removed using a filter-aided-sample-preparation (FASP) method (Wisniewski et al., Nat. Methods, 2009, 6, 359-362.). After buffer exchange, 100 µL of buffer (ammonium bicarbonate, pH 7.8, 50 mM) was pipetted into the Microcon® filtration unit (YM-30) and trypsin was added (1 µg in 1 µL). The digest was incubated for 4 h at 37° C. and then overnight in a humid chamber after the addition of another aliquot of trypsin. The digest was acidified (5 µL of neat formic acid) and the peptides were recovered by centrifugation to the lower chamber. The acidified peptides were treated with ethyl acetate as previously described (Erde et al., J. Proteome Res., 2014, 13, 1885-1895). The peptides were desalted by solid phase extraction on a Beckman BioMek NxP robot with C4 and porous graphite carbon Nutips (Glygen) (Chen et al., Mol. Cell. Proteomics, 2012, 11, M111.011445). The peptides that eluted with acetonitrile (60% in 1% formic acid) were combined, dried in a vacuum centrifuge, dissolved in acetonitrile/formic acid (1%/0.1%) (16 µL). An aliquot (2 µL) was taken for analysis using a fluorescent assay (ThermoFisher Scientific) and the remainder was pipetted into autosampler vials (SUN-SRi), concentrated by vacuum centrifugation and dissolved in aqueous TFA (0.1%) (0.6/µg) for LC-MS analysis (see below).

NADase Assay and Metabolite Extraction.

Ten microliters of beads incubated with the indicated cell lysate were incubated with 5 µM NAD in reaction buffer (92.4 mM NaCl and 0.64×PBS). Reactions were carried out at 25° C. for the indicated amount of time and stopped by addition of 1M of perchloric acid ($HClO_4$) and placing the tube on ice. NAD+ metabolites were extracted using $HClO_4$/$K_2CO_3$ method and quantified by HPLC (see HPLC for metabolite measurement). For LC-MS/MS analysis, the extraction was performed using 50% Methanol in distilled water and chloroform (see LC-MS/MS metabolite measurement for further details).

HPLC Metabolite Measurement.

Metabolites were isolated from enzyme reaction mixture by extracting with 1M $HClO_4$, then neutralized with 3M $K_2CO_3$, and followed by separation by centrifugation. The supernatant (90 µL) containing the extracted metabolites was mixed with 0.5M Potassium Phosphate buffer (10 µL) and metabolites were analyzed by HPLC (Nexera X2) with Kinetex (100×3 mm, 2.6 µm; Phenomenex) column. Internal standards for NAD+, Nicotinamide (Nam), Nicotinic Acid Adenine Dinucleotide (NaAD), ADP Ribose (ADPR) or cADPR were used to generate standard curves for quantification of the respective compounds. The levels for each compound in each experimental sample were normalized to the 0 min time point that was analyzed concurrently.

LC-MS/MS Metabolite Measurement.

Samples were prepared by mixing the reactions with 50% methanol in distilled water. The samples were placed on ice, and centrifuged.

Soluble metabolites in the supernatant were extracted with chloroform, and the aqueous phase was lyophilized and stored at −20° C. until LC-MS/MS analysis.

For LC-MS/MS, the metabolite samples were reconstituted with 5 mM ammonium formate, centrifuged 12,000×g for 10 min, and the cleared supernatant was applied to the LC-MS/MS for metabolite identification and quantification. Liquid chromatography was performed using an HPLC system (1290; Agilent) with a Synergi Fusion-RP (4.6×150 mm, 4 µm; Phenomenex) column. Samples (10 µl) were injected at a flow rate of 0.55 ml/min with 5 mM ammonium formate for mobile phase A and 100% methanol for mobile phase B. Metabolites were eluted with gradients of 0-7 min, 0-70% B; 7-8 min, 70% B; 9-12 min, 0% B. The metabolites were detected with a Triple Quad mass spectrometer (6460 MassHunter; Agilent) under positive ESI multiple reaction monitoring (MRM). Metabolites were quantified with the aid of a MassHunter quantitative analysis tool (Agilent) with standard curves. Standard curves for each compound were generated by analyzing NAD+, ADPR, and Nam reconstituted in 5 mM ammonium formate. The levels for each compound in each experimental sample were normalized to the 0 min time point that was analyzed concurrently. Sample identity was blinded to individual performing experiment.

Endogenous Bacterial and Mammalian Cell $NAD^+$ Quantification.

Overnight cultures of E. coli harboring a SARM1-TIR construct were diluted and grown at 30° C. until they reached A600=0.4-0.8. IPTG (0.1 mM final concentration) was added to induce protein expression and the cultures were harvested 60 min later. The cultures were normalized to A600=0.5±0.05 and the pellet from 500 µl of culture suspension was lysed by adding 0.5M $HClO_4$. NAD+ metabolites were extracted using $HClO_4$/$K_2CO_3$ method and measured by HPLC. Two hundred thousand NRK1-HEK293T cells grown in presence of NR were transfected with 1 µg SARM1-TIR expression construct. After two days, the NAD+ metabolites were extracted with 0.5M $HClO_4$ and 3M $K_2CO_3$ and measured by HPLC.

SYPRO Ruby Gel Staining.

Purified bead-SARM1-TIR protein complexes were boiled in Laemmli buffer for 10 min and separated on a 10% Bis-Tris Plus gel. After electrophoresis, the gel was fixed in 50% Methanol/7% acetic acid for 30 min×2, then incubated overnight in SYPRO Ruby Protein Gel stain (Thermo Fisher). The next day, the gel was washed with 10% methanol/7% acetic acid solution for 30 min, rinsed in distilled water for 5 minutes×2, and stained proteins were visualized with a UV transilluminator.

Enzyme Kinetics Studies.

V max, Km, kcat were determined from the reaction velocity of NAD+ consumption in the first 60 seconds of reaction for increasing substrate (NAD+) concentration, and fitting the data to the Michaelis-Menten equation using nonlinear curve fit in GraphPad Prism 7 (GraphPad Software, Inc., La Jolla, CA). kcat was calculated per dimer of purified hSARM1-TIR. Data are presented as Mean±SEM from three independents biological samples and reaction measurements. Enzyme concentration was determined via densitometry analysis on a SYPRO Ruby gel of purified protein, with carbonic anhydrase used as a standard.

Enzyme Inhibition Studies.

Purified bacterial hSARM1-TIR was tested in the NADase assay with the addition of 1 mM Nam or 1 mM ADPR in the reaction mixture. For dose-response inhibition experiments, varying concentrations of Nam (1, 10, 102, 103, 104 µM) were added to the reaction mixture. The reaction was stopped after 5 min and NAD+ metabolites were extracted by the perchloric acid method and measured by HPLC as indicated above.

Axonal NAD+ Measurement.

SARM1−/− DRGs were transduced with lentivirus as described above. Cells were supplemented with fresh media every 2 days. On DIV 7, axons were severed with a razor blade. At the indicated timepoint, cell bodies were removed then axonal NAD+ was extracted using perchloric acid/sodium carbonate method and separated with high performance liquid chromatography as previously described (Sasaki et al., J. Neurosci., 2009, 29, 5525-5535).

Modeling SARM1-TIR Domain.

The human SARM1 TIR domain (aa559-724) was analyzed for structural homologs in the protein data bank (PDB) using HHpred (Söding, J. et al., Nucleic Acids Res., 2005, 33, W244-248) and PHYRE2 (Kelley, L. A., et al., Nat. Protoc., 2015, 10, 845-858.). Protein sequence alignments were generated by HHpred and formatted with JalView. Hits with an E-value greater than 0.1 and score below 40 have a reduced probability of accurate prediction and were excluded. PHYRE2 and SWISS-MODEL (Arnold, K., et al., Bioinformatics, 2006, 22, 195-201) were used to generate 3D structural models of the SARM1 TIR domain using MilB CMP-glycosidase as a template (PDB: 4JEM) or nucleoside 2-deoxyribsoyltransrferase (PDB: 1F8Y). These structures were visualized and superimposed with Chimera (Pettersen, E. F., et al., J. Comput. Chem., 2004, 25, (1605-12)

Statistical Analyses.

Statistical methods were not used to predetermine sample size. Number and description of n is indicated in each figure legend or appropriate method section. One-way analysis of variance (ANOVA) comparisons were performed for multiple groups and unpaired t-tests or unpaired two-tailed t-tests were used for individual comparisons. Data meets the assumptions of all statistical tests performed with similar variance between groups. All error bars represent SEM and are an estimate of variation within sample groups. Samples from NADase mini-timecourse (1-4 min) experiments that were performed later than initial 5, 10 min reactions and kinetic assays, that had enzymatic activities that were partially reduced either due to increasing storage of bacteria pellets or other technical/biological phenomenon, were excluded from analysis. Fresh bacteria preparations were subsequently prepared. For quantification of Venus expression, DRGs were fixed in paraformaldyhyde and Venus fluorescence visualized by microscopy from multiple fields of axons for each experiment.

DRGs were co-stained for beta tubulin (Mouse anti-beta3 tubulin (TUJ1); from Biolegend) to assess total axon area for each field. Axon degeneration was quantified in distal axons from brightfield images using an ImageJ macro (Sasaki, Y., et al., J. Neurosci., 2009, 29, 5525-5535) that measures the ratio of fragmented axon area to total axon area. For an individual experiment, six fields were analyzed from 2-3 wells per condition. Other data analyses were done with Graph Pad Prism 7, Image J macro, Microsoft Excel, Adobe Illustrator and Photoshop.

Data and Software Availability

Recombinant DNA sequences have been deposited in BankIt with Accession numbers: KY584388-KY584401.

Example 1

This example illustrates a SAM-TIR assay for NADase activity and use of the assay to identify and/or characterize compounds that block SARM1-mediated NAD+ cleavage, a crucial step in the elimination of damaged or unhealthy axons. This assay can be utilized, for example, to identify and/or characterize compounds that inhibit TIR domain catalyzed NAD+ cleavage and potentially those that disrupt SAM-mediated multimerization. This assay makes use of a fragment of the SARM1 molecule encompassing the SAM and TIR domains. As demonstrated herein, expression of this fragment without the autoinhibitory N-terminal domain generates an active enzyme that cleaves NAD+.

Preparation of SARM1 SAM-TIR Lysate (STL)

NRK1-HEK293T cells represent a cell line that has been stably transfected with an FCIV expression vector that expresses human Nicotinamide Riboside Kinase 1 (NRK1), an enzyme that converts the NAD+ biosynthetic precursor nicotinamide riboside (NR) to NMN, the immediate precursor of NAD+. This expression vector has the DNA sequence:
gtcgacggatcgggagatctcccgatccctatggtgcactctcagta-
caatctgctctgatgccgcatagttaagccagtatctgctccc tgcttgtgtgttg-
gaggtcgctgagtagtgcgcgagcaaaatttaagcta-
caacaaggcaaggcttgaccgacaattgcatgaagaatct
gcttaggggttaggcgttttgcgctgcttcgcgatgtacgggccaga-
tatacgcgttgacattgattattgactagttattaatagtaatcaatt acggggtcatt-
agttcatagcccatatatggagttccgcgttacataact-
tacggtaaatggcccgcctggctgaccgcccaacgacccc
cgcccattgacgtcaataatgacgtatgttcccatagtaacgccaataggggactttc-
cattgacgtcaatgggtggagtatttacggtaaac tgcccacttggcagtacat-
caagtgtatcatatgccaagtacgccccctattgacgt-
caatgacggtaaatggcccgcctggcattatgcc
cagtacatgaccttatgggactttcctacttggcagtacatctacgtattagtcatcgc-
tattaccatggtgatgcggttttggcagtacatca atggcgtgga-
tagcggtttgactcacggggatttccaagtctccaccccattgacgtcaatgg-
gagtttgttttggcaccaaaatcaacg
ggactttccaaaatgtcgtaacaactccgccccat-
tgacgcaaatgggcggtaggcgtgtacggtgggaggtctatataagcagcgcgt
tttgcctgtactgggtctctctggttagaccagatctgagcctgg-
gagctctctggctaactagggaacccactgcttaagcctcaataaag cttgcctt-
gagtgctt-
caagtagtgtgtgcccgtctgttgtgtgactctggtaactagagatccctcagac-
ccttttagtcagtgtggaaaatc tctagcagtggcgcccgaacagggactt-
gaaagcgaaaggggaaaccagaggagctctctcgacgcaggactcggcttgct-
gaagcg cgcacggcaagaggcgaggggcggcgactggtgagtacgc-
caaaaattttgactagcggaggctagaaggagagagatgggtgcg
agagcgtcagtattaagcggggggagaattagatcgcgatgggaaaaaattcggt-
taaggccaggggggaagaaaaaatataaattaaa
acatatagtatgggcaagcagggagctagaacgattcgcagttaatcctggcctgt-
tagaaacatcagaaggctgtagacaaatactgg gacagctacaaccatccttca-
gacaggatcagaagaacttagatcattatataatacagtagcaaccctctat-
tgtgtgcatcaaaggat
agagataaaagacaccaaggaagctttagacaagatagag-
gaagagcaaaacaaaagtaagaccaccgcacagcaagcggccgct gatcttca-
gacctggaggaggagatatgagggacaattggagaagtgaat-
tatataaatataaagtagtaaaaattgaaccattaggagt
agcacccac-
caaggcaaagagaagagtggtgcagagagaaaaaagagcagtgggaatag-
gagctttgttccttggttcttgggagc agcaggaagcactatgggcgcagcgt-
caatgacgctgacggtacaggccagacaattattgtctggtatagtgcagcagc-
agaacaat ttgctgagggctattgaggcgcaacagcatctgttgcaact-
cacagtctggggcatcaagcagctccaggcaagaatcctggctgtgga aaga-
tacctaaaggatcaacagctcctggggatttgggggttgctctggaaaactcat-
ttgcaccactgctgtgccttggaatgctagttgg
agtaataaatctctgaacagatttggaatcacacgacctggatg-
gagtgggacagagaaattaacaattacacaagcttaatacactcct taatt-
gaagaatcgcaaaaccagcaagaaaagaatgaacaagaattattggaattaga-
taaatgggcaagtttgtggaattggtttaacat
aacaaattggctgtgtatataaaattattcataatgatagtag-
gagggcttggtaggtttaagaatagttttgctgtactttctatagtgaatag agt-
taggcagggatattcaccattatcgtttcagaccccacctcc-
caaccccgaggggacccgacaggcccgaaggaatagaagaaga
aggtggagagagagacagagacagatccattcgattagtgaacg-
gatcggcactgcgtgcgccaattctgcagacaaatggcagtatt catccacaattt-
taaaagaaaaggggggattgggggtacagtgcaggggaaagaatagtaga-
cataatagcaacagacatacaaact
aaagaattacaaaaacaaattacaaaaattcaaaattttcgggtttatta-
cagggacagcagagatccagtttggttaattaagggtgcagc
ggcctccgcgccggttttggcgcctcccgcgggcgccccctcct-
cacggcgagcgctgccacgtcagacgaagggcgcaggag cgttcct-
gatccttccgcccggacgctcaggacagcggcccgctgctcataa-
gactcggccttagaaccccagtatcagcagaaggac
attttaggacgggacttgggtgactctagggcactggttttcttccagagagcg-
gaacaggcgaggaaaagtagtccctctcggcgat tctgcggagg-
gatctccgtggggcggtgaacgccgatgat-
tatataaggacgcgccgggtgtggcacagctagttccgtcgcagccg
ggatttgggtcgcggttcttgtttgtggatcgctgtgatcgtcacttggt-
gagttgcgggctgctgggctggccggggctttcgtggccgc
cgggccgctcggtgggacggaagcgtgtggagagaccgc-
caagggctgtagtctgggtccgcgagcaaggttgccctgaactggg
ggttgggggggagcgcacaaaatggcggctgttcccgagtcttgaatggaa-
gacgcttgtaaggcgggctgtgaggtcgttgaaacaa ggtgggggg-
catggtggcgcaagaacccaaggtcttgaggccttcgctaatgcgg-
gaaagctcttattcgggtggagatgggctgg
ggcaccatctggggaccctgacgtgaagtttgtcactgactg-
gagaactcgggtttgtcgtctggttgcggggggcggcagttatgcggt
gccgttgggcagtgcacccgtacctttgg-
gagcgcgcgcctcgtcgtgtcgtgacgtcacccgttctgttggct-
tataatcagggtggg
gccacctgccggtaggtgtgcggtaggctttctccgtcgcaggacgcaggt-
tcgggcctagggtaggctctcctgaatcgacaggc gccggacctctggt-
gaggggagggataagtgaggcgtcagtttctttggtcggttttatgtacctatcttct-
taagtagctgaagctccggtt ttgaac-
tatgcgctcgggttggcgagtgtgttttgtgaagttttttaggcaccttttgaaa-
tgtaatcatttgggtcaatatgtaattttcagtgt
tagactagtaaagcttctgcaggtcgactctagaaaattgtccgctaaat-
tctgccgttttggcttttttgttagacgaagcttgggctgca ggtcgactctagag-
gatcatgaagagatttgtcattggaattggtggtgtgacaaacggagggaa-
gacgacactggctaagagcttgca
gaagcaccttcccaactgcagcgtcatatctcaggatgacttctt-
caagccagagtctgagatagacatagatgaaaatggttttttgcagt
atgatgtgcttgaagcgctaaatatggaaaaaatgatgtcagcagtttcctgttg-
gatggaaaacccaggaagctctgcgggaccagca gccttggaaagtgct-
caaggggttcccatttaattattgaaggtttcctttctctttaattataagcctctggacaccatatggaacagaagtta
cttcctgaccgttccatatgaagaatgtaagaggagaaggagtaccagagtatat-
gagcctccagaccctccaggg tacttcgatggcc acgtgtggcc-
catgtacctaaagcacagacaggaaatgagctccatcacctgggacattgtt-
tacctggatggaacaaggtctgaagag
gacctcttctctcaggtgtatgaagatgtcaagcag-
gaactagagaagcaaaatggtttgGACTATAAAGATGATGAT
GATAAGTAAgctagctaccggt-
gatccgcccctctccctcccccccccctaacgttactggccgaagccgcttg-
gaataaggc cggtgtgcgtttgtctatatgttattttccaccatat-
gccgtcttttggcaatgtgagggcccggaaacctggccctgtcttcttgacgagca
ttcctaggggtctttcccctctcgccaaaggaatgcaaggtctgttgaatgtcgt-
gaaggaagcagttcctctggaagcttcttgaagaca
aacaacgtctgtagcgaccctttgcaggcagcggaaccccc-
cacctggcgacaggtgcctctgcggccaaaagccacgtgtataaga
tacacctgcaaaggcggcacaaccccagtgccacgttgtgagttggatagttgtg-
gaaagagtcaaatggctctcctcaagcgtattcaa caaggggct-
gaaggatgcccagaaggtaccccattgtatgggatct-
gatctggggcctcggtgcacatgctttacatgtgtttagtcgag
gttaaaaaaacgtctaggcccccccgaaccacggggacgtggttttcctt-
gaaaaacacgatgataatatggccacaaccATGGatg
gccaagttgaccagtgccgttccggtgctcaccgcgcgcgacgtcgccg-
agcggtcgagttctggaccgaccggctcgggttctcc cgggacttcgtg-
gaggacgacttcgccggtgtggtccgggacgacgtgaccctgtt-
catcagcgcggtccaggaccaggtggtgccg
gacaacaccctggcctgggtgtgggtgcgcggcctggacgagctgtacgcc-
agtggtcggaggtcgtgtccacgaacttcccggaa cgcctccgggccggc-
catgaccgagatcggcgagcagccgtggggcgg-
gagttcgccctgcgcgacccggccggcaactgcgt gcacttcgtggccgag-
gagcaggactgagaattcgatatcaagcttatcgataatcaacctctggattac-
aaaatttgtgaaagattgact ggtattcttaactatgttgctccttttacgctatgtgga-
tacgctgcttaatgcctttgtatcatgctattgcttcccgtatggctttcattttctcct
ccttgtataaatcctggttgctgtctctttatgag-
gagttgtggcccgttgtcaggcaacgtggcgtggtgtgcactgtgtttgctgac-
gcaa ccccactggttggggcattgccac-
cacctgtcagctccttccgggactttgctttcccctcccctattgccacggcg-
gaactcatcgc
cgcctgccttgcccgctgctggacaggggctcggctgttgggcactgacaat-
tccgtggtgttgtcggggaaatcatcgtcctttccttgg ctgctcgcctgtgttgc-
cacctggattctgcgcgggacgtccttctgctacgtcccttcggccct-
caatccagcggaccttccttcccgcg
gcctgctgccggctctgcggcctcttccgcgtcttcgccttcgccctca-
gacgagtcggatctccctttgggccgcctccccgcatcgat accgtcgacctcga-
gacctagaaaaacatggagcaatcacaagtagcaatacagcagctaccaatgct-
gattgtgcctggctagaagc
acaagaggaggaggaggtgggttttccagtcacacctcaggtacctttaagac-
caatgacttacaaggcagctgtagatcttagccactt
tttaaaagaaaaggggggactggaagggctaattcactcccaacgaagacaaga-
tatccttgatctgtggatctaccacacacaaggct acttccctgattggcagaacta-
cacaccagggccagggatcagatatccactgacctttggatggtgcta-
caagctagtaccagttgagc
aagagaaggtagaagaagccaatgaaggagagaacacccgcttgtta-
caccctgtgagcctgcatgggatggatgacccggagaga gaagtattagagtg-
gaggtttgacagccgcctagcatttcatcacatggcccgagagctg-
catccggactgtactgggtctctctggttag
accagatctgagcctgggagctctctggctaactagggaacccactgcttaagcct-
caataaagcttgccttgagtgcttcaagtagtgtg
tgcccgtctgttgtgtgactctggtaactagagatccctcagacccttt-
agtcagtgtggaaaatctctagcagggcccgtttaaacccgc
tgatcagcctcgactgtgccttctagttgccagc-
catctgttgtttgcccctcccccgtgccttccttgaccctggaaggtgccactcccact
gtcctttcctaataaaatgaggaaattgcatcgcattgtctgagtaggtgtcattctat
tctggggggtgggtgggcaggacagcaagg gggaggattgggaa-
gacaatagcaggcatgctggggatgcggtgggctctatgcttctgaggcg-
gaaagaaccagctggggctcta
gggggtatccccacgcgccctgtagcggcgcat-
taagcgcggcgggtgtggtggttacgcgcagcgtgaccgctacacttgccagcg
ccctagcgcccgctccttttcgctttcttcccttccttttctcgc-
cacgttgccggctttccccgtcaagctctaaatcgggggctcccttttagg gttcc-
gatttagtgctttacggcacctcgaccccaaaaaacttgattagggtgatggtt-
cacgtagtgggccatcgccctgatagacggttt
ttcgccctttgacgttggagtccacgttctttaatagtggactcttgttccaaactg-
gaacaacactcaaccctatctcggtctattctttttgattt ataagggattttgccgat-
ttcggcctattggttaaaaaatgagctgatttaacaaaaatttaacgcgaattaat-
tctgtggaatgtgtgtcagtt
agggtgtggaaagtccccaggctccccagcaggcagaagtatgcaaagcatg-
catctcaattagtcagcaaccaggtgtggaaagtcc
ccaggctccccagcaggcagaagtatgcaaagcatgcatctcaatt-
agtcagcaaccatagtcccgcccctaactccgcccatcccgc
ccctaactccgcccagttccgcccattctccgccccatggctgactaatttttttatt-
tatgcagaggccgaggccgcctctgcctctgagc tattccagaagtagtgag-
gaggcttttttggaggcctaggcttttgcaaaaagctcccgggagcttgtatatccat-
tttcggatctgatcagc
acgtgttgacaattaatcatcggcatagtatatcggcatagtataatacgacaaggt-
gaggaactaaaccatggccaagttgaccagtgcc cgttccggtgct-
caccgcgcgcgacgtcgccg-
gagcggtcgagttctggaccgaccggctcgggttctcccgggacttcgtggagga
cgacttcgccggtgtggtccgggacgacgtgaccctgtt-
catcagcgcggtccaggaccaggtggtgccggacaacaccctggcctg
ggtgtgggtgcgcgccctggacgagctgtacgccgagtggtcggaggtcgtgtc-
cacgaacttcccggacgcctccgggccggcca
tgaccgagatcggcgagcagccgtggggggcgg-
gagttcgccctgcgcgacccggccggcaactgcgtgcacttcgtggccgagga
gcaggactgacacgtgctacgagatttcgattccaccgccgccttctat-
gaaaggttgggcttcggaatcgttttccgggacgccggctg gat-
gatcctccagcgcggggatctcatgctgagttcttcgcccaccccaacttgtttat-
gcagcttataatggttacaaataaagcaata
gcatcacaaatttcacaaataaagcattttttttcactgcattctagttgtggtttgtc-
caaactcatcaatgtatcttatcatgtctgtataccgtc
gacctctagctagagcttggcgtaatcatggtcatagctgtttcctgtgtgaaattgt-
tatccgctcacaattccacacaacatacgagccg gaagcat-
aaagtgtaaagcctggggtgcctaatgagtgagctaactcacattaat-
tgcgttgcgctcactgcccgctttccagtcgggaa
acctgtcgtgccagctgcattaatgaatcggccaacgcgcggg-
gagaggcggtttgcgtattgggcgctcttccgcttcctcgctcactg
actcgctgcgctcggtcgttcggctgcggcgagcggtatcagctcact-
caaaggcggtaatacggttatccacagaatcaggggataa cgcaggaaagaa-
catgtgagcaaaaggccagcaaaaggcag-
gaaccgtaaaaaggccgcgttgctggcgtttttccataggctccg
cccccctgacgagcatcacaaaaatcgacgct-
caagtcagaggtggcgaaacccgacaggactataaaga-
taccaggcgtttcccct
ggaagctccctcgtgcgctctcctgttccgaccctgccgcttaccgga-
tacctgtccgcctttctcccttcgggaagcgtggcgctttctca tagct-
cacgctgtaggtatctcagttcggtgtaggtcgttcgctc-
caagctgggctgtgtgcacgaaccccccgttcagcccgaccgctg
cgccttatccggtaactatcgtcttgagtccaacccggtaagacacgacttatcgc-
cactggcagcagccactggtaacaggattagcag
agcgaggtatgtaggcggtgctacagagttcttgaagtggtggcctaactacggc-
tacactagaagaacagtatttggtatctgcgctctg ctgaagccagttaccttcg-
gaaaaagagttggtagctcttgatccggcaaacaaac-
caccgctggtagcggtggtttttttgtttgcaagc
agcagattacgcgcagaaaaaaaggatctcaagaagatcctttgatcttttc-
tacggggtctgacgctcagtggaacgaaaactcacgtt aagggattttggtcat-
gagattatcaaaaaggatcttcacctagatccttttaaattaaaaatgaagttttaaat-
caatctaaagtatatatgagt
aaacttggtctgacagttaccaatgcttaatcagtgaggcacctatctcagc-
gatctgtctatttcgttcatccatagttgcctgactccccgt cgtgtagataactac-
gatacgggagggcttaccatctggccccagtgctgcaatgataccgcgagacc-
cacgctcaccggctccagatt
tatcagcaataaaccagccagccg-
gaagggccgagcgcagaagtggtcctgcaactttatccgcctccatccagtctat-
taattgttgcc gggaagctagagtaagtagttcgccagt taatagtttgcgcaacgttgttgccattgctacaggcatcgtggtgtcacgctcgtcgtttggt atggcttcattcagctccggttcccaacgatcaaggcgagttacatgatcccc-catgttgtgcaaaaaagcggttagctccttcggtcctcc gatcgttgtcagaagtaagttggccgcagtgttatcactcatggt-tatggcagcactgcataattctcttactgtcatgccatccgtaagatg cttttctgtgactggtgagtactcaaccaagtcattct-gagaatagtgtatgcggcgaccgagttgctcttgcccggcgtcaatacgggata ataccgcgccacatagcagaactttaaaagtgctcatcattg-gaaaacgttcttcggggcgaaaactctcaaggatcttaccgctgttgag atccagttcgatgtaacccactcgtgcacccaactgatcttcagcatcttttacttt-caccagcgtttctgggtgagcaaaaacaggaaggc aaaatgccgcaaaaaagg-gaataagggcgacacggaaatgttgaatactcatactcttcctttttcaatattatt-gaagcatttatcagggtt attgtctcatgagcggatacatatttgaatgtatt-tagaaaaataaacaaataggggttccgcgcacatttccccgaaaagtgc-cacctgac (SEQ ID NO: 7). When these NRK1-expressing cells are supplemented with NR, $NAD^+$ levels are augmented and cell viability is enhanced to enable efficient production and purification of the constitutively active human SARM1 SAM-TIR (SEQ ID NO: 1) protein fragment.

To express SARM1 SAM-TIR, the SARM1 N-terminal auto-inhibitory domain was deleted, keeping only the initiator Met.

Downstream from this initiator Met, the resulting protein has an N-terminal STREP-TAG® and is composed of human SARM1 residues 410 to 721: MSAWSHPQFEKGGGSGGGSGG-SAWSHPQFEKGGGSSGGGGGGSSGGGASVPSWKE AEVQTWLQQIGFSKYCESFREQQVDGDLLLRL-TEEELQTDLGMKSGITRKRFFRELTE LKTFA-NYSTCDRSNLADWLGSLDPRFRQYTYGLVSCGL-DRSLLHRVSEQQLLEDCGI HLGVHRARILTAAREMLHSPLPCTGGKPSGDTPDVFI-SYRRNSGSQLASLLKVHLQLH GFSVFID-VEKLEAGKFEDKLIQSVMGARNFVLVLSP-GALDKCMQDHDCKDWVHKEI VTALSCGKNIVPIIDGFEW-PEPQVLPEDMQAVLTFNGIKWSHEYQEATIEKIIR-FLQGR SSRDSSAGSDTSLEGAAPMGPT (SEQ ID NO: 8). The fragment encoding the SARM1 SAM-TIR protein was cloned into the FCIV expression construct by standard methods to generate the FCIV-SST vector. The resultant vector has the following sequence:

```
                                                                        (SEQ ID NO: 9)
gtcgacggatcgggagatctcccgatcccctatggtgcactctcagtacaatctgctctgatgccgcatagttaagcca gtatctgctccctgcttgtgtgttggaggtcgctgagtagtgcgcgagcaaaatttaagctacaacaaggcaaggcttg accgacaattgcatgaagaatctgcttagggttaggcgttttgcgctgcttcgcgatgtacgggccagatatacgcgtt gacattgattattgactagttattaatagtaatcaattacggggtcattagttcatagcccatatatggagttccgcgt tacataacttacggtaaatggcccgcctggctgaccgcccaacgacccccgcccattgacgtcaataatgacgtatgtt cccatagtaacgccaatagggactttccattgacgtcaatgggtggagtatttacggtaaactgcccacttggcagtac atcaagtgtatcatatgccaagtacgccccctattgacgtcaatgacggtaaatggcccgcctggcattatgcccagta catgaccttatgggactttcctacttggcagtacatctacgtattagtcatcgctattaccatggtgatgcggttttgg cagtacatcaatgggcgtggatagcggtttgactcacggggatttccaagtctccaccccattgacgtcaatgggagtt tgttttggcaccaaaatcaacgggactttccaaaatgtcgtaacaactccgccccattgacgcaaatgggcggtaggcg tgtacggtgggaggtctatataagcagcgcgttttgcctgtactgggtctctctggttagaccagatctgagcctggga gctctctggctaactagggaacccactgcttaagcctcaataaagcttgccttgagtgcttcaagtagtgtgtgcccgt ctgttgtgtgactctggtaactagagatccctcagacccttttagtcagtgtggaaaatctctagcagtggcgcccgaa cagggacttgaaagcgaaagggaaaccagaggagctctctcgacgcaggactcggcttgctgaagcgcgcacggcaaga ggcgaggggcggcgactggtgagtacgccaaaaattttgactagcggaggctagaaggagagagatgggtgcgagagcg tcagtattaagcgggggagaattagatcgcgatgggaaaaaattcggttaaggccagggggaaagaaaaaatataaatt aaaacatatagtatgggcaagcagggagctagaacgattcgcagttaatcctggcctgttagaaacatcagaaggctgt agacaaatactgggacagctacaaccatcccttcagacaggatcagaagaacttagatcattatataatacagtagcaa ccctctattgtgtgcatcaaaggatagagataaaagacaccaaggaagctttagacaagatagaggaagagcaaaacaa aagtaagaccaccgcacagcaagcggccgctgatcttcagacctggaggaggagatatgagggacaattggagaagtga attatataaatataaagtagtaaaaattgaaccattaggagtagcacccaccaaggcaaagagaagagtggtgcagaga gaaaaaagagcagtgggaataggagctttgttccttgggttcttgggagcagcaggaagcactatgggcgcagcgtcaa tgacgctgacggtacaggccagacaattattgtctggtatagtgcagcagcagaacaatttgctgagggctattgaggc gcaacagcatctgttgcaactcacagtctggggcatcaagcagctccaggcaagaatcctggctgtggaaagataccta aaggatcaacagctcctggggatttggggttgctctggaaaactcatttgcaccactgctgtgccttggaatgctagtt
```

-continued ggagtaataaatctctggaacagatttggaatcacacgacctggatggagtgggacagagaaattaacaattacacaag
cttaatacactccttaattgaagaatcgcaaaaccagcaagaaaagaatgaacaagaattattggaattagataaatgg
gcaagtttgtggaattggtttaacataacaaattggctgtggtatataaaattattcataatgatagtaggaggcttgg
taggtttaagaatagttttttgctgtactttctatagtgaatagagttaggcagggatattcaccattatcgtttcagac
ccacctcccaaccccgaggggacccgacaggcccgaaggaatagaagaagaaggtggagagagagacagagacagatcc
attcgattagtgaacggatcggcactgcgtgcgccaattctgcagacaaatggcagtattcatccacaattttaaaaga
aaaggggggattgggggggtacagtgcaggggaaagaatagtagacataatagcaacagacatacaaactaaagaattac
aaaaacaaattacaaaaattcaaaattttcgggtttattacagggacagcagagatccagtttggttaattaagggtgc
agcggcctccgcgccgggttttggcgcctcccgcgggcgccccctcctcacggcgagcgctgccacgtcagacgaagg
gcgcaggagcgttcctgatccttccgcccggacgctcaggacagcggcccgctgctcataagactcggccttagaaccc
cagtatcagcagaaggacattttaggacgggacttgggtgactctagggcactggttttctttccagagagcggaacag
gcgaggaaaagtagtcccttctcggcgattctgcggagggatctccgtggggcggtaacgccgatgattatataagga
cgcgccgggtgtggcacagctagttccgtcgcagccgggatttgggtcgcggttcttgtttgtggatcgctgtgatcgt
cacttggtgagttgcgggctgctgggctggccggggctttcgtggccgccgggccgctcggtgggacggaagcgtgtgg
agagaccgccaagggctgtagtctgggtccgcgagcaaggttgccctgaactgggggttgggggggagcgcacaaaatgg
cggctgttcccgagtcttgaatggaagacgcttgtaaggcgggctgtgaggtcgttgaaacaaggtgggggggcatggtg
ggcggcaagaacccaaggtcttgaggccttcgctaatgcgggaaagctcttattcgggtgagatgggctggggcaccat
ctggggaccctgacgtgaagtttgtcactgactggagaactcgggtttgtcgtctggttgcgggggcggcagttatgcg
gtgccgttgggcagtgcacccgtacctttgggagcgcgcgcctcgtcgtgtcgtgacgtcacccgttctgttggcttat
aatgcagggtggggccacctgccggtaggtgtgcggtaggcttttctccgtcgcaggacgcagggttcgggcctagggt
aggctctcctgaatcgacaggcgccggacctctggtgaggggagggataagtgaggcgtcagtttctttggtcggtttt
atgtacctatcttcttaagtagctgaagctccggttttgaactatgcgctcggggttggcgagtgtgttttgtgaagtt
ttttaggcacctttgaaatgtaatcatttgggtcaatatgtaattttcagtgttagactagtaaagcttctgcaggtc
gactctagaaaattgtccgctaaattctggccgttttggctttttgttagacgaagcttgggctgcaggtcgactct
agaggatccGGATCCGCCACCATGTCAgctTGGAGCCACCCACAATTCGAAAAAGGCGGTGGCTCAGGCGGTGGCTCAG
GTGGCTCAGCTTGGAGCCACCCACAATTCGAAAAAGGCGGTGGCTCATCTGGCGGAGGTGGCGGTGGCTCATCTGGCGG
AGGTGCTAGCgtgcccagctggaaggaggccgaggttcagacgtggctgcagcagatcggttctccaagtactgcgag
agcttccgggagcagcaggtggatggcgacctgcttctgcggctcacggaggaggaactccagaccgacctgggcatga
aatcgggcatcacccgcaagaggttctttagggagctcacggagctcaagaccttcgccaactattctacgtgcgaccg
cagcaacctggcggactggctgggcagcctggacccgcgcttccgccagtacacctacggcctggtcagctgcgggcctg
gaccgctccctgctgcaccgcgtgtctgagcagcagctgctggaagactgcggcatccacctgggcgtgcaccgcgccc
gcatcctcacggcggccagagaaatgctacactcccgctgccctgtactggtggcaaacccagtggggacactccaga
tgtcttcatcagctaccgccggaactcaggttcccagctggccagtctcctgaaggtgcacctgcagctgcatggcttc
agtgtcttcattgatgtggagaagctggaagcaggcaagttcgaggacaaactcatccagagtgtcatgggtgcccgca
actttgtgttggtgctatcacctggagcactggacaagtgcatgcaagaccatgactgcaaggattgggtgcataagga
gattgtgactgctttaagctgcggcaagaacattgtgcccatcattgatggcttcgagtggcctgagccccaggtcctg
cctgaggacatgcaggctgtgcttactttcaacggtatcaagtggtcccacgaataccaggaggccaccattgagaaga
tcatccgcttcctgcagggccgctcctcccgggactcatctgcaggctctgacaccagtttggaggggtgctgcacccat
gggtccaacctaaactctagaattcgatatcaagcttatcgataatcaacctctggattacaaaatttgtgaaagattg
actggtattcttaactatgttgctccttttacgctatgtggatacgctgattaatgcctttgtatcatgctattgcttc
ccgtatggctttcattttctcctccttgtataaatcctggttgctgtctctttatgaggagttgtggcccgttgtcagg -continued

```
caacgtggcgtggtgtgcactgtgtttgctgacgcaaccccactggttggggcattgccaccacctgtcagctcctt
ccgggactttcgctttccccctccctattgccacggcggaactcatcgccgcctgccttgcccgctgctggacaggggc
tcggctgttgggcactgacaattccgtggtgttgtcggggaaatcatcgtcctttccttggctgctcgcctgtgttgcc
acctggattctgcgcgggacgtccttctgctacgtcccttcggccctcaatccagcggaccttccttcccgcggcctgc
tgccggctctgcggcctcttccgcgtcttcgccttcgccctcagacgagtcggatctccctttgggccgcctcccgca
tcgataccgtcgacctcgagacctagaaaaacatggagcaatcacaagtagcaatacagcagctaccaatgctgattgt
gcctggctagaagcacaagaggaggaggaggtgggttttccagtcacacctcaggtacctttaagaccaatgacttaca
aggcagctgtagatcttagccacttttaaaagaaaaggggggactggaagggctaattcactcccaacgaagacaaga
tatccttgatctgtggatctaccacacacaaggctacttccctgattggcagaactacacaccagggccagggatcaga
tatccactgacctttggatggtgctacaagctagtaccagttgagcaagagaaggtagaagaagccaatgaaggagaga
acaccgcttgttacaccctgtgagcctgcatgggatggatgacccggagagagaagtattagagtggaggtttgacag
ccgcctagcatttcatcacatggcccgagagctgcatccggactgtactgggtctctctggttagaccagatctgagcc
tgggagctctctggctaactagggaacccactgcttaagcctcaataaagcttgccttgagtgcttcaagtagtgtgtg
cccgtctgttgtgtgactctggtaactagagatccctcagacccttttagtcagtgtggaaaatctctagcagggcccg
tttaaaccgctgatcagcctcgactgtgccttctagttgccagccatctgttgtttgcccctcccccgtgccttcctt
gaccctggaaggtgccactcccactgtcctttcctaataaaatgaggaaattgcatcgcattgtctgagtaggtgtcat
tctattctggggggtggggtggggcaggacagcaaggggggaggattgggaagacaatagcaggcatgctggggatgcgg
tgggctctatggcttctgaggcggaaagaaccagctggggctctagggggtatcccacgcgccctgtagcggcgcatt
aagcgcggcgggtgtggtggttacgcgcagcgtgaccgctacacttgccagcgccctagcgcccgctcctttcgctttc
ttcccttcctttctcgccacgttcgccggctttccccgtcaagctctaaatcggggctcccttagggttccgattta
gtgctttacggcacctcgaccccaaaaaacttgattagggtgatggttcacgtagtgggccatcgccctgatagacggt
ttttcgccctttgacgttggagtccacgttctttaatagtggactcttgttccaaactggaacaacactcaaccctatc
tcggtctattcttttgatttataagggattttgccgatttcggcctattggttaaaaaatgagctgatttaacaaaaat
ttaacgcgaattaattctgtggaatgtgtgtcagttagggtgtggaaagtccccaggctccccagcaggcagaagtatg
caaagcatgcatctcaattagtcagcaaccaggtgtggaaagtccccaggctccccagcaggcagaagtatgcaaagca
tgcatctcaattagtcagcaaccatagtcccgcccctaactccgcccatcccgcccctaactccgcccagttccgccca
ttctccgccccatggctgactaatttttttattatgcagaggccgaggccgcctctgcctctgagctattccagaag
tagtgaggaggcttttttggaggcctaggcttttgcaaaaagctcccgggagcttgtatatccatttcggatctgatc
agcacgtgttgacaattaatcatcggcatagtatatcggcatagtataatacgacaaggtgaggaactaaaccatggcc
aagttgaccagtgccgttccggtgctcaccgcgcgcgacgtcgccggagcggtcgagttctggaccgaccggctcggt
tctcccgggacttcgtggaggacgacttcgccggtgtggtccgggacgacgtgaccctgttcatcagcgcggtccagga
ccaggtggtgccggacaacaccctggcctgggtgtgggtgcgcggcctggacgagctgtacgccgagtggtcggaggtc
gtgtccacgaacttccgggacgcctccggccggccatgaccgagatcggcgagcagccgtggggcgggagttcgccc
tgcgcgacccggccggcaactgcgtgcacttcgtggccgaggagcaggactgacacgtgctacgagatttcgattccac
cgccgccttctatgaaaggttgggcttcggaatcgttttccgggacgccggctggatgatcctccagcgcgggatctc
atgctggagttcttcgcccaccccaacttgtttattgcagcttataatggttacaaataaagcaatagcatcacaaatt
tcacaaataaagcatttttttcactgcattctagttgtggtttgtccaaactcatcaatgtatcttatcatgtctgtat
accgtcgacctctagctagagcttggcgtaatcatggcatagctgtttcctgtgtgaaattgttatccgctcacaatt
ccacacaacatacgagccggaagcataaagtgtaaagcctggggtgcctaatgagtgagctaactcacattaattgcgt
tgcgctcactgcccgctttccagtcgggaaacctgtcgtgccagctgcattaatgaatcggccaacgcgcggggagagg
```

-continued

```
cggtttgcgtattgggcgctcttccgcttcctcgctcactgactcgctgcgctcggtcgttcggctgcggcgagcggta tcagctcactcaaaggcggtaatacggttatccacagaatcaggggataacgcaggaaagaacatgtgagcaaaaggcc agcaaaaggccaggaaccgtaaaaaggccgcgttgctggcgtttttccataggctccgcccccctgacgagcatcacaa aaatcgacgctcaagtcagaggtggcgaaacccgacaggactataaagataccaggcgtttccccctggaagctccctc gtgcgctctcctgttccgaccctgccgcttaccggatacctgtccgcctttctcccttcgggaagcgtggcgctttctc atagctcacgctgtaggtatctcagttcggtgtaggtcgttcgctccaagctgggctgtgtgcacgaaccccccgttca gcccgaccgctgcgccttatccggtaactatcgtcttgagtccaacccggtaagacacgacttatcgccactggcagca gccactggtaacaggattagcagagcgaggtatgtaggcggtgctacagagttcttgaagtggtggcctaactacggct acactagaagaacagtatttggtatctgcgctctgctgaagccagttaccttcggaaaaagagttggtagctcttgatc cggcaaacaaccaccgctggtagcggtggttttttttgtttgcaagcagcagattacgcgcagaaaaaaaggatctcaa gaagatcctttgatcttttctacggggtctgacgctcagtggaacgaaaactcacgttaagggattttggtcatgagat tatcaaaaaggatcttcacctagatccttttaaattaaaaatgaagttttaaatcaatctaaagtatatatgagtaaac ttggtctgacagttaccaatgcttaatcagtgaggcacctatctcagcgatctgtctatttcgttcatccatagttgcc tgactccccgtcgtgtagataactacgatacgggagggcttaccatctggccccagtgctgcaatgataccgcgagacc cacgctcaccggctccagatttatcagcaataaaccagccagccggaagggccgagcgcagaagtggtcctgcaacttt atccgcctccatccagtctattaattgttgccgggaagctagagtaagtagttcgccagttaatagtttgcgcaacgtt gttgccattgctacaggcatcgtggtgtcacgctcgtcgtttggtatggcttcattcagctccggttcccaacgatcaa ggcgagttacatgatccccatgttgtgcaaaaaagcggttagctccttcggtcctccgatcgttgtcagaagtaagtt ggccgcagtgttatcactcatggttatggcagcactgcataattctcttactgtcatgccatccgtaagatgcttttct gtgactggtgagtactcaaccaagtcattctgagaatagtgtatgcggcgaccgagttgctcttgcccggcgtcaatac gggataataccgcgccacatagcagaactttaaaagtgctcatcattggaaaacgttcttcgggggcgaaaactctcaag gatcttaccgctgttgagatccagttcgatgtaacccactcgtgcacccaactgatcttcagcatcttttactttcacc agcgtttctgggtgagcaaaaacaggaaggcaaaatgccgcaaaaaagggaataagggcgacacggaaatgttgaatac tcatactcttccttttcaatattattgaagcatttatcagggttattgtctcatgagcggatacatatttgaatgtat ttagaaaaataaacaaatagggggttccgcgcacatttccccgaaaagtgccacctgac.
```

NRK1-HEK293T cells were seeded onto 150 cm² plates at 20×10⁶ cells per plate. The next day, the cells were transfected with 15 μg FCIV-SST (SAM-TIR expression plasmid, SEQ ID NO: 9) using X-TREMEGENE™ 9 DNA Transfection Reagent (Roche product #06365787001). The cultures were supplemented with 1 mM NR at time of transfection to minimize toxicity from SAM-TIR overexpression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (cOmplete™ protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants (containing SARM1 SAM-TIR protein) were stored at −80° C. for later use in the in vitro SARM1 SAM-TIR NADase assay (see below). Protein concentration was determined by the Bicinchoninic (BCA) method and used to normalize lysate concentrations.

Compound Library

The NCI Diversity IV compound library and the Pharmacon 1600 compound library were screened for SARM1 SAM-TIR inhibitors. The stock concentration for each compound is 10 mM (in DMSO). The compounds were first diluted 10-fold to produce a 1 mM stock (in DMSO). This stock was further diluted 20-fold into 20% DMSO/80% water to produce 50 μM working stocks of each compound.

In Vitro SARM1 SAM-TIR NADase Assays and Inhibitor Screen

HPLC-Based Assay 1.

Reaction mixtures were prepared on ice by mixing SARM1 SAM-TIR cell lysate (0.14 μg total protein), compound stock (5 μM final concentration), and PBS (pH 7.4) to a final volume of 12 μl. NAD+ (5 μM final concentration) was then added for a final reaction volume of 20 μl. The mixture was incubated at 37° C. for 60 min; reaction was then stopped by addition of 180 μl of 0.55 M perchloric acid (HClO₄). The reactions were then placed on ice for 10 min, and the reaction plates were centrifuged for 10 min at 4,000 rpm (Sorvall ST 16R centrifuge). The supernatant (120 μl) was transferred to a new plate and 10 μl of 3M K₂CO₃ was added to neutralize the solution. Precipitated salts were removed by centrifugation 10 min at 4,000 rpm (Sorvall ST 16R centrifuge). The supernatant was transferred and analyzed by HPLC (Shimadzu Nexera X2) with KINETEX® (100×3 mm, 2.6 μm; PHENOMENEX®) column and metabolites were monitored with absorbance at 254 nm.

Results.

SARM1 SAM-TIR Lysate Cleaves NAD+.

Figure 4A:
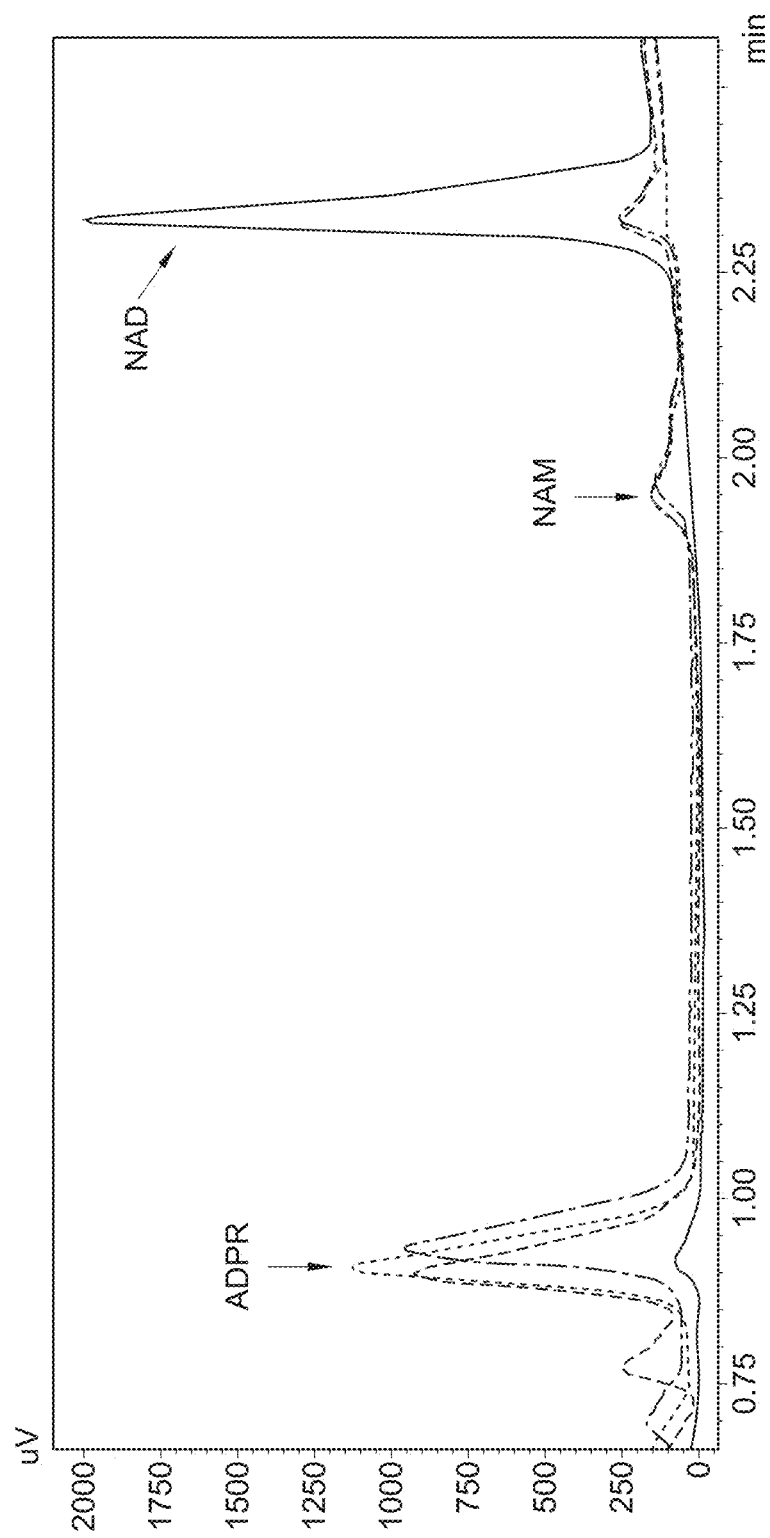
FIG. 4A-E illustrates cleavage of NAD+ by a cell lysate comprising SARM1 SAM-TIR.
Figure 4B:
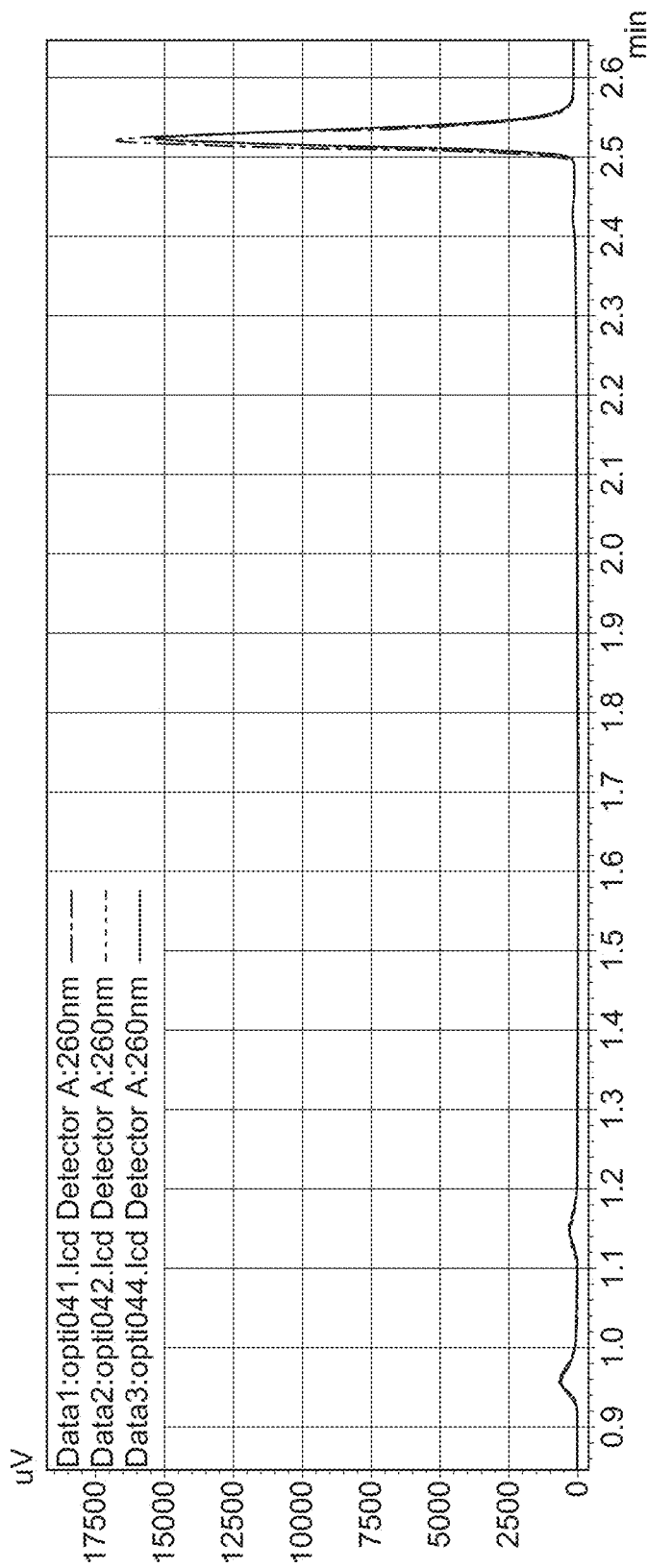

Using HPLC-based assay 1, the SARM1 SAM-TIR lysate cleaved NAD+ in a dose- and time-dependent manner (FIG. 4A, C, D), whereas control lysate prepared from non-transfected NRK1-HEK293T cells showed no NAD+ cleavage (FIG. 4B). Loss of NAD+ was accompanied by an increase in nicotinamide (Nam) and ADP ribose (ADPR), indicating that cleavage of the nicotinamide-ribosyl bond of NAD+ (FIG. 4A). SARM1 SAM-TIR lysate was incubated with NAD+ (5 μM) for indicated times. The NAD+ levels are shown in FIG. 4A (peak at 2.52 min in HPLC traces) were reduced and ADPR levels were increased (peak at 1.15 min) with time. Trace color: black—NAD alone; green—lysate; blue—on beads, green in eluate.

Figure 4C:
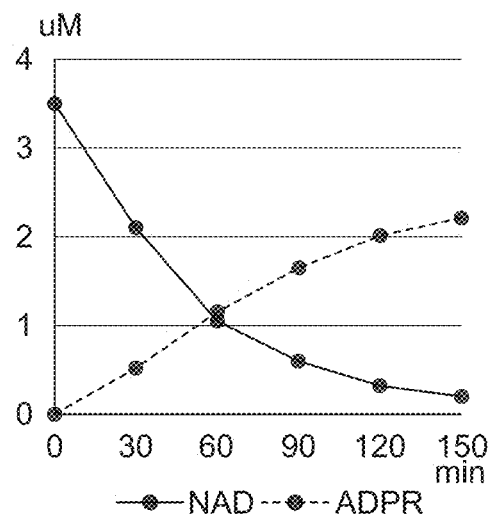
Figure 4D:
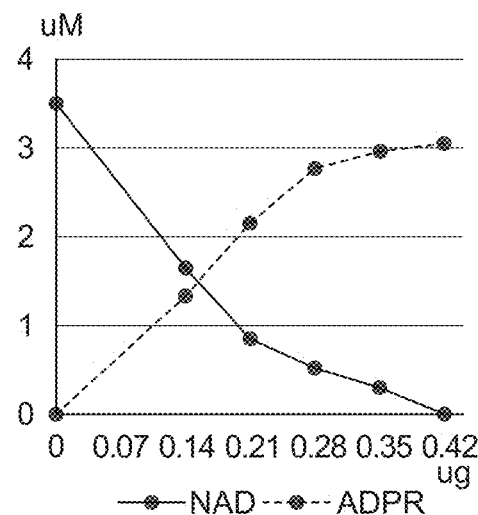
Figure 4E:
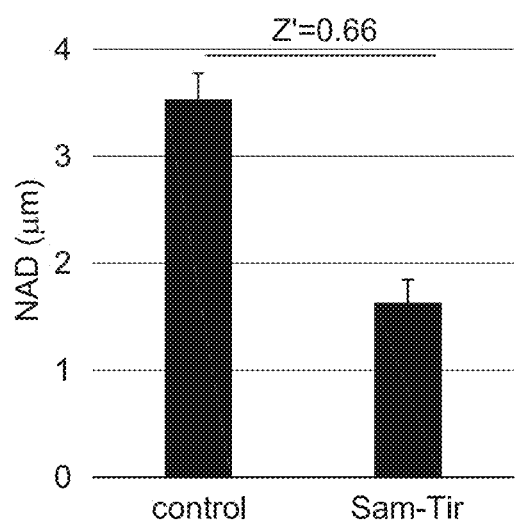

For FIG. 4A, the SARM1 Sam-TIR protein was purified by Strep Tag affinity methods. HEK-NRK1 lysate (100 ul) was incubated with 20 μL MagStrep (Strep-Tactin) type 3 XT beads suspension (IBA Lifesciences) for 30 min (in buffer W: 100 mM Tris/HCl, pH 8.0; 150 mM NaCl; 1 mM EDTA). The beads were then washed three times with buffer W, and bound proteins were eluted from MagStrep type 3 XT beads with 25 mM biotin in buffer W for 30 min. Supernatant containing the eluted protein can be used for NADase activity assay. Pierce protease inhibitors (ThermoFisher cat #88266) were added into all buffers. FIG. 4A shows HPLC traces for the starting substrate, NAD, and the cleavage products, ADPR and Nicotinamide (NAM), that are generated by active SARM1 TIR NADase. The black trace shows NAD without added enzyme. The red trace shows that SAM-TIR-containing lysate has potent NADase activity (NAD is lost and the products, ADPR and NAM, are generated). The Blue trace shows that the SAM-TIR enzyme can be purified on beads as described above and this enzyme is active (again, loss of NAD and generation of ADPR and NAM). Finally, the green trace shows that active SAM-TIR enzyme can be eluted from the beads and remains active (loss of NAD, generation of ADPR and NAM). FIG. 4B shows that control lysate didn't consume NAD+ after the same period of incubation. FIG. 4C shows quantitative values of NAD+ and ADPR of HPLC traces in FIG. 4A. FIG. 4D shows that cleavage of NAD+ by SARM1 SAM-TIR lysate is dose-dependent. The indicated amount of SARM1 SAM-TIR lysate was incubated with NAD+ (5 μM) at 37° C. for 60 min and conversion of NAD+ to ADPR was monitored. FIG. 4E shows that quantitation of NAD+/ADPR ratio after 60 min reaction using 0.14 μg protein of either control and SAM-TIR lysate. These results are consistent with the NADase activity observed using TIR Assay (see FIG. 8).

In summary, the present Example demonstrates that a lysate containing the SARM1-TIR domain contains NADase activity.

Identification and/or Characterization of SARM1 SAM-TIR NADase Inhibitors.

Figure 5A:
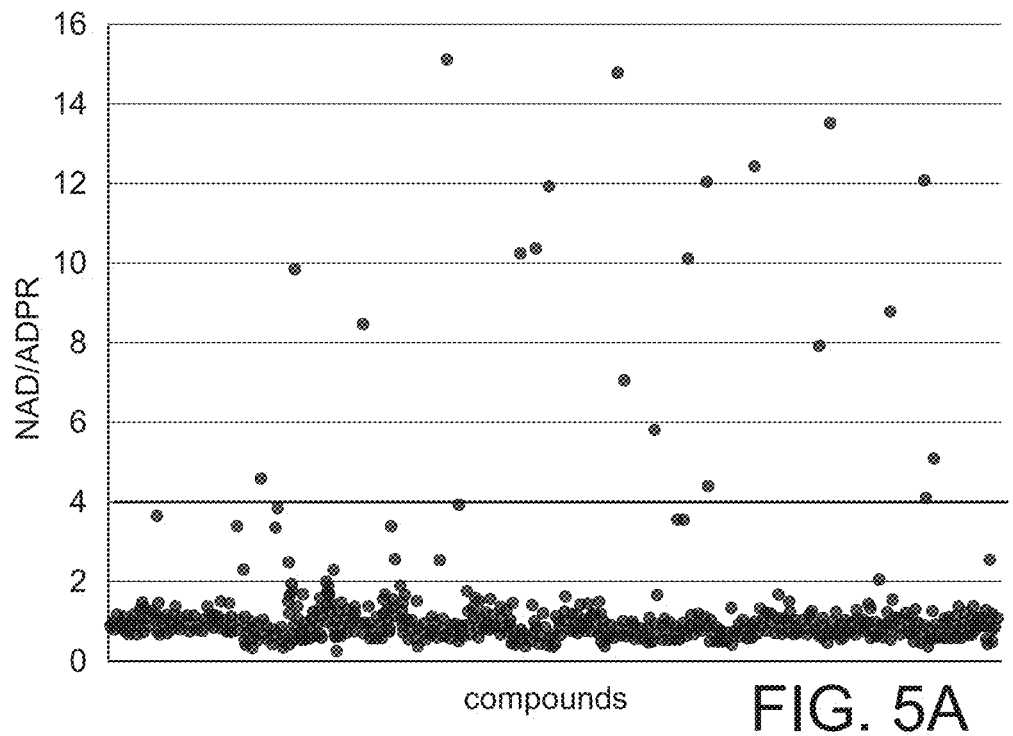
FIG. 5A-B illustrates a screen of candidate SAM-TIR NADase inhibitors from the NCI diversity IV compound library.
Figure 5B:
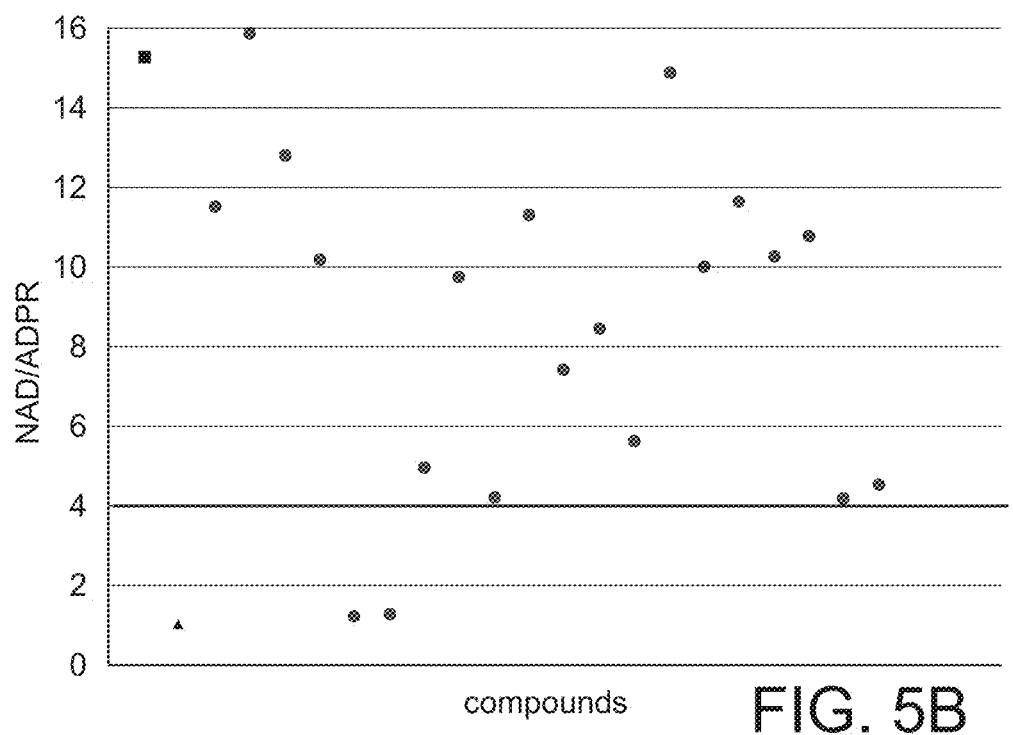

To identify inhibitors of SARM1 NADase activity, the levels of NAD+ and the enzymatic cleavage product ADPR in the reactions were quantified by HPLC. From these values, the NAD+/ADPR ratio for each compound was calculated and the ratio used as a measure of NAD+ cleavage activity (Note: there is a small residual but detectable ADPR signal in control samples derived from the HEK293 lysate). This ratio was compared to the ratio generated in the absence of compound inhibitors. A significant reduction of NADase activity (defined as NAD+/ADPR ratio>4) was used to identify compounds that inhibited SAM-TIR catalyzed NAD+ cleavage (FIG. 5A-B). FIG. 5A illustrates a primary screen of all 1600 compounds from the library (5 μM compound with 5 μM NAD+). In FIG. 5B, the 20 positive hits (NAD+/ADPR>4 from the top panel were re-tested. Eighteen of the 20 original 'positive hits' were again identified as inhibitors in the secondary screen (controls: square, no reaction time; triangle: DMSO control).

Identification and Characterization of Compounds that Inhibit SARM1 SAM-TIR NADase Activity The NAD+/ADPR ratio was used to determine the NAD+ cleavage activity of the SARM1 SAM-TIR lysate using the HPLC based assay 1. It will be appreciated that any precise, quantitative method of measuring NAD+ levels could be used for the detection of SARM1 NADase activity. An NAD+/ADPR ratio=~1 was established as a baseline control (without inhibitor). The assay was robust (Z'=0.537, control lysate (n=14) NAD+/ADPR=19.52±2.25; SAM-TIR lysate (n=14) NAD+/ADPR=1.186±0.607 (mean±SD). In the control condition, a small amount of ADPR is detected by HPLC) (FIG. 4A-B). An empirically generated (NAD+/ADPR) cutoff value of 4:1 was used, where NAD+/ADPR>4 represents significant suppression of SARM1 SAM-TIR lysate NADase activity.

Figure 6A:
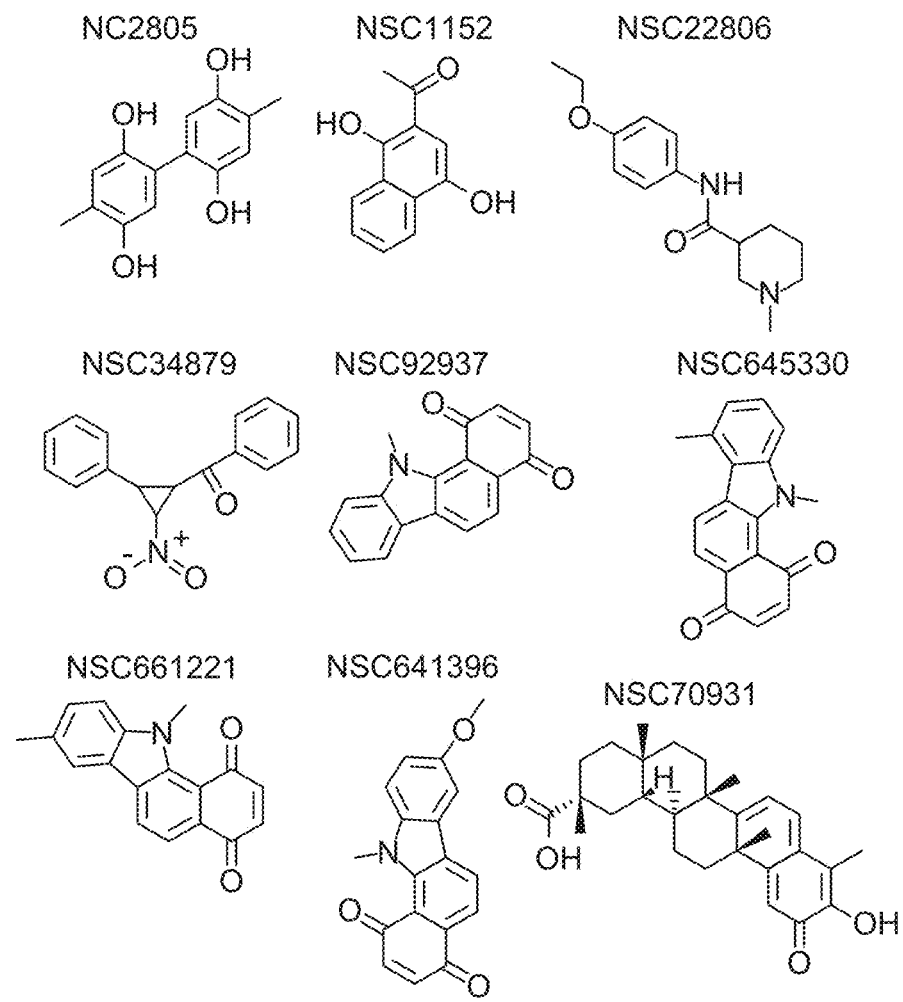

Twenty compounds out of 1600 from the NCI Diversity IV compound library were identified as inhibitors in the primary screen (FIG. 5A). Eighteen of these were identified as positive 'hits' in a secondary screen, with 10 of them showing robust inhibition of SARM1 SAM-TIR activity (i.e., NAD+/ADPR>10 (FIG. 5B; FIG. 6A-C).

Figure 7A:
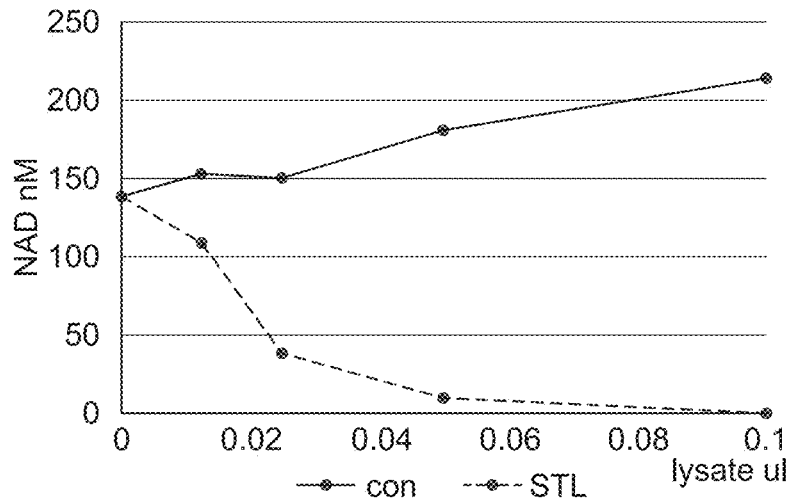
FIG. 7A-D illustrates an NAD+ cycling assay as an additional screening assay for SAM-TIR NADase inhibitors.
Figure 7B:
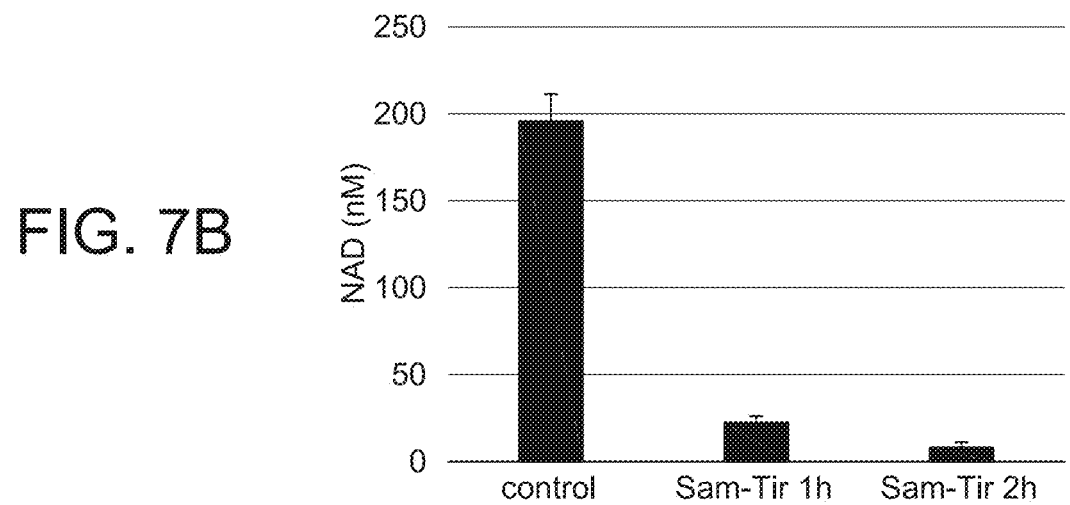
Figure 7C:
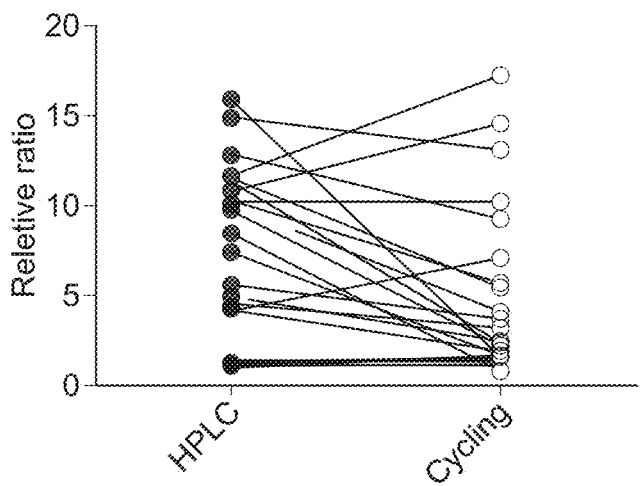
Figure 7D:
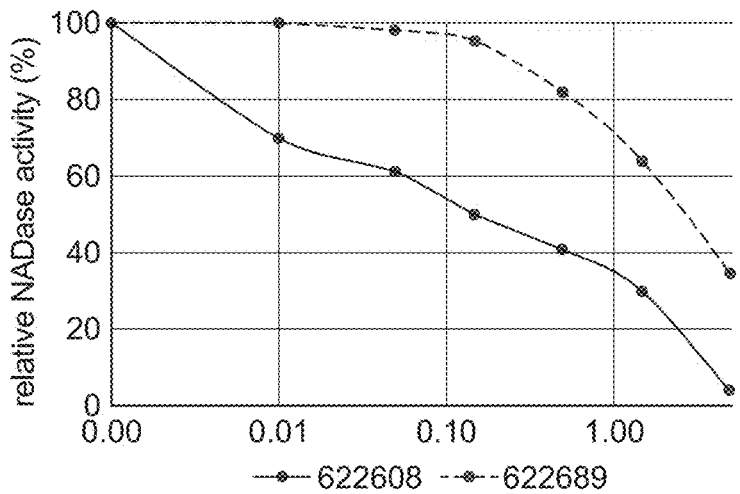

Inhibitors identified in the initial screen were then tested in the NAD+ Glo assay (see section infra), which employ an enzymatic cycling reaction to determine NAD+ concentration. The assay itself is highly reproducible (FIG. 7A-B). FIG. 7A illustrates SAM-TIR lysate (STL) but not control (con) lysate decreased NAD+ determined by NAD+ Glo assay. The elevated NAD+ levels in high dose lysate conditions are mostly likely derived from lysate itself. FIG. 7B illustrates that the assay is very robust (Z'=0.66 control 2 h reaction time vs SAM-TIR 1 h reaction time; Z'=0.71 control 2 h reaction time vs SAM-TIR 2 h reaction time). Control 2 h NAD+=196.20±15.66 nM; SAM-TIR 1 h NAD+=22.48±3.98 nM; SAM-TIR 2 h NAD+=8.18±2.79 nM. Most hits identified in the initial HPLC assay (14/18) showed significant inhibition of SAM-TIR NADase activity in NAD+-Glo assay (FIG. 7C). Cycling assay is highly correlated with HPLC assay. 14 out of 18 hits from HPLC also blocked NADase activity significantly (2 fold increase of luminescence intensity). Relative ratio for HPLC assay 1 represents the NAD+/ADPR ratio, while for the cycling assay, it represents the ratio of $IC_{50}\approx150$ nM (FIG. 7D). Two compounds showed the best inhibition in NAD+ Glo assay. $IC_{50}$ for NSC622608≈150 nM.

Luminescence-based assay. This assay can complement the results obtained by HPLC, and can permit a higher throughput of compound library screening than is possible with HPLC methods. This assay is an adaptation of the NAD+/NADH-GLO™ assay (Promega G9071, Promega Corporation, Madison, WI). In this assay, NAD+ cycling enzymes convert NAD+ into NADH. In the presence of NADH, the reductase enzymatically converts a pro-luciferin reductase substrate into luciferin. Luciferin is detected using ULTRA-GLO™ rLuciferase, and the chemiluminescence intensity is proportional to the amount of NAD+ and NADH in the sample. Under the present assay conditions, the amount of NAD+ and NADH present in the lysate is undetectable with this assay, precluding any endogenous contribution to the final NAD+ detected. The assay was set up as follows: 2 μl candidate inhibitor (final concentration 1

µM, 2% DMSO), 0.07 µg lysate (2 µl), and 2 µl of 400 nM NAD+. The reaction was incubated at 37° C. for 60 min, then 6 µl NAD+/NADH-GLO™ detection reagent was added. After 30 min at room temperature, the luminescent signals were quantified using a CYTATION™ 5 imaging reader (BIOTEK®). The SARM1 SAM-TIR lysate catalyzed a dose-dependent depletion of NAD+, whereas NAD+ levels did not decline when reactions were performed with lysate prepared from control NRK1-HEK293T cells (FIG. 7A-D).

Example 2

The present Example describes a SARM1 TIR-based Assay. This assay is similar to the assay described in Example 1, but allows for the identification and/or characterization of compounds that directly interact with the TIR domain, whereas the assay described in Example 1 can also identify compounds that disrupt SAM domain interactions. This assay makes use of the bacterial expression of a tagged version of the SARM1 TIR fragment that can be affinity purified. Displaying this artificial SARM1 TIR domain on a solid surface (i.e. affinity beads) generates an active NAD+ cleavage enzyme.

Materials and Methods

```
Tagged proteins included the following:
StrepTag-humanSARM1-TIR-6xHisTag
                                 (SEQ ID NO: 10)
MSAWSHPQFEKGGGSGGGSGGSAWSHPQFEKGGGSSGGGASTPDVFISYR

RNSGSQLASLLKVHLQLHGFSVFIDVEKLEAGKFEDKLIQSVMGARNFVL

VLSPGALDKCMQDHDCKDWVHKEIVTALSCGKNIVPIIDGFEWPEPQVLP

EDMQAVLTFNGIKWSHEYQEATIEKIIRFLQGRSSRDSSAGSDTSLEGAA

PMGPTHHHHHH

StrepTag-mouseSARM1-TIR-6xHisTag
                                 (SEQ ID NO: 11)
MSAWSHPQFEKGGGSGGGSGGSAWSHPQFEKGGGSSGGGASTPDVFISYR

RNSGSQLASLLKVHLQLHGFSVFIDVEKLEAGKFEDKLIQSVIAARNFVL

VLSAGALDKCMQDHDCKDWVHKEIVTALSCGKNIVPIIDGFEWPEPQALP

EDMQAVLTFNGIKWSHEYQEATIEKIIRFLQGRPSQDSSAGSDTSLEGAT

PMGLPHHHHHH

StrepTag-zebrafishSARM1-TIR-6xHisTag
                                 (SEQ ID NO: 12)
MSAWSHPQFEKGGGSGGGSGGSAWSHPQFEKGGGSSGGGASPDVFISYRR

TTGSQLASLLKVHLQLRGFSVFIDVEKLEAGRFEEKLITSVQRARNFILV

LSANALDKCMGDVAMKDWVHKEIVTALNGKKNIVPVTDNFVWPDPTSLPE

DMSTILKFNGIKWSHEYQEATIEKILRFLEGCPSQEKPDGAKTDKKEPQK

KHHHHHH
```

Bacterial Protein Expression and Tandem Affinity Purification (TAP).

The TIR domain of SARM1 was tagged with a tandem STREP-TAG® at the N-terminus, and a polyhistidine tag at the C-terminus, and was cloned into a pET30a+ plasmid. The construct was then transformed into SHuffle® T7 Express Competent E. coli (New England BioLabs, Ipswich, MA) and single colonies were grown overnight. The next day, cultures were diluted in LB media, grown at 30° C. until they reached A600=0.4-0.8, when IPTG (0.5 mM final concentration) was added. The bacteria were grown for an additional 4 h, pelleted by centrifugation, washed with PBS and stored at −80° C. For protein purification, the frozen bacterial pellet was thawed on ice, resuspended in binding buffer (without protease inhibitors) and incubated with 100 µg/mL lysozyme for 15 min on ice. Protease inhibitor cocktail was then added and the cells were lysed by sonication.

The SARM1 TIR protein was first purified by Strep Tag affinity methods where bacterial lysates were incubated with 204 MagStrep (STREP-TACTIN®, IBA GmBH, Gottingen Germany) type 3 XT beads suspension (IBA Lifesciences) for 30 min. The beads were then washed three times with binding buffer, and bound proteins were eluted from MagStrep type 3 XT beads with 22.5 mM biotin for 25 min. Supernatant containing the eluted protein was separated from MagStrep beads, and incubated with 10 µL Co2+ DYNABEAD® (ThermoFisher Scientific, Waltham, MA) suspension for 30 min to bind SARM1-TIR proteins via the His tag. The beads were then washed at least two times with binding buffer and resuspended in 100 µL of binding buffer for NADase assay.

Figure 8:
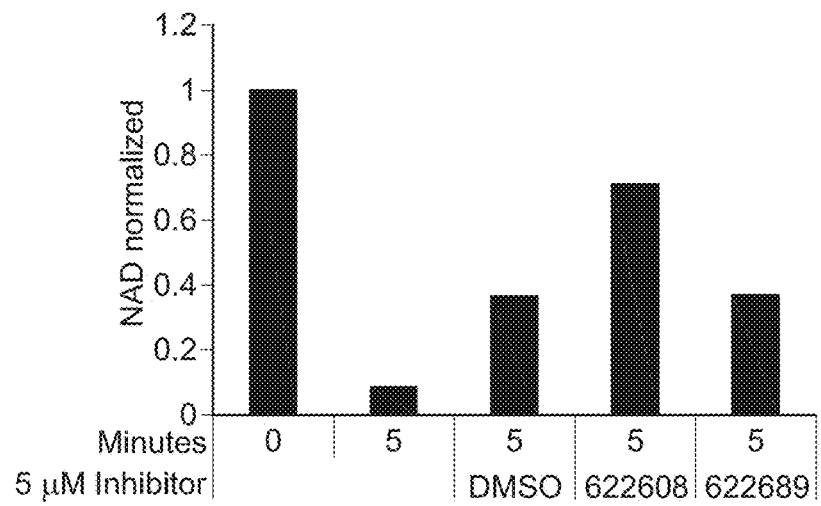
FIG. 8 illustrates in vitro NAD+ cleavage by SARM1 TIR protein expressed and purified from bacteria.

Ten microliters of purified SARM1-TIR laden beads were incubated with 5 µM NAD+ in reaction buffer (92.4 mM NaCl and 0.64×PBS). Reactions were carried out at 25° C. for the indicated amount of time and stopped by addition of 1M of perchloric acid ($HClO_4$) and placing the tube on ice. NAD+ metabolites were extracted using $HClO_4/K_2CO_3$ method and quantified by HPLC (see metabolite measurement below). For LC-MS/MS analysis, the extraction was performed using 50% methanol in distilled water and chloroform (see LC-MS/MS metabolite measurement below). FIG. 8 shows that some compounds identified as inhibitors in the SARM1 SAM-TIR assay also inhibit NADase activity of purified SARM1 TIR in the in vitro assay. Select potent inhibitors (622608, 622689) identified from SARM1 SAM-TIR lysate screen were added to the reaction at 5 µM. NAD normalized to control at 0 min.

HPLC Metabolite Measurement.

Metabolites were isolated from enzyme reaction mixture by extracting with 1M $HClO_4$, then neutralized with 3M $K_2CO_3$, and followed by separation by centrifugation. The supernatant (90 µL) containing the extracted metabolites was mixed with 0.5M Potassium Phosphate buffer (10 µL) and metabolites were analyzed by HPLC (Nexera X2) with KINETEX® (100×3 mm, 2.6 µm; PHENOMENEX®) column and metabolites are monitored with absorbance at 254 nm. Internal standards for NAD+, Nicotinamide (Nam), ADP Ribose (ADPR) were used to generate standard curves for quantification of the respective compounds. The levels for each compound in each experimental sample was normalized to the 0 min time point that was analyzed concurrently.

LC-MS/MS Metabolite Measurement.

Samples were prepared by mixing the reactions with 50% methanol in distilled water. The samples were placed on ice, centrifuged, soluble metabolites in the supernatant were extracted with chloroform, and the aqueous phase was lyophilized and stored at −20° C. until LC-MS/MS analysis. For LC-MS/MS, the metabolite samples were reconstituted with 5 mM ammonium formate, centrifuged 12,000×g for 10 min, and the cleared supernatant was applied to the LC-MS/MS for metabolite identification and quantification. Liquid chromatography was performed by HPLC system (1290; Agilent) with SYNERGI™ Fusion-RP (4.6×150 mm, 4 µm; PHENOMENEX®, Phenomenex, Torance, CA) column. Samples (10 µl) were injected at a flow rate of 0.55 ml/min with 5 mM ammonium formate for mobile phase A and 100% methanol for mobile phase B and metabolites were eluted with gradients of 0-7 min, 0-70% B; 7-8 min, 70% B; 9-12 min, 0% B. Metabolites were detected with Triple Quad mass spectrometer (6460 MassHunter; AGILENT®) under positive ESI multiple reaction monitoring (NAD+: 664>428 with 160V (fragmentation), 22V (collision), 7V (post-acceleration)). Metabolites were quantified by MassHunter quantitative analysis tool (AGILENT®) with standard curves. Standard curves for each compound were generated by analyzing NAD+, ADPR, and Nam reconstituted in 5 mM ammonium formate. The levels for each compound in each experimental sample were normalized to the 0 min time point that was analyzed concurrently. Sample identity was blinded to individual performing experiment.

Example 3

This example illustrates an NAD flux assay which allows for the identification and/or characterization of compounds that inhibit SARM1-mediated NAD consumption in axons of cultured neurons. This assay utilizes the full-length SARM1 protein activated by a neuronal injury in neurons. This assay measures the injury-activated SARM1-dependent degradation of NAD+ in axons. This method allows for the independent assessment of NAD+ synthesis and NAD+ consumption.

DRG Neuronal Culture.

Mouse dorsal root ganglion (DRG) were dissected from embryonic days 13.5 CD1 mouse embryo (~50 ganglion per embryo) and incubated with 0.05% Trypsin solution containing 0.02% EDTA (Gibco) at 37° C. for 15 min. Then cell suspensions are triturated by gentle pipetting and washed 3 times with DRG growth medium (Neurobasal medium (Gibco) containing 2% B27 (Invitrogen), 100 ng/ml 2.5S NGF (Harlan Bioproducts), 1 µM uridine (Sigma), 1 µM 5-fluoro-2'-deoxyuridine (Sigma), penicillin, and streptomycin). Cells were suspended in DRG growth medium at a ratio of 100 µl medium/50 DRGs. The cell density of these suspensions was ~7×106 cells/ml. Cell suspension (10 µl) was placed in the center of the well using 24-well tissue culture plates (Corning) coated with poly-D-Lysine (0.1 mg/ml; Sigma) and laminin (3 µg/ml; Invitrogen). Cells were allowed to adhere in humidified tissue culture incubator (5% CO2) for 15 min and then DRG growth medium was gently added (500 µl).

Axonal Metabolite Collection.

At DIV6, neuronal cell bodies and axons were separated using a microsurgical blade under the microscope at 0 (for control NAD+ consumption) or 4 (for axotomized axonal NAD+ consumption) hours prior to metabolite collection. Then the DRG cultures were placed on ice, culture medium was replaced with ice-cold 0.9% NaCl solution (0.5 µl), and the DRG cell bodies were removed using a pipet. The 0.9% NaCl solution was removed, and the axonal metabolites were extracted by incubation with ice-cold 1:1 mixture of MeOH and water (150 µl per well) on ice for 10 min. The metabolite containing solutions were transferred into test tubes and extracted twice with chloroform (100 µl per sample). The aqueous phase (1200 was lyophilized and reconstituted with 50 µl of 5 mM ammonium formate and cleared supernatants after centrifugation at 12,000×g for 10 min were transferred to sample vials and measured.

NAD+ Measurement Using LC-MS/MS.

Serial dilutions of NAD+ (25 µM to 320 pM, Sigma) in 5 mM ammonium formate were used for calibration. Liquid chromatography was performed with 10 µl of each sample injected at a flow rate of 0.55 ml/min with 5 mM ammonium formate for mobile phase A and 100% methanol for mobile phase B (HPLC:1290; Agilent with Synergi Fusion-RP (4.6×150 mm, 4 µm; Phenomenex)). Metabolites were eluted with gradients of 0-7 min, 0-70% B; 7-8 min, 70% B; 9-12 min, 0% B. The metabolites were detected with a Triple Quad mass spectrometer (6460 MassHunter; Agilent) under positive ESI multiple reaction monitoring (MRM) (D4-NAD+:668>428, D3-NAD+:667>428, NAD+:664>428 with 160V (fragmentation), 22V (collision), 7V (post-acceleration)). Metabolites were quantified by MassHunter quantitative analysis tool (Agilent) with standard curves.

NAD+ Consumption Measurement.

Figure 9:
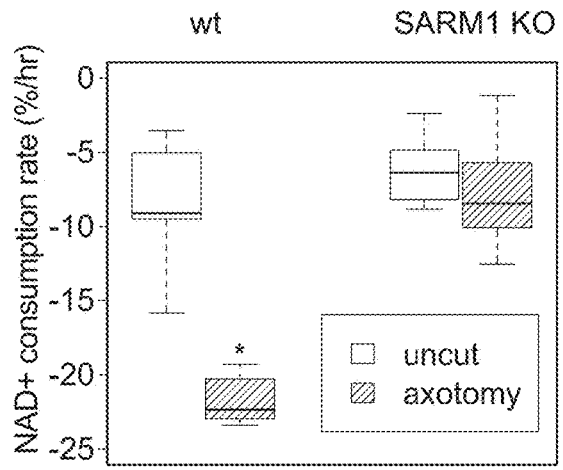
FIG. 9 illustrates that NAD+ consumption rate is increased after axotomy in wt axons.

For NAD+ consumption measurements, DRG neurons were incubated with D4-Nam (300 µM: 2, 3, 4, 5 deuterium Nam; C/D/N Isotopes Inc., D-3457) for 4 hours and axonal metabolites were collected as described above. For NAD+ flux measurements after axonal injury, D4-Nam was added at the same time as axotomy. Labeled (heavy) or non-labeled (light) NAD+ was quantified by LC-MS/MS. For heavy-labeled NAD+, D3-NAD+ as well as D4-NAD+ was observed. This is due to the replacement of deuterium at C4 position with non-labeled proton during NAD+-NADH cycling. The values of D3-NAD+ and D4-NAD+ were added and used this combined value as the amount of heavy NAD+. The net rate of NAD+ consumption were calculated by % decrease of light NAD+ over total NAD+ (sum of heavy and light NAD+) at 4 hours after D4-Nam application and expressed %/hr. Axonal NAD+ consumption was −8.5±3.8%/hr without axotomy and increased to −21.7±1.6%/hr in axotomized axons. This acceleration of NAD+ consumption is completely blocked in SARM1 KO axons (−6.3±2.4%/hr uninjured vs. −7.9±3.7%/hr after axotomy) and can be used for a read out of SARM1 activation after injury (FIG. 9). FIG. 9 shows that the depletion of SARM1 completely blocked the increase of NAD+ consumption. Thus the increased NAD+ consumption can be used as a read out of SARM1 activation in injured neurons. one-way ANOVA F(3,32)=50.6, p=3×10-12. * p<0.005 denotes significant difference from control uncut with Holm-Bonferroni multiple comparison (n=9).

NAD+ Consumption Assay for Assessing the Efficacy of SARM1 Inhibitors in Neurons.

Selected chemical compounds (final concentration 5 µM at 30 min prior to D4-Nam addition) as well as 300 µM D4-Nam were added to DRG culture medium and axons were immediately transected (3 wells) or keep intact (3 wells). Axonal metabolites were collected at 4 hours post D4-Nam addition and metabolites can be analyzed as described above. NAD+ consumption rate before and after axotomy can be calculated. Shown here is a demonstration that in the absence of SARM1 (SARM1 knockout, KO), there is no axotomy-induced increase in NAD+ consumption rate (FIG. 9). Thus the inhibitory effects of compounds on SARM1 activation can be assessed by a decrease in the post-injury NAD+ consumption rate. This assay tests the efficacy of SARM1 inhibitors in axons of cultured neurons.

Example 4

This example illustrates an in vitro axon degeneration assay and application of this assay to characterize compounds. In this example, this assay was used to test whether inhibitors of SARM1 NADase activity can inhibit axon degeneration that rapidly follows axonal NAD+ loss after injury.

Axonal degeneration was induced by axotomy or by the addition of vincristine (0.04 µM) using DRG drop cultures in 96 well at DIV 6. Axotomy was performed by separating cell bodies and axons using a micro surgical blade under the microscope. Bright field images of axons (6 fields per well) were taken at 0-72 hours after axotomy using a high content imager (Operetta; Perkin-Elmer) with a 20× objective. Axon degeneration was quantified using degeneration index (DI) calculated using ImageJ (NIH, Sasaki et al., 2009, J. Neurosci., 19(17): 5525-5535). The average DI from 6 fields per well was obtained and averaged for each independent well. The DI was calculated from axon images from the same fields before (0 hour) and after (9-72 hours) axotomy. Compounds (in FIG. 10A) with a significant blockade of SARM1 NADase activity from the assays in Examples 1-3 were tested for their effects on axon degeneration in cultures of DRG neurons as described above. All 18 positive hits from HPLC screen were tested (at 5 µM) for their ability to inhibit axon degeneration. The candidate compounds are added to the culture medium at the concentration of 0.05 to 5 µM 30 min before axotomy. Axon degeneration was monitored by imaging axons before injury, and various time points after axotomy.

Results

Figure 10A:
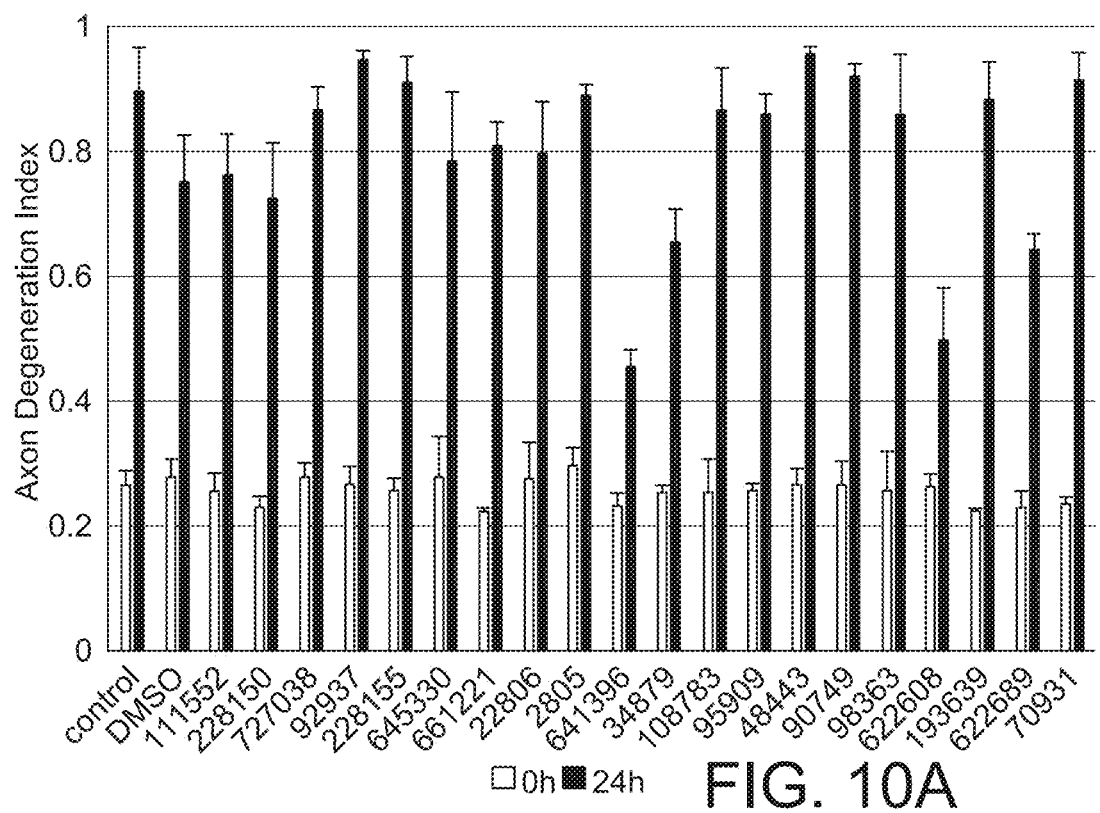
Figure 10B:
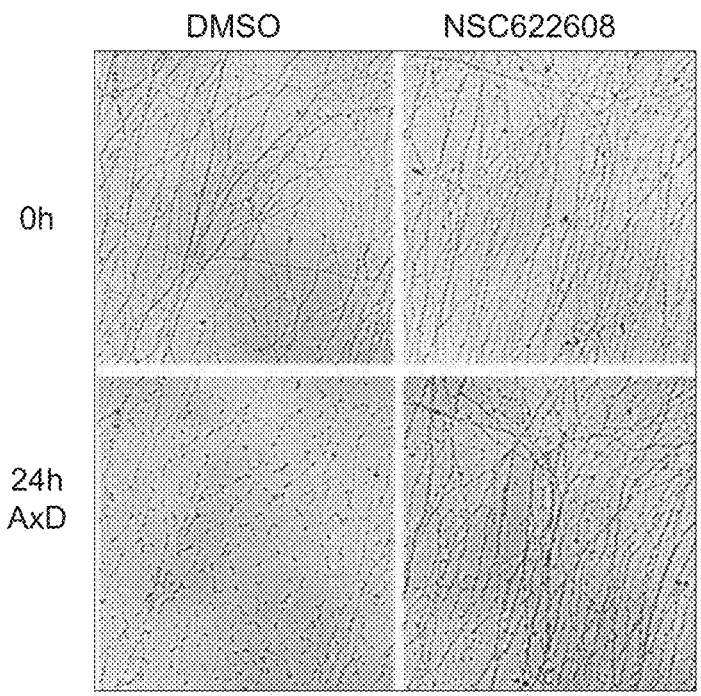

FIG. 10A illustrates the axon degeneration indices before injury and 24 h after injury (axotomy). A higher degeneration index indicates more axon degeneration (i.e. less inhibition). FIG. 10B illustrates a representative compound showing significant protection (NSC622608). The representative images before and after axotomy are shown. FIG. 10C illustrates dose dependent inhibition of axon degeneration by compound NSC622608.

Thus, the present Example demonstrates successful development of an axon degeneration assay to characterize compounds. Moreover, the present Example demonstrates that a compound identified in the present disclosure as an inhibitor of SARM1-TIR NADase activity also inhibits axon degeneration in a dose-dependent manner.

Example 5

The present Example demonstrates that a SARM1-TIR complex purified from mammalian cells cleaves NAD+.

This example also illustrates application of an NAD+ depletion assay.

Figure 2C:
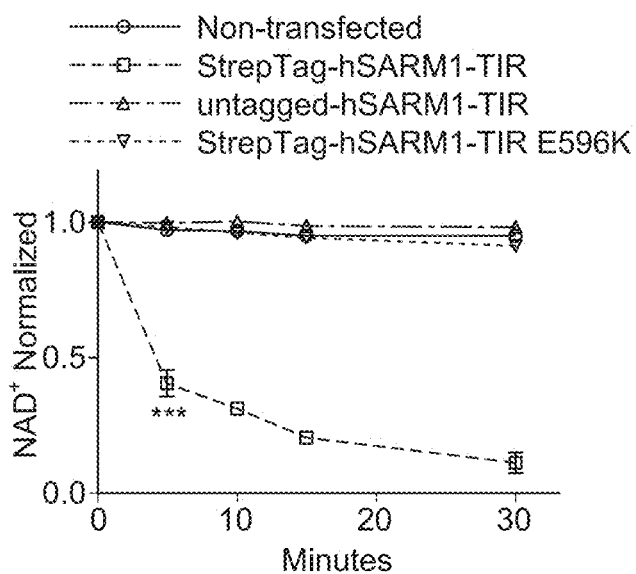

The human SARM1-TIR domain was engineered with a tandem StrepTag II at the N-terminus, a Venus fluorescent tag at the C-terminus, and expressed it transiently in NRK1-HEK293T cells supplemented with NR. Cell lysates were subsequently prepared by lysing cells under native conditions by sonication, and the recombinant SARM1-TIR protein complexes were affinity purified using MagStrep (Strep-Tactin) magnetic beads. Beads with SARM1-TIR complexes were incubated with NAD+ (5 µM) for up to 30 minutes, metabolites were extracted, and then NAD+ levels were measured using HPLC (FIG. 2B). NAD+ levels dropped precipitously, within 5 minutes, when beads loaded with SARM1-TIR complexes were tested (FIG. 2C). In contrast, no decrease in NAD+ was observed if beads exposed to lysates were prepared from either non-transfected NRK1-HEK293T cells or from NRK1-HEK293T cells expressing SARM1-TIR lacking the StrepTag II (FIG. 2C). A TIR domain mutant [SARM1(E596K)] that is incapable of supporting injury-induced axonal NAD+ depletion and degeneration was also tested. Magnetic beads loaded with complexes assembled on this SARM1(E596K) mutant failed to degrade NAD+ in this in vitro assay (FIG. 2C).

The substrate specificity of the SARM1-TIR in vitro NADase reaction was examined.

Figure 2D:
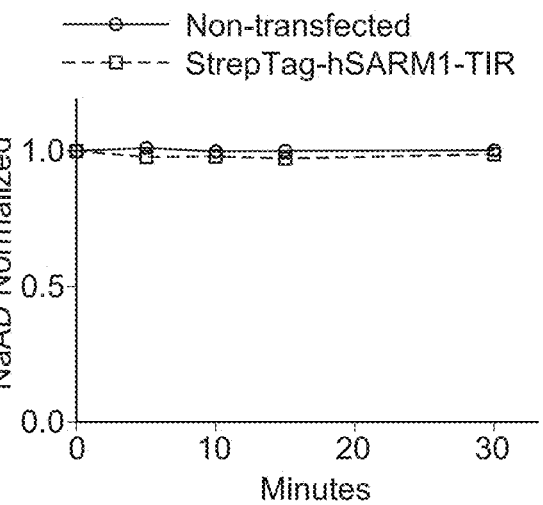

Gerdts, J., et al. (Science, 2015, 348, 453-457) previously showed that Nicotinic Acid Adenine Dinucleotide (NaAD), a closely related analog of NAD+, was not cleaved after SARM1 activation. Using this in vitro assay, it was found that wild type SARM1-TIR complexes do not degrade NaAD (FIG. 2D). Together, these results show that the purified SARM1-TIR complex actively degrades NAD+ in a manner consistent with previous characterization of the axon degeneration process.

Figure 2E:
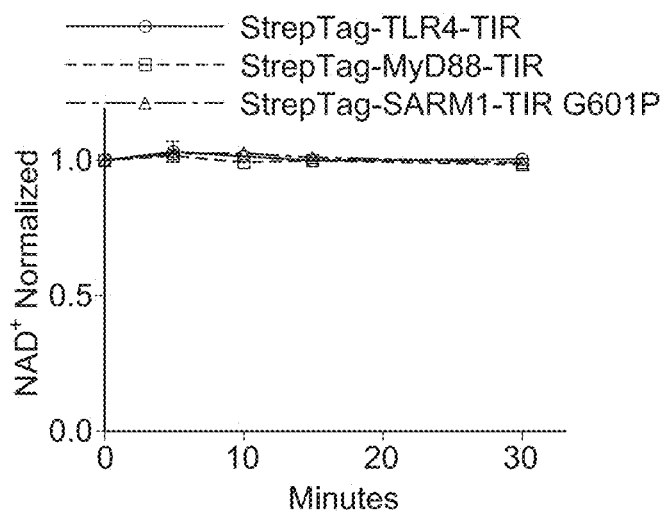
Figure 2F:
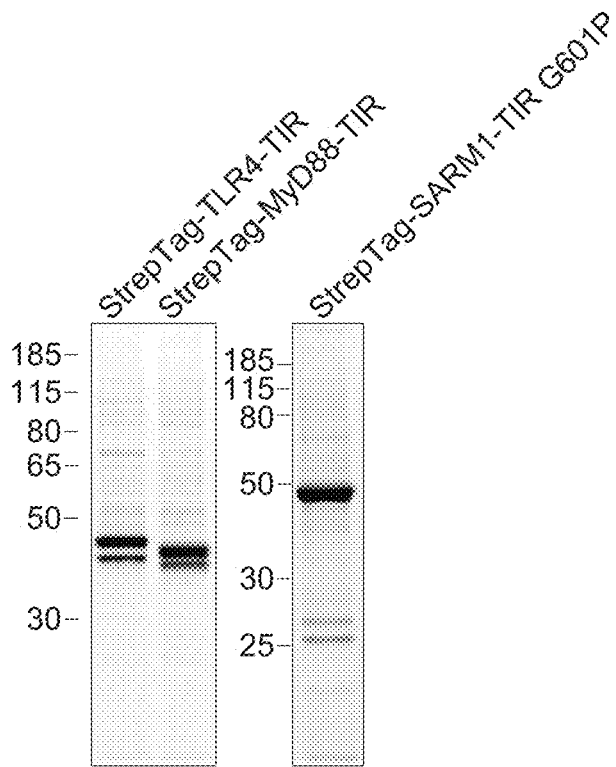

Whether the enzymatic activity was unique to complexes associated with the SARM1-TIR domain or whether TIR domains from other proteins could also assemble complexes that exhibit NADase activity was then explored. The TIR domains of TLR4, a Toll-like receptor, and MyD88, another member of the TIR adaptor family, were expressed and purified from NRK1-HEK293T cells and tested them in the in vitro NAD+ depletion assay. Both TLR4 and MyD88 TIR containing complexes showed no NADase activity (FIGS. 2E and 2F). These results support the previously reported unique roles of SARM1 among TIR adaptor proteins (Gerdts, J, et al., Science, 2015, 348, 453-457; O'Neill, L. A., et al., Nat. Rev. Immunol., 2013, 13, 453-460, Summers, D. W., et al., Proc. Natl. Acad. Sci. USA., 2016, 113, E6271-E6280) in promoting axonal degeneration and neuronal NAD+ depletion.

Example 6

The present Example demonstrates that NAD+ cleavage activity observed in other experiments described herein is not due to other proteins that co-purify with SARM1-TIR and that therefore the SARM1-TIR domain possesses intrinsic NAD+ cleavage activity. Moreover, the present Example describes characterizations of this NAD+ cleavage activity and that the SARM1-TIR enzymatic reaction comprises both cyclase and glycohydrolase activities.

Figure 11C:
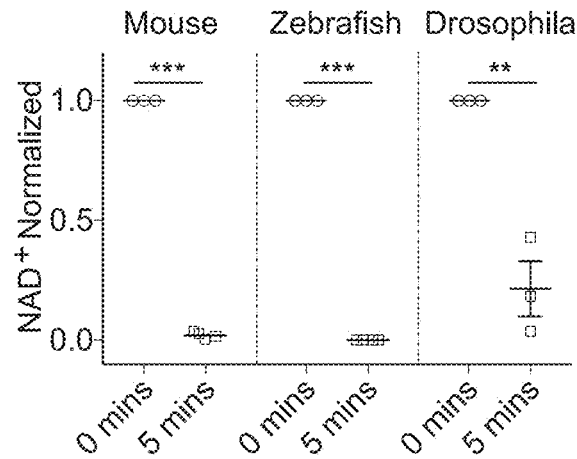
Figure 11D:
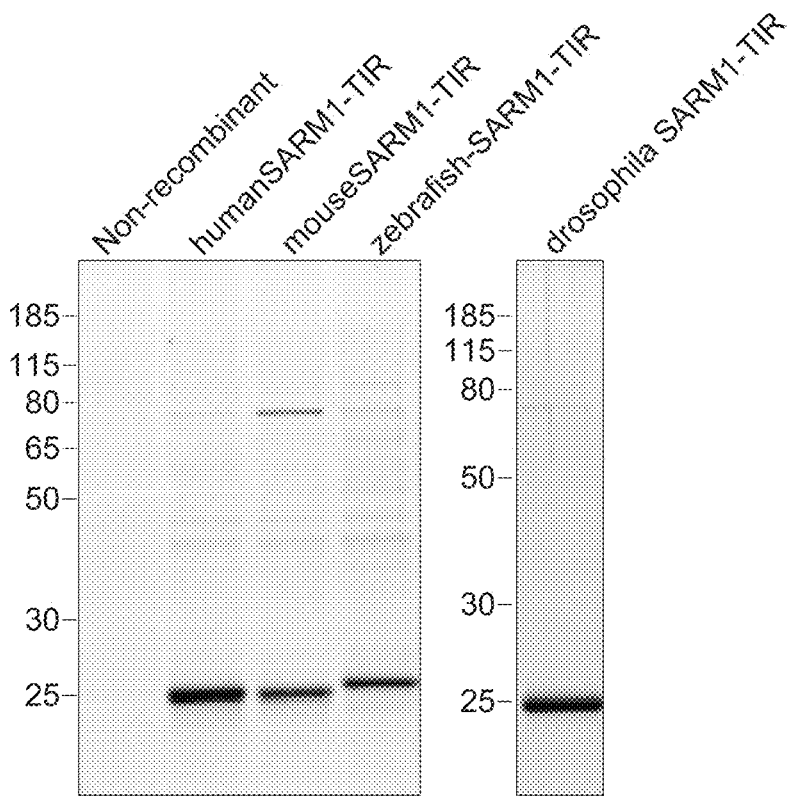
Figure 11E:
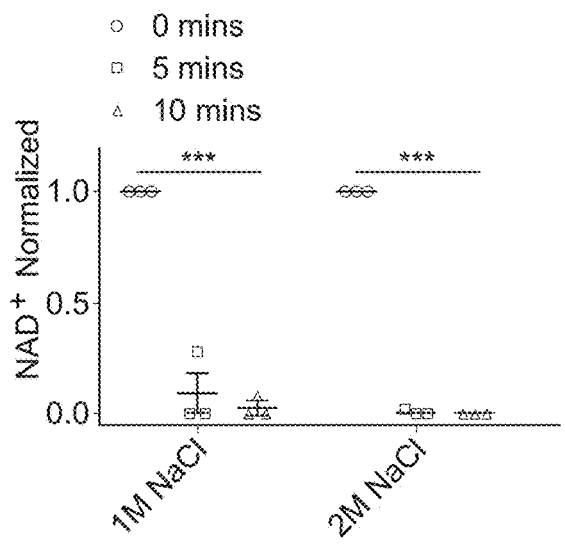
Figure 11F:
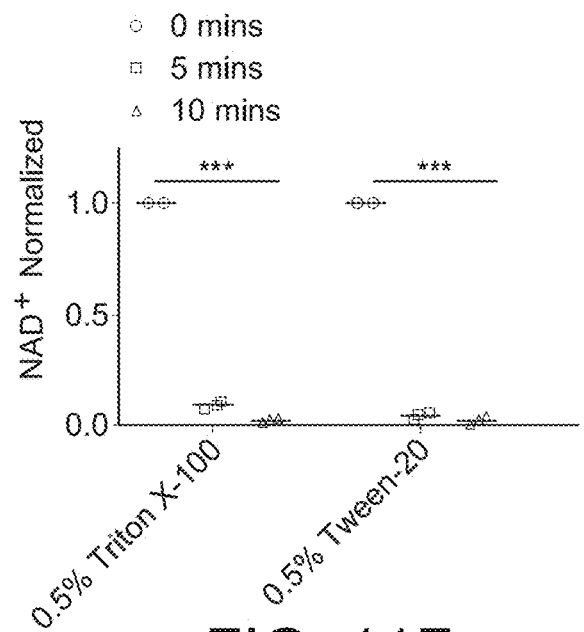

Human SARM1-TIR was expressed in E. coli so that proteins with NADase activity would not be co-purified. SARM1-TIR expression in E. coli was induced by IPTG addition, endogenous metabolites were extracted, and NAD+ levels were assessed by HPLC. Bacteria producing wild type SARM1-TIR had remarkably low (almost undetectable) levels of endogenous NAD+ within 60 minutes after IPTG addition when compared to bacteria harboring non-recombinant vector. Further, bacteria harboring mutant SARM1-TIR (E596K) had NAD+ levels comparable to bacteria harboring non-recombinant vector or to bacteria in which wild type SARM1 was not induced (FIG. 11A). FIG. 11A illustrates endogenous NAD+ levels in bacteria after IPTG induction of human SARM1-TIR. The bacterially expressed SARM1-TIR was purified using TAP and tested for NADase activity. Consistent with the results using SARM1-TIR complexes isolated from mammalian cells in example 5, NAD+ was rapidly consumed by bacterially produced SARM1-TIR protein (FIG. 11B). FIG. 11B illustrates in vitro NAD+ cleavage reaction by human SARM1-TIR protein expressed and purified from bacteria. Although it is highly unlikely that human SARM1-TIR would associate with an E. coli NADase, the intrinsic nature of the SARM1 NADase activity was tested by stringently washing the SARM1 TIR purified complexes with either high salt or detergents to remove potential associated proteins. Using these washed SARM1 TIR beads, they found no decrease in NAD+ cleavage activity, indicating that SARM1 itself has NADase activity (FIGS. 11E and 11F).

Mouse, zebrafish and *Drosophila* SARM1-TIR domains were expressed and purified in *E. coli*. The purified proteins were then tested for their ability to cleave NAD+. Similar to human SARM1-TIR domain, bacterially-expressed mouse, zebrafish and *Drosophila* SARM1-TIR domains also rapidly degrade NAD+ in vitro (FIG. 11C-D). FIG. 11C illustrates that bacterially expressed mouse, zebrafish and *Drosophila* SARM1-TIR proteins cleave NAD+ in the in vitro NADase assay. FIG. 11D illustrates a SYPRO Ruby gel of SARM1-TIR laden beads purified from bacteria used in NADase assay; representative of three independent experiments. These bacterially expressed proteins lack the Venus fluorescent tag and thus run at a different size than the proteins expressed in NRK1-HEK293T cells. Data were generated from at least three independent reaction experiments using purified protein from at least three independent bacteria clones. Data are presented as mean±SEM; Error bars: SEM; *** P<0.001 unpaired two tailed Student's t-test.

Figure 11G:
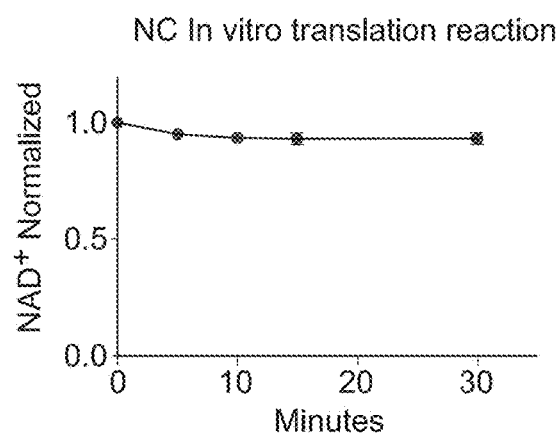

To demonstrate definitively that SARM1-TIR itself possessed the enzymatic activity, human SARM1-TIR was synthesized in a cell-free protein expression system that utilizes purified *E. coli* components for transcription and translation. None of the purified *E. coli* transcription/translation components are known NADases (Shimizu et al., Nat. Biotechnol., 2001, 19, 751-755), and these experiments confirmed that these purified components do not exhibit NADase activity (FIG. 11G). To test if SARM1-TIR purified from this in vitro translation system could cleave NAD+, the human SARM1-TIR plasmid DNA was first incubated with the purified transcription and translation reagents and RNase inhibitor for 2.5 hours at 37° C. Next, they purified the newly synthesized protein from the reaction by TAP, and tested for NADase activity in the assay (FIG. 30). The purified SARM1-TIR from this cell-free protein translation system rapidly cleaved NAD+, consistent with prior findings with SARM1-TIR purified from both mammalian cells and bacteria (FIGS. 31 and 32). Without being limited by theory, the finding that the SARM1-TIR domain depletes NAD+ in bacteria and that bacterially synthesized SARM1-TIR from multiple species cleaves NAD+ in vitro demonstrates that the SARM1-TIR domain has intrinsic NADase activity, and shows that SARM1 itself is responsible for the NAD+ depletion observed after axon injury. Moreover, these findings reveal for the first time that a TIR domain, previously demonstrated to function as a protein interaction domain, can also harbor enzymatic activity.

Figure 12A:
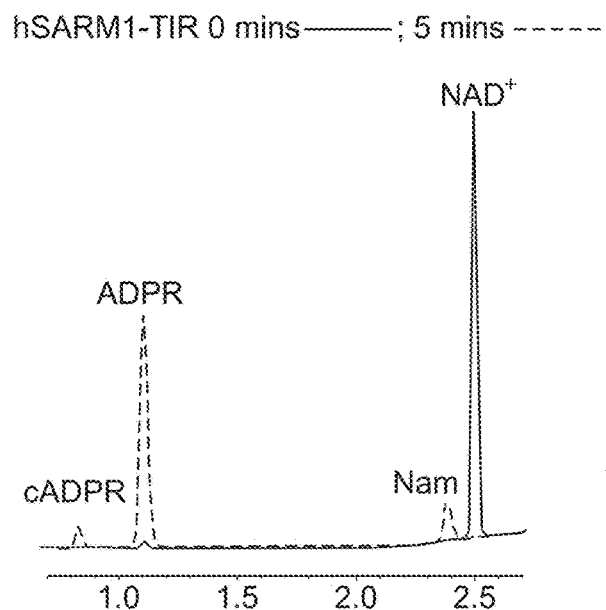
FIGS. 12A-M illustrate characterization of the SARM1-TIR NAD+ cleavage reaction.
Figure 12B:
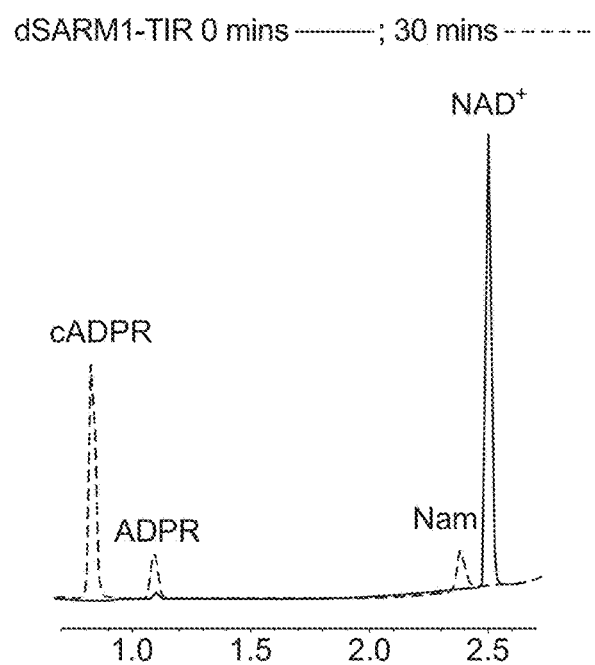
Figure 12C:
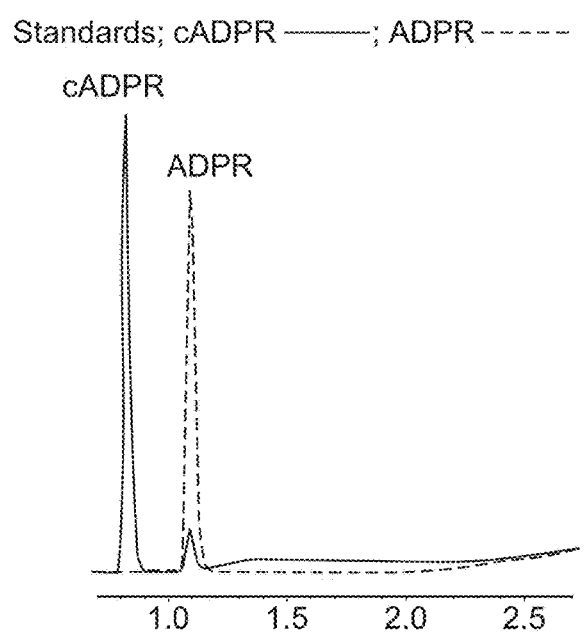
Figure 12D:
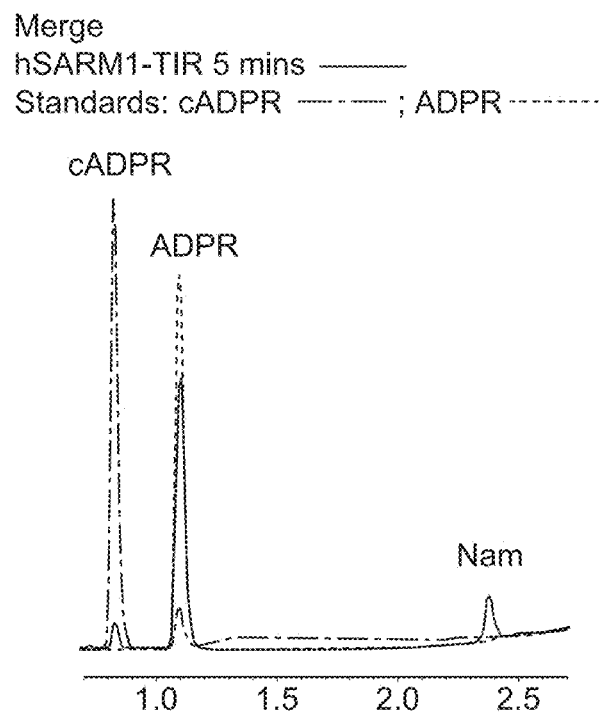
Figure 12E:
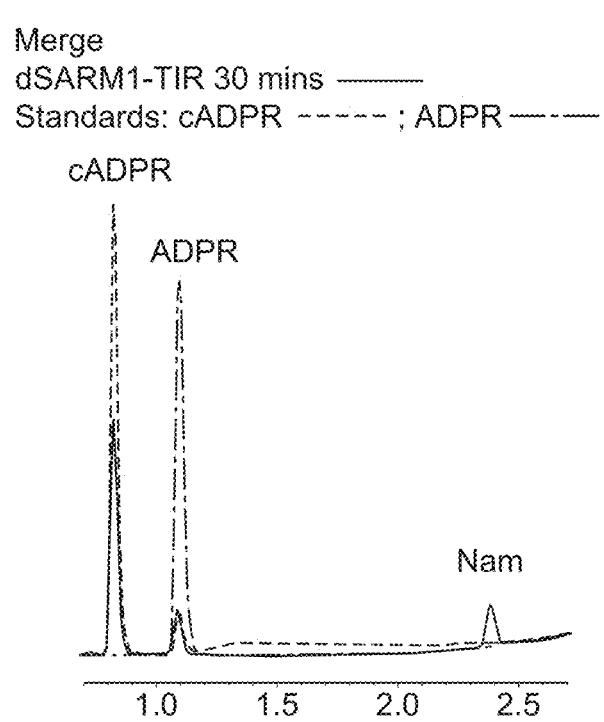
Figure 12F:
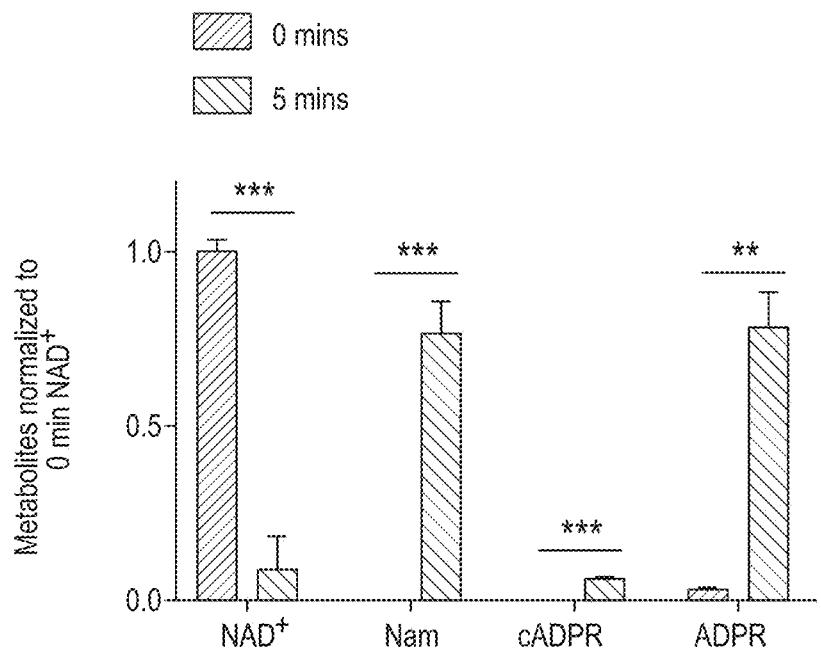
Figure 12G:
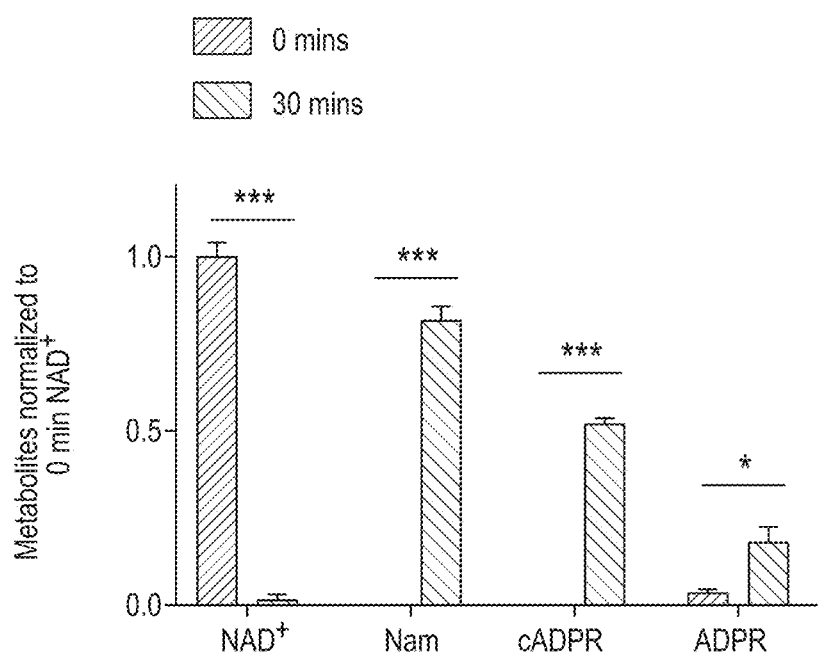
Figure 12H:
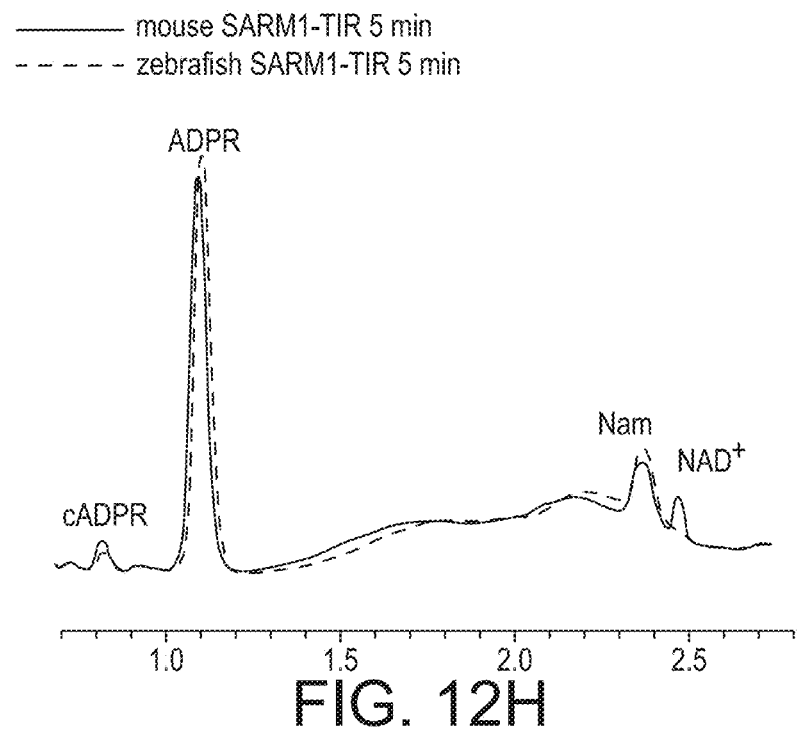

To further characterize the SARM1-TIR NADase activity, the NAD+ cleavage products of this enzymatic reaction were identified and reaction parameters were established. HPLC and LC-MS/MS analysis of the metabolites produced by human SARM1-TIR was performed; Nam and ADP Ribose (ADPR) were identified as major products, and cyclic ADPR (cADPR) as a minor product (FIG. 12A-G). While the mouse and zebrafish orthologs generated a similar ratio of reaction products as the human enzyme (FIG. 12H), the *Drosophila* SARM1-TIR purified either from bacteria or NRK1-293T cells generated more cADPR than ADPR (FIG. 12A-G). This finding is similar to results with the ADPRibosyl cyclase family of NADases (Liu et al., J. Biol. Chem., 2009, 284, 27637-27645), in which the mammalian ADP Ribosyl Cyclase CD38 cleaves NAD+ to generate ADPR as the major product, with minor amounts of cADPR; while the ADP Ribosyl Cyclase isolated from the sea mollusk *Aplysia californica* cleaves NAD+ into cADPR (Liu et al., J. Biol. Chem., 2009, 284, 27637-27645). This difference in reaction products between the *Drosophila* and vertebrate SARM1-TIR NADase may provide insights into the divergent enzymatic activities of the ADP Ribosyl cyclase family of enzymes.

Figure 12I:
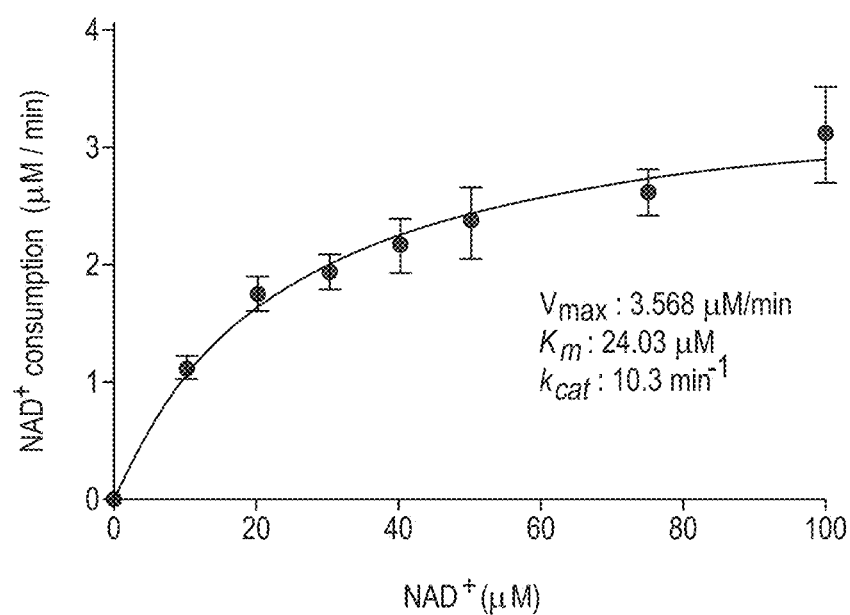

Furthermore, kinetic assays of the SARM1-TIR enzyme revealed saturation kinetics (FIG. 12I), a distinguishing feature of enzyme catalysts, with an estimated Michaelis constant (Km) of 24 µM, maximum velocity (V max) of 3.6 µM/min, and turnover number (kcat) of 10.3 min-1 (FIG. 12I). Kinetic parameters for SARM1-TIR cleavage reaction. V max, Km, kcat were determined by fitting the data to the Michaelis-Menten equation and are presented as mean±SEM for three independent biological samples and experiment. Although the estimated kcat is lower than the reported values for other ADP-Ribosyl cyclases and NAD+ glycohydrolases (Ghosh et al., J. Biol. Chem., 2010, 285, 5683-5694), the estimated Km values are similar (Cantó et al., Cell Metab., 2015, 22, 31-53).

Figure 12J:
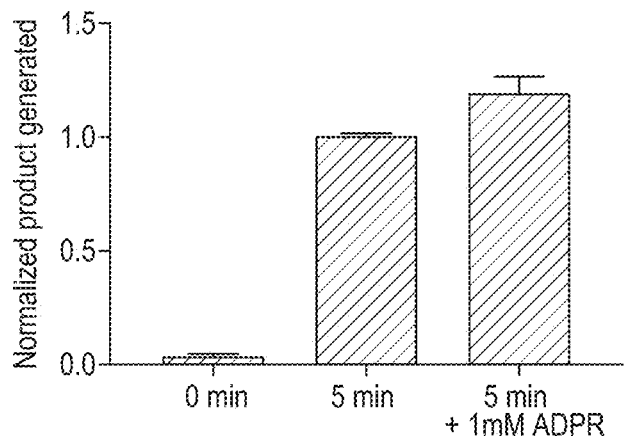
Figure 12K:
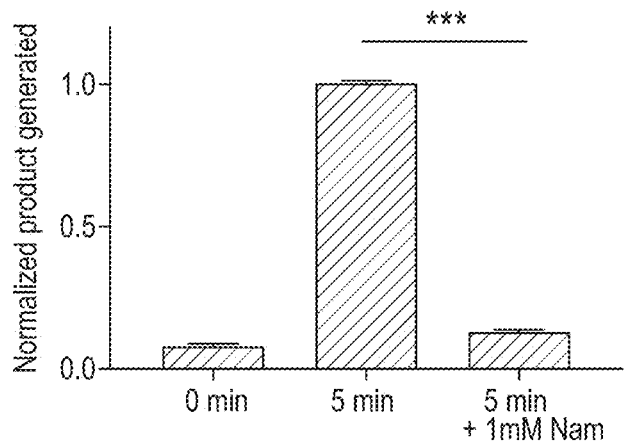
Figure 12L:
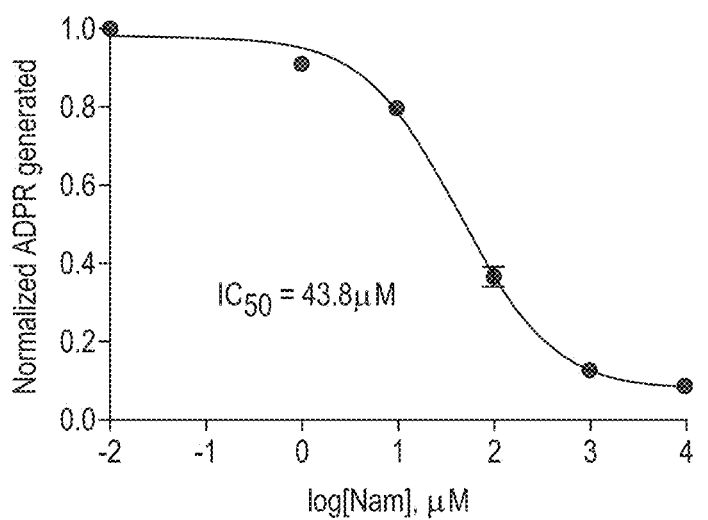
Figure 12M:
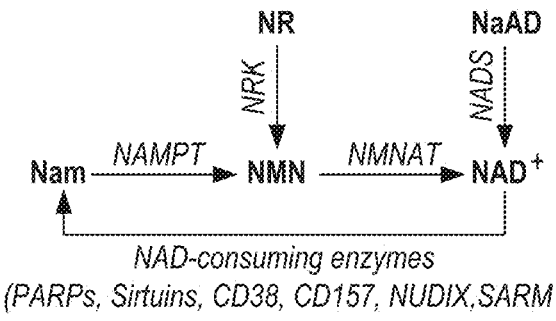
Figure 13:
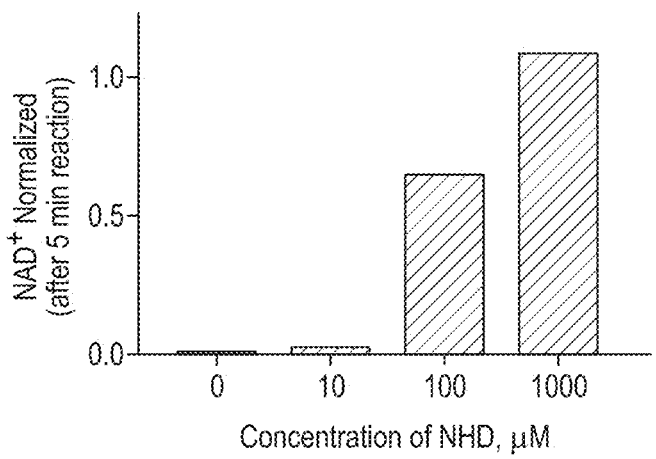
FIG. 13 illustrates that Nicotinamide Hypoxanthine dinucleotide (NHD) inhibits SARM1 TIR NAD+ cleavage.
Figure 14:
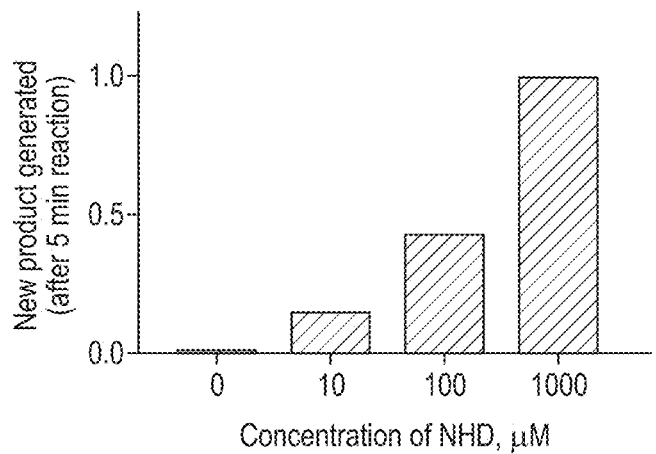
FIG. 14 illustrates that Nicotinamide Hypoxanthine dinucleotide (NHD) is a substrate for the SARM1 TIR enzyme.
Figure 15:
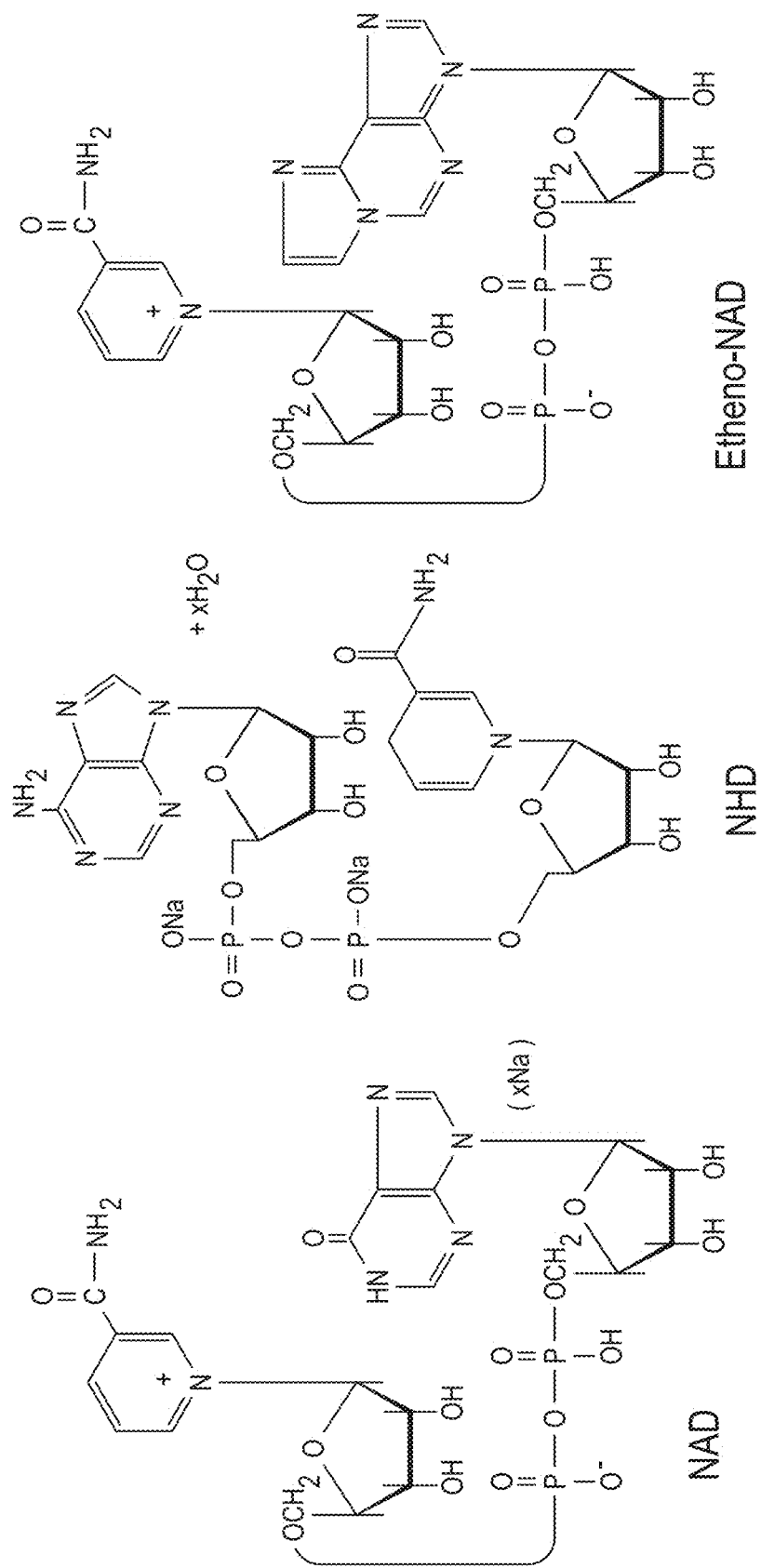
FIG. 15 illustrates chemical structures of candidate analogs represented in the Table 1, Example 7.

The reaction products were tested to determine whether they could inhibit the enzymatic activity of SARM1-TIR. While ADPR did not inhibit SARM1-TIR NADase activity (FIG. 12J; activity normalized to Nam generated at 5 min), Nam could inhibit the enzymatic activity with an IC50 of 43.8 µM, which is about 9-fold higher than the starting reaction NAD+ concentration (FIG. 12K-L). FIG. 12K illustrates that Nam inhibits SARM1-TIR enzymatic activity (normalized to ADPR generated at 5 min). FIG. 12L illustrates Nam dose response inhibition of SARM1-TIR enzymatic activity. Inhibitors of the SARM1-TIR domain modeled after nicotinamide can be useful in preventing the early stages of axon degeneration (Gerdts, J et al., Neuron, 2016, 89, 449-460; Fliegert, R., et al., Biochem. Soc. Trans., 2007, 35, 109-114).

These data demonstrated that the TIR domain of SARM1 cleaves NAD+ into Nam and ADPR. SARM1-TIR appears to be unique in this regard, as other tested TIR domains do not have this activity. A crystal structure of the SARM1-TIR domain can be important in identifying the NAD+ binding pocket as well as other key residues involved in NAD+ cleavage.

In summary, these results describe the first enzymatic activity intrinsic to a TIR domain. These data establish that NADase activity is integral to a conserved axon death program. The discovery that SARM1 is the axonal NADase (FIG. 12J) now provides an identified target for the design of inhibitors as novel therapeutic candidates for the treatment of neurodegenerative diseases.

Example 7

This example describes characterization of analogs of nicotinamide (a known SARM1 NADase inhibitor) and analogs of NAD+ with respect to activity as inhibitors of SARM1 enzymatic activity and/or as substrates for the cleavage reaction. These analogs were tested using an assay that makes use of a bacterially-expressed tagged version of the SARM1 TIR fragment, as described in Example 2. Displaying this artificial SARM1 TIR domain on a solid surface (i.e. affinity beads) generates an active NAD+ cleavage enzyme.

| # | Candidate Analogs | Inhibitor | Substrate |
|---|---|---|---|
| 1 | Thionicotinamide | No | No |
| 2 | 6-aminonicotinamide | No | No |
| 3 | 3-acetylpyridine | No | No |
| 4 | Nicotinaldehyde | No | No |

| # | Candidate Analogs | Inhibitor | Substrate |
|---|---|---|---|
| 5 | Benzamide (PARP inhibitor) | No | No |
| 6 | Ex-527 (Sirtuin inhibitor) | Unclear (might inhibit at very higher doses of 1 mM) | No |
| 7 | Nicotinamide adenine dinucleotide 2'-phosphate, reduced (NADPH) | Unclear | Yes (at higher doses of at least 100 μM) |
| 8 | Nicotinamide Hypoxanthine dinucleotide (NHD) | Yes | Yes |
| 9 | Nicotinamide 1, N6-ethenoadenine dinucleotide | Unclear (might inhibit at high doses of 1 mM) | No |

Table 4: Substrates and Inhibitors of the SARM1 TIR NAD cleavage activity as determined by an assay which uses a bacterially expressed, tagged version of the SARM1 TIR fragment. Nicotinamide Hypoxanthine dinucleotide (NHD) was both a substrate and an inhibitor.

Example 8

This example illustrates that Glutamic Acid 642 is a catalytic residue in the active site of the SARM1-TIR enzyme.

Since there is no reported crystal structure of the SARM1-TIR domain, an unbiased template-based prediction (Söding, J., et al., Nucleic Acids Res., 2005, 33, W244-248) was used to identify protein homologs of SARM1-TIR. A recent bioinformatics study showed that some TIR domains share strong structural similarity to nucleotide/nucleoside hydrolases (Burroughs, A. M., et al., Nucleic Acids Res., 2015, 43, 10633-10654). From domain prediction analysis using SARM1-TIR, other TIR domains were identified as expected. However, in addition to these TIR domains, a number of nucleotide hydrolase/transferase enzymes were also detected. For some of these enzymes, residues that contribute to catalytic activity have been established (Sikowitz, M. D., et al., Biochemistry, 2013, 52, 4037-4047; Armstrong, S. R., et al., Structure, 1995, 4, 97-107). Structural modeling and sequence alignments were used to identify putative residues in the SARM1-TIR domain that might contribute to enzymatic activity (FIG. 16 and FIG. 17). The SARM1-TIR domain was modeled using the crystal structure of two enzymes identified from the prediction: MilB Cytidine 5' monophosphate (CMP) Hydrolase (PDB: 4JEM) (FIG. 17) and Nucleoside 2-deoxyribosyltransferase (PDB: 1F8Y). A glutamic acid E642 in the SARM1-TIR domain aligned with both the key catalytic glutamic acid residue in CMP hydrolase (Sikowitz, M. D., et al., Biochemistry, 2013, 52, 4037-4047) and the proposed nucleophilic glutamic acid in the active site of nucleoside 2-deoxyribosyltransferase (Armstrong, S. R., et al., Structure, 1995, 4, 97-107) (FIG. 16 and FIG. 17). Moreover, glutamic acid residues are also known catalytic residues in other NADases (Ghosh, J., et al., J. Biol. Chem., 2010, 285, 5683-5694). To test if SARM1 TIR E642 had similar catalytic properties, this residue was mutated to an Alanine (E642A) in SARM1-TIR, purified the protein from the cell-free protein translation system, and tested it for NAD+ cleavage activity. Purified SARM1-TIR E642A failed to cleave NAD+ in the NADase assay (FIG. 18 and FIG. 19). E642 in the SARM1-TIR domain is a key catalytic residue within the active site that is responsible for NAD+ cleavage.

Example 9

This example illustrates that SARM1 enzymatic activity functions in axons to promote pathological axonal degeneration.

Figure 21:
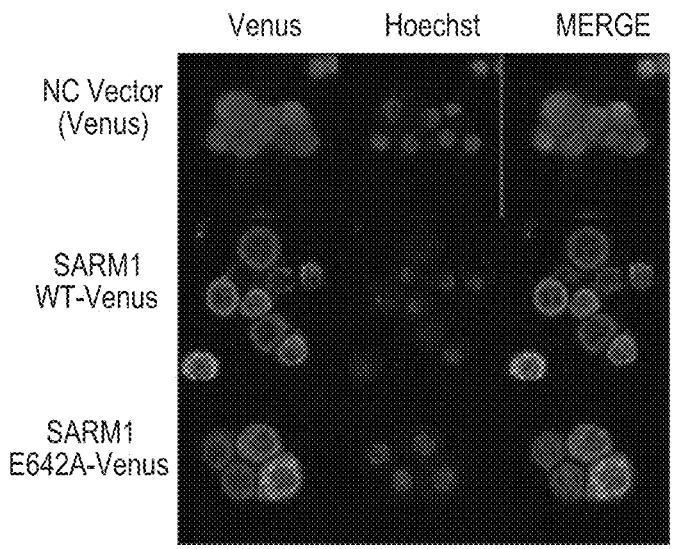
FIG. 21 illustrates Venus expression of indicated constructs in DRG cell bodies, co-stained with Hoechst to assess total nuclei in each field.

Having demonstrated that the SARM1 TIR domain is an enzyme and having identified its catalytic residue, enzymatic activity of the SARM1-TIR domain and, in particular, the identified glutamate, were investigated to determine whether either are required for the pro-degenerative functions of full-length SARM1 in neurons. In wild type neurons, axotomy triggers rapid depletion of axonal NAD+ and axonal degeneration, while in SARM1-deficient neurons axonal degeneration is blocked and NAD+ levels remain significantly higher than in injured wild type axons (Gerdts et al., Science, 2015, 348, 453-457). First, the SARM1 NADase activity was tested to determine whether such activity is necessary for injury-induced axonal NAD+ depletion and subsequent axonal degeneration. In these experiments, either wild type (enzymatically active) full-length SARM1 or mutant (enzymatically disabled) SARM1 (E642A) were expressed in cultured SARM1-deficient DRG neurons. FIG. 20 and FIG. 21 illustrate that both were well expressed in axons. Following axotomy, axonal NAD+ levels and axonal degeneration were measured.

Expression of enzymatically active, wild type SARM1 in SARM1-deficient DRG neurons promotes both axonal NAD+ depletion and axonal degeneration after axotomy.

Figure 22:
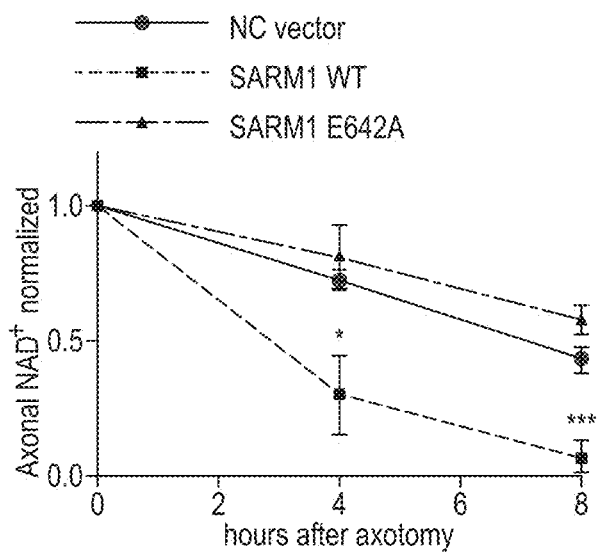
FIG. 22 illustrates axonal NAD+ levels after axotomy (normalized to control at 0 hr). NC vector, SARM1 WT, and SARM1 E642A constructs were expressed in SARM1−/− DRG neurons, and levels of NAD+ were obtained at indicated timepoints after axotomy.
Figure 23:
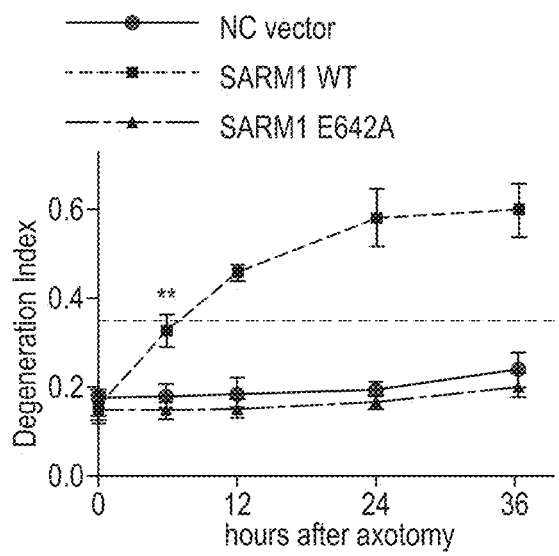
FIG. 23 illustrates axonal degeneration time course after axotomy, quantified as degeneration index (DI) where a DI of 0.35 (indicated by dotted line) or above represents degenerated axons.
Figure 24:
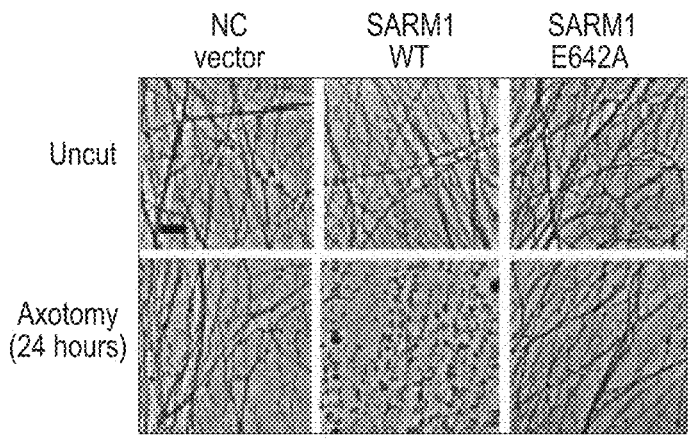
FIG. 24 illustrates bright-field micrographs of axons expressing indicated constructs represented in FIG. 23.

In contrast to wild type SARM1, when the enzymatically disabled SARM1(E642A) mutant is expressed in these neurons, axotomy did not induce axonal degeneration or rapid NAD+ depletion (FIG. 22-24).

The requirement for SARM1 enzyme activity was also tested in another injury model—vincristine-induced neurotoxicity. Cultured SARM1-deficient DRG axons are protected from vincristine-induced axonal degeneration (Gerdts, J., et al., J. Neurosci., 2013, 33, 13569-13580). Moreover, SARM1 is required in mice for the development of vincristine-induced peripheral neuropathy (Geisler et al., 2016, Brain, 139, 3092-3108). As with axotomy, either wild type (enzymatically active) full-length SARM1 or mutant (enzymatically disabled) SARM1(E642A) was expressed in cultured SARM1-deficient DRG neurons. Enzymatically active SARM1 mediates axon loss in response to the chemotherapeutic vincristine, while enzymatically disabled SARM1 does not promote axon loss following vincristine administration (FIG. 25, and FIG. 26). Altogether, these findings demonstrate that the intrinsic NADase activity of SARM1 (FIG. 27) is necessary to promote axonal degeneration after both traumatic and neurotoxic injuries, and suggest that inhibitors of the SARM1 NADase could block pathological axonal degeneration.

Example 10

This example illustrates the identification and characterization of a family of small molecules that effectively inhibit SARM1 NADase activity.

Initial screening using methods of the present teachings identified dexlansoprazole and tenatorprazole as SARM1 NADase inhibitors. These molecules are both members of a class of molecules referred to as protein pump inhibitors. The rest of the drug class was screened using the HPLC-based SARM1 SAM-TIR NADase assay described in detail in Example 1, with 5 μM NAD. FIG. 28 illustrates testing at 5 μM (Series 1), 15 μM (Series 2), and 50 μM (Series 3): omeprazole (1), lansoprazole (2), esomeprazole magnesium hydrate (3), pantoprazole sodium sesquihydrate (4), rabeprazole sodium (5), dexlansoprazole (6) and tenatoprazole (7). Each member of the family exhibited at least some inhibitory activity (FIG. 28). Based on these results, a dose-response analysis of rabeprozole (FIG. 29) was performed. This molecule showed 95% inhibition at 10 μM and 98.8% inhibition at 30 μM. These results indicate that this family of molecules has SARM1 NADase activity.

```
GenBankSend:
Homo sapiens sterile alpha and TIR motif containing protein 1
isoform a (SARM1) mRNA, complete cds GenBank: AY444166.1

LOCUS AY444166 2193 bp mRNA linear PRI 16-JAN-2004

DEFINITION Homo sapiens sterile alpha and TIR motif containing
protein 1 isoform a (SARM1) mRNA, complete cds. ACCESSION AY444166
VERSION AY444166.1 GI: 38326778

SOURCE Homo sapiens (human) ORGANISM Homo sapiens

REFERENCE 1 (bases 1 to 2193)

AUTHORS Bousson, J.-C., Casteran, C. and Tiraby, G. TITLE SARM1
isoforms nucleotide sequence JOURNAL Unpublished REFERENCE 2 (bases 1 to 2193)

AUTHORS Bousson, J.-C., Casteran, C. and Tiraby, G. TITLE Direct
Submission

JOURNAL Submitted (21-OCT-2003) CAYLA, BP4437, 5 rue Jean
Rodier, Toulouse cedex 4 31405, France FEATURES Location/Qualifiers source 1 . . . 2193

/organism = "Homo sapiens"

/mol_type = "mRNA"

/db_xref = "taxon:9606"

/chromosome = "17"

/map = "17q11" gene 1 . . . 2193

/gene = "SARM1"

/gene_synonym = "KIAA0524"

/gene_synonym = "SAMD2"

/gene_synonym = "SARM" CDS 1 . . . 2175

/gene = "SARM1"

/gene_synonym = "KIAA0524"

/gene_synonym = "SAMD2"

/gene_synonym = "SARM"

/note = "SARM1a; receptor"

/codon_start = 1

/product = "sterile alpha and TIR motif containing protein 1
isoform a"

/protein_id = "AAR17520.1"

/db_xref = "GI: 38326779"

/translation = "MVLTLLLSAYKLCRFFAMSGPRPGAERLAVPGPDGGGGTGPWWAAGGRG

PREVSPGAGTEVQDALERALPELQQALSALKQAGGARAVGAGLAEVFQLVEEAWLLPAVGREV

AQGLCDAIRLDGGLDLLLRLLQAPELETRVQAARLLEQILVAENRDRVARIGLGVILNLAKER
```

EPVELARSVAGILEHMFKHSEETCQRLVAAGGLDAVLYWCRRTDPALLRHCALALGNCALHGG

QAVQRRMVEKRAAEWLFPLAFSKEDELLRLHACLAVAVLATNKEVEREVERSGTLALVEPLVA

SLDPGRFARCLVDASDTSQGRGPDDLQRLVPLLDSNRLEAQCIGAFYLCAEAAIKSLQGKTKV

FSDIGAIQSLKRLVSYSTNGTKSALAKRALRLLGEEVPRPILPSVPSWKEAEVQTWLQQIGFS

KYCESFREQQVDGDLLLRLTEEELQTDLGMKSGITRKRFFRELTELKTFANYSTCDRSNLADW

LGSLDPRFRQYTYGLVSCGLDRSLLHRVSEQQLLEDCGIHLGVHRARILTAAREMLHSPLPCT

GGKPSGDTPDVFISYRRNSGSQLASLLKVHLQLHGFSVFIDVEKLEAGKFEDKLIQSVMGARN

FVLVLSPGALDKCMQDHDCKDWVHKEIVTALSCGKNIVPIIDGFEWPEPQVLPEDMQAVLTFN

GIKWSHEYQEATIEKIIRFLQGRSSRDSSAGSDTSLEGAAPMGPT" ORIGIN

```
    1 atggtcctga cgctgcttct ctccgcctac aagctgtgtc gcttcttcgc catgtcgggc
   61 ccacggccgg gcgccgagcg gctggcggtg cctgggccag atggggggcgg tggcacgggc
  121 ccatggtggg ctgcggtgg ccgcggggccc cgcgaagtgt cgccggggc aggcaccgag
  181 gtgcaggacg ccctggagcg cgcgctgccg gagctgcagc aggccttgtc cgcgctgaag
  241 caggcgggcg gcgcgcgggc cgtgggcgcc ggcctgccg aggtcttcca actggtggag
  301 gaggcctggc tgctgccggc cgtgggccgc gaggtagccc agggtctgtg cgacgccatc
  361 cgcctcgatg gcggcctcga cctgctgttg cggctgctgc aggcgccgga gttggagacg
  421 cgtgtgcagg ccgcgcgcct gctggagcag atcctggtgg ctgagaaccg agaccgcgtg
  481 gcgcgcattg gctgggcgt gatcctgaac ctggcgaagg aacgcgaacc cgtagagctg
  541 gcgcggagcg tggcaggcat cttggagcac atgttcaagc attcggagga gacatgccag
  601 aggctggtgg cggccggcgg cctggacgcg gtgctgtatt ggtgccgccg cacggacccc
  661 gcgctgctgc gccactgcgc gctggcgctg ggcaactgcg cgctgcacgg gggccaggcg
  721 gtgcagcgac gcatggtaga gaagcgcgca gccgagtggc tcttcccgct cgccttctcc
  781 aaggaggacg agctgcttcg gctgcacgcc tgcctcgcag tagcggtgtt ggcgactaac
  841 aaggaggtgg agcgcgaggt ggagcgctcg ggcacgctgg cgctcgtgga gccgcttgtg
  901 gcctcgctgg accctggccg cttcgcccgc tgtctggtgg acgccagcga cacaagccag
  961 ggccgcgggc ccgacgacct gcagcgcctc gtgccgttgc tcgactctaa ccgcttggag
 1021 gcgcagtgca tcggggcttt ctacctctgc gccgaggctg ccatcaagag cctgcaaggc
 1081 aagaccaagg tgttcagcga catcggcgcc atccagagcc tgaaacgcct ggtttcctac
 1141 tctaccaatg gcactaagtc ggcgctggcc aagcgcgcgc tgcgcctgct gggcgaggag
 1201 gtgccacggc ccatcctgcc ctccgtgccc agctggaagg aggccgaggt tcagacgtgg
 1261 ctgcagcaga tcggtttctc caagtactgc gagagcttcc gggagcagca ggtggatggc
 1321 gacctgcttc tgcggctcac ggaggaggaa ctccagaccg acctgggcat gaaatcgggc
 1381 atcacccgca agaggttctt tagggagctc acggagctca gaccttcgc caactattct
 1441 acgtgcgacc gcagcaacct ggcggactgg ctgggcagcc tggaccgcg cttccgccag
 1501 tacacctacg gcctggtcag ctgcggcctg accgctccc tgctgcaccg cgtgtctgag
 1561 cagcagctgc tggaagactg cggcatccac ctgggcgtgc accgcgcccg catcctcacg
 1621 gcggccagag aaatgctaca ctcccgctg ccctgtactg gtggcaaacc cagtggggac
 1681 actccagatg tcttcatcag ctaccgccgg aactcaggtt cccagctggc cagtctcctg
 1741 aaggtgcacc tgcagctgca tggcttcagt gtcttcattg atgtggagaa gctggaagca
 1801 ggcaagttcg aggacaaact catccagagt gtcatgggtg cccgcaactt tgtgttggtg
```

```
1861 ctatcacctg gagcactgga caagtgcatg caagaccatg actgcaagga ttgggtgcat 1921 aaggagattg tgactgcttt aagctgcggc aagaacattg tgcccatcat tgatggcttc 1981 gagtggcctg agccccaggt cctgcctgag gacatgcagg ctgtgcttac tttcaacggt 2041 atcaagtggt cccacgaata ccaggaggcc accattgaga agatcatccg cttcctgcag 2101 ggccgctcct cccgggactc atctgcaggc tctgacacca gtttggaggg tgctgcaccc 2161 atgggtccaa cctaaccagt ccccagttcc cca Also Known As: MyD88-5, SAMD2, SARM Homologs of the SARM1 gene The SARM1 gene is conserved in chimpanzee, Rhesus monkey, dog,
mouse, rat, chicken, zebrafish, fruit fly, mosquito,
C. elegans, and frog.
```

Examples 11-16

As depicted in the Examples below, in certain exemplary embodiments, compounds are prepared according to the following general procedures. It will be appreciated that, although the general methods depict the synthesis of certain compounds of the present disclosure, the following general methods, and other methods known to one of ordinary skill in the art, can be applied to all compounds and subclasses and species of each of these compounds, as described herein.

General Procedures

The following is a description of the assays used to determine SARM1 NADase activity for the compounds of formula $I^A$ and formula $I^B$.

Assay 1. Preparation of SARM1 SAM-TIR Lysate (STL)

NRK1-HEK293T cells represent a polyclonal cell line that has been stably transfected with an FCIV expression vector that expresses human Nicotinamide Riboside Kinase 1 (NRK1), an enzyme that converts the NAD+ biosynthetic precursor nicotinamide riboside (NR) to NMN, the immediate precursor of NAD+. This expression vector has the DNA sequence: gtcgacggatcgggagatctcccgatcccc-tatggtgcactctcagtacaatctgctctgatgccgcatagt-taagccagtatctgctccctgc ttgtgtgttggaggtcgct-gagtagtgcgcgagcaaaatttaagctacaacaaggcaaggcttgaccgacaattg-catgaagaatctgcttag
ggttaggcgttttgcgctgcttcgcgatgtacgggccagatatacgcgttgacatt-gattattgactagttattaatagtaatcaattacggggtc attagttcatagcc-catatatggagttccgcgttacataact-
tacggtaaatggcccgcctggctgaccgcccaacgacccccgcccattgac gtcaataatgacgtatgttcccatagtaacgccaataagggacttccattgacgt-caatggtggagtatttacggtaaactgcccacttggca gtacatcaagtgtat-catatgccaagtacgcccccctattgacgtcaatgacggtaaatggcccgcctgg-cattatgcccagtacatgacctat
gggactttcctacttggcagtacatctacgtattagtcatcgctattaccatggt-gatgcggttttggcagtacatcaatgggcgtggatagcgg tttgactcacggg-gatttccaagtctccaccccattgacgtcaatgggagtttgttttggcaccaaaat-caacgggactttccaaatgtcgtaa
caactccgccccattgacgcaaatgggcggtaggcgtgtacggtgggaggtc-tatataagcagcgcgttttgcctgtactgggtctctctggt tagaccagatct-gagcctgggagctctctggctaactagggaacccactgcttaagcct-caataaagcttgccttgagtgcttcaagtagtgt
gtgcccgtctgttgtgtgactctggtaactagagatccctcagacccttt-tagtcagtgtggaaaatctctagcagtggcgcccgaacaggga ctt-gaaagcgaaagggaaaccagaggagctctctcgacgcaggactcggcttgct-gaagcgcgcacggcaagaggcgaggggcggc
gactggtgagtacgccaaaaattttgactagcg-gaggctagaaggagagagatgggtgcgagagcgtcagtattaagcgggg-gagaatt agatcgcgatgggaaaaattcggttaaggccagggg-gaaagaaaaaatataaattaaaacatatagtatgggcaagcagggagctagaa cgattcgcagttaatcctggcctgttagaaacatcagaaggctgta-gacaaatactgggacagctacaaccatcccttcagacaggatcaga agaactta-gatcattatataatacagtagcaaccctctattgtgtgcatcaaaggatagaga-taaaagacaccaaggaagctttagacaagat
agaggaagagcaaaacaaaagtaagaccaccgcacagcaagcggccgct-gatcttcagacctggaggaggagatatgagggacaattg gagaagtgaat-tatataaatataaagtagtaaaaattgaaccattaggagtagcacccac-caaggcaaagagaagagtggtgcagagaga
aaaaagagcagtgggaataggagctttgttccttgggttcttgggagcagcag-gaagcactatgggcgcagcgtcaatgacgctgacggt acaggccagacaattat-tgtctggtatagtgcagcagcagaacaatttgctgagggctatt-gaggcgcaacagcatctgttgcaactcacagt
ctggggcatcaagcagctccaggcaagaatcctggctgtggaaaga-tacctaaaggatcaacagctcctggggatttggggttgctctgga aaactcat-ttgcaccactgctgtgccttggaatgctagttggagtaataaatctctggaacagat-ttggaatcacacgacctggatggagtggg
acagagaaattaacaattacacaagcttaatacactccttaatt-gaagaatcgcaaaaccagcaagaaaagaatgaacaagaattattggaat taga-taaatgggcaagtttgtggaattggtttaacataacaaattggctgtggtatataaaat-tattcataatgatagtaggaggcttggtaggttt
aagaatagttttttgctgtacttctatagtgaatagagttaggcagggatattcaccat-tatcgtttcagacccacctcccaaccccgaggggac
ccgacaggcccgaaggaatagaagaagaaggtggagagagagacagagaca-gatccattcgattagtgaacggatcggcactgcgtgc gccaattctgca-gacaaatggcagtattcatccacaattttaaaagaaaaggggggattgggggta-cagtgcaggggaaagaatagtaga
cataatagcaacagacatacaaactaaagaattacaaaaacaaattacaaaaatt-caaaattttcgggtttattacagggacagcagagatcc agtttggttaat-taagggtgcagcggcctccgcgccgggttttggcgcctcccgcgggcgcccc-cctcctcacggcgagcgctgccacgt cagacgaagggcgcaggagcgttcct-gatccttccgcccggacgctcaggacagcggcccgctgctcataa-
gactcggccttagaaccc cagtatcagcagaaggacattt-taggacgggacttgggtgactctagggcactggttttcttccagagagcggaa-caggcgaggaaaagt agtcccttctcggcgattctgcggagg-gatctccgtgggcggtgaacgccgatgat-
tatataaggacgcgccgggtgtggcacagctagt tccgtcgcagccgggat-ttgggtcgcggttcttgtttgtggatcgctgtgatcgtcacttggtgagttgcgggc-tgctgggctggccggggct ttcgtggccgccgggccgctcggtgggacg-gaagcgtgtggagagaccgc-
caagggctgtagtctgggtccgcgagcaaggttgccct gaactgggggttgggggggagcgcacaaaatggcggctgttcccgagtctt-gaatggaagacgcttgtaaggcgggctgtgaggtcgttga aacaaggtgggggcatggtgggcggcaagaacccaaggtctt-gaggccttcgctaatgcgggaaagctcttattcgggtgagatgggct ggggcac-catctggggaccctgacgtgaagtttgtcactgactg-gagaactcgggtttgtcgtctggttgcggggcggcagttatgcggt gccgttgggcagtgcaccccgtaccttttgg-gagcgcgcgcctcgtcgtgtcgtgacgtcacccgttctgttggct-tataatgcagggtggggc cacctgccggtaggtgtgcggtaggcttttctccgtcgcaggacgcagggtcgggcctagggtaggctctcctgaatcgacaggcgccg gacctctggtgagggagggataagtgaggcgtcagtttcttggtcggttttatgtacctatcttctaagtagctgaagctccggttttgaact
atgcgctcggggttggcgagtgtgttttgtgaagttttttaggcacctttt gaaatgtaatcatttgggtcaatatgtaatttcagtgttagactagt
aaagcttctgcaggtcgactctagaaaattgtccgctaaat tctggccgttttggcttttttgttagacgaagcttgggctgcaggtcgactcta gaggatcatgaagagatttgtcattggaattggtggtgtgacaaacggagggaagacgacactggctaagagcttgcagaagcaccttccc
aactgcagcgtcatatctcaggatgacttcttcaagccagagtctgagatagacatagatgaaaatggttttttgcagtatgatgtgcttgaagc gctaaatatggaaaaaatgatgtcagcagtttcctgttggatggaaaacccaggaagctctgcgggaccagcagccttggaaagtgctcaa
ggggttcccattttaattattgaaggtttccttctctttaattataagcctctggacaccatatggaacagaagttacttcctgaccgttccatatga agaatgtaagaggagaaggagtaccagagtatatgagcctccagaccctccagggtacttcgatggccacgtgtggcccatgtacctaaa
gcacagacaggaaatgagctccatcacctgggacattgtttacctggatggaacaaggtctgaagaggacctcttctctcaggtgtatgaag atgtcaagcaggaactagagaagcaaaatggttttgGACTATAAAGATGATGATGATAAGTAAgctagctaccgg
tgatccgcccctctccctcccccccccctaacgttactggccgaagccgcttggaataaggccggtgtgcgtttgtctatatgttattttccacc atatgccgtcttttggcaatgtgagggcccggaaacctggccctgtcttcttgacgagcattcctaggggtctttcccctctcgccaaaggaa
tgcaaggtctgttgaatgtcgtgaaggaagcagttcctctggaagcttcttgaagacaaacaacgtctgtagcgacccttcgcaggcagcgg aaccccccacctggcgacaggtgcctctgcgggccaaaagccacgtgtataagatacacctgcaaaggcggcacaaccccagtgccacgt
tgtgagttggatagttgtgaaagagtcaaatggctctcctcaagcgtattcaacaaggggctgaaggatgcccagaaggtaccccattgtat gggatctgatctggggcctcggtgcacatgctttacatgtgtttagtcgaggttaaaaaaacgtctaggccccccgaaccacggggacgtgg
ttttccctttgaaaaacacgatgaataatatggccacaaccATGGatggccaagttgaccagtgccgttccggtgctcaccgcgcgcgacgt cgccggagcggtcgagttctggaccgaccggctcgggttctcccgggacttcgtgaggacgacttcgccggtgtggtccgggacgacg
tgaccctgtt catcagcgcggtccaggaccaggtggtgccggacaacaccctggcctgggtgtgggtgcgcggcctggacgagctgtac gccgagtggtcggaggtcgtgtcacgaacttccgggacgcctccgggccggccatgaccgagatcggcgagcagccgtggggggcgg
gagttcgccctgcgcgacccggccggcaactgcgtgcacttcgtggccgaggagcaggactgacacgtgctacgagatttcgattccaccgcc gccttctatgaaaggttgggcttcggaatcgttttccgggacgccggctggatgatcctccagcgcggggatctcatgctggagttcttcgccca
caaaatttgtaaaggtgaaagattgactggtattcttaactatgttgctccttttacgctatgtgatacgctgctttaatgcctttgtatca tgctattgcttcccgtatggcttcatttctcctccttgtataaatcctggttgctgtctctttatgaggagttgtggcccgttgtcaggcaacgtgg
cgtggtgtgcactgtgtttgctgacgcaaccccactggttggggcattgccaccacctgtcagctccttccgggactttcgctttcccctcc ctattgccacggcgaactcatcgccgcctgcctgcccgctgctggacaggggctcggctgttgggcactgacaattccggtggttgtcg gggaat
catcgtcctttccttggctgctcgcctgtgttgccacctggattctgcgcgggacgtccttctgctacgtcccttcggccctcaatcc agcggaccttccttcccgcggcctgctgccggctctgcggcctcttccgcgtcttcgccttcgccctcagacgagtcggatctcccttggggc cgcctccccgcatcgataccgtcgacctcgagacctagaaaaacatggagcaatcacaagtagcaatacagcagctaccaatgctgattgt gcctggctagaagcacaagaggaggaggaggtgggttttccagtcacacctcaggtacctttaagaccaatgacttacaaggcagctgtag atcttagccactttttaaaagaaaaggggggactggaagggctaattcactcccaacgaagacaagatatccttgatctgtggatctaccaca cacaaggctacttccctgattggcagaactacacaccagggccagggatcagatatccactgacctttggatggtgctacaagctagtacca gttgagcaagagaaggtagaagaagccaatgaaggagagaacacccgcttgtta cacctgtgagcctgcatgggatggatgacccgga gagagaagtattagagtgagggtttgacagccgcctagcattttcatcacatggcccgagagctgcatccggactgtactgggtctctctggtt
agaccagatctgagcctgggagctctctggctaactagggaacccactgcttaagcctcaataaagcttgccttgagtgcttcaagtagtgtg tgcccgtctgttgtgtgactctggtaactagagatccctcagacccctttagtcagtgtggaaaatctctagcagggcccgtttaaacccgctga tcagcctcgactgtgccttctagttgccagc
catcgttgtttgcccctccccgtgccttccttgaccctggaaggtgccactccactgtcctt tcctaataaaatgaggaaattgcatcgcattgtctgagtaggtgtcattctattctgggggtggggtggggcaggacagcaaggggggagg attgggaagacaatagcaggcatgctggggatgcggtgggctctatggcttctgaggcggaaagaaccagctggggctcagggggtatc
cccacgcgccctgtagcggcgcattaagcgcggcgggtgtggtggttacgcgcagcgtgaccgctacacttgccagcgccctagcgccc gctccttcgctttcttcccttccttctcgccacgttcgccgctttccccgtcaagctctaaatcgggggctcccttagggttccgatttagtgc tttacggcacctcgaccccaaaaaacttgattagggtgatggttcacgtagtgggccatcgccctgatagacggtttttcgcccttgacgttg gagtccacgttctttaatagtggactcttgttccaaactggaacaacactcaacccctatctcggtctattctttttgatttataaggggattttgccgatt
tcggcctattggttaaaaaatgagctgatttaacaaaaatttaacgcgaattaatctgtggaatgtgtgtcagttaggtgtggaaagtcccca ggctccccagcaggcagaagtatgcaaagcatgcatctcaatt agtcagcaaccaggtgtggaaagtcccccaggctccccagcaggcag aagtatgcaaagcatgcatctcaattagtcagcaaccat agtcccgccctaactccgcccatcccgcccctaactccgcccagttccgccc attctccgccccatggctgactaatttttttattt
tatgcagaggccgaggccgcctctgcctctgagctattcagaagtagtgag gaggcttttt ttggaggcctaggcttttgcaaaaagctcccgggagcttgtatatc cattttcggatctgatcagcacgtgttgacaattaatcatcggcatagt atatcggcatagtataatacgacaaggtgaggaactaaaccatggccaagttgaccagtgccgttccggtgctcaccgcgcgcgacgtcgc
cggagcggtcgagttctggaccgaccggctcgggttctcccgggacttcgtg gaggacgacttcgccggtgtggtccgggacgacgtga ccctgtt catcagcgcggtccaggaccaggtggtgccggacaacaccctggcctgg gtgtgggtgcgcggcctggacgagctgtacgcc gagtggtcggaggtcgtgtc cacgaacttccgggacgcctccgggccggc catgaccgagatcggcgagcagccgtgggggcgggag
ttcgccctgcgcgacccggccgcaactgcgtgcacttcgtggccgag gagcaggactgacacgtgctacgagatttcgattccaccgcc gccttctat gaaaggttgggcttcggaatcgttttccgggacgccggctggat gatcctccagcgcggggatctcatgctggagttcttcgcc
caccccaacttgtttattgcagcttataatggttacaaataaagcaatagcat cacaaatttcacaaataaagcatttttttcactgcattctagttgt ggtttgtccaaact catcaatgtatcttatcatgtctgtataccgtcgacctctagctagagcttggcgtaat catggtcatagctgtttcctgtgtg
aaattgttatccgctcacaattccacacaacatacgagccggaagcat aaagtgtaaagcctggggtgcctaatgagtgagctaactcacatt aat tgcgttgcgctcactgcccgctttccagtcgggaaacctgtcgtgccagctgcat taatgaatcggccaacgcgcggggagaggcggt ttgcgtattgggcgctcttccgcttcctcgct cactgactcgctgcgctcggtcgttcggctgcggcgagcggtatcagctcact
caaaggcg gtaatacggttatccacagaatcaggggataacgcaggaaagaa catgtgagcaaaaggccagcaaaaggccaggaaccgtaaaagg ccgcgttgctggcgtttttccataggctccgcccccctgacgagcat cacaaaaatcgacgctcaagtcagaggtggcgaaacccgacag gactataaa gataccaggcgtttccccctg
gaagctccctcgtgcgctctcctgttccgaccctgccgcttaccggatacctg tccgcctttct cccttcgggaagcgtggcgctttctcatagct cacgctgtaggtatctcagttcggtgtaggtcgttcgct caagctgggctgtgcacga accccccgttcagcccgaccgctgcgcct tatccggtaactatcgtcttgagtccaacccggtaagacacgacttatcgcca ctggcagcag ccactggtaacaggattagcagagcgaggtatgtaggcggtg tacagagttcttgaagtggtggcctaactacggctacactagaagaac agtat ttggtatctgcgctctgctgaagccagttaccttcggaaaaagagttggtagctctt gatccggcaaacaaaccaccgctggtagcgg
tggtttttttgtttgcaagcagcagattacgcgcagaaaaaaaggatctcaagaa-
gatcctttgatcttttctacggggtctgacgctcagtgga acgaaaactcacgt-
taagggattttggtcatgagattatcaaaaaggatcttcacctagatccttttaaat-
taaaaatgaagttttaaatcaatcta
aagtatatatgagtaaacttggtctgacagttaccaatgcttaatcagtgaggcacc-
tatctcagcgatctgtctatttcgttcatccatagttgcc tgactccccgtcgtgtaga-
taactacgatacgggagggcttaccatctggccccagtgctgcaatga-
taccgcgagacccacgctcaccgg
ctccagatttatcagcaataaaccagccagccg-
gaagggccgagcgcagaagtggtcctgcaactttatccgcctccatccagtctat-
taatt gttgccgggaagctagagtaagtagttcgccagt-
taatagtttgcgcaacgttgttgccattgctacaggcatcgtggtgtcacgctcgtcgttt
ggtatggcttcattcagctccggttcccaacgatcaaggcgagttacatgatcccc-
catgttgtgcaaaaaagcggttagctccttcggtcctc
cgatcgttgtcagaagtaagttggccgcagtgttatcactcatggt-
tatggcagcactgcataattctcttactgtcatgccatccgtaagatgct
tttctgtgactggtgagtactcaaccaagtcattct-
gagaatagtgtatgcggcgaccgagttgctcttgcccggcgtcaatacggga-
taatac cgcgccacatagcagaactttaaaagtgctcatcattg-
gaaaacgttcttcggggcgaaaactctcaaggatcttaccgctgttgagatccag
ttcgatgtaacccactcgtgcacccaactgatcttcagcatcttttacttt-
caccagcgtttctgggtgagcaaaaacaggaaggcaaaatgcc gcaaaaaagg-
gaataagggcgacacggaaatgttgaatactcatactcttcctttttcaatattatt-
gaagcatttatcagggttattgtctcatga
gcggatacatatttgaatgtatttagaaaaataaacaaataggggttccgcgcacat-
ttccccgaaaagtgccacctgac (SEQ ID NO: 7). When these NRK1-expressing cells are supplemented with NR, NAD+ levels are augmented and cell viability is enhanced to enable efficient production and purification of the constitutively active human SARM1 SAM-TIR protein fragment. To express SARM1 SAM-TIR, the SARM1 N-terminal auto-inhibitory domain was deleted, keeping only the initiator Met. Downstream from this imitator Met, the resulting protein consists of human SARM1 residues 410 to 721: MSAWSHPQFEKGGGSGGGSGG-
SAWSHPQFEKGGGSSGGGGGGSSGG-
GASVPSWKEAE VQTWLQQIGFSKY-
CESFREQQVDGDLLLRLTEEELQTDLGMKSGITR-
KRFFRELTELKTF ANYSTCDRSNLADWLGSLDPR-
FRQYTYGLVSCGLDRSLLHRVSE-
QQLLEDCGIHLGVH RARILTAA-
REMLHSPLPCTGGKPSGDTPDVFISYRRNSGSQLA-
SLLKVHLQLHGFSVFID
VEKLEAGKFEDKLIQSVMGARNFVLVLSP-
GALDKCMQDHDCKDWVHKEIVTALSCGK NIVPI-
IDGFEW-
PEPQVLPEDMQAVLTFNGIKWSHEYQEATIEKIIR-
FLQGRSSRDSSAGSD TSLEGAAPMGPT (SEQ ID NO: 8). The fragment encoding the SARM1 SAM-TIR protein was cloned into the FCIV expression construct by standard methods to generate the FCIV-SST vector. The resultant vector has the following sequence:

```
                                                     (SEQ ID NO: 9)
gtcgacggatcgggagatctcccgatcccctatggtgcactctcagtacaatctgctctgatgccgcatagt taagccagtatctgctccctgcttgtgtgttggaggtcgctgagtagtgcgcgagcaaaatttaagctacaa caaggcaaggcttgaccgacaattgcatgaagaatctgcttagggttaggcgttttgcgctgcttcgcgatg tacgggccagatatacgcgttgacattgattattgactagttattaatagtaatcaattacggggtcattag ttcatagcccatatatggagttccgcgttacataacttacggtaaatggcccgcctggctgaccgcccaacg acccccgcccattgacgtcaataatgacgtatgttcccatagtaacgccaatagggactttccattgacgtc aatgggtggagtatttacggtaaactgcccacttggcagtacatcaagtgtatcatatgccaagtacgcccc ctattgacgtcaatgacggtaaatggcccgcctggcattatgcccagtacatgaccttatgggactttccta cttggcagtacatctacgtattagtcatcgctattaccatggtgatgcggttttggcagtacatcaatgggc gtggatagcggtttgactcacggggatttccaagtctccaccccattgacgtcaatgggagtttgttttggc accaaaatcaacgggactttccaaaatgtcgtaacaactccgccccattgacgcaaatgggcggtaggcgtg tacggtgggaggtctatataagcagcgcgttttgcctgtactgggtctctctggttagaccagatctgagcc tgggagctctctggctaactagggaacccactgcttaagcctcaataaagcttgccttgagtgcttcaagta gtgtgtgcccgtctgttgtgtgactctggtaactagagatccctcagacccttttagtcagtgtggaaaatc tctagcagtggcgcccgaacagggacttgaaagcgaaagggaaaccagaggagctctctcgacgcaggactc ggcttgctgaagcgcgcacggcaagaggcgaggggcggcgactggtgagtacgccaaaaattttgactagcg gaggctagaaggagagagatgggtgcgagagcgtcagtattaagcgggggagaattagatcgcgatgggaaa aaattcggttaaggccagggggaaagaaaaaatataaattaaaacatatagtatgggcaagcagggagctag aacgattcgcagttaatcctggcctgttagaaacatcagaaggctgtagacaaatactgggacagctacaac catcccttcagacaggatcagaagaacttagatcattatataatacagtagcaaccctctattgtgtgcatc aaaggatagagataaaagacaccaaggaagctttagacaagatagaggaagagcaaaacaaaagtaagacca ccgcacagcaagcggccgctgatcttcagacctggaggaggagatatgagggacaattggagaagtgaatta tataaatataaagtagtaaaaattgaaccattaggagtagcacccaccaaggcaaagagaagagtggtgcag agagaaaaaagagcagtgggaataggagctttgttccttgggttcttgggagcagcaggaagcactatgggc
```

-continued gcagcgtcaatgacgctgacggtacaggccagacaattattgtctggtatagtgcagcagcagaacaatttg ctgagggctattgaggcgcaacagcatctgttgcaactcacagtctggggcatcaagcagctccaggcaaga atcctggctgtggaaagatacctaaaggatcaacagctcctggggatttggggttgctctggaaaactcatt tgcaccactgctgtgccttggaatgctagttggagtaataaatctctggaacagatttggaatcacacgacc tggatggagtgggacagagaaattaacaattacacaagcttaatacactccttaattgaagaatcgcaaaac cagcaagaaaagaatgaacaagaattattggaattagataaatgggcaagtttgtggaattggtttaacata acaaattggctgtggtatataaaattattcataatgatagtaggaggcttggtaggtttaagaatagttttt gctgtactttctatagtgaatagagttaggcagggatattcaccattatcgtttcagacccacctcccaacc ccgaggggacccgacaggcccgaaggaatagaagaagaaggtggagagagagacagagacagatccattcga ttagtgaacggatcggcactgcgtgcgccaattctgcagacaaatggcagtattcatccacaattttaaaag aaaaggggggattgggggtacagtgcaggggaaagaatagtagacataatagcaacagacatacaaactaa agaattacaaaaacaaattacaaaaattcaaaattttcgggtttattacagggacagcagagatccagtttg gttaattaagggtgcagcggcctccgcgccgggttttggcgcctcccgcgggcgccccctcctcacggcga gcgctgccacgtcagacgaagggcgcaggagcgttcctgatccttccgcccggacgctcaggacagcggcc gctgctcataagactcggccttagaaccccagtatcagcagaaggacattttaggacgggacttgggtgact ctagggcactggttttctttccagagagcggaacaggcgaggaaaagtagtcccttctcggcgattctgcgg agggatctccgtggggcggtgaacgccgatgattatataaggacgcgccgggtgtggcacagctagttccgt cgcagccgggatttgggtcgcggttcttgtttgtggatcgctgtgatcgtcacttggtgagttgcgggctgc tgggctggccggggctttcgtggccgccgggccgctcggtgggacggaagcgtgtggagagaccgccaaggg ctgtagtctgggtccgcgagcaaggttgccctgaactgggggttgggggagcgcacaaaatggcggctgtt cccgagtcttgaatggaagacgcttgtaaggcgggctgtgaggtcgttgaaacaaggtgggggcatggtgg gcggcaagaacccaaggtcttgaggccttcgctaatgcgggaaagctcttattcgggtgagatgggctgggg caccatctggggaccctgacgtgaagtttgtcactgactggagaactcgggtttgtcgtctggttgcgggg cggcagttatgcggtgccgttgggcagtgcacccgtacctttgggagcgcgcgcctcgtcgtgtcgtgacgt cacccgttctgttggcttataatgcagggtggggccacctgccggtaggtgtgcggtaggcttttctccgtc gcaggacgcagggttcgggcctagggtaggctctcctgaatcgacaggcgccggacctctggtgaggggagg gataagtgaggcgtcagtttctttggtcggttttatgtacctatcttcttaagtagctgaagctccggtttt gaactatgcgctcggggttggcgagtgtgttttgtgaagttttttaggcaccttttgaaatgtaatcatttg ggtcaatatgtaattttcagtgttagactagtaaagatctgcaggtcgactctagaaaattgtccgctaaat tctggccgttttttggctttttttgttagacgaagcttgggctgcaggtcgactctagaggatccGCCATGTCAgctTGGAGCCACCCACAATTCGAAAAAGGCGGTGGCTCAGGCGGTGGCTCAGGTGGCTCAGCTTGGAGCCACCCACAATTCGAAAAAGGCGGTGGCTCATCTGGCGGAGGTGGCGGTGGCTCATCTGGCGGAGGTGCTAGCgtgcccagctggaaggaggccgaggttcagacgtggctgcagcagatcggtttctccaagtactgc gagagcttccgggagcagcaggtggatggcgacctgcttctgcggctcacggaggaggaactccagaccgac ctgggcatgaaatcgggcatcacccgcaagaggttctttaggagctcacggagctcaagaccttcgccaac tattctacgtgcgaccgcagcaacctggcggactggctgggcagcctggacccgcgcttccgccagtacacc tacgcctggtcagctgcggcctggaccgctccctgctgcaccgcgtgtctgagcagcagctgctggaagac tgcggcatccacctgggcgtgcaccgcgcccgcatcctcacggcggccagagaaatgctacactccccgctg ccctgtactggtggcaaacccagtggggacactccagatgtcttcatcagctaccgccggaactcaggttcc cagctggccagtctcctgaaggtgcacctgcagctgcatggcttcagtgtcttcattgatgtgggagaagctg -continued gaagcaggcaagttcgaggacaaactcatccagagtgtcatgggtgcccgcaactttgtgttggtgctatca cctggagcactggacaagtgcatgcaagaccatgactgcaaggattgggtgcataaggagattgtgactgct ttaagctgcggcaagaacattgtgcccatcattgatggcttcgagtggcctgagccccaggtcctgcctgag gacatgcaggctgtgcttactttcaacggtatcaagtggtcccacgaataccaggaggccaccattgagaag atcatccgcttcctgcagggccgctcctcccgggactcatctgcaggctctgacaccagtttggagggtgct gcacccatgggtccaacctaaactctagaattcgatatcaagcttatcgataatcaacctctggattacaaa atttgtgaaagattgactggtattcttaactatgttgctccttttacgctatgtggatacgctgctttaatg cctttgtatcatgctattgcttcccgtatggctttcattttctcctccttgtataaatcctggttgctgtct ctttatgaggagttgtggcccgttgtcaggcaacgtggcgtggtgtgcactgtgtttgctgacgcaaccccc actggttggggcattgccaccacctgtcagctccttccgggactttcgctttccccctccctattgccacg gcggaactcatcgccgcctgccttgcccgctgctggacagggctcggctgttgggcactgacaattccgtg gtgttgtcggggaaatcatcgtcctttccttggctgctcgcctgtgttgccacctggattctgcgcgggacg tccttctgctacgtcccttcggccctcaatccagcggaccttccttcccgcggcctgctgccggctctgcgg cctcttccgcgtcttcgccttcgccctcagacgagtcggatctccctttgggccgcctccccgcatcgatac cgtcgacctcgagacctagaaaaacatggagcaatcacaagtagcaatacagcagctaccaatgctgattgt gcctggctagaagcacaagaggaggaggaggtgggttttccagtcacacctcaggtacctttaagaccaatg acttacaaggcagctgtagatcttagccacttttaaaagaaaaggggggactggaagggctaattcactcc caacgaagacaagatatccttgatctgtggatctaccacacacaaggctacttccctgattggcagaactac acaccagggccagggatcagatatccactgacctttggatggtgctacaagctagtaccagttgagcaagag aaggtagaagaagccaatgaaggagagaacacccgcttgttacaccctgtgagcctgcatgggatggatgac ccggagagagaagtattagagtggaggtttgacagccgcctagcatttcatcacatggcccgagagctgcat ccggactgtactgggtctctctggttagaccagatctgagcctgggagctctctggctaactagggaaccca ctgcttaagcctcaataaagcttgccttgagtgcttcaagtagtgtgtgcccgtctgttgtgtgactctggt aactagagatccctcagacccttttagtcagtgtggaaaatctctagcagggcccgtttaaacccgctgatc agcctcgactgtgccttctagttgccagccatctgttgtttgcccctcccccgtgccttccttgaccctgga aggtgccactcccactgtcctttcctaataaaatgaggaaattgcatcgcattgtctgagtaggtgtcattc tattctggggggtggggtggggcaggacagcaaggggggaggattgggaagacaatagcaggcatgctgggga tgcggtgggctctatggcttctgaggcggaaagaaccagctggggctctaggggtatccccacgcgccctg tagcggcgcattaagcgcggcgggtgtggtggttacgcgcagcgtgaccgctacacttgccagcgccctagc gcccgctcctttcgctttcttcccttcctttctcgccacgttcgccggctttccccgtcaagctctaaatcg gggctccctttagggttccgatttagtgctttacggcacctcgaccccaaaaaacttgattagggtgatgg ttcacgtagtgggccatcgccctgatagacggttttcgccctttgacgttggagtccacgttctttaatag tggactcttgttccaaactggaacaacactcaaccctatctcggtctattctttgatttataagggatttt gccgatttcggcctattggttaaaaaatgagctgatttaacaaaaatttaacgcgaattaattctgtggaat gtgtgtcagttagggtgtggaaagtccccaggctccccagcaggcagaagtatgcaaagcatgcatctcaat tagtcagcaaccaggtgtggaaagtccccaggctccccagcaggcagaagtatgcaaagcatgcatctcaat tagtcagcaaccatagtcccgcccctaactccgcccatcccgcccctaactccgcccagttccgcccattct ccgccccatggctgactaatttttttatttatgcagaggccgaggccgcctctgcctctgagctattccag aagtagtgaggaggcttttttggaggcctaggcttttgcaaaaagctcccgggagcttgtatatccatttc ggatctgatcagcacgtgttgacaattaatcatcggcatagtatatcggcatagtataatacgacaaggtga ggaactaaaccatggccaagttgaccagtgccgttccggtgctcaccgcgcgcgacgtcgccggagcggtcg -continued

```
agttctggaccgaccggctcgggttctcccgggacttcgtggaggacgacttcgccggtgtggtccgggacg
acgtgaccctgttcatcagcgcggtccaggaccaggtggtgccggacaacaccctggcctgggtgtgggtgc
gcggcctggacgagctgtacgccgagtggtcggaggtcgtgtccacgaacttccgggacgcctccgggccgg
ccatgaccgagatcggcgagcagccgtgggggcgggagttcgccctgcgcgacccggccggcaactgcgtgc
acttcgtggccgaggagcaggactgacacgtgctacgagatttcgattccaccgccgccttctatgaaggt
tgggcttcggaatcgttttccgggacgccggctggatgatcctccagcgcggggatctcatgctggagttct
tcgcccaccccaacttgtttattgcagcttataatggttacaaataaagcaatagcatcacaaatttcacaa
ataaagcattttttcactgcattctagttgtggtttgtccaaactcatcaatgtatcttatcatgtctgta
taccgtcgacctctagctagagcttggcgtaatcatggtcatagctgtttcctgtgtgaaattgttatccgc
tcacaattccacacaacatacgagccggaagcataaagtgtaaagcctggggtgcctaatgagtgagctaac
tcacattaattgcgttgcgctcactgcccgctttccagtcgggaaacctgtcgtgccagctgcattaatgaa
tcggccaacgcgcggggagaggcggtttgcgtattgggcgctcttccgcttcctcgctcactgactcgctgc
gctcggtcgttcggctgcggcgagcggtatcagctcactcaaaggcggtaatacggttatccacagaatcag
gggataacgcaggaaagaacatgtgagcaaaaggccagcaaaaggccaggaaccgtaaaaaggccgcgttgc
tggcgtttttccataggctccgcccccctgacgagcatcacaaaaatcgacgctcaagtcagaggtggcgaa
acccgacaggactataaagataccaggcgtttccccctggaagctccctcgtgcgctctcctgttccgaccc
tgccgcttaccggatacctgtccgcctttctcccttcgggaagcgtggcgctttctcatagctcacgctgta
ggtatctcagttcggtgtaggtcgttcgctccaagctgggctgtgtgcacgaaccccccgttcagcccgacc
gctgcgccttatccggtaactatcgtcttgagtccaacccggtaagacacgacttatcgccactggcagcag
ccactggtaacaggattagcagagcgaggtatgtaggcggtgctacagagttcttgaagtggtggcctaact
acggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgc
gcagaaaaaaaggatctcaagaagatcctttgatcttttctacggggtctgacgctcagtggaacgaaaact
cacgttaagggattttggtcatgagattatcaaaaaggatcttcacctagatccttttaaattaaaaatgaa
gttttaaatcaatctaaagtatatatgagtaaacttggtctgacagttaccaatgcttaatcagtgaggcac
ctatctcagcgatctgtctatttcgttcatccatagttgcctgactccccgtcgtgtagataactacgatac
gggagggcttaccatctggccccagtgctgcaatgataccgcgagacccacgctcaccggctccagatttat
cagcaataaaccagccagccggaagggccgagcgcagaagtggtcctgcaactttatccgcctccatccagt
ctattaattgttgccgggaagctagagtaagtagttcgccagttaatagtttgcgcaacgttgttgccattg
ctacaggcatcgtggtgtcacgctcgtcgtttggtatggcttcattcagctccggttcccaacgatcaaggc
gagttacatgatcccccatgttgtgcaaaaaagcggttagctccttcggtcctccgatcgttgtcagaagta
agttggccgcagtgttatcactcatggttatggcagcactgcataattctcttactgtcatgccatccgtaa
gatgcttttctgtgactggtgagtactcaaccaagtcattctgagaatagtgtatgcggcgaccgagttgct
cttgcccggcgtcaatacgggataataccgcgccacatagcagaactttaaaagtgctcatcattggaaaac
gttcttcggggcgaaaactctcaaggatcttaccgctgttgagatccagttcgatgtaacccactcgtgcac
ccaactgatcttcagcatcttttactttcaccagcgtttctgggtgagcaaaaacaggaaggcaaaatgccg
caaaaaagggaataagggcgacacggaaatgttgaatactcatactcttcctttttcaatattattgaagca
tttatcagggttattgtctcatgagcggatacatatttgaatgtatttagaaaaataaacaaataggggttc
cgcgcacatttccccgaaaagtgccacctgac.
```

NRK1-HEK293T cells were seeded onto 150 cm² plates at 20×10⁶ cells per plate in 25 mL growth medium comprised of 90% DMEM (Gibco 11965-084) and 10% FBS (Sigma F0926). The next day, cells were transfected by first premixing 15 ug FCIV-SST SST (SAM-TIR expression plasmid from Washington University) with 45 ul X-tremeGENE 9 DNA Transfection Reagent (Roche product #06365787001) and 750 ul OptiMEM (Gibco 31985062) and then adding this mix directly to the cells. The cultures were supplemented with 1 mM nicotinamide riboside (Thorne Research THR-00467) at time of transfection to minimize toxicity from SAM-TIR overexpression. Forty-eight hours after transfection, cells were harvested, pelleted by centrifugation at 1,000 rpm (Eppendorf Centrifuge 5804R, 15 Amp Version), and washed once with cold PBS (0.01 M phosphate buffered saline NaCl 0.138 M; KCl 0.0027 M; pH 7.4). The cells were resuspended in 0.5 ml PBS with protease inhibitors (Complete protease inhibitor cocktail, Roche product #11873580001). Cell lysates were prepared by sonication (Misonix Microson Ultrasonic Cell Disruptor, output=3, 20 episodes of stroke). The lysates were centrifuged at 12,000×g for 10 min at 4° C. (Eppendorf Centrifuge 5415C) to remove cell debris and the aliquots of supernatant (containing SARM1 SAM-TIR protein) were stored at −80° C. for later use. Protein concentration was determined by the Bicinchoninic (BCA) method and used to normalize lysate concentrations.

Assay 2. Luminescence-Based Assay (NAD GLo)

This assay is an adaptation of the NAD+/NADH Glo assay (Promega G9071). In this assay, NAD+ cycling enzymes convert NAD+ into NADH. In the presence of NADH, the reductase enzymatically converts a pro-luciferin reductase substrate into luciferin. Luciferin is detected using Ultra-Glo™ rLuciferase, and the chemiluminescence intensity is proportional to the amount of NAD+ and NADH in the sample. In our assay conditions, the amount of NAD+ and NADH present in the lysate is undetectable with this assay, precluding any endogenous contribution to the final NAD+ detected. The assay was set up as follows: 2 μl inhibitor (final concentration 1 μM, 2% DMSO), 0.07 μg lysate (2 μl), and 2 μl of 400 nM NAD+. The reaction was incubated at 37° C. for 60 min, then 6 μl NAD+/NADH Glo detection reagent was added. After 30 min at room temperature, the luminescent signals were quantified using an Analyst HT reader (LJL Biosystems). The SARM1 SAM-TIR lysate catalyzed a dose-dependent depletion of NAD+, whereas NAD+ levels did not decline when reactions were performed with lysate prepared from control NRK1-HEK293T cells.

Assay 3. HPLC-Based Assay 2

Reaction mixtures were prepared on ice by mixing 10 ul of SARM1 SAM-TIR cell lysate (320 fold dilution of lysate 11-3-2016, or 80 fold lysate dilution for assessment of time dependence) in PBS (pH 7.4) with 5 ul of compound stock. Compounds were first dissolved DMSO at 10 mM (final stock concentration). A 10 point compound dilution curve was prepared first with a 20 ul to 40 ul serial dilution in DMSO, followed by a 10 fold dilution (12 ul+108 ul) in PBS. Top concentration of compound in the assay is 250 uM. Compound and lysate were then preincubated, in duplicate, for various amounts of time (zero or 120 minutes for analysis of time dependence). 5 ul of 20 uM NAD$^+$ (5 μM final concentration) was then added for a final reaction volume of 20 μl. The reaction was incubated at 37° C. for 60 (or 10 minutes @ room temp for assessment of time dependence), then stopped by addition of 180 μl of 0.55 M perchloric acid (HClO$_4$). The reactions were then place on for 10 min, 16.6 μl of 3 M K$_2$CO$_3$ was added to neutralize the solution. Precipitated salts were removed by centrifugation 10 min at 4,000 rpm (Sorvall ST 16R centrifuge). 80 ul of the supernatant was analyzed by HPLC (Waters 2695) with Kinetex (50×4.6 mm, 5 μm; Phenomenex). NAD and metabolites were eluted with a 1 ml/min gradient from 100% A: KPO$_4$ (5.026 g K$_2$HPO$_4$ and 2.876 KH$_2$PO$_4$ in 1 L H2O) to 3% methanol in 1 minute, followed by a linear gradient to 15% methanol in 1.5 minutes, held for 1 minute before returning to 0% methanol for 2.5 minutes for re-equilibration. NAD (3 minutes) and ADPR (1.5 min) were monitored by absorbance at 260 nm. Percent control conversion was established for each compound concentration. Blank (no lysate NAD only) values for ADPR were subtracted from samples and control (lysate+NAD) and control values from NAD depletion were subtracted from samples and blank to determine maximal ADPR conversion or NAD depletion (lysate dilutions used typically produced about a 50% conversion). Blanks and controls were run in triplicate (or more) then averaged. Duplicate data points from the 10 point dose curves were plotted using Grafit and IC$_{50}$'s were calculated using a 4 Parameter log fit.

Example 11

Synthesis of Compound I$^A$-6.

Compound I$^A$-6 was prepared in accordance with Scheme 1$^A$, supra. The sidechain was prepared according to Scheme 2$^A$, below.

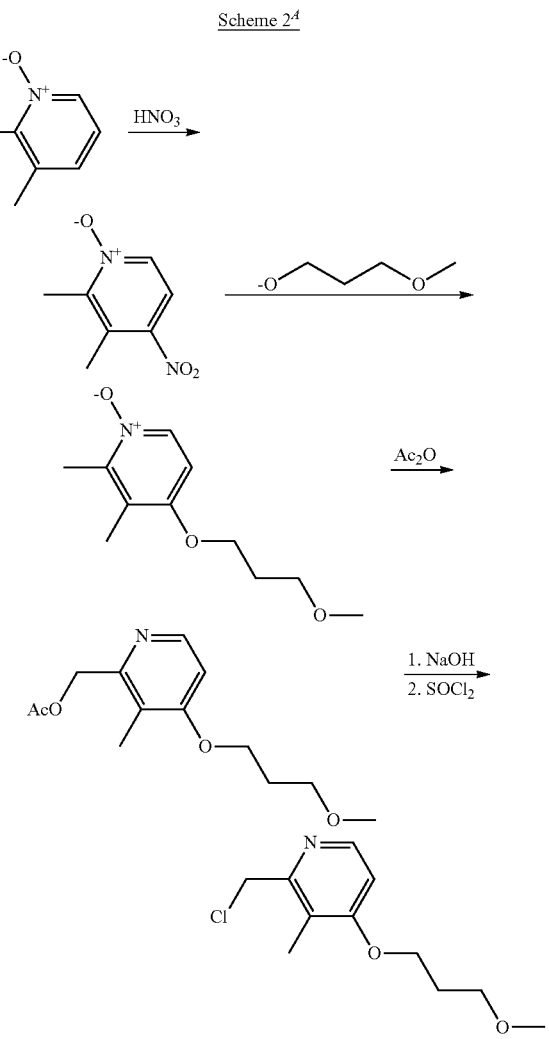

Scheme 2$^A$

This molecule was then used to prepare Compound I⁴-6 in accordance with Scheme I⁴, supra. The synthetic route is shown below.

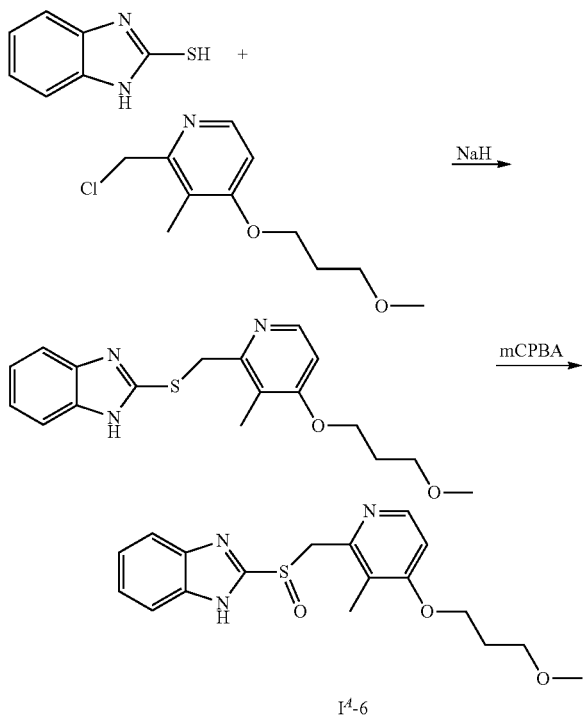

Example 12

10 Point Dose Curves of SARM1 NADase Activity Inhibition with Compounds I⁴-2, I⁴-3, I⁴-6 and I⁴-8.

Compounds I⁴-2, I⁴-3, I⁴-6 and I⁴-8 demonstrate inhibition of SARM1 NADase activity, as shown in FIG. 33. Assay 3 (HPLC-based assay 2), described above, was used to assess NAD consumption and ADPR production from duplicate samples of a 10 point compound curve (average of n=2) ranging from 0.01-250 uM of compounds I⁴-2, I⁴-3, I⁴-6 and I⁴-8. The results are shown in FIG. 33, whereby FIG. 33A shows NAD consumption as a function of concentration of compounds I⁴-2, I⁴-3, I⁴-6 and I⁴-8 and FIG. 33B shows ADPR production as a function of concentration of compounds I⁴-2, I⁴-3, I⁴-6 and I⁴-8. As can be seen, increasing concentration of these compound I⁴-6 from 0.01-250 uM leads to higher NAD consumption and lower ADPR production. The IC₅₀ for these compounds in Assay 3 are provided below in Table 5⁴.

TABLE 5⁴

IC₅₀ Values for SARM1 NADase Activity Inhibition with Compounds I⁴-2, I⁴-3, I⁴-6 and I⁴-8.

| Compound | IC₅₀ (μM, NAD Consumption) | IC₅₀ (μM, ADPR Production) |
|---|---|---|
| I⁴-2 | 3.5 | 3.3 |
| I⁴-3 | 21.4 | 28.3 |
| I⁴-6 | 3.3 | 3.2 |
| I⁴-8 | 7.4 | 8.7 |

Example 13

Screening of SARM1 NADase Activity Inhibition with Compounds I⁴-3, I⁴-8, I⁴-9, I⁴-10, and I⁴-13.

Compounds I⁴-3, I⁴-8, I⁴-9, I⁴-10, I⁴-11 and I⁴-13 demonstrates inhibition of SARM1 NADase activity, as shown below in Table 6⁴. Assay 3 (HPLC-based assay), described above, was used to assess NAD consumption and ADPR production from duplicate samples of a single point screening (average of n=2) at 150 μM of each of Compounds I⁴-3, I⁴-8, I⁴-9, I⁴-10, I⁴-11 and I⁴-13. In Table 6⁴, Compounds I⁴-3, I⁴-8, I⁴-9, I⁴-10, I⁴-11 and I⁴-13 are categorized by their ability to control NAD consumption, with "A" indicating >75%, "B" indicating between 50%-75% and "C" indicating <50%. Compounds I⁴-3, I⁴-8, I⁴-9, I⁴-10, I⁴-11 and I⁴-13 are also categorized by their ability to control ADPR production, with "A" indicating >75%, "B" indicating between 50%-75% and "C" indicating <50%.

TABLE 6⁴

Single Point Screens of SARM1 NADase Activity Inhibition with Compounds I⁴-3, I⁴-8, I⁴-9, I⁴-10, I⁴-11 and I⁴-13.

| Compound | NAD Consumption (%) | ADPR Production (%) |
|---|---|---|
| I⁴-3 | A | C |
| I⁴-8 | B | C |
| I⁴-9 | A | A |
| I⁴-10 | A | A |
| I⁴-11 | A | A |
| I⁴-13 | A | B |

Without wishing to be bound by any particular theory, it is believed that the compounds of Formula I⁴ described herein may act by a unique mechanism that requires double protonation (in parietal cells which have pH of ~1), followed by rearrangement to an activated tetracyclic intermediate which rapidly inactivates the H+-K+ ATPase. This is believed to arise from a precise arrangement of the sulfoxide group of the compounds of Formula I⁴ to the two activated rings of the compounds of Formula I⁴. The data presented herein is indicative of a subtle SAR/discrimination with the benzimidazole-pyridine-sulfoxide scaffold of the compounds of Formula I⁴ and inhibition of SARM1 NADase activity.

Example 14

Synthesis of Compound I^B-1.

Compound I^B-1 was prepared in accordance with Scheme 1^B, supra. The synthetic route is shown below.

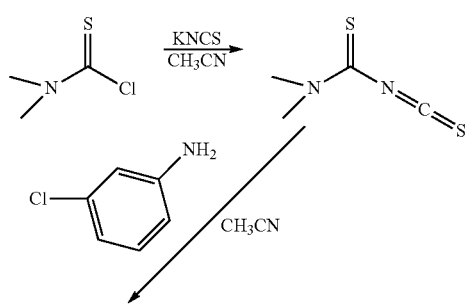

-continued

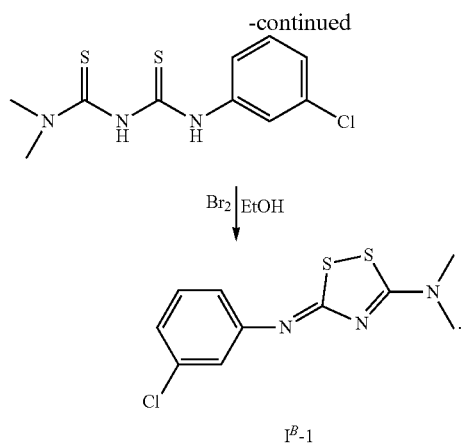

I$^B$-1

Example 15

Synthesis of Compound I$^B$-2.

Compound I$^B$-2 was prepared in accordance with Scheme 1$^B$, supra. The synthetic route is shown below.

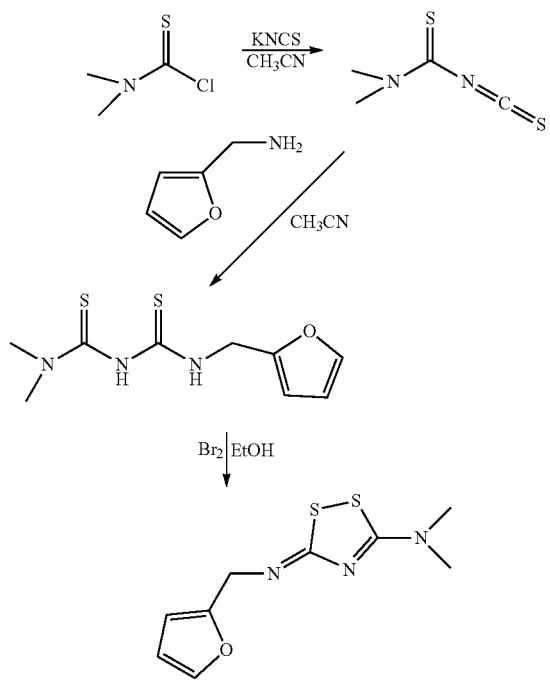

Example 16

Dose Curves of SARM1 NADase Activity Inhibition with Compounds I$^B$-1 and I$^B$-2

Compounds I$^B$-1 and I$^B$-2 demonstrate inhibition of SARM1 NADase activity, as shown in FIG. 34. Assay 3 (HPLC-based assay), described above, was used to assess NAD consumption from duplicate samples of a 7 point compound curve (average of n=2) ranging from 0-about 6 uM of compounds I$^B$-1 and I$^B$-2. The results are shown in FIG. 34, whereby it is shown that NADase activity decreases with increasing concentration of compounds I$^B$-1 and I$^B$-2. The upper curve represents compound I$^B$-1 and the lower curve represents I$^B$-2. The IC$_{50}$ for compound I$^B$-2 in Assay 3 was determined to be about 150 nM and the IC$_{50}$ for compound I$^B$-1 in Assay 3 was determined to be about 0.7 µM.

Example 17

Prevention of Axonal Degeneration with Compound I$^B$-2.

Mouse DRG Drop Culture: Mouse dorsal root ganglion (DRG) was dissected from embryonic days 13.5 CD1 mouse embryo (50 ganglion per embryo) and incubated with 0.05% Trypsin solution containing 0.02% EDTA (Gibco) at 37° C. for 15 min. Then cell suspensions are triturated by gentle pipetting and washed 3 times with the DRG growth medium (Neurobasal medium (Gibco) containing 2% B27 (Invitrogen), 100 ng/ml 2.5S NGF (Harlan Bioproduts), 1 mM uridine (Sigma), 1 mM 5-fluoro-2'-deoxyuridine (Sigma), penicillin, and streptomycin). Cells were suspended in DRG growth medium at a ratio of 100 ml medium/50 DRGs. The cell density of these suspensions was ~7×10$^6$ cells/ml. Cell suspensions (1.5 ml/96 well, 10 ml/24 well) were placed in the center of the well using either 96- or 24-well tissue culture plates (Corning) coated with poly-D-Lysine (0.1 mg/ml; Sigma) and laminin (3 mg/ml; Invitrogen). Cells were allowed to adhere in humidified tissue culture incubator (5% CO$_2$) for 15 min and then DRG growth medium was gently added (100 ml/96 well, 500 ml/24 well). Lentiviruses were added (1-10×10$^3$ pfu) at 1-2 days in vitro (DIV) and metabolites were extracted or axon degeneration assays were performed at 6-7 DIV. When using 24 well DRG cultures, 50% of the medium was exchanged for a fresh medium at DIV4. NR (100 mM) was added 24 hr before axotomy or metabolite collection.

Axon Denegeneration Assay: Axons from DRG drop cultures in 96 well were transected using a micro surgical blade under micro-scope at DIVE. Bright field images of distal axons (6 fields per well) were taken at 0-72 hr after axotomy using a high content imager (Operetta; Perkinelmer) with 20× objective. Axon degeneration was quantified using degeneration index (DI) calculated using ImageJ (NIH). The average DI from 6 fields per well was obtained and averaged for each independent well. The DI was calculated from axon images from the same fields before (0 hr) and after (9-72 hr) axotomy. Experiments were repeated 3 times with 3 independent wells (n=9). For statistical analysis, DI was compared using one-way ANOVA and Holm-Bonferroni multiple comparison using R (RRID:SCR 002394). Data from this experiment is represented below as a bar graph in FIG. 35 and the images are shown in FIG. 36.

Compound I$^B$-2 demonstrates prevention of axonal degeneration in a mouse dorsal root ganglion (DRG) drop culture assay, as described above. FIG. 35 shows a control sample (grouping on left side of FIG. 35) and a sample that includes compound I$^B$-2 (grouping on right side of FIG. 35) and the level of axonal degeneration after exposure to both samples at intervals of 0 hours, 6 hours, 12 hours and 24 hours. As can be seen, axons exposed to compound I$^B$-2 showed a substantial decrease in axonal degeneration compared to the control sample after intervals of 6 hours, 12 hours and 24 hours.

FIG. 36 shows SEM micrographs of injured axons under degenerating conditions with (FIG. 36A) and without (FIG. 36B) exposure to compound I$^B$-2. As can be seen, axons exposed to compound I$^B$-2 were intact under degenerating conditions, whereas axons not exposed to compound I$^B$-2 were degenerated.

Example 18

The present Example demonstrates successful development of an in vitro assay using a full-length SARM1. The assay described in this Example can be used, for example, to identify and/or characterize compounds that inhibit full-length SARM1 in vivo.

Cells expressing SARM1 show decreased expression after extended growth. NAD+ levels are lower in SARM1-expressing cells, but these cells do not die. Moreover, a C-terminal GFP tag decreased SARM1 NADase activity. The presently described assay overcame these challenges.

Full-length SARM1 lacking the mitochondrial targeting sequence (MTS) (FL-MTS SARM1) was produced and tested as described below.

Production of Affinity Tagged FL-MTS SARM1.

NRK1-HEK293T cells represent a polyclonal cell line that has been stably transfected with an FCIV expression vector that expresses human Nicotinamide Riboside Kinase 1 (NRK1), an enzyme that converts the NAD+ biosynthetic precursor nicotinamide riboside (NR) to NMN, the immediate precursor of NAD+. When these NRK1-expressing cells are supplemented with NR, NAD+ levels are augmented and cell viability is enhanced to enable efficient production and purification of SARM1.

For these experiments, human SARM1 lacking the first 26 residues, which correspond to the SARM1 mitochondrial targeting sequence, was engineered with a StrepTag affinity tag on the N-terminus (referred to as FL-MTS SARM1; see FIG. 37A). This modified SARM1 protein was cloned into the lentiviral vector FCIV to generate an FL-MTS SARM1 mammalian expression vector. A similar construct was generated in which the catalytic Glu residue at SARM1 position 642 was changed to Ala. This inactive mutant FL-MTS SARM1(E642A) was used as a negative control in assays described in this Example. Finally, an active SARM1 mutant (SAM-TIR) was similarly constructed with an N-terminal StrepTag fused to SARM1 residues 409-724 and used as a positive control in these assays.

To produce the StrepTag-FL-MTS SARM1 and StrepTag-FL-MTS SARM1(E642A) or the active SARM1 SAM-TIR protein, NRK1-HEK293T cells were seeded onto 150 cm$^2$ plates at 20×10$^6$ cells per plate. The next day, the cells were transfected with 15 µg FCIV-FL-MTS SARM1 or FCIV FL-MTS SARM1(E642A) or SARM1 SAM-TIR expression vector using X-tremeGENE 9 DNA Transfection Reagent (Roche product #06365787001). The cultures were supplemented with 1 mM NR at the time of transfection to minimize toxicity from SARM1 protein expression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (Complete protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants containing the affinity-tagged FL-MTS SARM1 or FL-MTS SARM1(E642A) or SARM1 SAM-TIR protein were stored at −80° C. for later use. For affinity purification, the supernatants were incubated with 100 µL MagStrep (Strep-Tactin) type 3 XT beads suspension (IBA Lifesciences) for 30 min. The beads bound with FL-MTS SARM1 or FL-MTS SARM1(E642A) or SARM1 SAM-TIR protein were then washed three times with binding buffer and resuspended in 100 µL of binding buffer for enzymatic assays.

Assaying for NAD Cleavage Activity

Reaction mixtures were prepared using MagStrep beads laden with affinity tagged FL-MTS SARM1 or FL-MTS SARM1(E642A) protein (1 to 30 ng on 1-4 ul of beads or the active SAM-TIR protein (0.25 ng) and PBS (pH 7.4) to a final volume of 12 µl. NAD (5 final concentration) was then added for a final reaction volume of 20 µl. The reaction was incubated at 37° C. for 60 min, and then stopped by addition of 180 µl of 0.55 M perchloric acid (HClO$_4$) and placed on ice. After 10 min on ice, the reaction plates were centrifuged for 10 min at 4,000 rpm (Sorvall ST 16R centrifuge). The supernatant (120 µl) was transferred to a new plate and 10 µl of 3M K2CO3 was added to neutralize the solution. Precipitated salts were removed by centrifugation for 10 min at 4,000 rpm (Sorvall ST 16R centrifuge). The supernatant (90 µl) containing the extracted metabolites was mixed with 0.5 M Potassium Phosphate buffer (10 µL) and metabolites were analyzed by HPLC (Shimadzu Nexera X2) with C18 reverse phase column (Kinetex 100×3 mm, 2.6 µm; Phenomenex) to quantify the amounts of NAD and ADPR, a product of the NAD cleavage reaction. Internal standards for NAD and ADPR were used to generate standard curves for quantification of the respective compounds. The levels for each compound in each experimental sample were normalized to the 0 min time point that was analyzed concurrently. From these values, the NAD/ADPR ratio was calculated as a measure of NAD cleavage activity.

FIG. 37B shows HPLC traces from an assay, with peaks corresponding to NAD, NAM, and ADPR delineated with arrows. As shown in FIGS. 37C and 37D, full-length SARM1 showed significantly lower NADase activity than SAM-TIR, while the FL SARM1 E642A mutant had significantly lower NADase activity than full-length SARM1.

Thus, the presently described assay successfully measures NADase activity using full-length SARM1.

While we have described a number of embodiments of this disclosure, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

We claim:

1. A method of inhibiting SARM1 NADase activity, comprising contacting SARM1 with a SARM1 NADase inhibitor, wherein the SARM1 NADase inhibitor is a compound of formula $I^A$:

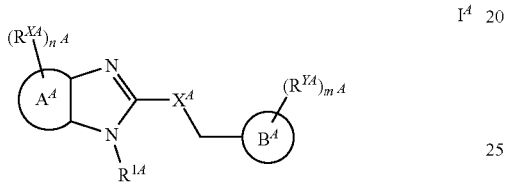

or a pharmaceutically acceptable salt thereof, wherein:

$X^A$ is —S—, —SO— or —SO$_2$—;

$R^{1A}$ is hydrogen, $C_{1-4}$ aliphatic, alkali metal, alkaline earth metal, ammonium or $N^+(C_{1-4}alkyl)_4$;

Ring $A^A$ is selected from a benzo fused ring and a 5-6 membered heteroaromatic fused ring having 1-3 heteroatoms independently selected from nitrogen, oxygen, and sulfur;

Ring $B^A$ is selected from phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^{XA}$ and $R^{YA}$ are independently hydrogen, $C_{1-4}$ aliphatic optionally substituted with 1-4 halogen, —OR$^A$, —SR$^A$, —N(R$^A$)$_2$, —N(R$^A$)C(O)R$^A$, —C(O)N(R$^A$)$_2$, —N(R$^A$)C(O)N(R$^A$)$_2$, —N(R$^A$)C(O)OR$^A$, —OC(O)N(R$^A$)$_2$, —N(R)S(O)$_2$R$^A$, —S(O)$_2$N(R$^A$)$_2$, —C(O)R$^A$, —C(O)OR$^A$, —OC(O)R$^A$, —S(O)R$^A$, —S(O)$_2$R$^A$, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^A$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

$m^A$ and $n^A$ are independently 0, 1, 2, or 3.

2. The method according to claim 1, wherein the compound of formula $I^A$ is selected from the group consisting of:

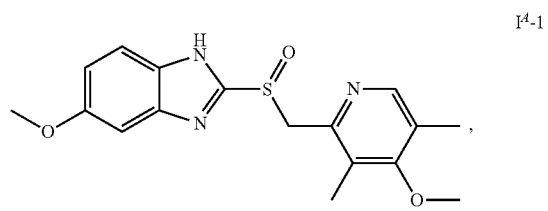

$I^A$-1

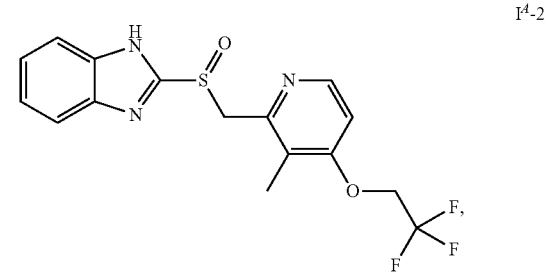

$I^A$-2

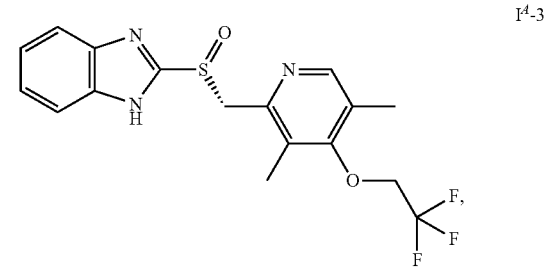

$I^A$-3

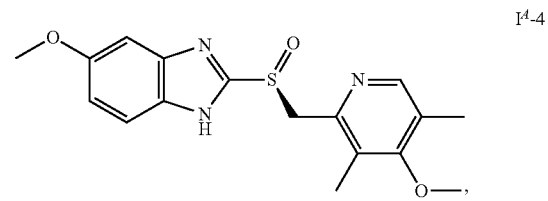

$I^A$-4

-continued
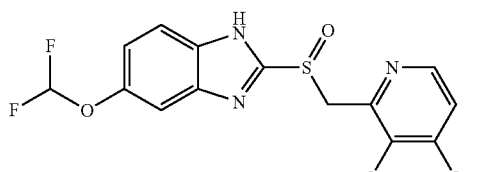
I⁴-5
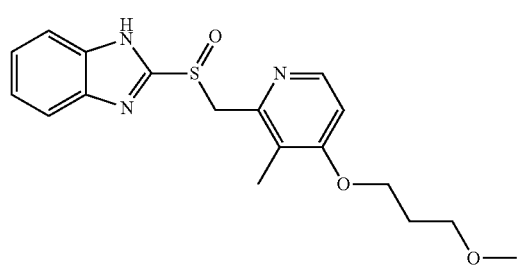
I⁴-6
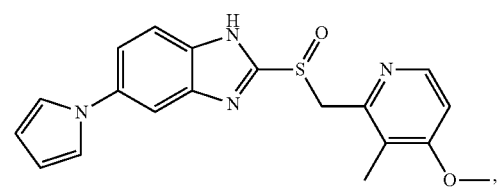
I⁴-7
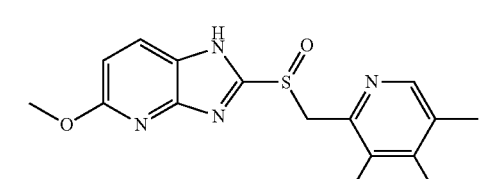
I⁴-8
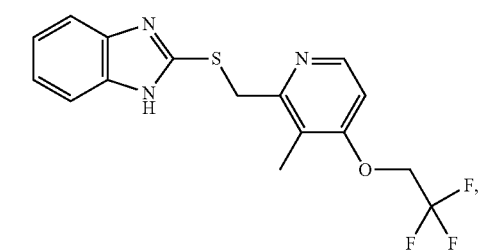
I⁴-9
-continued
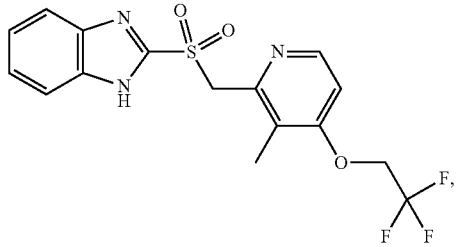
I⁴-10
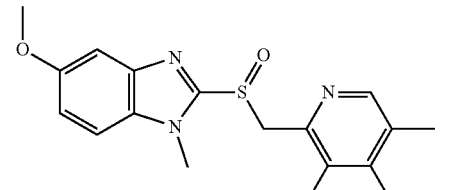
I⁴-11
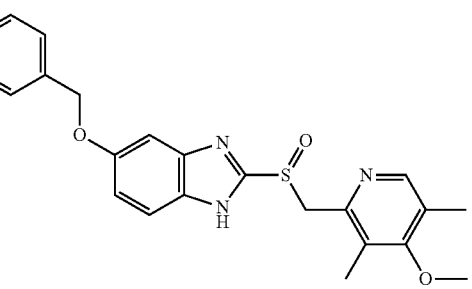
I⁴-12
and
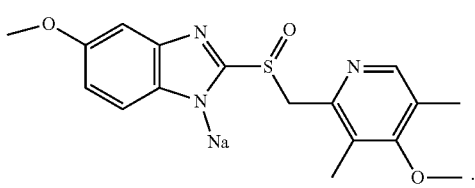
I⁴-13
3. The method according to claim 1, wherein the SARM1 NADase inhibitor is a proton pump inhibitor.
* * * * *

SEQUENCE LISTING

```
<160> NUMBER OF SEQ ID NOS: 16

<210> SEQ ID NO 1
<211> LENGTH: 316
<212> TYPE: PRT
<213> ORGANISM: Homo sapiens

<400> SEQUENCE: 1
```

-continued

```
Val Pro Ser Trp Lys Glu Ala Glu Val Gln Thr Trp Leu Gln Gln Ile
1               5                   10                  15

Gly Phe Ser Lys Tyr Cys Glu Ser Phe Arg Glu Gln Val Asp Gly
            20                  25                  30

Asp Leu Leu Leu Arg Leu Thr Glu Glu Leu Gln Thr Asp Leu Gly
        35                  40                  45

Met Lys Ser Gly Ile Thr Arg Lys Arg Phe Phe Arg Glu Leu Thr Glu
50                  55                  60

Leu Lys Thr Phe Ala Asn Tyr Ser Thr Cys Asp Arg Ser Asn Leu Ala
65                  70                  75                  80

Asp Trp Leu Gly Ser Leu Asp Pro Arg Phe Arg Gln Tyr Thr Tyr Gly
                85                  90                  95

Leu Val Ser Cys Gly Leu Asp Arg Ser Leu Leu His Arg Val Ser Glu
            100                 105                 110

Gln Gln Leu Leu Glu Asp Cys Gly Ile His Leu Gly Val His Arg Ala
        115                 120                 125

Arg Ile Leu Thr Ala Ala Arg Glu Met Leu His Ser Pro Leu Pro Cys
130                 135                 140

Thr Gly Gly Lys Pro Ser Gly Asp Thr Pro Asp Val Phe Ile Ser Tyr
145                 150                 155                 160

Arg Arg Asn Ser Gly Ser Gln Leu Ala Ser Leu Leu Lys Val His Leu
                165                 170                 175

Gln Leu His Gly Phe Ser Val Phe Ile Asp Val Glu Lys Leu Glu Ala
            180                 185                 190

Gly Lys Phe Glu Asp Lys Leu Ile Gln Ser Val Met Gly Ala Arg Asn
        195                 200                 205

Phe Val Leu Val Leu Ser Pro Gly Ala Leu Asp Lys Cys Met Gln Asp
210                 215                 220

His Asp Cys Lys Asp Trp Val His Lys Glu Ile Val Thr Ala Leu Ser
225                 230                 235                 240

Cys Gly Lys Asn Ile Val Pro Ile Ile Asp Gly Phe Glu Trp Pro Glu
                245                 250                 255

Pro Gln Val Leu Pro Glu Asp Met Gln Ala Val Leu Thr Phe Asn Gly
            260                 265                 270

Ile Lys Trp Ser His Glu Tyr Gln Glu Ala Thr Ile Glu Lys Ile Ile
        275                 280                 285

Arg Phe Leu Gln Gly Arg Ser Ser Arg Asp Ser Ser Ala Gly Ser Asp
290                 295                 300

Thr Ser Leu Glu Gly Ala Ala Pro Met Gly Pro Thr
305                 310                 315

<210> SEQ ID NO 2
<211> LENGTH: 164
<212> TYPE: PRT
<213> ORGANISM: Homo sapiens

<400> SEQUENCE: 2

Thr Pro Asp Val Phe Ile Ser Tyr Arg Arg Asn Ser Gly Ser Gln Leu
1               5                   10                  15

Ala Ser Leu Leu Lys Val His Leu Gln Leu His Gly Phe Ser Val Phe
            20                  25                  30

Ile Asp Val Glu Lys Leu Glu Ala Gly Lys Phe Glu Asp Lys Leu Ile
        35                  40                  45

Gln Ser Val Met Gly Ala Arg Asn Phe Val Leu Val Leu Ser Pro Gly
```

-continued

```
                    50                  55                  60
Ala Leu Asp Lys Cys Met Gln Asp His Asp Cys Lys Asp Trp Val His
 65                  70                  75                  80

Lys Glu Ile Val Thr Ala Leu Ser Cys Gly Lys Asn Ile Val Pro Ile
                 85                  90                  95

Ile Asp Gly Phe Glu Trp Pro Glu Pro Gln Val Leu Pro Glu Asp Met
                100                 105                 110

Gln Ala Val Leu Thr Phe Asn Gly Ile Lys Trp Ser His Glu Tyr Gln
            115                 120                 125

Glu Ala Thr Ile Glu Lys Ile Ile Arg Phe Leu Gln Gly Arg Ser Ser
        130                 135                 140

Arg Asp Ser Ser Ala Gly Ser Asp Thr Ser Leu Glu Gly Ala Ala Pro
145                 150                 155                 160

Met Gly Pro Thr

<210> SEQ ID NO 3
<211> LENGTH: 164
<212> TYPE: PRT
<213> ORGANISM: Mus sp.

<400> SEQUENCE: 3

Thr Pro Asp Val Phe Ile Ser Tyr Arg Arg Asn Ser Gly Ser Gln Leu
 1               5                  10                  15

Ala Ser Leu Leu Lys Val His Leu Gln Leu His Gly Phe Ser Val Phe
                20                  25                  30

Ile Asp Val Glu Lys Leu Glu Ala Gly Lys Phe Glu Asp Lys Leu Ile
            35                  40                  45

Gln Ser Val Ile Ala Ala Arg Asn Phe Val Leu Val Leu Ser Ala Gly
        50                  55                  60

Ala Leu Asp Lys Cys Met Gln Asp His Asp Cys Lys Asp Trp Val His
 65                  70                  75                  80

Lys Glu Ile Val Thr Ala Leu Ser Cys Gly Lys Asn Ile Val Pro Ile
                 85                  90                  95

Ile Asp Gly Phe Glu Trp Pro Glu Pro Gln Ala Leu Pro Glu Asp Met
                100                 105                 110

Gln Ala Val Leu Thr Phe Asn Gly Ile Lys Trp Ser His Glu Tyr Gln
            115                 120                 125

Glu Ala Thr Ile Glu Lys Ile Ile Arg Phe Leu Gln Gly Arg Pro Ser
        130                 135                 140

Gln Asp Ser Ser Ala Gly Ser Asp Thr Ser Leu Glu Gly Ala Thr Pro
145                 150                 155                 160

Met Gly Leu Pro

<210> SEQ ID NO 4
<211> LENGTH: 160
<212> TYPE: PRT
<213> ORGANISM: Danio rerio

<400> SEQUENCE: 4

Pro Asp Val Phe Ile Ser Tyr Arg Arg Thr Thr Gly Ser Gln Leu Ala
 1               5                  10                  15

Ser Leu Leu Lys Val His Leu Gln Leu Arg Gly Phe Ser Val Phe Ile
                20                  25                  30

Asp Val Glu Lys Leu Glu Ala Gly Arg Phe Glu Glu Lys Leu Ile Thr
            35                  40                  45
```

```
Ser Val Gln Arg Ala Arg Asn Phe Ile Leu Val Leu Ser Ala Asn Ala
    50                  55                  60

Leu Asp Lys Cys Met Gly Asp Val Ala Met Lys Asp Trp Val His Lys
65                  70                  75                  80

Glu Ile Val Thr Ala Leu Asn Gly Lys Lys Asn Ile Val Pro Val Thr
                85                  90                  95

Asp Asn Phe Val Trp Pro Asp Pro Thr Ser Leu Pro Glu Asp Met Ser
            100                 105                 110

Thr Ile Leu Lys Phe Asn Gly Ile Lys Trp Ser His Glu Tyr Gln Glu
        115                 120                 125

Ala Thr Ile Glu Lys Ile Leu Arg Phe Leu Gly Cys Pro Ser Gln
    130                 135                 140

Glu Lys Pro Asp Gly Ala Lys Thr Asp Lys Lys Glu Pro Gln Lys Lys
145                 150                 155                 160
```

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

```
Trp Ser His Pro Gln Phe Glu Lys
1               5
```

<210> SEQ ID NO 6
<211> LENGTH: 195
<212> TYPE: PRT
<213> ORGANISM: Artificial Sequence
<220> FEATURE:
<223> OTHER INFORMATION: Synthetic polypeptide

<400> SEQUENCE: 6

```
Met Lys Arg Phe Val Ile Gly Ile Gly Gly Val Thr Asn Gly Gly Lys
1               5                   10                  15

Thr Thr Leu Ala Lys Ser Leu Gln Lys His Leu Pro Asn Cys Ser Val
                20                  25                  30

Ile Ser Gln Asp Asp Phe Phe Lys Pro Glu Ser Glu Ile Asp Ile Asp
            35                  40                  45

Glu Asn Gly Phe Leu Gln Tyr Asp Val Leu Glu Ala Leu Asn Met Glu
        50                  55                  60

Lys Met Met Ser Ala Val Ser Cys Trp Met Glu Asn Pro Gly Ser Ser
65                  70                  75                  80

Ala Gly Pro Ala Ala Leu Glu Ser Ala Gln Gly Val Pro Ile Leu Ile
                85                  90                  95

Ile Glu Gly Phe Leu Leu Phe Asn Tyr Lys Pro Leu Asp Thr Ile Trp
            100                 105                 110

Asn Arg Ser Tyr Phe Leu Thr Val Pro Tyr Glu Glu Cys Lys Arg Arg
        115                 120                 125

Arg Ser Thr Arg Val Tyr Glu Pro Pro Asp Pro Pro Gly Tyr Phe Asp
    130                 135                 140

Gly His Val Trp Pro Met Tyr Leu Lys His Arg Gln Glu Met Ser Ser
145                 150                 155                 160

Ile Thr Trp Asp Ile Val Tyr Leu Asp Gly Thr Arg Ser Glu Glu Asp
                165                 170                 175

Leu Phe Ser Gln Val Tyr Glu Asp Val Lys Gln Glu Leu Glu Lys Gln
            180                 185                 190
```

Asn Gly Leu
   195

<210> SEQ ID NO 7
<211> LENGTH: 10809
<212> TYPE: DNA
<213> ORGANISM: Artificial Sequence
<220> FEATURE:
<223> OTHER INFORMATION: Synthetic polynucleotide

<400> SEQUENCE: 7

| | | |
|---|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctgggattt | 1920 |
| tggggttgct ctggaaaact catttgcacc actgctgtgc cttggaatgc tagttggagt | 1980 |

```
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggggat    2460 tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420 accttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgagggagg    3600 gataagtgag gcgtcagttt cttggtcgg ttttatgtac ctatcttctt aagtagctga    3660
agctccggtt ttgaactatg cgctcggggt tggcgagtgt gttttgtgaa gtttttagg    3720 caccttttga aatgtaatca tttgggtcaa tatgtaattt tcagtgttag actagtaaag    3780
cttctgcagg tcgactctag aaaattgtcc gctaaattct ggccgttttt ggctttttg    3840 ttagacgaag cttgggctgc aggtcgactc tagaggatca tgaagagatt tgtcattgga    3900
attggtggtg tgacaaacgg agggaagacg acactggcta agagcttgca gaagcacctt    3960
cccaactgca gcgtcatatc tcaggatgac ttcttcaagc cagagtctga gatagacata    4020
gatgaaaatg gttttttgca gtatgatgtg cttgaagcgc taaatatgga aaaaatgatg    4080
tcagcagttt cctgttggat ggaaaaccca ggaagctctg cgggaccagc agccttggaa    4140
agtgctcaag gggttcccat tttaattatt gaaggtttcc ttctctttaa ttataagcct    4200
ctggacacca tatggaacag aagttacttc ctgaccgttc catatgaaga atgtaagagg    4260
agaaggagta ccagagtata tgagcctcca gaccctccag ggtacttcga tggccacgtg    4320
```

-continued

```
tggcccatgt acctaaagca cagacaggaa atgagctcca tcacctggga cattgtttac    4380
ctggatggaa caaggtctga agaggacctc ttctctcagg tgtatgaaga tgtcaagcag    4440
gaactagaga agcaaaatgg tttggactat aaagatgatg atgataagta agctagctac    4500
cggtgatccg cccctctccc tcccccccc ctaacgttac tggccgaagc cgcttggaat    4560
aaggccggtg tgcgtttgtc tatatgttat tttccaccat attgccgtct tttggcaatg    4620
tgagggcccg gaaacctggc cctgtcttct gacgagcat tcctaggggt ctttcccctc    4680
tcgccaaagg aatgcaaggt ctgttgaatg tcgtgaagga agcagttcct ctggaagctt    4740
cttgaagaca acaacgtct gtagcgaccc tttgcaggca gcggaacccc ccacctggcg    4800
acaggtgcct ctgcggccaa agccacgtg tataagatac acctgcaaag gcggcacaac    4860
cccagtgcca cgttgtgagt tggatagttg tggaaagagt caaatggctc tcctcaagcg    4920
tattcaacaa ggggctgaag gatgcccaga aggtacccca ttgtatggga tctgatctgg    4980
ggcctcggtg cacatgcttt acatgtgttt agtcgaggtt aaaaaaacgt ctaggccccc    5040
cgaaccacgg ggacgtggtt ttcctttgaa aaacacgatg ataatatggc cacaaccatg    5100
gatggccaag ttgaccagtg ccgttccggt gctcaccgcg cgcgacgtcg ccggagcggt    5160
cgagttctgg accgaccggc tcgggttctc ccgggacttc gtggaggacg acttcgccgg    5220
tgtggtccgg gacgacgtga ccctgttcat cagcgcggtc caggaccagg tggtgccgga    5280
caacaccctg gctgggtgt gggtgcgcgg cctggacgag ctgtacgccg agtggtcgga    5340
ggtcgtgtcc acgaacttcc gggacgcctc cgggccggcc atgaccgaga tcggcgagca    5400
gccgtggggg cggagttcg ccctgcgcga cccggccggc aactgcgtgc acttcgtggc    5460
cgaggagcag gactgagaat tcgatatcaa gcttatcgat aatcaacctc tggattacaa    5520
aatttgtgaa agattgactg gtattcttaa ctatgttgct ccttttacgc tatgtggata    5580
cgctgcttta atgcctttgt atcatgctat tgcttcccgt atggctttca ttttctcctc    5640
cttgtataaa tcctggttgc tgtctcttta tgaggagttg tggcccgttg tcaggcaacg    5700
tggcgtggtg tgcactgtgt ttgctgacgc aacccccact ggttggggca ttgccaccac    5760
ctgtcagctc ctttccggga ctttcgcttt ccccctccct attgccacgg cggaactcat    5820
cgccgcctgc cttgcccgct gctggacagg ggctcggctg ttgggcactg acaattccgt    5880
ggtgttgtcg gggaaatcat cgtccttttc ttggctgctc gcctgtgttg ccacctggat    5940
tctgcgcggg acgtccttct gctacgtccc ttcggccctc aatccagcgg accttccttc    6000
ccgcggcctg ctgccggctc tgcggcctct tccgcgtctt cgccttcgcc ctcagacgag    6060
tcggatctcc ctttgggccg cctccccgca tcgataccgt cgacctcgag acctagaaaa    6120
acatggagca atcacaagta gcaatacagc agctaccaat gctgattgtg cctggctaga    6180
agcacaagag gaggaggagg tgggttttcc agtcacacct caggtacctt taagaccaat    6240
gacttacaag gcagctgtag atcttagcca ctttttaaaa gaaagggggg actggaagg    6300
gctaattcac tcccaacgaa gacaagatat ccttgatctg tggatctacc acacacaagg    6360
ctacttccct gattggcaga actacacacc agggccaggg atcagatatc cactgacctt    6420
tggatggtgc tacaagctag taccagttga gcaagagaag gtagaagaag ccaatgaagg    6480
agagaacacc cgcttgttac accctgtgag cctgcatggg atggatgacc cggagagaga    6540
agtattagag tggaggtttg acagccgcct agcatttcat cacatggccc gagagctgca    6600
tccggactgt actgggtctc tctgttagac cagatctga gcctgggagc tctctggcta    6660
actagggaac ccactgctta agcctcaata aagcttgcct tgagtgcttc aagtagtgtg    6720
```

```
tgcccgtctg ttgtgtgact ctggtaacta gagatccctc agacccttt  agtcagtgtg   6780 gaaaatctct agcagggccc gtttaaaccc gctgatcagc ctcgactgtg ccttctagtt   6840
gccagccatc tgttgtttgc cctcccccg  tgccttcctt gaccctggaa ggtgccactc   6900
ccactgtcct ttcctaataa aatgaggaaa ttgcatcgca ttgtctgagt aggtgtcatt   6960
ctattctggg gggtggggtg gggcaggaca gcaaggggga ggattgggaa gacaatagca   7020
ggcatgctgg ggatgcggtg ggctctatgg cttctgaggc ggaaagaacc agctggggct   7080 ctaggggta  tccccacgcg ccctgtagcg gcgcattaag cgcggcgggt gtggtggtta   7140
cgcgcagcgt gaccgctaca cttgccagcg ccctagcgcc cgctcctttc gctttcttcc   7200
cttcctttct cgccacgttc gccggctttc cccgtcaagc tctaaatcgg gggctccctt   7260
tagggttccg atttagtgct ttacggcacc tcgaccccaa aaaacttgat tagggtgatg   7320
gttcacgtag tgggccatcg ccctgataga cggtttttcg ccctttgacg ttggagtcca   7380
cgttctttaa tagtggactc ttgttccaaa ctggaacaac actcaaccct atctcggtct   7440
attcttttga tttataaggg attttgccga tttcggccta ttggttaaaa aatgagctga   7500
tttaacaaaa atttaacgcg aattaattct gtggaatgtg tgtcagttag ggtgtggaaa   7560
gtccccaggc tccccagcag gcagaagtat gcaaagcatg catctcaatt agtcagcaac   7620
caggtgtgga aagtccccag gctccccagc aggcagaagt atgcaaagca tgcatctcaa   7680
ttagtcagca accatagtcc cgcccctaac tccgcccatc cgcccctaa  ctccgcccag   7740 ttccgcccat tctccgcccc atggctgact aattttttt  atttatgcag aggccgaggc   7800
cgcctctgcc tctgagctat tccagaagta gtgaggaggc tttttggag  gcctaggctt   7860 ttgcaaaaag ctcccgggag cttgtatatc cattttcgga tctgatcagc acgtgttgac   7920
aattaatcat cggcatagta tatcggcata gtataatacg acaaggtgag gaactaaacc   7980
atggccaagt tgaccagtgc cgttccggtg ctcaccgcgc gcgacgtcgc cggagcggtc   8040
gagttctgga ccgaccggct cgggttctcc cgggacttcg tggaggacga cttcgccggt   8100
gtggtccggg acgacgtgac cctgttcatc agcgcggtcc aggaccaggt ggtgccggac   8160
aacaccctgg cctgggtgtg ggtgcgcggc ctggacgagc tgtacgccga gtggtcggag   8220
gtcgtgtcca cgaacttccg ggacgcctcc gggccggcca tgaccgagat cggcgagcag   8280
ccgtgggggc gggagttcgc cctgcgcgac cggccggca  actgcgtgca cttcgtggcc   8340
gaggagcagg actgacacgt gctacgagat ttcgattcca ccgccgcctt ctatgaaagg   8400
ttgggcttcg gaatcgtttt ccgggacgcc ggctggatga tcctccagcg cggggatctc   8460
atgctggagt tcttcgccca ccccaacttg tttattgcag cttataatgg ttacaaataa   8520
agcaatagca tcacaaattt cacaaataaa gcatttttt  cactgcattc tagttgtggt   8580
ttgtccaaac tcatcaatgt atcttatcat gtctgtatac cgtcgacctc tagctagagc   8640
ttggcgtaat catggtcata gctgtttcct gtgtgaaatt gttatccgct cacaattcca   8700
cacaacatac gagccggaag cataaagtgt aaagcctggg gtgcctaatg agtgagctaa   8760
ctcacattaa ttgcgttgcg ctcactgccc gctttccagt cgggaaacct gtcgtgccag   8820
ctgcattaat gaatcggcca acgcgcgggg agaggcggtt tgcgtattgg gcgctcttcc   8880
gcttcctcgc tcactgactc gctgcgctcg gtcgttcggc tgcggcgagc ggtatcagct   8940
cactcaaagg cggtaatacg gttatccaca gaatcagggg ataacgcagg aaagaacatg   9000
tgagcaaaag gccagcaaaa ggccaggaac cgtaaaaagg ccgcgttgct ggcgtttttc   9060
```

```
cataggctcc gccccctga cgagcatcac aaaaatcgac gctcaagtca gaggtggcga      9120
aacccgacag gactataaag ataccaggcg tttccccctg gaagctccct cgtgcgctct     9180
cctgttccga ccctgccgct taccggatac ctgtccgcct ttctcccttc gggaagcgtg     9240
gcgctttctc atagctcacg ctgtaggtat ctcagttcgg tgtaggtcgt tcgctccaag     9300
ctgggctgtg tgcacgaacc ccccgttcag cccgaccgct gcgccttatc cggtaactat     9360
cgtcttgagt ccaacccggt aagacacgac ttatcgccac tggcagcagc cactggtaac     9420
aggattagca gagcgaggta tgtaggcggt gctacagagt tcttgaagtg gtggcctaac     9480
tacggctaca ctagaagaac agtatttggt atctgcgctc tgctgaagcc agttaccttc     9540 ggaaaagag ttggtagctc ttgatccggc aaacaaacca ccgctggtag cggtggtttt      9600
tttgtttgca agcagcagat tacgcgcaga aaaaaaggat ctcaagaaga tcctttgatc      9660
ttttctacgg ggtctgacgc tcagtggaac gaaaactcac gttaagggat tttggtcatg     9720
agattatcaa aaaggatctt cacctagatc ctttttaaatt aaaaatgaag ttttaaatca     9780
atctaaagta tatatgagta aacttggtct gacagttacc aatgcttaat cagtgaggca     9840
cctatctcag cgatctgtct atttcgttca tccatagttg cctgactccc cgtcgtgtag     9900
ataactacga tacgggaggg cttaccatct ggccccagtg ctgcaatgat accgcgagac     9960
ccacgctcac cggctccaga tttatcagca ataaaccagc cagccggaag ggccgagcgc     10020
agaagtggtc ctgcaacttt atccgcctcc atccagtcta ttaattgttg ccgggaagct     10080
agagtaagta gttcgccagt taatagtttg cgcaacgttg ttgccattgc tacaggcatc     10140
gtggtgtcac gctcgtcgtt tggtatggct tcattcagct ccggttccca acgatcaagg     10200
cgagttacat gatcccccat gttgtgcaaa aaagcggtta gctccttcgg tcctccgatc     10260
gttgtcagaa gtaagttggc cgcagtgtta tcactcatgg ttatggcagc actgcataat     10320
tctcttactg tcatgccatc cgtaagatgc ttttctgtga ctggtgagta ctcaaccaag     10380
tcattctgag aatagtgtat gcggcgaccg agttgctctt gcccggcgtc aatacggat      10440 aataccgcgc cacatagcag aactttaaaa gtgctcatca ttggaaaacg ttcttcgggg     10500
cgaaaactct caaggatctt accgctgttg agatccagtt cgatgtaacc cactcgtgca     10560
cccaactgat cttcagcatc ttttactttc accagcgttt ctgggtgagc aaaaacagga     10620
aggcaaaatg ccgcaaaaaa gggaataagg gcgacacgga aatgttgaat actcatactc     10680
ttcctttttc aatattattg aagcatttat cagggttatt gtctcatgag cggatacata     10740
tttgaatgta tttagaaaaa taaacaaata ggggttccgc gcacatttcc ccgaaaagtg     10800
ccacctgac                                                              10809
```

<210> SEQ ID NO 8
<211> LENGTH: 365
<212> TYPE: PRT
<213> ORGANISM: Artificial Sequence
<220> FEATURE:
<223> OTHER INFORMATION: Synthetic polypeptide

<400> SEQUENCE: 8

Met Ser Ala Trp Ser His Pro Gln Phe Glu Lys Gly Gly Gly Ser Gly
1               5                   10                  15

Gly Gly Ser Gly Gly Ser Ala Trp Ser His Pro Gln Phe Glu Lys Gly
            20                  25                  30

Gly Gly Ser Ser Gly Gly Gly Gly Gly Ser Ser Gly Gly Gly Ala
        35                  40                  45

| | | | | | | | | | | | |
|---|---|---|---|---|---|---|---|---|---|---|---|
|Ser|Val|Pro|Ser|Trp|Lys|Glu|Ala|Glu|Val|Gln|Thr|Trp|Leu|Gln|Gln|
| |50| | | |55| | | |60| | |

Ser Val Pro Ser Trp Lys Glu Ala Glu Val Gln Thr Trp Leu Gln Gln
       50                  55                  60

Ile Gly Phe Ser Lys Tyr Cys Glu Ser Phe Arg Glu Gln Gln Val Asp
 65              70                  75                      80

Gly Asp Leu Leu Leu Arg Leu Thr Glu Glu Leu Gln Thr Asp Leu
                85                  90                  95

Gly Met Lys Ser Gly Ile Thr Arg Lys Arg Phe Phe Arg Glu Leu Thr
            100                 105                 110

Glu Leu Lys Thr Phe Ala Asn Tyr Ser Thr Cys Asp Arg Ser Asn Leu
            115                 120                 125

Ala Asp Trp Leu Gly Ser Leu Asp Pro Arg Phe Arg Gln Tyr Thr Tyr
        130                 135                 140

Gly Leu Val Ser Cys Gly Leu Asp Arg Ser Leu Leu His Arg Val Ser
145                 150                 155                 160

Glu Gln Gln Leu Leu Glu Asp Cys Gly Ile His Leu Gly Val His Arg
                165                 170                 175

Ala Arg Ile Leu Thr Ala Ala Arg Glu Met Leu His Ser Pro Leu Pro
            180                 185                 190

Cys Thr Gly Gly Lys Pro Ser Gly Asp Thr Pro Asp Val Phe Ile Ser
            195                 200                 205

Tyr Arg Arg Asn Ser Gly Ser Gln Leu Ala Ser Leu Leu Lys Val His
    210                 215                 220

Leu Gln Leu His Gly Phe Ser Val Phe Ile Asp Val Glu Lys Leu Glu
225                 230                 235                 240

Ala Gly Lys Phe Glu Asp Lys Leu Ile Gln Ser Val Met Gly Ala Arg
                245                 250                 255

Asn Phe Val Leu Val Leu Ser Pro Gly Ala Leu Asp Lys Cys Met Gln
                260                 265                 270

Asp His Asp Cys Lys Asp Trp Val His Lys Glu Ile Val Thr Ala Leu
        275                 280                 285

Ser Cys Gly Lys Asn Ile Val Pro Ile Ile Asp Gly Phe Glu Trp Pro
        290                 295                 300

Glu Pro Gln Val Leu Pro Glu Asp Met Gln Ala Val Leu Thr Phe Asn
305                 310                 315                 320

Gly Ile Lys Trp Ser His Glu Tyr Gln Glu Ala Thr Ile Glu Lys Ile
                325                 330                 335

Ile Arg Phe Leu Gln Gly Arg Ser Ser Arg Asp Ser Ser Ala Gly Ser
            340                 345                 350

Asp Thr Ser Leu Glu Gly Ala Ala Pro Met Gly Pro Thr
            355                 360                 365

<210> SEQ ID NO 9
<211> LENGTH: 10329
<212> TYPE: DNA
<213> ORGANISM: Artificial Sequence
<220> FEATURE:
<223> OTHER INFORMATION: Synthetic polynucleotide

<400> SEQUENCE: 9

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
```

```
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca gtctccaccc cattgacgtc aatgggagtt tgttttggc    720 accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt   1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggat   2460 tgggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
```

```
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt aacgccgat  gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420 accttttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgagggagg    3600 gataagtgag gcgtcagttt cttggtcgg  ttttatgtac ctatcttctt aagtagctga    3660
agctccggtt ttgaactatg cgctcggggt tggcgagtgt gttttgtgaa gttttttagg    3720
caccttttga aatgtaatca tttgggtcaa tatgtaattt tcagtgttag actagtaaag    3780
cttctgcagg tcgactctag aaaattgtcc gctaaattct ggccgttttt ggctttttg    3840 ttagacgaag cttgggctgc aggtcgactc tagaggatcc ggatccgcca ccatgtcagc    3900
ttggagccac ccacaattcg aaaaaggcgg tggctcaggc ggtggctcag gtggctcagc    3960
ttggagccac ccacaattcg aaaaaggcgg tggctcatct ggcggaggtg gcggtggctc    4020
atctggcgga ggtgctagcg tgcccagctg gaaggaggcc gaggttcaga cgtggctgca    4080
gcagatcggt ttctccaagt actgcgagag cttccgggag cagcaggtgg atggcgacct    4140
gcttctgcgg ctcacggagg aggaactcca gaccgacctg ggcatgaaat cgggcatcac    4200
ccgcaagagg ttcttaggg  agctcacgga gctcaagacc ttcgccaact attctacgtg    4260
cgaccgcagc aacctggcgg actggctggg cagcctggac ccgcgcttcc gccagtacac    4320
ctacggcctg gtcagctgcg gcctggaccg ctccctgctg caccgcgtgt ctgagcagca    4380
gctgctggaa gactgcggca tccacctggg cgtgcaccgc gcccgcatcc tcacggcggc    4440
cagagaaatg ctacactccc cgctgccctg tactggtggc aaacccagtg gggacactcc    4500
agatgtcttc atcagctacc gccggaactc aggttcccag ctggcagtc  tcctgaaggt    4560 gcacctgcag ctgcatggct tcagtgtctt cattgatgtg gagaagctgg aagcaggcaa    4620
gttcgaggac aaactcatcc agagtgtcat gggtgcccgc aactttgtgt tggtgctatc    4680
acctggagca ctggacaagt gcatgcaaga ccatgactgc aaggattggg tgcataagga    4740
gattgtgact gctttaagct gcggcaagaa cattgtgccc atcattgatg gcttcgagtg    4800
gcctgagccc caggtcctgc ctgaggacat gcaggctgtg cttactttca acggtatcaa    4860
gtggtcccac gaataccagg aggccaccat tgagaagatc atccgcttcc tgcagggccg    4920
ctcctcccgg gactcatctg caggctctga caccagtttg gagggtgctg cacccatggg    4980
tccaacctaa actctagaat tcgatatcaa gcttatcgat aatcaacctc tggattacaa    5040
```

```
aatttgtgaa agattgactg gtattcttaa ctatgttgct cctttttacgc tatgtggata   5100 cgctgcttta atgcctttgt atcatgctat tgcttcccgt atggctttca ttttctcctc   5160
cttgtataaa tcctggttgc tgtctcttta tgaggagttg tggcccgttg tcaggcaacg   5220
tggcgtggtg tgcactgtgt ttgctgacgc aaccccccact ggttgggggca ttgccaccac   5280 ctgtcagctc ctttccggga ctttcgcttt cccctccct attgccacgg cggaactcat   5340
cgccgcctgc cttgcccgct gctggacagg ggctcggctg ttgggcactg acaattccgt   5400
ggtgttgtcg gggaaatcat cgtccttttcc ttggctgctc gcctgtgttg ccacctggat   5460
tctgcgcggg acgtccttct gctacgtccc ttcggccctc aatccagcgg accttccttc   5520
ccgcggcctg ctgccggctc tgcggcctct tccgcgtctt cgccttcgcc ctcagacgag   5580
tcggatctcc ctttgggccg cctccccgca tcgataccgt cgacctcgag acctagaaaa   5640
acatggagca atcacaagta gcaatacagc agctaccaat gctgattgtg cctggctaga   5700
agcacaagag gaggaggagg tgggttttcc agtcacacct caggtacctt taagaccaat   5760
gacttacaag gcagctgtag atcttagcca ctttttaaaa gaaaaggggg gactggaagg   5820
gctaattcac tcccaacgaa gacaagatat ccttgatctg tggatctacc acacacaagg   5880
ctacttccct gattggcaga actacacacc agggccaggg atcagatatc cactgacctt   5940
tggatggtgc tacaagctag taccagttga gcaagagaag gtagaagaag ccaatgaagg   6000
agagaacacc cgcttgttac accctgtgag cctgcatggg atggatgacc cggagagaga   6060
agtattagag tggaggtttg acagccgcct agcatttcat cacatggccc gagagctgca   6120
tccggactgt actgggtctc tctggttaga ccagatctga gcctgggagc tctctggcta   6180
actagggaac ccactgctta agcctcaata aagcttgcct tgagtgcttc aagtagtgtg   6240
tgcccgtctg ttgtgtgact ctggtaacta gagatccctc agaccctttt agtcagtgtg   6300
gaaaatctct agcagggccc gtttaaaccc gctgatcagc ctcgactgtg ccttctagtt   6360
gccagccatc tgttgtttgc ccctcccccg tgccttcctt gaccctggaa ggtgccactc   6420
ccactgtcct ttcctaataa aatgaggaaa ttgcatcgca ttgtctgagt aggtgtcatt   6480
ctattctggg gggtggggtg gggcaggaca gcaaggggga ggattgggaa gacaatagca   6540
ggcatgctgg ggatgcggtg ggctctatgg cttctgaggc ggaaagaacc agctggggct   6600 ctaggggggta tccccacgcg ccctgtagcg gcgcattaag cgcggcgggt gtggtggtta   6660
cgcgcagcgt gaccgctaca cttgccagcg ccctagcgcc cgctccttc gctttcttcc   6720 cttcctttct cgccacgttc gccggctttc cccgtcaagc tctaaatcgg ggctcccctt   6780
tagggttccg atttagtgct ttacggcacc tcgaccccaa aaaacttgat tagggtgatg   6840
gttcacgtag tgggccatcg ccctgataga cggtttttcg ccctttgacg ttggagtcca   6900
cgttctttaa tagtggactc ttgttccaaa ctggaacaac actcaaccct atctcggtct   6960
attcttttga tttataaggg attttgccga tttcggccta ttggttaaaa aatgagctga   7020
tttaacaaaa atttaacgcg aattaattct gtggaatgtg tgtcagttag ggtgtggaaa   7080
gtccccaggc tccccagcag gcagaagtat gcaaagcatg catctcaatt agtcagcaac   7140
caggtgtgga aagtccccag gctccccagc aggcagaagt atgcaaagca tgcatctcaa   7200
ttagtcagca accatagtcc cgcccctaac tccgcccatc ccgcccctaa ctccgcccag   7260
ttccgcccat tctccgcccc atggctgact aatttttttt atttatgcag aggccgaggc   7320
cgcctctgcc tctgagctat tccagaagta gtgaggaggc ttttttggag gcctaggctt   7380
```

```
ttgcaaaaag ctcccgggag cttgtatatc cattttcgga tctgatcagc acgtgttgac    7440
aattaatcat cggcatagta tatcggcata gtataatacg acaaggtgag gaactaaacc    7500
atggccaagt tgaccagtgc cgttccggtg ctcaccgcgc gcgacgtcgc cggagcggtc    7560
gagttctgga ccgaccggct cgggttctcc cgggacttcg tggaggacga cttcgccggt    7620
gtggtccggg acgacgtgac cctgttcatc agcgcggtcc aggaccaggt ggtgccggac    7680
aacaccctgg cctgggtgtg ggtgcgcggc ctggacgagc tgtacgccga gtggtcggag    7740
gtcgtgtcca cgaacttccg ggacgcctcc gggccggcca tgaccgagat cggcgagcag    7800 ccgtggggc gggagttcgc cctgcgcgac cggccggca actgcgtgca cttcgtggcc    7860
gaggagcagg actgacacgt gctacgagat ttcgattcca ccgccgcctt ctatgaaagg    7920
ttgggcttcg gaatcgtttt ccgggacgcc ggctggatga tcctccagcg cggggatctc    7980
atgctggagt tcttcgccca ccccaacttg tttattgcag cttataatgg ttacaaataa    8040
agcaatagca tcacaaattt cacaaataaa gcattttttt cactgcattc tagttgtggt    8100
ttgtccaaac tcatcaatgt atcttatcat gtctgtatac cgtcgacctc tagctagagc    8160
ttggcgtaat catggtcata gctgtttcct gtgtgaaatt gttatccgct cacaattcca    8220
cacaacatac gagccggaag cataaagtgt aaagcctggg gtgcctaatg agtgagctaa    8280
ctcacattaa ttgcgttgcg ctcactgccc gctttccagt cgggaaacct gtcgtgccag    8340
ctgcattaat gaatcggcca acgcgcgggg agaggcggtt tgcgtattgg gcgctcttcc    8400
gcttcctcgc tcactgactc gctgcgctcg gtcgttcggc tgcggcgagc ggtatcagct    8460
cactcaaagg cggtaatacg gttatccaca gaatcagggg ataacgcagg aaagaacatg    8520
tgagcaaaag gccagcaaaa ggccaggaac cgtaaaaagg ccgcgttgct ggcgtttttc    8580
cataggctcc gccccctga cgagcatcac aaaaatcgac gctcaagtca gaggtggcga    8640
aacccgacag gactataaag ataccaggcg tttccccctg gaagctccct cgtgcgctct    8700
cctgttccga ccctgccgct taccggatac ctgtccgcct ttctcccttc gggaagcgtg    8760
gcgctttctc atagctcacg ctgtaggtat ctcagttcgg tgtaggtcgt tcgctccaag    8820
ctgggctgtg tgcacgaacc ccccgttcag cccgaccgct gcgccttatc cggtaactat    8880
cgtcttgagt ccaacccggt aagacacgac ttatcgccac tggcagcagc cactggtaac    8940
aggattagca gagcgaggta tgtaggcggt gctacagagt tcttgaagtg gtggcctaac    9000
tacggctaca ctagaagaac agtatttggt atctgcgctc tgctgaagcc agttaccttc    9060
ggaaaaagag ttggtagctc ttgatccggc aaacaaacca ccgctggtag cggtggtttt    9120
tttgtttgca agcagcagat tacgcgcaga aaaaaaggat ctcaagaaga tcctttgatc    9180
ttttctacgg ggtctgacgc tcagtggaac gaaaactcac gttaagggat tttggtcatg    9240
agattatcaa aaaggatctt cacctagatc cttttaaatt aaaaatgaag ttttaaatca    9300
atctaaagta tatatgagta aacttggtct gacagttacc aatgcttaat cagtgaggca    9360
cctatctcag cgatctgtct atttcgttca tccatagttg cctgactccc cgtcgtgtag    9420
ataactacga tacgggaggg cttaccatct ggccccagtg ctgcaatgat accgcgagac    9480
ccacgctcac cggctccaga tttatcagca ataaaccagc cagccggaag ggccgagcgc    9540
agaagtggtc ctgcaacttt atccgcctcc atccagtcta ttaattgttg ccgggaagct    9600
agagtaagta gttcgccagt taatagtttg cgcaacgttg ttgccattgc tacaggcatc    9660
gtggtgtcac gctcgtcgtt tggtatggct tcattcagct ccggttccca acgatcaagg    9720
cgagttacat gatcccccat gttgtgcaaa aaagcggtta gctccttcgg tcctccgatc    9780
```

```
gttgtcagaa gtaagttggc cgcagtgtta tcactcatgg ttatggcagc actgcataat  9840
tctcttactg tcatgccatc cgtaagatgc ttttctgtga ctggtgagta ctcaaccaag  9900
tcattctgag aatagtgtat gcggcgaccg agttgctctt gcccggcgtc aatacgggat  9960
aataccgcgc cacatagcag aactttaaaa gtgctcatca ttggaaaacg ttcttcgggg 10020
cgaaaactct caaggatctt accgctgttg agatccagtt cgatgtaacc cactcgtgca 10080
cccaactgat cttcagcatc ttttactttc accagcgttt ctgggtgagc aaaaacagga 10140
aggcaaaatg ccgcaaaaaa gggaataagg gcgacacgga aatgttgaat actcatactc 10200
ttcctttttc aatattattg aagcatttat cagggttatt gtctcatgag cggatacata 10260
tttgaatgta tttagaaaaa taaacaaata ggggttccgc gcacatttcc ccgaaaagtg 10320
ccacctgac                                                        10329
```

<210> SEQ ID NO 10
<211> LENGTH: 211
<212> TYPE: PRT
<213> ORGANISM: Artificial Sequence
<220> FEATURE:
<223> OTHER INFORMATION: Synthetic polypeptide

<400> SEQUENCE: 10

```
Met Ser Ala Trp Ser His Pro Gln Phe Glu Lys Gly Gly Ser Gly
1               5                   10                  15

Gly Gly Ser Gly Gly Ser Ala Trp Ser His Pro Gln Phe Glu Lys Gly
            20                  25                  30

Gly Gly Ser Ser Gly Gly Gly Ala Ser Thr Pro Asp Val Phe Ile Ser
            35                  40                  45

Tyr Arg Arg Asn Ser Gly Ser Gln Leu Ala Ser Leu Leu Lys Val His
        50                  55                  60

Leu Gln Leu His Gly Phe Ser Val Phe Ile Asp Val Glu Lys Leu Glu
65                  70                  75                  80

Ala Gly Lys Phe Glu Asp Lys Leu Ile Gln Ser Val Met Gly Ala Arg
                85                  90                  95

Asn Phe Val Leu Val Leu Ser Pro Gly Ala Leu Asp Lys Cys Met Gln
            100                 105                 110

Asp His Asp Cys Lys Asp Trp Val His Lys Glu Ile Val Thr Ala Leu
        115                 120                 125

Ser Cys Gly Lys Asn Ile Val Pro Ile Ile Asp Gly Phe Glu Trp Pro
    130                 135                 140

Glu Pro Gln Val Leu Pro Glu Asp Met Gln Ala Val Leu Thr Phe Asn
145                 150                 155                 160

Gly Ile Lys Trp Ser His Glu Tyr Gln Glu Ala Thr Ile Glu Lys Ile
                165                 170                 175

Ile Arg Phe Leu Gln Gly Arg Ser Ser Arg Asp Ser Ser Ala Gly Ser
            180                 185                 190

Asp Thr Ser Leu Glu Gly Ala Ala Pro Met Gly Pro Thr His His His
        195                 200                 205

His His His
    210
```

<210> SEQ ID NO 11
<211> LENGTH: 211
<212> TYPE: PRT
<213> ORGANISM: Artificial Sequence
<220> FEATURE:

<223> OTHER INFORMATION: Synthetic polypeptide

<400> SEQUENCE: 11

```
Met Ser Ala Trp Ser His Pro Gln Phe Glu Lys Gly Gly Ser Gly
 1               5                  10                  15

Gly Gly Ser Gly Gly Ser Ala Trp Ser His Pro Gln Phe Glu Lys Gly
            20                  25                  30

Gly Gly Ser Ser Gly Gly Ala Ser Thr Pro Asp Val Phe Ile Ser
            35                  40                  45

Tyr Arg Arg Asn Ser Gly Ser Gln Leu Ala Ser Leu Leu Lys Val His
 50                  55                  60

Leu Gln Leu His Gly Phe Ser Val Phe Ile Asp Val Glu Lys Leu Glu
 65                  70                  75                  80

Ala Gly Lys Phe Glu Asp Lys Leu Ile Gln Ser Val Ile Ala Ala Arg
                85                  90                  95

Asn Phe Val Leu Val Leu Ser Ala Gly Ala Leu Asp Lys Cys Met Gln
                100                 105                 110

Asp His Asp Cys Lys Asp Trp Val His Lys Glu Ile Val Thr Ala Leu
            115                 120                 125

Ser Cys Gly Lys Asn Ile Val Pro Ile Ile Asp Gly Phe Glu Trp Pro
130                 135                 140

Glu Pro Gln Ala Leu Pro Glu Asp Met Gln Ala Val Leu Thr Phe Asn
145                 150                 155                 160

Gly Ile Lys Trp Ser His Glu Tyr Gln Glu Ala Thr Ile Glu Lys Ile
                165                 170                 175

Ile Arg Phe Leu Gln Gly Arg Pro Ser Gln Asp Ser Ser Ala Gly Ser
                180                 185                 190

Asp Thr Ser Leu Glu Gly Ala Thr Pro Met Gly Leu Pro His His His
            195                 200                 205

His His His
    210
```

<210> SEQ ID NO 12
<211> LENGTH: 207
<212> TYPE: PRT
<213> ORGANISM: Artificial Sequence
<220> FEATURE:
<223> OTHER INFORMATION: Synthetic polypeptide

<400> SEQUENCE: 12

```
Met Ser Ala Trp Ser His Pro Gln Phe Glu Lys Gly Gly Ser Gly
 1               5                  10                  15

Gly Gly Ser Gly Gly Ser Ala Trp Ser His Pro Gln Phe Glu Lys Gly
            20                  25                  30

Gly Gly Ser Ser Gly Gly Gly Ala Ser Pro Asp Val Phe Ile Ser Tyr
            35                  40                  45

Arg Arg Thr Thr Gly Ser Gln Leu Ala Ser Leu Leu Lys Val His Leu
 50                  55                  60

Gln Leu Arg Gly Phe Ser Val Phe Ile Asp Val Glu Lys Leu Glu Ala
 65                  70                  75                  80

Gly Arg Phe Glu Glu Lys Leu Ile Thr Ser Val Gln Arg Ala Arg Asn
                85                  90                  95

Phe Ile Leu Val Leu Ser Ala Asn Ala Leu Asp Lys Cys Met Gly Asp
                100                 105                 110

Val Ala Met Lys Asp Trp Val His Lys Glu Ile Val Thr Ala Leu Asn
            115                 120                 125
```

```
Gly Lys Lys Asn Ile Val Pro Val Thr Asp Asn Phe Val Trp Pro Asp
            130                 135                 140

Pro Thr Ser Leu Pro Glu Asp Met Ser Thr Ile Leu Lys Phe Asn Gly
145                 150                 155                 160

Ile Lys Trp Ser His Glu Tyr Gln Glu Ala Thr Ile Glu Lys Ile Leu
                165                 170                 175

Arg Phe Leu Glu Gly Cys Pro Ser Gln Glu Lys Pro Asp Gly Ala Lys
            180                 185                 190

Thr Asp Lys Lys Glu Pro Gln Lys Lys His His His His His
            195                 200                 205

<210> SEQ ID NO 13
<211> LENGTH: 724
<212> TYPE: PRT
<213> ORGANISM: Homo sapiens

<400> SEQUENCE: 13

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
            20                  25                  30

Pro Asp Gly Gly Gly Gly Thr Gly Pro Trp Trp Ala Ala Gly Gly Arg
        35                  40                  45

Gly Pro Arg Glu Val Ser Pro Gly Ala Gly Thr Glu Val Gln Asp Ala
50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Lys His Ser Glu Glu Thr Cys Gln Arg Leu Val Ala Ala Gly Gly Leu
        195                 200                 205

Asp Ala Val Leu Tyr Trp Cys Arg Arg Thr Asp Pro Ala Leu Leu Arg
210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
        275                 280                 285

Arg Ser Gly Thr Leu Ala Leu Val Glu Pro Leu Val Ala Ser Leu Asp
```

```
            290                 295                 300
Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
                340                 345                 350

Ala Ala Ile Lys Ser Leu Gln Gly Lys Thr Lys Val Phe Ser Asp Ile
                355                 360                 365

Gly Ala Ile Gln Ser Leu Lys Arg Leu Val Ser Tyr Ser Thr Asn Gly
                370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
                420                 425                 430

Phe Arg Glu Gln Gln Val Asp Gly Asp Leu Leu Leu Arg Leu Thr Glu
                435                 440                 445

Glu Glu Leu Gln Thr Asp Leu Gly Met Lys Ser Gly Ile Thr Arg Lys
450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
                500                 505                 510

Ser Leu Leu His Arg Val Ser Glu Gln Leu Leu Glu Asp Cys Gly
                515                 520                 525

Ile His Leu Gly Val His Arg Ala Arg Ile Leu Thr Ala Ala Arg Glu
                530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
                580                 585                 590

Ile Asp Val Glu Lys Leu Glu Ala Gly Lys Phe Glu Asp Lys Leu Ile
                595                 600                 605

Gln Ser Val Met Gly Ala Arg Asn Phe Val Leu Val Leu Ser Pro Gly
                610                 615                 620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
                645                 650                 655

Ile Asp Gly Phe Glu Trp Pro Glu Pro Gln Val Leu Pro Glu Asp Met
                660                 665                 670

Gln Ala Val Leu Thr Phe Asn Gly Ile Lys Trp Ser His Glu Tyr Gln
                675                 680                 685

Glu Ala Thr Ile Glu Lys Ile Ile Arg Phe Leu Gln Gly Arg Ser Ser
                690                 695                 700

Arg Asp Ser Ser Ala Gly Ser Asp Thr Ser Leu Glu Gly Ala Ala Pro
705                 710                 715                 720
```

Met Gly Pro Thr

<210> SEQ ID NO 14
<211> LENGTH: 2193
<212> TYPE: DNA
<213> ORGANISM: Homo sapiens

<400> SEQUENCE: 14

| | | | | | |
|---|---|---|---|---|---|
| atggtcctga | cgctgcttct | ctccgcctac | aagctgtgtc | gcttcttcgc | catgtcgggc | 60 |
| ccacggccgg | gcgccgagcg | gctggcggtg | cctgggccag | atggggggcgg | tggcacgggc | 120 |
| ccatggtggg | ctgcgggtgg | ccgcgggccc | cgcgaagtgt | cgccggggc | aggcaccgag | 180 |
| gtgcaggacg | ccctggagcg | cgcgctgccg | gagctgcagc | aggccttgtc | cgcgctgaag | 240 |
| caggcgggcg | gcgcgcgggc | cgtgggcgcc | ggcctggccg | aggtcttcca | actggtggag | 300 |
| gaggcctggc | tgctgccggc | cgtgggccgc | gaggtagccc | agggtctgtg | cgacgccatc | 360 |
| cgcctcgatg | gcgccctcga | cctgctgttg | cggctgctgc | aggcgccgga | gttggagacg | 420 |
| cgtgtgcagg | ccgcgcgcct | gctggagcag | atcctggtgg | ctgagaaccg | agaccgcgtg | 480 |
| gcgcgcattg | gctgggcgt | gatcctgaac | ctggcgaagg | aacgcgaacc | cgtagagctg | 540 |
| gcgcggagcg | tggcaggcat | cttggagcac | atgttcaagc | attcggagga | gacatgccag | 600 |
| aggctggtgg | cggccggcgg | cctggacgcg | gtgctgtatt | ggtgccgccg | cacggacccc | 660 |
| gcgctgctgc | gccactgcgc | gctggcgctg | ggcaactgcg | cgctgcacgg | gggccaggcg | 720 |
| gtgcagcgac | gcatggtaga | gaagcgcgca | gccgagtggc | tcttcccgct | cgccttctcc | 780 |
| aaggaggacg | agctgcttcg | gctgcacgcc | tgcctcgcag | tagcggtgtt | ggcgactaac | 840 |
| aaggaggtgg | agcgcgaggt | ggagcgctcg | ggcacgctgg | cgctcgtgga | gccgcttgtg | 900 |
| gcctcgctgg | accctggccg | cttcgcccgc | tgtctggtgg | acgccagcga | cacaagccag | 960 |
| ggccgcgggc | ccgacgacct | gcagcgcctc | gtgccgttgc | tcgactctaa | ccgcttggag | 1020 |
| gcgcagtgca | tcggggcttt | ctacctctgc | gccgaggctg | ccatcaagag | cctgcaaggc | 1080 |
| aagaccaagg | tgttcagcga | catcggcgcc | atccagagcc | tgaaacgcct | ggtttcctac | 1140 |
| tctaccaatg | gcactaagtc | ggcgctggcc | aagcgcgcgc | tgcgcctgct | gggcgaggag | 1200 |
| gtgccacggc | ccatcctgcc | ctccgtgccc | agctggaagg | aggccgaggt | tcagacgtgg | 1260 |
| ctgcagcaga | tcggtttctc | caagtactgc | gagagcttcc | gggagcagca | ggtggatggc | 1320 |
| gacctgcttc | tgcggctcac | ggaggaggaa | ctccagaccg | acctgggcat | gaaatcgggc | 1380 |
| atcacccgca | agaggttctt | tagggagctc | acggagctca | agaccttcgc | caactattct | 1440 |
| acgtgcgacc | gcagcaacct | ggcggactgg | ctgggcagcc | tggacccgcg | cttccgccag | 1500 |
| tacacctacg | gcctggtcag | ctgcggcctg | gaccgctccc | tgctgcaccg | cgtgtctgag | 1560 |
| cagcagctgc | tggaagactg | cggcatccac | ctgggcgtgc | accgcgcccg | catcctcacg | 1620 |
| gcggccagag | aaatgctaca | ctccccgctg | ccctgtactg | gtggcaaacc | cagtggggac | 1680 |
| actccagatg | tcttcatcag | ctaccgccgg | aactcaggtt | cccagctggc | cagtctcctg | 1740 |
| aaggtgcacc | tgcagctgca | tggcttcagt | gtcttcattg | atgtggagaa | gctggaagca | 1800 |
| ggcaagttcg | aggacaaact | catccagagt | gtcatgggtg | cccgcaactt | tgtgttggtg | 1860 |
| ctatcacctg | gagcactgga | caagtgcatg | caagaccatg | actgcaagga | ttgggtgcat | 1920 |
| aaggagattg | tgactgcttt | aagctgcggc | aagaacattg | tgcccatcat | tgatggcttc | 1980 |
| gagtggcctg | agccccaggt | cctgcctgag | gacatgcagg | ctgtgcttac | tttcaacggt | 2040 |

```
atcaagtggt cccacgaata ccaggaggcc accattgaga agatcatccg cttcctgcag    2100
ggccgctcct cccgggactc atctgcaggc tctgacacca gtttggaggg tgctgcaccc    2160
atgggtccaa cctaaccagt ccccagttcc cca                                 2193
```

<210> SEQ ID NO 15
<211> LENGTH: 166
<212> TYPE: PRT
<213> ORGANISM: Artificial Sequence
<220> FEATURE:
<223> OTHER INFORMATION: Synthetic polypeptide

<400> SEQUENCE: 15

```
Gly Asp Thr Pro Asp Val Phe Ile Ser Tyr Arg Arg Asn Ser Gly Ser
1               5                   10                  15

Gln Leu Ala Ser Leu Leu Lys Val His Leu Gln Leu His Gly Phe Ser
            20                  25                  30

Val Phe Ile Asp Val Glu Lys Leu Glu Ala Gly Lys Phe Glu Asp Lys
        35                  40                  45

Leu Ile Gln Ser Val Met Gly Ala Arg Asn Phe Val Leu Val Leu Ser
    50                  55                  60

Pro Gly Ala Leu Asp Lys Cys Met Gln Asp His Asp Cys Lys Asp Trp
65                  70                  75                  80

Val His Lys Glu Ile Val Thr Ala Leu Ser Cys Gly Lys Asn Ile Val
                85                  90                  95

Pro Ile Ile Asp Gly Phe Glu Trp Pro Glu Pro Gln Val Leu Pro Glu
            100                 105                 110

Asp Met Gln Ala Val Leu Thr Phe Asn Gly Ile Lys Trp Ser His Glu
        115                 120                 125

Tyr Gln Glu Ala Thr Ile Glu Lys Ile Ile Arg Phe Leu Gln Gly Arg
    130                 135                 140

Ser Ser Arg Asp Ser Ser Ala Gly Ser Asp Thr Ser Leu Glu Gly Ala
145                 150                 155                 160

Ala Pro Met Gly Pro Thr
                165
```

<210> SEQ ID NO 16
<211> LENGTH: 154
<212> TYPE: PRT
<213> ORGANISM: Artificial Sequence
<220> FEATURE:
<223> OTHER INFORMATION: Synthetic polypeptide

<400> SEQUENCE: 16

```
Val Gly Ser Val Phe Leu Gly Gly Pro Phe Arg Gln Leu Val Asp Pro
1               5                   10                  15

Arg Thr Gly Val Met Ser Ser Gly Asp Gln Asn Val Phe Ser Arg Leu
            20                  25                  30

Ile Glu His Phe Glu Ser Arg Gly Thr Thr Val Tyr Asn Ala His Arg
        35                  40                  45

Arg Glu Ala Trp Gly Ala Glu Phe Leu Ser Pro Ala Glu Ala Thr Arg
    50                  55                  60

Leu Asp His Asp Glu Ile Lys Ala Ala Asp Val Phe Ala Phe Pro
65                  70                  75                  80

Gly Val Pro Ala Ser Pro Gly Thr His Val Glu Ile Gly Trp Ala Ser
                85                  90                  95

Gly Met Gly Lys Pro Met Val Leu Leu Leu Glu Arg Asp Glu Asp Tyr
            100                 105                 110
```

```
Ala Phe Leu Val Thr Gly Leu Glu Ser Gln Ala Asn Val Glu Ile Leu
        115                 120                 125
Arg Phe Ser Gly Thr Glu Glu Ile Val Glu Arg Leu Asp Gly Ala Val
    130                 135                 140
Ala Arg Val Leu Gly Arg Ala Gly Glu Pro
145                 150
```